(12) United States Patent
Berger et al.

(10) Patent No.: US 9,744,252 B2
(45) Date of Patent: Aug. 29, 2017

(54) COMPOUNDS FOR BINDING TO THE PLATELET SPECIFIC GLYCOPROTEIN IIB/IIIA AND THEIR USE FOR IMAGING OF THROMBI

(71) Applicant: PIRAMAL IMAGING SA, Matran (CH)

(72) Inventors: Markus Berger, Berlin (DE); Martin Kruger, Berlin (DE); Jessica Lohrke, Berlin (DE); Michael Reinhardt, Berlin (DE); Holger Siebeneicher, Berlin (DE)

(73) Assignee: PIRAMAL IMAGING SA, Matran (CH)

( * ) Notice: Subject to any disclaimer, the term of this patent is extended or adjusted under 35 U.S.C. 154(b) by 35 days.

(21) Appl. No.: 15/003,368

(22) Filed: Jan. 21, 2016

(65) Prior Publication Data
US 2016/0137629 A1 May 19, 2016

Related U.S. Application Data

(62) Division of application No. 14/239,065, filed as application No. PCT/EP2012/003583 on Aug. 17, 2012, now Pat. No. 9,345,793.

(30) Foreign Application Priority Data

Aug. 17, 2011 (EP) .................................... 11075195

(51) Int. Cl.
*A61K 51/08* (2006.01)
*C07D 211/60* (2006.01)
*C07D 401/04* (2006.01)
*C07D 401/06* (2006.01)
*C07K 5/06* (2006.01)
*A61J 1/06* (2006.01)
*A61K 49/04* (2006.01)
*C07D 401/14* (2006.01)

(52) U.S. Cl.
CPC ............... *A61K 51/088* (2013.01); *A61J 1/06* (2013.01); *A61K 49/0433* (2013.01); *C07D 211/60* (2013.01); *C07D 401/04* (2013.01); *C07D 401/06* (2013.01); *C07D 401/14* (2013.01); *C07K 5/06* (2013.01)

(58) Field of Classification Search
CPC .......... A61K 51/00; A61K 51/08; C07K 5/06; C07K 7/06; C07K 7/08
See application file for complete search history.

(56) References Cited

U.S. PATENT DOCUMENTS

| 6,066,651 | A | 5/2000 | Hoekstra |
| 6,069,254 | A | 5/2000 | Costanzo et al. |
| 6,191,145 | B1 | 2/2001 | Hoekstra |
| 2007/0189970 | A1 | 8/2007 | Murakami et al. |

FOREIGN PATENT DOCUMENTS

| WO | 9741102 A1 | 11/1997 |
| WO | 9921832 A2 | 5/1999 |
| WO | WO-9921832 | * 5/1999 |

OTHER PUBLICATIONS

Hoekstra, W. J. et al., "Potent, Orally Active GPIIb/IIIa Antagonists Containing a Nipecotic Acid Subunit. Structure-Activity Studies Leading to the Discovery of RWJ-53308," J. Med. Chem., 1999, vol. 42, pp. 5254-5265.
International Search Report for PCT/EP2012/003583 dated Sep. 24, 2012.

* cited by examiner

*Primary Examiner* — Jake Vu
*Assistant Examiner* — Jagadishwar Samala
(74) *Attorney, Agent, or Firm* — Millen White Zelano and Branigan, PC; John Sopp; Anthony Zelano

(57) ABSTRACT

The present invention relates to novel fluorine containing compounds, methods for their preparation, the intermediates of the synthesis, their use as diagnostic agents, especially for imaging of thrombi. The invention relates to positron emission tomography (PET) agents and associated precursor reagents, and methods for producing such radiolaveled agents for imaging of thrombi in a mammalian body. More particularly, the invention relates to small nonpeptide, high-affinity, specific-binding glycoprotein IIb/IIIa antagonists for imaging of thrombi.

15 Claims, 7 Drawing Sheets

1.

2.

3.

Affinity assay

Blood-to-clot ratio *in vitro* versus IC50 values of the investigated compounds

Biodistribution of the compound described in example 41 in mice.

Blood kinetics of the compound described in example 40 in cynomolgus monkey.

PET-Imaging of an arterial thrombus in a Cynomolgus monkey

PET-Imaging of an arterial thrombus in a cynomolgus monkey

Arterial thrombi removed from monkey 2:

0 – 15 min.   15 - 60 min.

PET-Imaging of arterial and venous thrombi in a cynomolgus monkey with the reduced tracer-dosage of 15 MBq per animal

COMPOUNDS FOR BINDING TO THE PLATELET SPECIFIC GLYCOPROTEIN IIB/IIIA AND THEIR USE FOR IMAGING OF THROMBI

FIELD OF THE INVENTION

The present invention relates to novel fluorine containing compounds, $^{19}$F and the corresponding $^{18}$F labeled compounds, methods for their preparation, the intermediates of the synthesis, their use as diagnostic agents, especially for imaging of thrombi. This invention relates to positron emission tomography (PET) agents and associated precursor reagents, and methods for producing such radiolabeled agents for imaging of thrombi in a mammalian body. More particularly, the invention relates to small, nonpeptide, high-affinity, specific-binding glycoprotein IIb/IIIa antagonists for imaging of thrombi.

BACKGROUND

1. Introduction

Myocardial infarction (MI), stroke, transient ischemic attacks (TIA) and pulmonary embolism (PE) are major causes of morbidity and mortality worldwide. These life-threatening clinical events are mostly caused by thrombi, which can be located in different vessels spread all over the body and can be of different size and composition. The origin of stroke or TIA can for example be a thrombus in the left atrium (LA) of the heart or in one of the big arteries between heart and brain like the carotid artery. In case of PE a venous thrombosis, often situated in the lower legs, can be the cause.

In a growing thrombus the final common step of platelet aggregation is characterized by the binding of activated glycoprotein IIb/IIIa to blood fibrinogen resulting in a crosslink inside the platelets. Design and development of glycoprotein IIb/IIIa inhibitors (Scarborough R. M., Gretler D. D., *J. Med. Chem.* 2000, 43, 3453-3473) has been of considerable interest in pharmacological research with respect to anti-platelet and anti-thrombotic activity.

However, health care professionals are in need not only for compounds that prevent thrombosis in an acute care setting, but also for a satisfactory method of imaging thrombi down to a size of 1 mm$^3$. More particularly, a thrombus imaging is important because clinical applications such as thrombolytic intervention require that the thrombus formation site is identified and enables the monitoring of therapy effects. In this way a thrombus imaging can help to avoid unnecessary prophylactic applications and therewith anticoagulant treatments which are associated with risks (e.g. severe bleedings due to the reduced coagulation capacity).

The patient population which may benefit from such a diagnostic procedure is huge. According to the "Heart disease and Stroke Statistics—2010 Update" of the American Heart Association 17.6 million people suffered from coronary heart disease only in the USA. Every year an estimated 785,000 Americans will have a new coronary attack, and approximately 470,000 will have a recurrent attack. Every year about 795,000 patients experience a new or a recurrent stroke. About 610,000 of these are first attacks. Of all strokes, 87% are ischemic, most of them due to a thromboembolic cause (Lloyd-Jones, D. et al., *Circulation*, 2010, 121(7): p. e46-215). The incidence of transient ischemic attack (TIA) in the United States has been estimated to be approximately 200,000 to 500,000 per year, with a population prevalence of 2.3%, which translates into about 5 million people (Easton, J. D. et al., Stroke, 2009, 40(6): p. 2276-2293). Individuals who have a TIA have a 90-day risk of stroke of 3.0% to 17.3% and a 10-year stroke risk of 18.8%. The combined 10-year stroke, myocardial infarction, or vascular death risk is even 42.8% (Clark, T. G., M. F. G. Murphy, and P. M. Rothwell, Journal of Neurology, Neurosurgery & Psychiatry, 2003. 74(5): p. 577-580).

Imaging is forefront in identifying thrombus. Currently, thrombus imaging relies on different modalities depending on the vascular territory. Carotid ultrasound is used to search for carotid thrombus, transesophageal echocardiography (TEE) searches for cardiac chamber clot, ultrasound searches for deep vein thrombosis, and CT has become the gold standard for PE detection.

2. Description of the Prior Art, Problem to be Solved and its Solution

Despite the success of these techniques, there continues to be a strong need for a molecular imaging solution for thrombus detection and monitoring: first, there are certain vascular territories that are underserved. For instance, despite best imaging efforts some 30% to 40% of ischemic strokes are "cryptogenic," that is, of indefinite cause, or in other words, the source of the thromboembolism is never identified (Guercini, F. et al., *Journal of Thrombosis and Haemostasis*, 2008. 6(4): p. 549-554). Underlying sources of cryptogenic stroke include atherosclerosis in the aortic arch or intracranial arteries. Plaque rupture in the arch or other major vessels, in particular, is thought to be a major source of cryptogenic strokes and can be difficult to detect with routine methods. Recent clinical trial data from transesophageal Echocardiography (TEE) studies showed that the presence of thickened vessel wall in the aortic arch was not predictive of ischemic stroke, although ulcerated aortic arch plaques are associated with cryptogenic stroke. A thrombus-targeted molecular imaging approach could potentially identify clot in the presence of atherosclerotic plaque. Finally, there is a need for an approach wherein a single modality could be used to identify thrombus throughout the body. For instance, in a TIA or stroke follow-up, currently multiple examinations are required to search for the source of the embolus (Ciesienski, K. L. and P. Caravan, *Curr Cardiovasc Imaging Rep.*, 2010. 4(1): p. 77-84).

As already mentioned the therapeutic application of glycoprotein IIb/IIIa inhibitors (Scarborough R. M., Gretler D. D., *J. Med. Chem.* 2000, 43, 3453-3473) has been of considerable interest in the past. Meanwhile three glycoprotein IIb/IIIa antagonists are commercially available: a recombinant antibody (Abciximab), a cyclic heptapeptide (Eptifibatid) and a synthetic, non-peptide inhibitor (Tirofiban). Tirofiban (brand name AGGRASTAT) belongs to the class of sulfonamides and is the only synthetic, small molecule among the above mentioned pharmaceuticals. Duggan et. al., 1994, U.S. Pat. No. 5,292,756 disclose sulfonamide fibrinogen receptor antagonist as therapeutic agents for the prevention and treatment of diseases caused by thrombus formation.

One attempt to fulfill the need of thrombus imaging is represented by the SPECT tracer apticide (AcuTect®). Apticide is a Tc-99m labeled peptide specifically binds to the GPIIb/IIIa receptor and is used for imaging of thrombi in a mammalian body. Dean et al., 1996, U.S. Pat. No. 5,508,020, disclosed radiolabeled peptides, methods and kits for making such peptides to image sites in a mammalian body labeled with technetium-99m via Tc-99m binding moieties. Dean and Lister-James describe peptides that specifically bind to GPIIb/IIIa receptors on the surface of activated platelets (U.S. Pat. Nos. 5,645,815; 5,830,856 and 6,028,056). Apticide was approved for the detection of deep vein thrombosis. The resolution reached by the technetium labeled peptide was found not to be satisfactory due to unspecific binding and high background.

Novel highly specific non-peptide glycoprotein IIb/IIIa antagonists have been described in the prior art (Damiano et. al., *Thrombosis Research* 2001 104, 113-126; Hoekstra, W. J., et al., *J. Med. Chem.*, 1999, 42, 5254-5265). These compounds have been known to be GPIIb/IIIa antagonist, effective as therapeutic agents with anti-platelet and anti-thrombotic activity (see WO95/08536, WO96/29309, WO97/33869, WO9701/60813, U.S. Pat. No. 6,515,130). The potential use of glycoprotein IIb/IIIa antagonists as contrast agents is also proposed (see US 2007/0189970 A1). However, a thrombus imaging with these compounds has not been demonstrated.

The F-18 radiolabeled compounds and their precursors described in this invention surprisingly show high metabolic stability, low protein binding and fast elimination. A non-invasive PET imaging of very small thrombi in vivo with an $^{18}$F-labeled tracer has been successfully demonstrated.

The images show strong signals in arterial and venous thrombi. In contrast to Apticide (U.S. Pat. Nos. 5,645,815; 5,830,856 and 6,028,056 there is no background visible in the whole body except the excreting organs liver and kidney. Most surprisingly, even very small thrombi (thickness <1 mm) can be detected and show a bright signal in the image. Detection of such small thrombi has not been described so far. The thrombi shown with Apticide had a size of 89 plus/minus 26 mg [mean plus/minus SEM](Lister-James, J., et al., *J Nucl Med*, 1996. 37(5): p. 775-81).

The imaging of small thrombi is particularly important with regard to thromboembolic diseases such as myocardial infarction, pulmonary embolism, stroke and transient ischemic attacks. Furthermore, a sensitive thrombus PET marker can be used for the regular health monitoring of cardiovascular risk patients, or the diagnosis of life threatening diseases such as aortic aneurism, chronic thromboembolic pulmonary hypertension (CETPH), atrial fibrillation and coronary thrombosis.

The in vivo clot-to-blood ratio of the disclosed compounds lies in a high, especially desirable range, which is a property that has never been observed before. In fact, it is the decisive property of the new compounds that is responsible for the clear advantage over the current state of the art compounds and enables a much lower radioactive dose to be administered to a potential patient (only 15 MBq needed for monkeys, which is at least 20-fold less the dose used in the closest prior art US 2007/0189970 A1).

SUMMARY

The present invention is directed to compounds that bind to glycoprotein IIb/IIIa and can be used as radiotracers for diagnostic imaging, in particular positron emission tomography (PET), of thrombi. The disclosed compounds enable the imaging of arterial and venous thrombi with a sensitivity that has never been observed before and that is sufficient to image the smallest thrombi in the single digit milligram range. Compared to the prior art, the disclosed compounds enable obtaining images with basically no background in relevant tissues and organs and the administration of radioactive doses in a much lower range.

DESCRIPTION

The present invention provides novel compounds of Formula I, Formula II and Formula III.

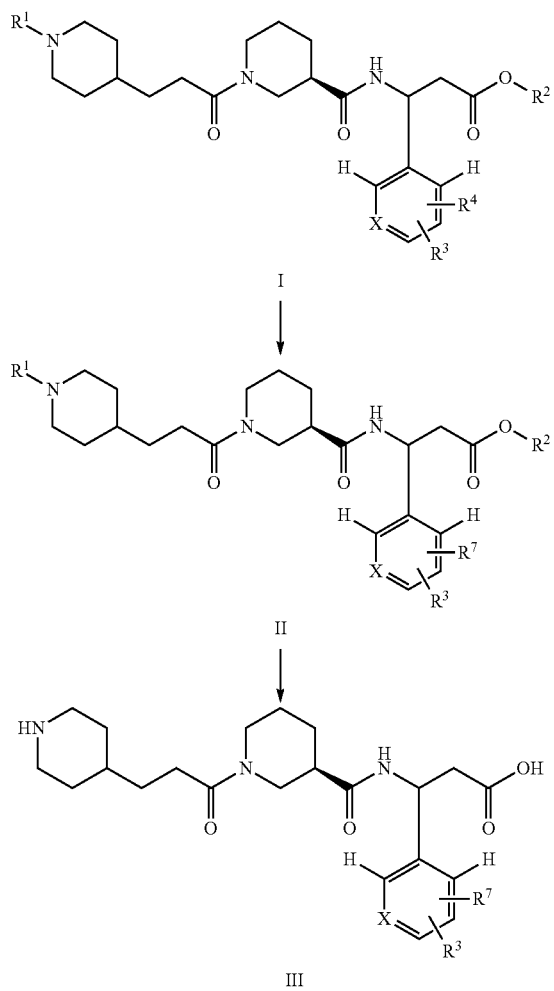

The invention furthermore provides a radiopharmaceutical composition of compounds of Formula III or pharmaceutically acceptable salts of an inorganic or organic acid or base thereof, hydrates, complexes and solvates thereof and optionally a pharmaceutically acceptable carrier, diluent, adjuvant or excipient.

The compounds of Formula III may exist as zwitterions. All forms of the compounds, including free acid, free-base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

The present invention also provides methods for manufacturing of compounds of Formula III that contain $^{18}$F:

Direct method:
   $^{18}$F radiolabeling of compounds of Formula I to obtain compounds of Formula II, and
   Cleavage of protecting groups of compounds of Formula II to obtain compounds of Formula III.

Indirect method:
   Reacting of compounds of Formula I with a $^{18}$F radiolabeled building block, and
   Cleavage of protecting groups to obtain compounds of Formula III.

The present invention also provides methods for manufacturing of compounds of Formula III that contain $^{19}F$:

Method 1:
$^{19}F$ Fluorination of compounds of Formula I to obtain compounds of Formula II, Cleavage of protecting groups of compounds of Formula II to obtain compounds of Formula III.

Method 2:
Reacting of compound of Formula I with a $^{19}F$ fluorine reagent or $^{19}F$ fluorinated building block,
Cleavage of protecting groups to obtain compounds of Formula III.

DETAILED DESCRIPTION

Ahead of the detailed description, the main compounds of Formula III are emphasized.

The main and third aspect of the present invention is directed to compounds of Formula III:

III wherein
$R^3$ is H, F, $CF_3$, CN or $NO_2$;
$R^7$ is Y, $-O(CH_2)_n-Y$, $-(OCH_2CH_2)_m-Y$, Z, $-OCH_2-Z$; $-CH_2-CH_2-Z$, $-CH=CH-Z$ or $-C\equiv C-Z$;
X is CH or N;
Y is $^{18}F$ or F;
Z is a group wherein * indicates the atom of connection of Z;
$R^5$ is H, $CF_3$, CN or $NO_2$;
$R^8$ is Y, $-O(CH_2)_n-Y$ or $-(OCH_2CH_2)_m-Y$;
n is 1-3;
and m is 2-3,
including E- and Z-isomers and diastereomers, mixtures thereof, and any pharmaceutically acceptable salt or complex thereof.

The first aspect of the present invention is directed to compounds of Formula I:

I wherein
$R^1$ is hydrogen or an amine-protecting group;
$R^2$ is hydrogen or a carboxyl-protecting group;
wherein at least one of $R^1$ and $R^2$ is not H;
$R^3$ is selected from the group consisting of H, F, $CF_3$, $COR^9$, $COOR^{10}$, $SOR^{10}$, $SO_2R^{10}$, CN and $NO_2$; preferably $R^3$ is selected from the group consisting of H, F, $CF_3$, CN, and $NO_2$;
$R^4$ is selected from the group consisting of OH, Halogen, $-NO_2$, $-N^+(Me)_3(W^-)$, $-I^+R^{11}(W^-)-O(CH_2)_n$-LG, $-(OCH_2CH_2)_m$-LG, Q, $-OCH_2$-Q; $-CH_2-CH_2$-Q, $-CH=CH$-Q and $-C\equiv C$-Q; preferably $R^4$ is selected from the group consisting of OH, Halogen, $-N^+(Me)_3(W^-)$, $-O(CH_2)_n$-LG, $-(OCH_2CH_2)_m$-LG, Q, $-OCH_2$-Q; $-CH_2-CH_2$-Q, $-CH=CH$-Q and $-C\equiv C$-Q;
X is selected from CH or N;
LG is a leaving group;
$R^9$ is hydrogen or $(C_1-C_6)$alkyl; preferably hydrogen or $(C_1-C_4)$alkyl, more preferably hydrogen, methyl, ethyl or tert-butyl;
$R^{10}$ is $(C_1-C_6)$alkyl; preferably $(C_1-C_4)$alkyl, more preferably methyl, ethyl or tert-butyl;
$R^{11}$ is selected from the group consisting of phenyl, (4-methyl)phenyl, (4-methoxy)phenyl, 2-furanyl and 2-thienyl; preferably $R^{11}$ is selected from the group consisting of (4-methoxy)phenyl and 2-thienyl;
$W^-$ is selected from the group comprising $CF_3(S(O)_2O^-$, iodide anion, bromide anion and $CF_3C(O)O^-$; preferably $W^-$ is selected from the group $CF_3(S(O)_2O^-$, bromide anion and $CF_3C(O)O^-$;
Q is a group wherein * indicates the atom of connection of Q;
$R^5$ is selected from the group consisting of H, $CF_3$, $COR^9$, $COOR^{10}$, $SOR^{10}$, $SO_2R^{10}$, CN and $NO_2$; preferably $R^5$ is selected from the group consisting of H, $CF_3$, CN, and $NO_2$
$R^6$ is selected from the group consisting of OH, Halogen, $-NO_2$, $-N^+(Me)_3(W^-)$, $-I^+R^{11}(W^-)$, $-O(CH_2)_n$-LG and $-(OCH_2CH_2)_m$-LG; preferably $R^6$ is selected from the group consisting of OH, Halogen, $-N^+(Me)_3(W^-)$, $-O(CH_2)_n$-LG and $-(OCH_2CH_2)_m$-LG;
n is 1-3;
and m is 2-3;

with the proviso that if $R^4$ has the meaning of Halogen, $-NO_2$, $-N^+(Me)_3(W^-)$ or $-I^+R^{11}(W^-)$, $R^3$ has the meaning of $CF_3$, $COR^9$, $COOR^{10}$, $SOR^{10}$, $SO_2R^{10}$, CN or $NO_2$ and with the proviso that if $R^6$ has the meaning of Halogen, $-NO_2$, $-N^+(Me)_3(W^-)$ or $-I^+R^{11}(W^-)$, $R^5$ has the meaning of $CF_3$, $COR^9$, $COOR^{10}$, $SOR^{10}$, $SO_2R^{10}$, CN or $NO_2$;

including E and Z-isomers and diastereomers, mixtures thereof, and any pharmaceutically acceptable salt or complex thereof.

Preferably, $R^1$ is an amine-protecting group comprising tert-butyloxycarbonyl (BOC), carbobenzyloxy (Cbz) and 9-fluorenylmethyloxycarbonyl (FMOC).

More preferably, $R^1$ is tert-butyloxycarbonyl (BOC) or carbobenzyloxy (Cbz).

Even more preferably, $R^1$ is tert-butyloxycarbonyl (BOC)

Preferably, $R^2$ is a carboxyl-protecting group selected from the group comprising methyl, ethyl, propyl, tert-butyl, benzyl and p-methoxybenzyl.

More preferably, $R^2$ is selected from the group comprising methyl and tert-butyl.

Preferably, $R^1$ is a nitrogen-protecting group and $R^2$ is a carboxyl-protecting group.

More preferably, $R^1$ is tert-butyloxycarbonyl (BOC) and $R^2$ is methyl or tert-butyl.

Preferably, X is N.

Preferably, $R^1$ is tert-butyloxycarbonyl (BOC), $R^2$ is methyl or tert-butyl, and X is N.

Preferably LG is a leaving group selected from the group comprising methylsulfonyloxy and (4-methylphenyl)sulfonyloxy.

More preferably, LG is (4-methylphenyl)sulfonyloxy.

In a preferred embodiment, X is N and $R^3$ is H and $R^4$ is $-O(CH_2)_n$-LG.

In a preferred embodiment, X is N and $R^3$ is H and $R^4$ is $-O(CH_2)_n$-LG and $R^1$ is Boc and $R^2$ is methyl or tert-butyl and LG is methylsulfonyloxy or (4-methylphenyl)sulfonyloxy.

Compounds of Formula I are defined by the general formula and/or the combination of the preferred features as defined above.

In a first embodiment, compounds of the Formula I are defined as single diastereomers of Formula I-A, see structure in table A.

In a second embodiment, compounds of the Formula I are defined as mixture of the two diastereomers of Formula I-A and Formula I-B, see structure in table A.

Preferred features as disclosed above are incorporated herein for all embodiments.

TABLE A

Formula I diastereomers

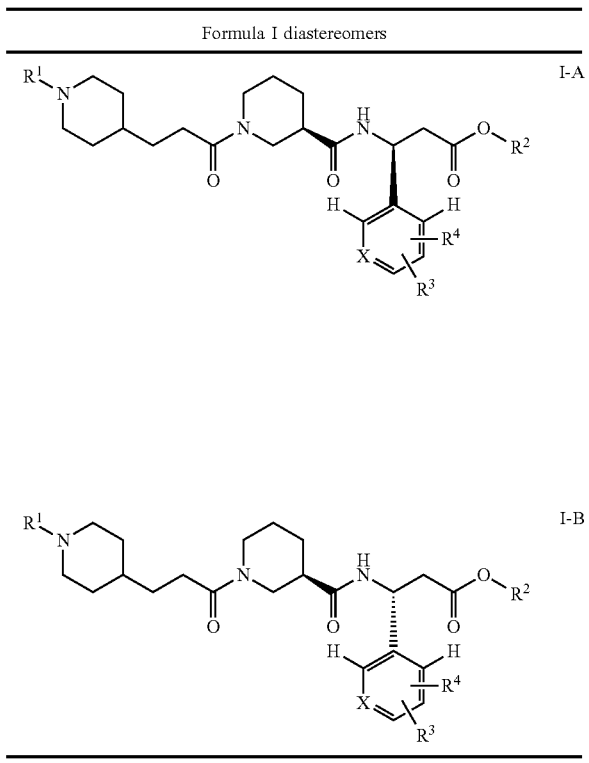

The compounds of Formula I-A and Formula I-B furthermore encompass pharmaceutically acceptable salts of an inorganic or organic acid or base thereof, hydrates, complexes, and solvates thereof and optionally a pharmaceutically acceptable carrier, diluent, adjuvant or excipients.

A preferred compound of Formula I is Example 21 tert-butyl 4-{3-[(3R)-3-({(1S)-3-methoxy-1-[3-(2-{[(4-methylphenyl)sulfonyl]oxy}ethoxy)-phenyl]-3-oxopropyl}carbamoyl)piperidin-1-yl]-3-oxopropyl}piperidine-1-carboxylate

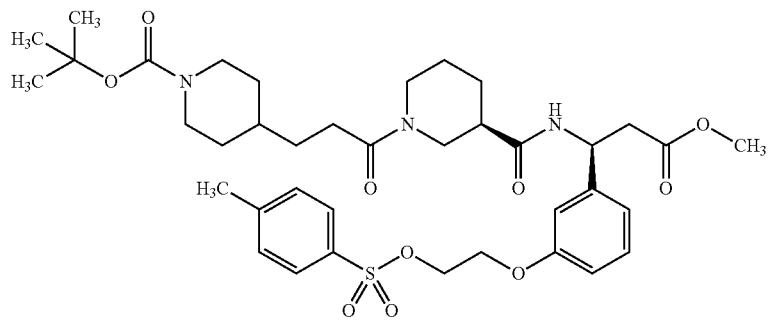 [SMILES: COC(=O)C[C@H](NC(=O)[C@@H]1CCCN(C(=O)CCC2CCN(C(=O)OC(C)(C)C)CC2)C1)c1cccc(OCCOS(=O)(=O)c2ccc(C)cc2)c1]

Another preferred compound of Formula I is Example 22 tert-butyl 4-{3-[(3R)-3-({3-methoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate

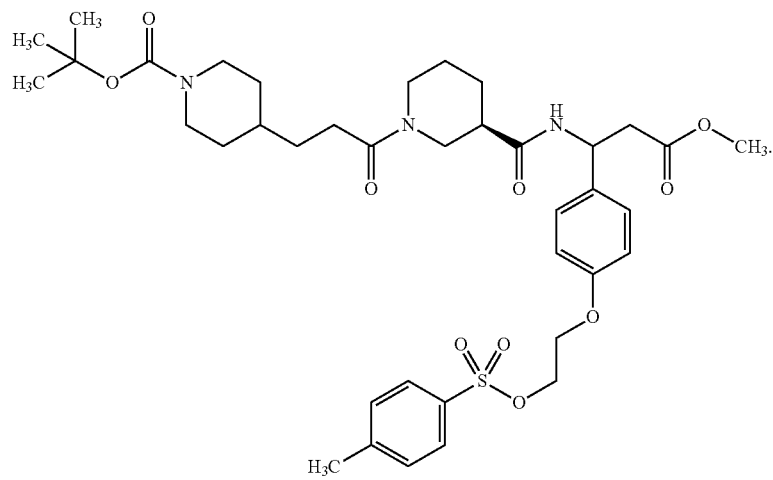 [SMILES: COC(=O)CC(NC(=O)[C@@H]1CCCN(C(=O)CCC2CCN(C(=O)OC(C)(C)C)CC2)C1)c1ccc(OCCOS(=O)(=O)c2ccc(C)cc2)cc1]

Another preferred compound of Formula I is Example 23 tert-butyl 4-{3-[(3R)-3-({(1S)-3-tert-butoxy-1-[4-(2-{[(4-methylphenyl)sulfonyl]oxy}ethoxy)-phenyl]-3-oxopropyl}carbamoyl)piperidin-1-yl]-3-oxopropyl}piperidine-1-carboxylate

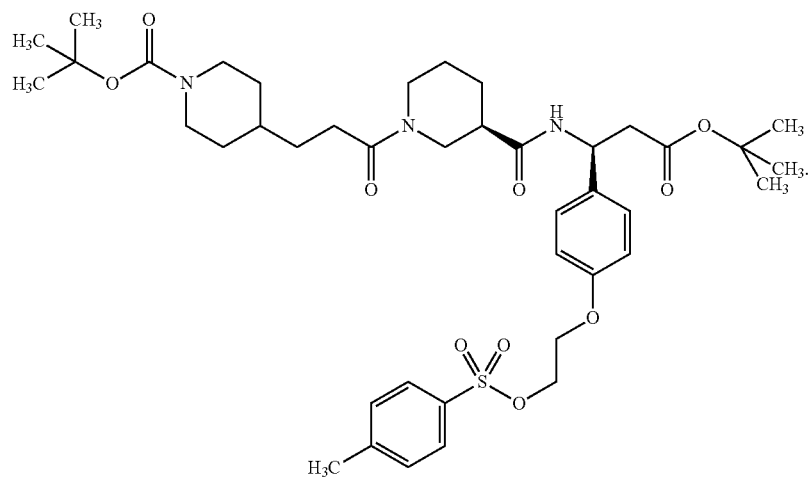 [SMILES: Cc1ccc(S(=O)(=O)OCCOc2ccc([C@H](CC(=O)OC(C)(C)C)NC(=O)[C@@H]3CCCN(C(=O)CCC4CCN(C(=O)OC(C)(C)C)CC4)C3)cc2)cc1]

Another preferred compound of Formula I is Example 24 tert-butyl 4-{3-[(3R)-3-({(1S)-3-methoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylat

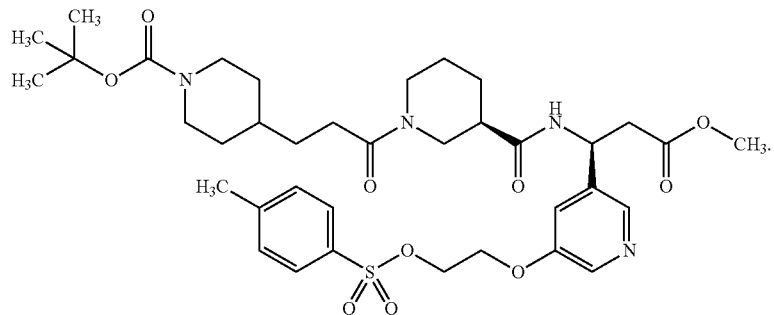 [SMILES: COC(=O)C[C@H](NC(=O)[C@@H]1CCCN(C(=O)CCC2CCN(C(=O)OC(C)(C)C)CC2)C1)c1cncc(OCCOS(=O)(=O)c2ccc(C)cc2)c1]

Another preferred compound of Formula I is Example 25 tert-butyl 4-{3-[(3R)-3-({(1S)-3-tert-butoxy-1-[5-(2-{[(4-methylphenyl)sulfonyl]oxy}ethoxy)-pyridin-3-yl]-3-oxopropyl}carbamoyl)piperidin-1-yl]-3-oxopropyl}piperidine-1-carboxylate

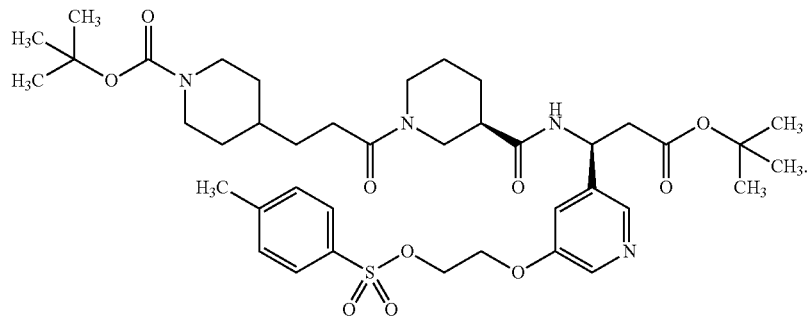 [SMILES: Cc1ccc(S(=O)(=O)OCCOc2cncc([C@H](CC(=O)OC(C)(C)C)NC(=O)[C@@H]3CCCN(C(=O)CCC4CCN(C(=O)OC(C)(C)C)CC4)C3)c2)cc1]

Another preferred compound of Formula I is Example 26 tert-butyl 4-{3-[(3R)-3-{[3-methoxy-1-{5-[4-(2-{[(4-methylphenyl)sulfonyl]oxy}ethoxy)phenyl]-pyridin-3-yl}-3-oxopropyl]carbamoyl}piperidin-1-yl]-3-oxopropyl}piperidine-1-carboxylate

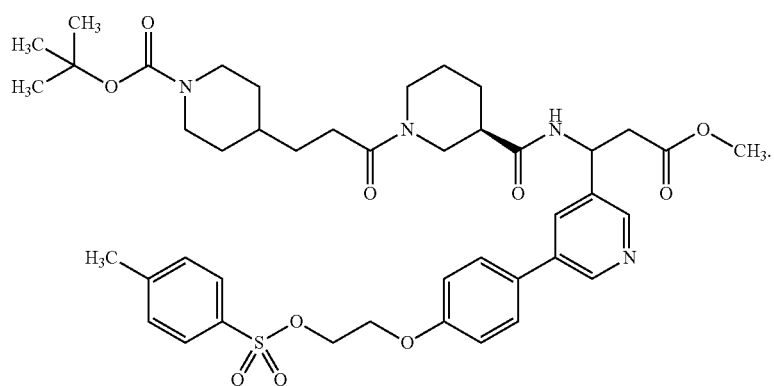 [SMILES: COC(=O)CC(NC(=O)[C@@H]1CCCN(C(=O)CCC2CCN(C(=O)OC(C)(C)C)CC2)C1)c1cncc(-c2ccc(OCCOS(=O)(=O)c3ccc(C)cc3)cc2)c1]

Another preferred compound of Formula I is Example 27 tert-butyl 4-{3-[(3R)-3-{[(1S)-3-tert-butoxy-1-{5-[4-(2-{[(4-methylphenyl)sulfonyl]oxy}ethoxy)-phenyl]pyridin-3-yl}-3-oxopropyl]carbamoyl}piperidin-1-yl]-3-oxopropyl}piperidine-1-carboxylate

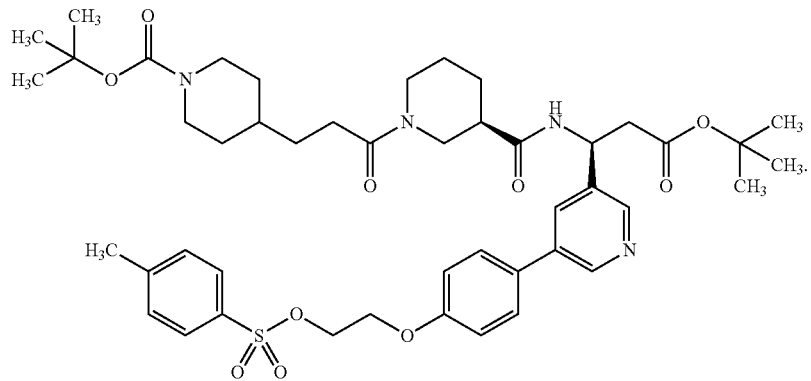 [SMILES: Cc1ccc(S(=O)(=O)OCCOc2ccc(-c3cncc([C@H](CC(=O)OC(C)(C)C)NC(=O)[C@@H]4CCCN(C(=O)CCC5CCN(C(=O)OC(C)(C)C)CC5)C4)c3)cc2)cc1]

Another preferred compound of Formula I is Example 28 tert-butyl 4-{3-[(3R)-3-({1-[5-(4-chloro-3-cyanophenyl)pyridin-3-yl]-3-methoxy-3-oxopropyl}-carbamoyl)piperidin-1-yl]-3-oxopropyl}piperidine-1-carboxylate

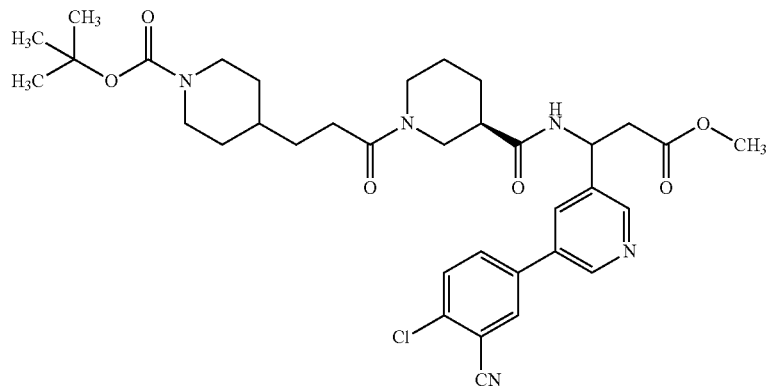 [SMILES: COC(=O)CC(NC(=O)[C@@H]1CCCN(C(=O)CCC2CCN(C(=O)OC(C)(C)C)CC2)C1)c1cncc(-c2ccc(Cl)c(C#N)c2)c1]

Another preferred compound of Formula I is Example 29 tert-butyl-4-{3-[(3R)-3-{[(1S)-1-{5-[(3-bromo-4-cyanobenzyl)oxy]pyridin-3-yl}-3-methoxy-3-oxopropyl]carbamoyl}piperidin-1-yl]-3-oxopropyl}piperidine-1-carboxylate

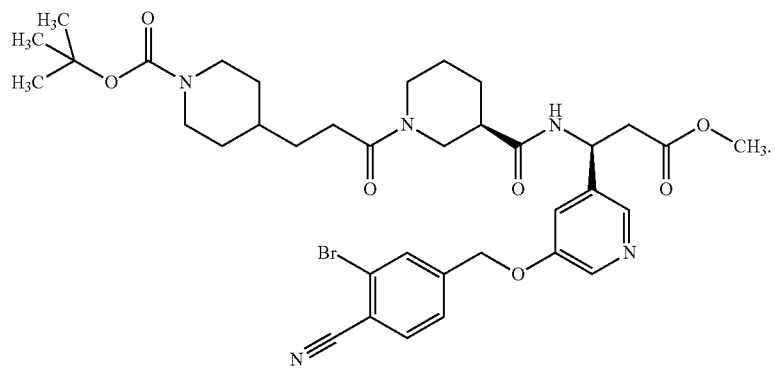 [SMILES: COC(=O)C[C@H](NC(=O)[C@@H]1CCCN(C(=O)CCC2CCN(C(=O)OC(C)(C)C)CC2)C1)c1cncc(OCc2ccc(C#N)c(Br)c2)c1]

Another preferred compound of Formula I is Example 30 tert-butyl 4-{3-[(3R)-3-{[3-methoxy-1-{5-[3-(2-{[(4-methylphenyl)sulfonyl]oxy}ethoxy)phenyl]-pyridin-3-yl}-3-oxopropyl]carbamoyl}piperidin-1-yl]-3-oxopropyl}piperidine-1-carboxylate

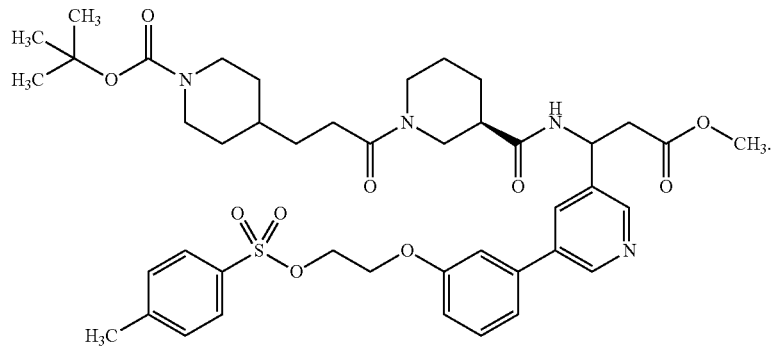 [SMILES: COC(=O)CC(NC(=O)[C@@H]1CCCN(C(=O)CCC2CCN(C(=O)OC(C)(C)C)CC2)C1)c1cncc(-c2cccc(OCCOS(=O)(=O)c3ccc(C)cc3)c2)c1]

Another preferred compound of Formula I is Example 31 tert-butyl 4-{3-[(3R)-3-{[3-methoxy-1-{5-[2-(2-{[(4-methylphenyl)sulfonyl]oxy}ethoxy)-phenyl]pyridin-3-yl}-3-oxopropyl]carbamoyl}piperidin-1-yl]-3-oxopropyl}piperidine-1-carboxylate

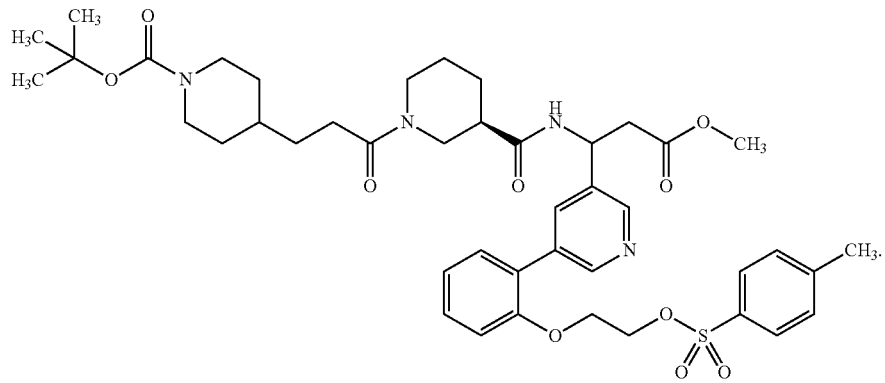 [SMILES: COC(=O)CC(NC(=O)[C@@H]1CCCN(C(=O)CCC2CCN(C(=O)OC(C)(C)C)CC2)C1)c1cncc(-c2ccccc2OCCOS(=O)(=O)c2ccc(C)cc2)c1]

Another preferred compound of Formula I is Example 32 tert-butyl 4-{3-[(3R)-3-({1-[5-(4-chloro-3-nitrophenyl)pyridin-3-yl]-3-methoxy-3-oxopropyl}-carbamoyl)piperidin-1-yl]-3-oxopropyl}piperidine-1-carboxylate

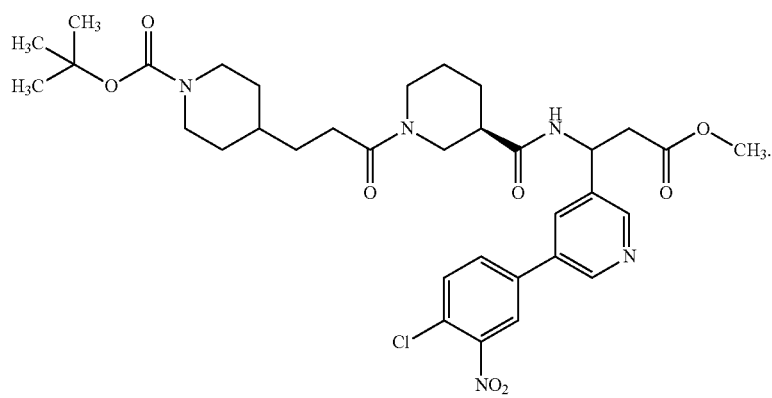 [SMILES: COC(=O)CC(NC(=O)[C@@H]1CCCN(C(=O)CCC2CCN(C(=O)OC(C)(C)C)CC2)C1)c1cncc(-c2ccc(Cl)c([N+](=O)[O-])c2)c1]

Another preferred compound of Formula I is Example 33 tert-butyl 4-{3-[(3R)-3-({1-[5-fluoro-4'-(2-{[(4-methylphenyl)sulfonyl]oxy}ethoxy)biphenyl-3-yl]-3-methoxy-3-oxopropyl}carbamoyl)piperidin-1-yl]-3-oxopropyl}piperidine-1-carboxylate

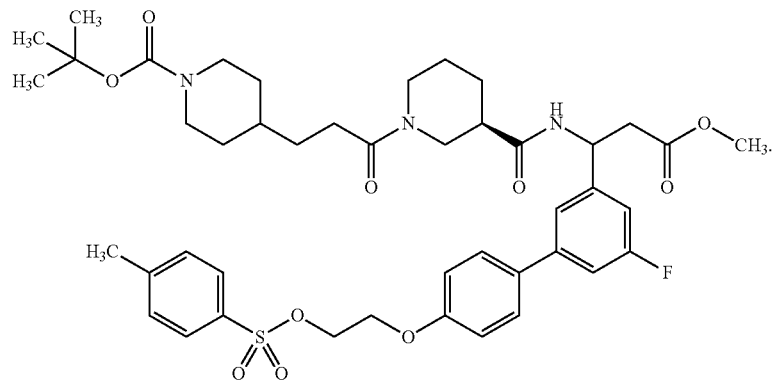 [SMILES: COC(=O)CC(NC(=O)[C@@H]1CCCN(C(=O)CCC2CCN(C(=O)OC(C)(C)C)CC2)C1)c1cc(F)cc(-c2ccc(OCCOS(=O)(=O)c3ccc(C)cc3)cc2)c1]

Another preferred compound of Formula I is Example 34 tert-butyl 4-{3-[(3R)-3-{[(1S)-3-tert-butoxy-1-(5-{[4-(2-{[(4-methylphenyl)sulfonyl]oxy}-ethoxy)phenyl]ethynyl}pyridin-3-yl)-3-oxopropyl]carbamoyl}piperidin-1-yl]-3-oxopropyl}-piperidine-1-carboxylate

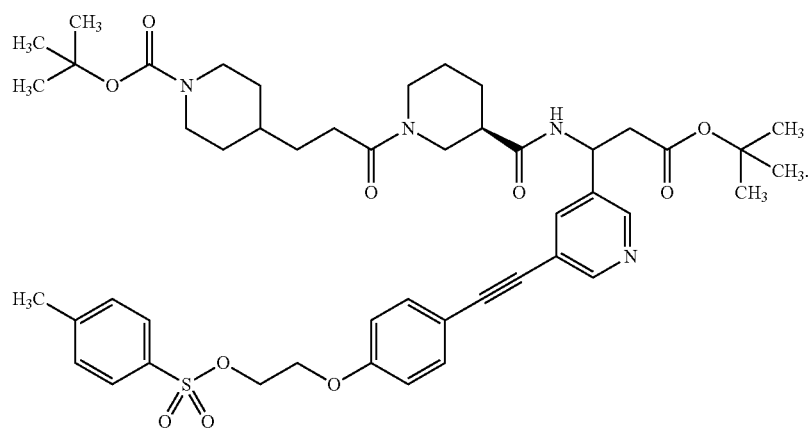 [SMILES: Cc1ccc(S(=O)(=O)OCCOc2ccc(C#Cc3cncc(C(CC(=O)OC(C)(C)C)NC(=O)[C@@H]4CCCN(C(=O)CCC5CCN(C(=O)OC(C)(C)C)CC5)C4)c3)cc2)cc1]

Another preferred compound of Formula I is Example 35 tert-butyl 4-{3-[(3R)-3-{[(1S)-3-tert-butoxy-1-(5-{[3-(2-{[(4-methylphenyl)sulfonyl]oxy}-ethoxy)phenyl]ethynyl}pyridin-3-yl)-3-oxopropyl]carbamoyl}piperidin-1-yl]-3-oxopropyl}-piperidine-1-carboxylate

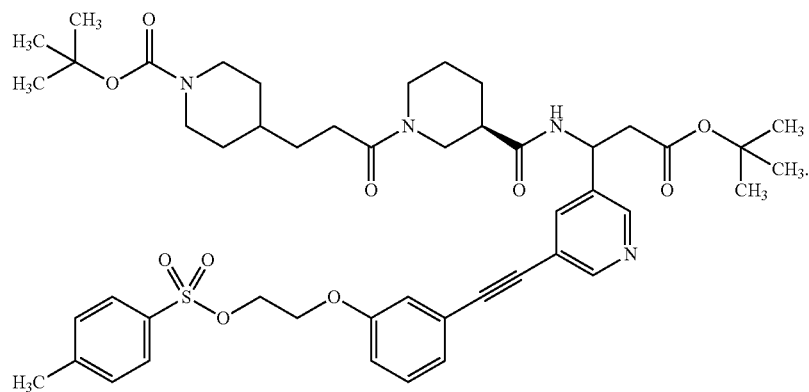 [SMILES: Cc1ccc(S(=O)(=O)OCCOc2cccc(C#Cc3cncc(C(CC(=O)OC(C)(C)C)NC(=O)[C@@H]4CCCN(C(=O)CCC5CCN(C(=O)OC(C)(C)C)CC5)C4)c3)c2)cc1]

Another preferred compound of Formula I is Example 36 tert-butyl 4-{3-[(3R)-3-{[(1S)-3-tert-butoxy-1-(5-{2-[4-(2-{[(4-methylphenyl)sulfonyl]oxy}-ethoxy)phenyl]ethyl}pyridin-3-yl)-3-oxopropyl]carbamoyl}piperidin-1-yl]-3-oxopropyl}-piperidine-1-carboxylate

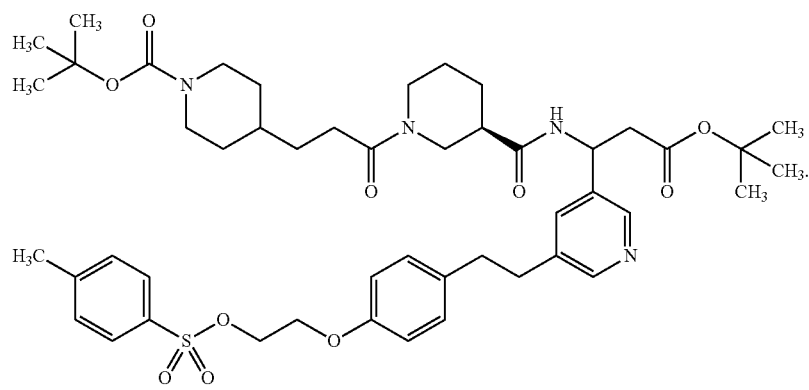 [SMILES: Cc1ccc(S(=O)(=O)OCCOc2ccc(CCc3cncc(C(CC(=O)OC(C)(C)C)NC(=O)[C@@H]4CCCN(C(=O)CCC5CCN(C(=O)OC(C)(C)C)CC5)C4)c3)cc2)cc1]

Another preferred compound of Formula I is Example 37 tert-butyl 4-{3-[(3R)-3-{[(1S)-3-tert-butoxy-1-(5-{2-[3-(2-{[(4-methylphenyl)sulfonyl]oxy}-ethoxy)phenyl]ethyl}pyridin-3-yl)-3-oxopropyl]carbamoyl}piperidin-1-yl]-3-oxopropyl}-piperidine-1-carboxylate

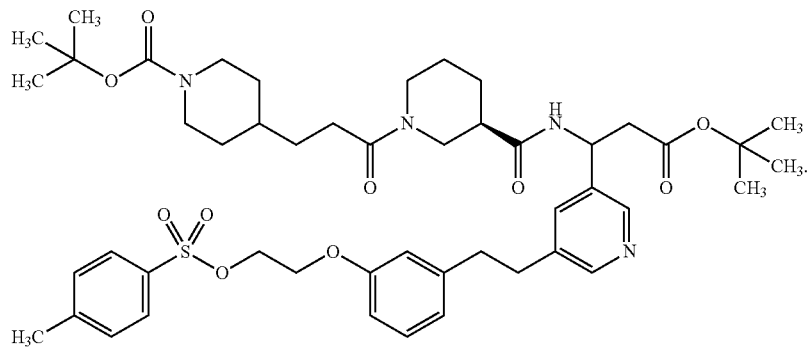 [SMILES: Cc1ccc(S(=O)(=O)OCCOc2cccc(CCc3cncc(C(CC(=O)OC(C)(C)C)NC(=O)[C@@H]4CCCN(C(=O)CCC5CCN(C(=O)OC(C)(C)C)CC5)C4)c3)c2)cc1]

Another preferred compound of Formula I is Example 2b tert-butyl 4-[3-((3R)-3-{[1-(4-hydroxyphenyl)-3-methoxy-3-oxopropyl]carbamoyl}piperidin-1-yl)-3-oxopropyl]piperidine-1-carboxylate

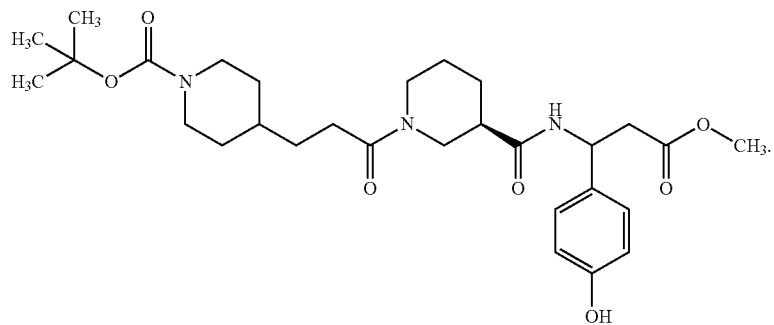 [SMILES: COC(=O)CC(NC(=O)[C@@H]1CCCN(C(=O)CCC2CCN(C(=O)OC(C)(C)C)CC2)C1)c1ccc(O)cc1]

Another preferred compound of Formula I is Example 4e tert-butyl 4-{3-[(3R)-3-({(1S)-1-[3-hydroxyphenyl]-3-methoxy-3-oxopropyl}carbamoyl)-piperidin-1-yl]-3-oxopropyl}piperidine-1-carboxylate e

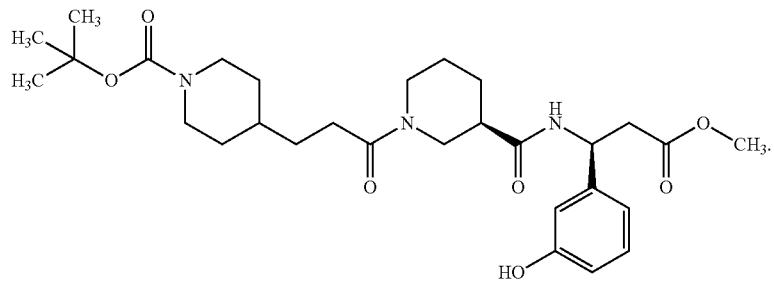 [SMILES: COC(=O)C[C@H](NC(=O)[C@@H]1CCCN(C(=O)CCC2CCN(C(=O)OC(C)(C)C)CC2)C1)c1cccc(O)c1]

Another preferred compound of Formula I is Example 5e tert-butyl 4-{3-[(3R)-3-({(1S)-1-[5-(hydroxy)pyri-
din-3-yl]-3-methoxy-3-oxopropyl}-carbamoyl)pip-
eridin-1-yl]-3-oxopropyl}piperidine-1-carboxylate

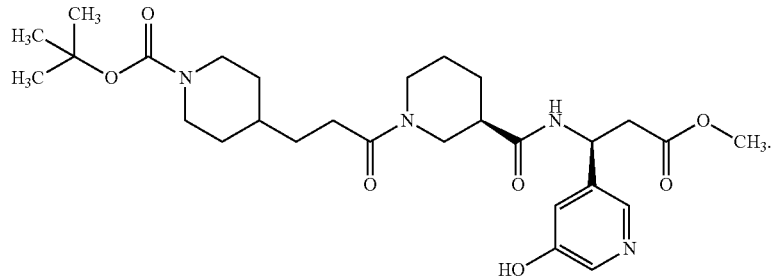 [SMILES: COC(=O)C[C@H](NC(=O)[C@@H]1CCCN(C(=O)CCC2CCN(C(=O)OC(C)(C)C)CC2)C1)c1cncc(O)c1]

Another preferred compound of Formula I is Example 6a tert-butyl 4-{3-[(3R)-3-({1-[5-(3-hydroxyphenyl)
pyridin-3-yl]-3-methoxy-3-oxopropyl}-carbamoyl)
piperidin-1-yl]-3-oxopropyl}piperidine-1-carboxy-
late

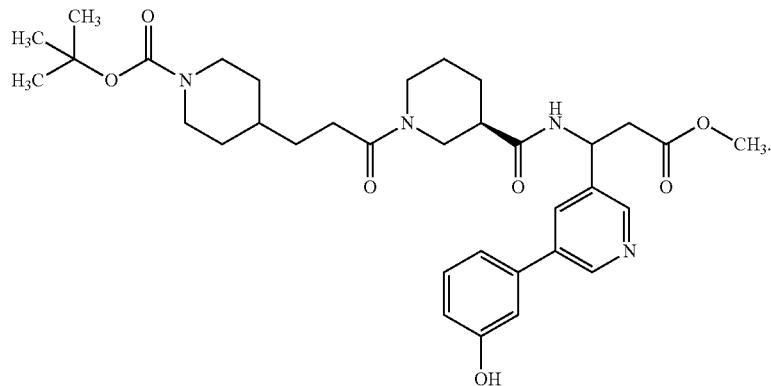 [SMILES: COC(=O)CC(NC(=O)[C@@H]1CCCN(C(=O)CCC2CCN(C(=O)OC(C)(C)C)CC2)C1)c1cncc(-c2cccc(O)c2)c1]

Another preferred compound of Formula I is Example 7a tert-butyl 4-{3-[(3R)-3-({1-[5-(4-hydroxyphenyl)
pyridin-3-yl]-3-methoxy-3-oxopropyl}-carbamoyl)
piperidin-1-yl]-3-oxopropyl}piperidine-1-carboxy-
late

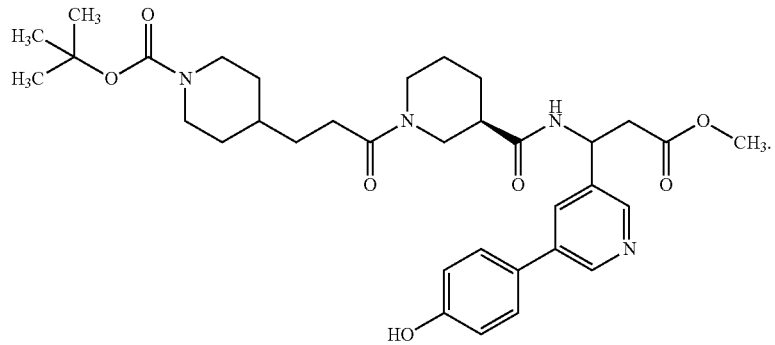 [SMILES: COC(=O)CC(NC(=O)[C@@H]1CCCN(C(=O)CCC2CCN(C(=O)OC(C)(C)C)CC2)C1)c1cncc(-c2ccc(O)cc2)c1]

Another preferred compound of Formula I is Example 8d tert-butyl 4-{3-[(3R)-3-({1-[5-(2-hydroxyphenyl)
pyridin-3-yl]-3-methoxy-3-oxopropyl}-carbamoyl)
piperidin-1-yl]-3-oxopropyl}piperidine-1-carboxy-
late

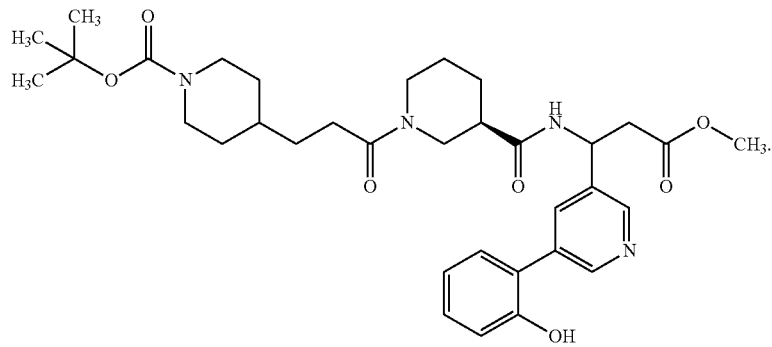 [SMILES: COC(=O)CC(NC(=O)[C@@H]1CCCN(C(=O)CCC2CCN(C(=O)OC(C)(C)C)CC2)C1)c1cncc(-c2ccccc2O)c1]

Another preferred compound of Formula I is Example 17d tert-butyl 4-{3-[(3R)-3-{[(1-(5-fluoro-4'-hydroxybi-
phenyl-3-yl)-3-methoxy-3-oxopropyl]-
carbamoyl}piperidin-1-yl]-3-oxopropyl}piperidine-
1-carboxylate

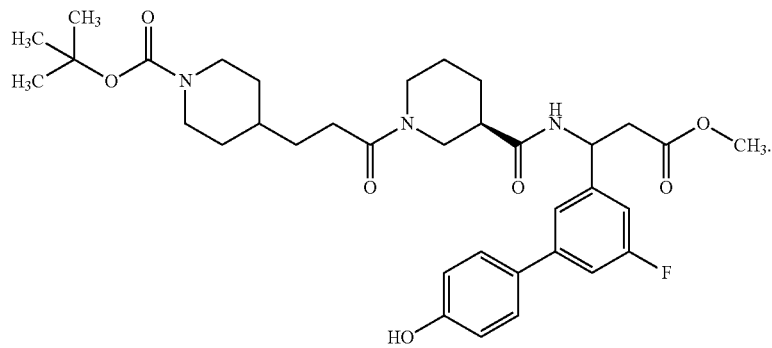 [SMILES: COC(=O)CC(NC(=O)[C@@H]1CCCN(C(=O)CCC2CCN(C(=O)OC(C)(C)C)CC2)C1)c1cc(F)cc(-c2ccc(O)cc2)c1]

Another preferred compound of Formula I is Example 23b tert-butyl 4-{3-[(3R)-3-{[(1S)-3-tert-butoxy-1-(4-
hydroxyphenyl)-3-oxopropyl]-carbamoyl}piperidin-
1-yl]-3-oxopropyl}piperidine-1-carboxylate

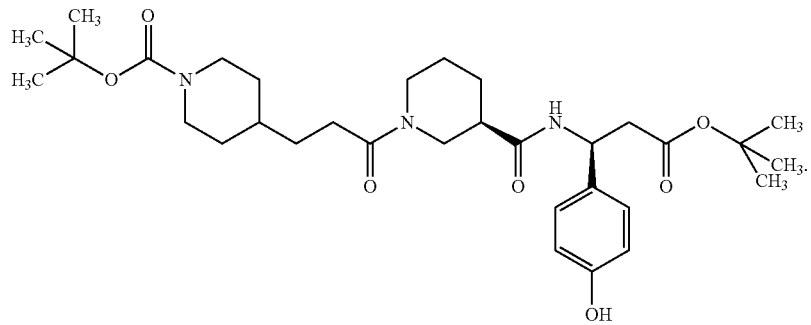 [SMILES: CC(C)(C)OC(=O)C[C@H](NC(=O)[C@@H]1CCCN(C(=O)CCC2CCN(C(=O)OC(C)(C)C)CC2)C1)c1ccc(O)cc1]

Another preferred compound of Formula I is Example 25e tert-butyl 4-{3-[(3R)-3-{[(1S)-3-tert-butoxy-1-(5-hydroxypyridin-3-yl)-3-oxopropyl]-carbamoyl}piperidin-1-yl]-3-oxopropyl}piperidine-1-carboxylate

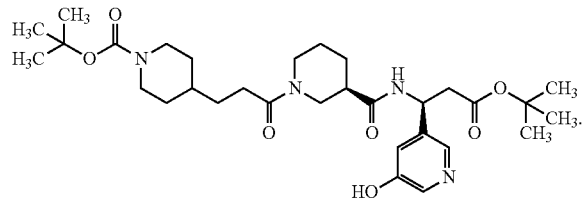 [SMILES: CC(C)(C)OC(=O)C[C@H](NC(=O)[C@@H]1CCCN(C(=O)CCC2CCN(C(=O)OC(C)(C)C)CC2)C1)c1cncc(O)c1]

Another preferred compound of Formula I is Example 27d tert-butyl 4-{3-[(3R)-3-({(1S)-3-tert-butoxy-1-[5-(4-hydroxyphenyl)pyridin-3-yl]-3-oxopropyl}carbamoyl)piperidin-1-yl]-3-oxopropyl}piperidine-1-carboxylate

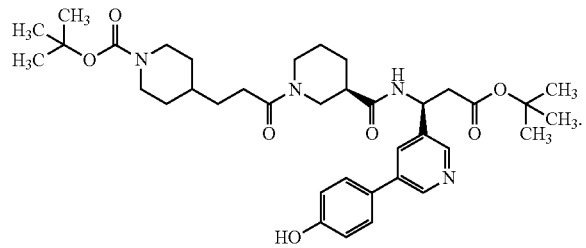 [SMILES: CC(C)(C)OC(=O)C[C@H](NC(=O)[C@@H]1CCCN(C(=O)CCC2CCN(C(=O)OC(C)(C)C)CC2)C1)c1cncc(-c2ccc(O)cc2)c1]

Another preferred compound of Formula I is Example 34a tert-butyl 4-(3-{(3R)-3-[(3-tert-butoxy-1-{5-[(4-hydroxyphenyl)ethynyl]pyridin-3-yl}-3-oxopropyl)carbamoyl]piperidin-1-yl}-3-oxopropyl)piperidine-1-carboxylate

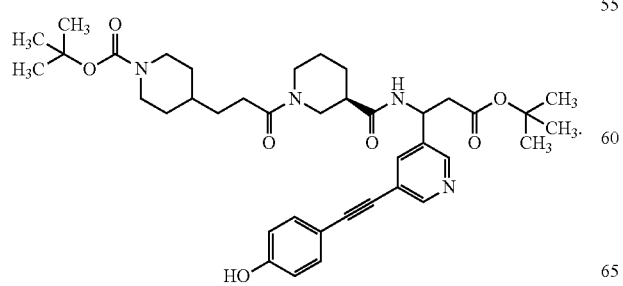

Another preferred compound of Formula I is Example 35a tert-butyl 4-{3-[(3R)-3-{[(1 S)-3-tert-butoxy-1-{5-[(3-hydroxyphenyl)ethynyl]pyridin-3-yl}-3-oxopropyl]carbamoyl}piperidin-1-yl]-3-oxopropyl}piperidine-1-carboxylate

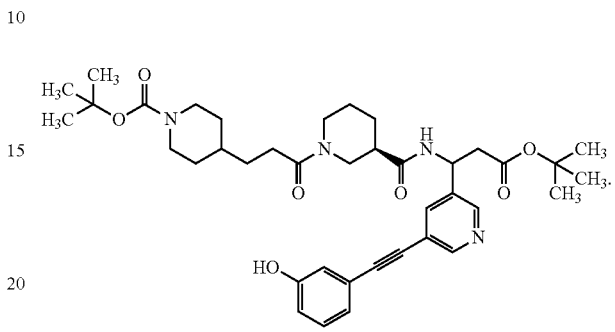

Another preferred compound of Formula I is Example 36a tert-butyl 4-(3-{(3R)-3-[(3-tert-butoxy-1-{5-[2-(4-hydroxyphenyl)ethyl]pyridin-3-yl}-3-oxopropyl)carbamoyl]piperidin-1-yl}-3-oxopropyl)piperidine-1-carboxylate

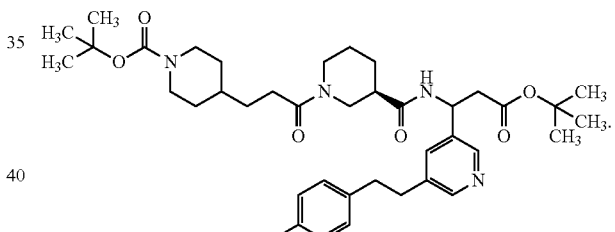

Another preferred compound of Formula I is Example 37a tert-butyl 4-(3-{(3R)-3-[(3-tert-butoxy-1-{5-[2-(3-hydroxyphenyl)ethyl]pyridin-3-yl}-3-oxopropyl)carbamoyl]piperidin-1-yl}-3-oxopropyl)piperidine-1-carboxylate

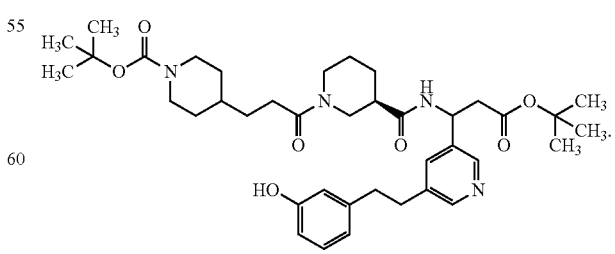

The second aspect of the present invention is directed to compounds of Formula II:

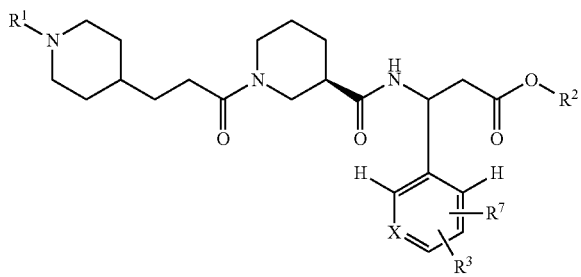

wherein
- R¹ is hydrogen or an amine-protecting group;
- R² is hydrogen or a carboxyl-protecting group;
- wherein at least one of R¹ and R² is not hydrogen;
- R³ is selected from the group consisting of H, F, $CF_3$, $COR^9$, $COOR^{10}$, $SOR^{10}$, $SO_2R^{10}$, CN and $NO_2$; preferably R³ is selected from the group consisting of H, F, $CF_3$, CN, $NO_2$;
- R⁷ is selected from the group consisting of Y, $-O(CH_2)_n-Y$, $-(OCH_2CH_2)_m-Y$, Z, $-OCH_2-Z$, $-CH_2-CH_2-Z$, $-CH=CH-Z$ and $-C\equiv C-Z$;
- X is selected from CH or N;
- Y is selected from $^{18}F$ or F;
- R⁹ is hydrogen or ($C_1$-$C_6$)alkyl; preferably hydrogen or ($C_1$-$C_4$)alkyl, more preferably hydrogen, methyl, ethyl or tert-butyl;
- R¹⁰ is ($C_1$-$C_6$)alkyl; preferably ($C_1$-$C_4$)alkyl, more preferably methyl, ethyl or tert-butyl;
- Z is a group

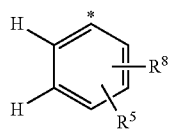

wherein * indicates the atom of connection of Z;
- R⁵ is selected from the group consisting of H, $CF_3$, $COR^9$, $COOR^{10}$, $SOR^{10}$, $SO_2R^{10}$, CN and $NO_2$; preferably R⁵ is selected from the group consisting of H, $CF_3$, CN, $NO_2$
- R⁸ is selected from the group consisting of Y, $-O(CH_2)_n-Y$ and $-(OCH_2CH_2)_m-Y$;
- n is 1-3;
- and m is 2-3;
- with the proviso that if R⁷ has the meaning Y, R³ has the meaning of $CF_3$, $COR^9$, $COOR^{10}$, $SOR^{10}$, $SO_2R^{10}$, CN or $NO_2$ and
- with the proviso that if R⁸ has the meaning Y, R⁵ has the meaning of $CF_3$, $COR^9$, $COOR^{10}$, $SOR^{10}$, $SO_2R^{10}$, CN or $NO_2$;
- including E and Z-isomers and diastereomers, mixtures thereof, and any pharmaceutically acceptable salt or complex thereof.

Preferably, R¹ is an amine-protecting group selected from the group comprising tert-butyloxycarbonyl (BOC), carbobenzyloxy (Cbz) and 9-fluorenylmethyloxycarbonyl (FMOC).

More preferably, R¹ is tert-butyloxycarbonyl (BOC) or carbobenzyloxy (Cbz).

Even more preferably, R¹ is tert-butyloxycarbonyl (BOC)

Preferably, R² is a carboxyl-protecting group selected from the group comprising methyl, ethyl, propyl, tert-butyl, benzyl and p-methoxybenzyl.

More preferably, R² is selected from the group comprising methyl and tert-butyl.

Preferably, R¹ is a nitrogen-protecting group and R² is a carboxyl-protecting group.

More preferably, R¹ is tert-butyloxycarbonyl (BOC) and R² is methyl or tert-butyl.

Preferably, X is N.

Preferably, R¹ is tert-butyloxycarbonyl (BOC), R² is methyl or tert-butyl, and X is N.

Preferably, Y is $^{18}F$.

Preferably, Y is F.

In a preferred embodiment, X is N and R³ is H and R⁷ is $-O(CH_2)_n-F$.

In a preferred embodiment, X is N and R³ is H and R⁷ is $-O(CH_2)_n-^{18}F$.

In a preferred embodiment, X is N and R³ is H and R⁷ is $-O(CH_2)_n-F$ and R¹ is BOC and R² is methyl or tert-butyl.

In a preferred embodiment, X is N and R³ is H and R⁷ is $-O(CH_2)_n-^{18}F$ and R¹ is BOC and R² is methyl or tert-butyl.

Compounds of Formula II are defined by the general formula and/or the combination of the preferred features as defined above.

In a first embodiment, compounds of the Formula II are defined as single diastereomers, of Formula II-A, see structure in table B.

In a second embodiment, compounds of the Formula II are defined as mixture of the two diastereomers of Formula II-A and Formula II-B, see structure in table B.

Preferred features as disclosed above are incorporated herein for all embodiments.

TABLE B

Formula II diastereomers

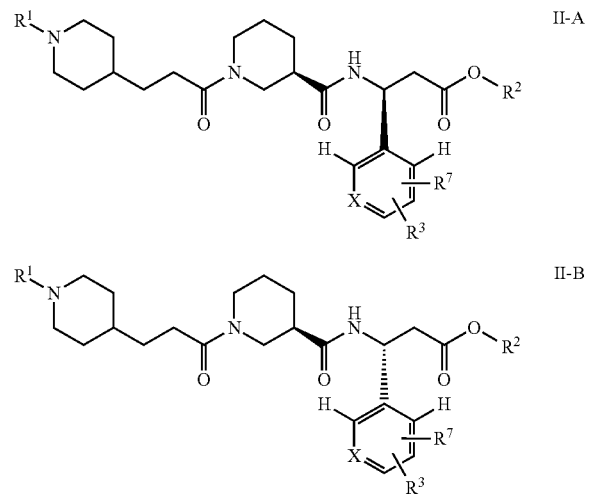

The compounds of Formula II-A and Formula II-B furthermore encompass pharmaceutically acceptable salts of an inorganic or organic acid or base thereof, hydrates, complexes, and solvates thereof and optionally a pharmaceutically acceptable carrier, diluent, adjuvant or excipients.

31

A preferred compound of Formula II is Example 1d tert-butyl 4-{3-[(3R)-3-({(1-[3-(2-fluoroethoxy)phenyl]-3-methoxy-3-oxopropyl}carbamoyl)-piperidin-1-yl]-3-oxopropyl}piperidine-1-carboxylate

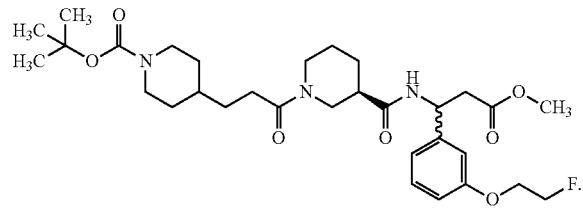 [SMILES: COC(=O)CC(NC(=O)[C@@H]1CCCN(C(=O)CCC2CCN(C(=O)OC(C)(C)C)CC2)C1)c1cccc(OCCF)c1]

Another preferred compound of Formula II is Example 1e 3-({[(3R)-1-{3-[1-(tert-butoxycarbonyl)piperidin-4-yl]propanoyl}piperidin-3-yl]carbonyl}amino)-3-[3-(2-fluoroethoxy)phenyl]propanoic acid

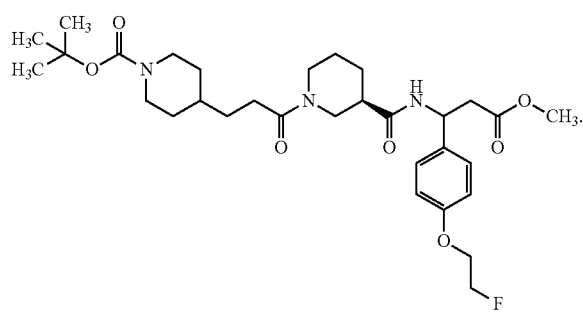 [SMILES: COC(=O)CC(NC(=O)[C@@H]1CCCN(C(=O)CCC2CCN(C(=O)OC(C)(C)C)CC2)C1)c1ccc(OCCF)cc1]

Another preferred compound of Formula II is Example 2c tert-butyl 4-{3-[(3R)-3-({1-[4-(2-fluoroethoxy)phenyl]-3-methoxy-3-oxopropyl}carbamoyl)-piperidin-1-yl]-3-oxopropyl}piperidine-1-carboxylate

32

Another preferred compound of Formula II is Example 2d 3-({[(3R)-1-{3-[1-(tert-butoxycarbonyl)piperidin-4-yl]propanoyl}piperidin-3-yl]carbonyl}amino)-3-[4-(2-fluoroethoxy)phenyl]propanoic acid

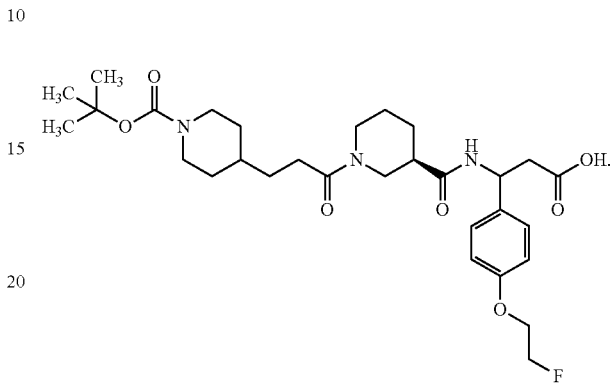

Another preferred compound of Formula II is Example 3a tert-butyl 4-{3-[(3R)-3-({(1S)-3-tert-butoxy-1-[5-(2-fluoroethoxy)pyridin-3-yl]-3-oxopropyl}-carbamoyl)piperidin-1-yl]-3-oxopropyl}piperidine-1-carboxylate

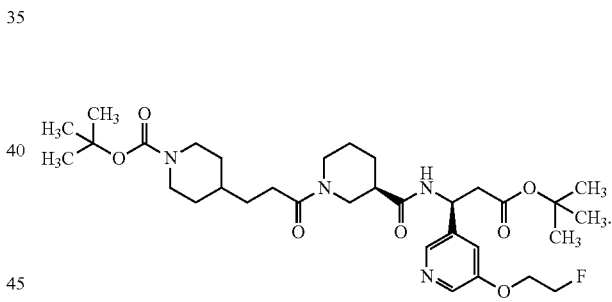

Another preferred compound of Formula II is Example 4f tert-butyl-4-{3-[(3R)-3-{[(1S)-1-(3-{2-[2-(2-fluoroethoxy)ethoxy]ethoxy}phenyl)-3-methoxy-3-oxopropyl]carbamoyl}piperidin-1-yl]-3-oxopropyl}piperidine-1-carboxylate

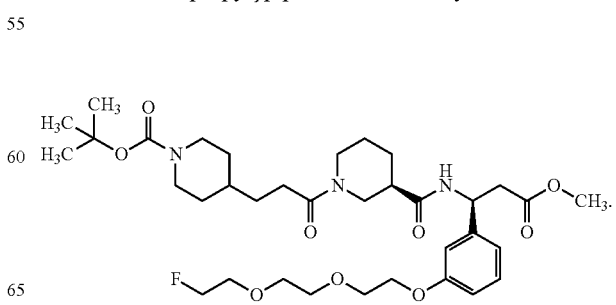

Another preferred compound of Formula II is Example 5f tert-butyl-4-{3-[(3R)-3-{[(1S)-1-(5-{2-[2-(2-fluoroethoxy)ethoxy]ethoxy}pyridin-3-yl)-3-methoxy-3-oxopropyl]carbamoyl}piperidin-1-yl]-3-oxopropyl}piperidine-1-carboxylate

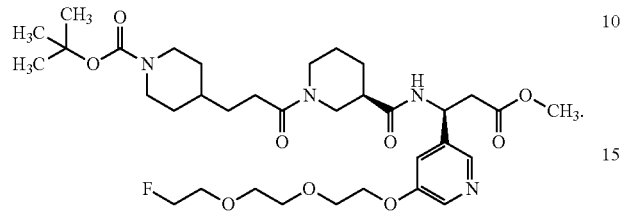

Another preferred compound of Formula II is Example 6b tert-butyl 4-{3-[(3R)-3-{[1-{5-[3-(2-fluoroethoxy)phenyl]pyridin-3-yl}-3-methoxy-3-oxopropyl]-carbamoyl}piperidin-1-yl]-3-oxopropyl}piperidine-1-carboxylate

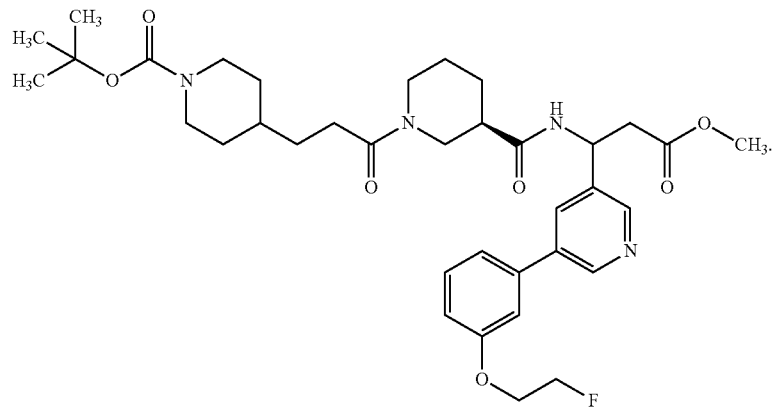 [SMILES: COC(=O)CC(NC(=O)[C@@H]1CCCN(C(=O)CCC2CCN(C(=O)OC(C)(C)C)CC2)C1)c1cncc(-c2cccc(OCCF)c2)c1]

Another preferred compound of Formula II is Example 6c 3-({[(3R)-1-{3-[1-(tert-butoxycarbonyl)piperidin-4-yl]propanoyl}piperidin-3-yl]carbonyl}amino)-3-{5-[3-(2-fluoroethoxy)phenyl]pyridin-3-yl}propanoic acid

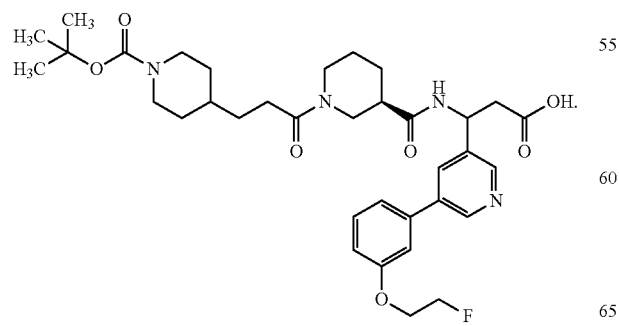

Another preferred compound of Formula II is Example 7b tert-butyl 4-(3-{(3R)-3-[(1-{5-[4-(2-fluoroethoxy)
phenyl]pyridin-3-yl}-3-methoxy-3-oxopropyl)-car-
bamoyl]piperidin-1-yl}-3-oxopropyl)piperidine-1-
carboxylate

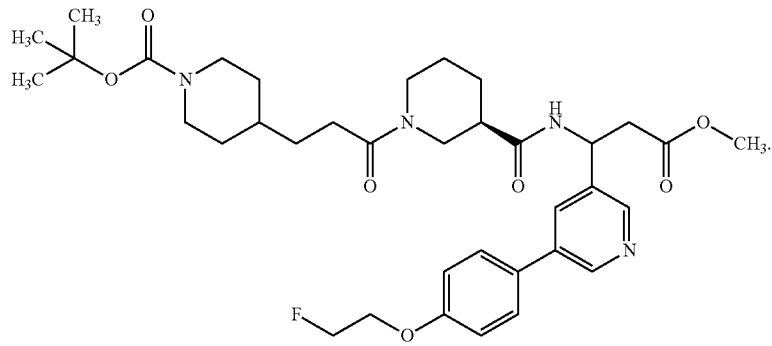 [SMILES: COC(=O)CC(NC(=O)[C@@H]1CCCN(C(=O)CCC2CCN(C(=O)OC(C)(C)C)CC2)C1)c1cncc(-c2ccc(OCCF)cc2)c1]

Another preferred compound of Formula II is Example 7c 3-({[(3R)-1-{3-[1-(tert-butoxycarbonyl)piperidin-4-
yl]propanoyl}piperidin-3-yl]carbonyl}amino)-3-{5-
[4-(2-fluoroethoxy)phenyl]pyridin-3-yl}propanoic
acid

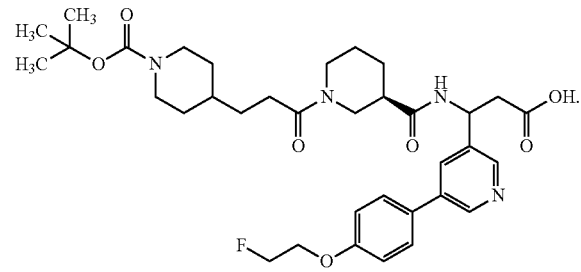 [SMILES: CC(C)(C)OC(=O)N1CCC(CCC(=O)N2CCC[C@@H](C(=O)NC(CC(=O)O)c3cncc(-c4ccc(OCCF)cc4)c3)C2)CC1]

Another preferred compound of Formula II is Example 8e tert-butyl 4-(3-{(3R)-3-[(1-{5-[2-(2-fluoroethoxy)
phenyl]pyridin-3-yl}-3-methoxy-3-oxopropyl)car-
bamoyl]piperidin-1-yl}-3-oxopropyl)piperidine-1-
carboxylate

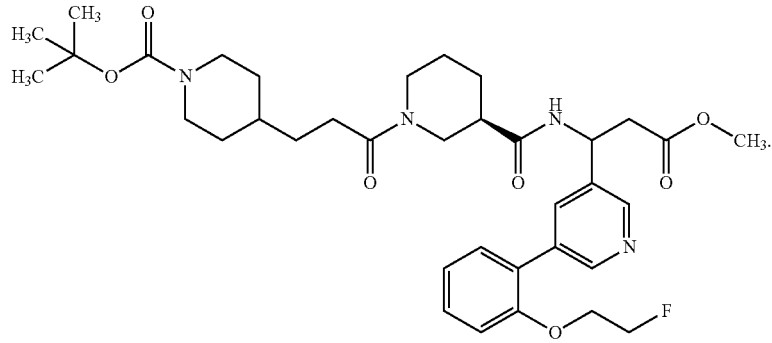 [SMILES: COC(=O)CC(NC(=O)[C@@H]1CCCN(C(=O)CCC2CCN(C(=O)OC(C)(C)C)CC2)C1)c1cncc(-c2ccccc2OCCF)c1]

Another preferred compound of Formula II is Example 8f 3-({[(3R)-1-{3-[1-(tert-butoxycarbonyl)piperidin-4-
yl]propanoyl}piperidin-3-yl]carbonyl}amino)-3-{5-
[2-(2-fluoroethoxy)phenyl]pyridin-3-yl}propanoic
acid

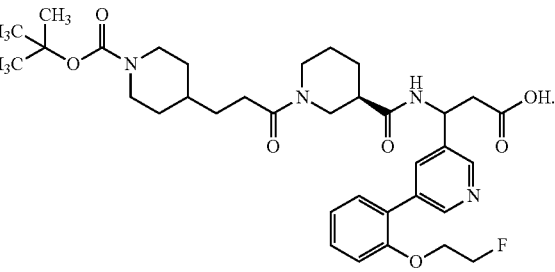

Another preferred compound of Formula II is Example 9a tert-butyl 4-{3-[(3R)-3-({1-[5-(3-cyano-4-fluorophenyl)pyridin-3-yl]-3-methoxy-3-oxopropyl}carbamoyl)piperidin-1-yl]-3-oxopropyl}piperidine-1-carboxylate

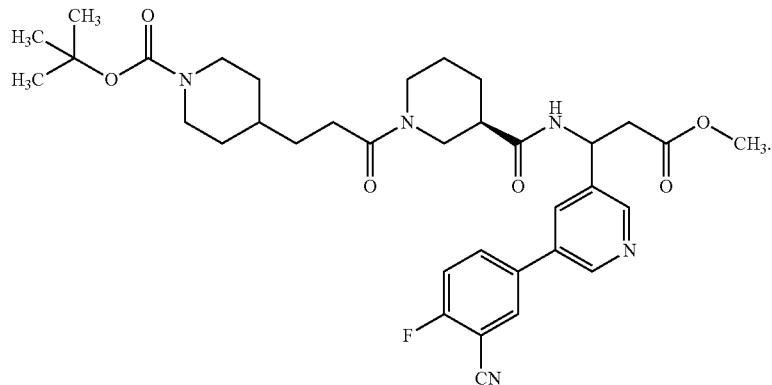 [SMILES: COC(=O)CC(NC(=O)[C@@H]1CCCN(C(=O)CCC2CCN(C(=O)OC(C)(C)C)CC2)C1)c1cncc(-c2ccc(F)c(C#N)c2)c1]

Another preferred compound of Formula II is Example 9b 3-({[(3R)-1-{3-[1-(tert-butoxycarbonyl)piperidin-4-yl]propanoyl}piperidin-3-yl]carbonyl}amino)-3-[5-(3-cyano-4-fluorophenyl)pyridin-3-yl]propanoic acid

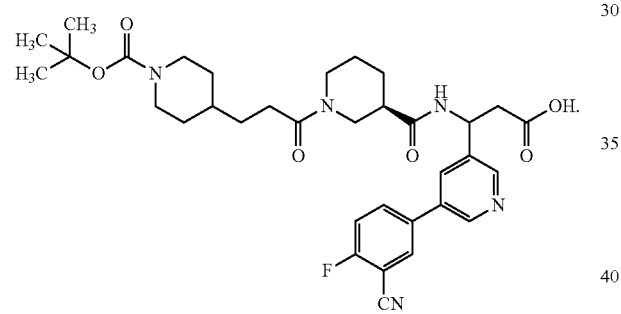

Another preferred compound of Formula II is Example 10a tert-butyl 4-{3-[(3R)-3-({1-[5-(4-cyano-3-fluorophenyl)pyridin-3-yl]-3-methoxy-3-oxopropyl}carbamoyl)piperidin-1-yl]-3-oxopropyl}piperidine-1-carboxylate

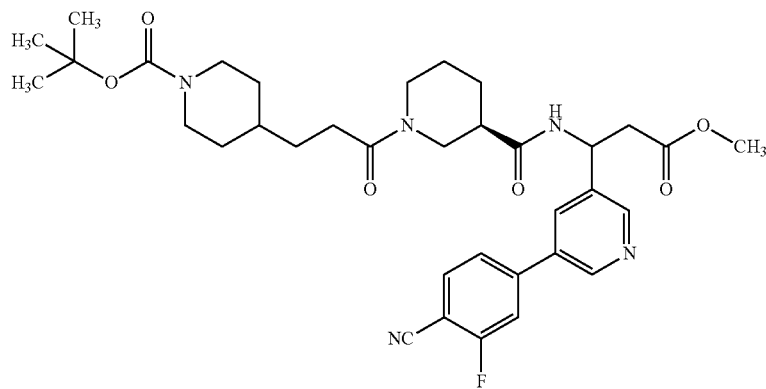 [SMILES: COC(=O)CC(NC(=O)[C@@H]1CCCN(C(=O)CCC2CCN(C(=O)OC(C)(C)C)CC2)C1)c1cncc(-c2ccc(C#N)c(F)c2)c1]

Another preferred compound of Formula II is Example 10b 3-({[(3R)-1-{3-[1-(tert-butoxycarbonyl)piperidin-4-yl]propanoyl}piperidin-3-yl]carbonyl}amino)-3-[5-(4-cyano-3-fluorophenyl)pyridin-3-yl]propanoic acid

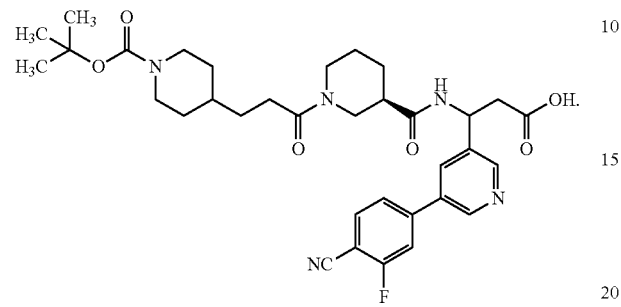

Another preferred compound of Formula II is Example 11a tert-butyl 4-{3-[(3R)-3-({1-[5-(4-fluoro-3-nitrophenyl)pyridin-3-yl]-3-methoxy-3-oxopropyl}carbamoyl)piperidin-1-yl]-3-oxopropyl}piperidine-1-carboxylate

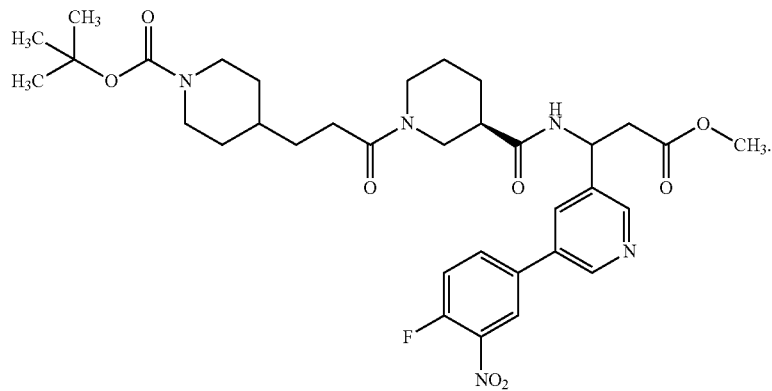

Another preferred compound of Formula II is Example 11b 3-({[(3R)-1-{3-[1-(tert-butoxycarbonyl)piperidin-4-yl]propanoyl}piperidin-3-yl]carbonyl}amino)-3-[5-(4-fluoro-3-nitrophenyl)pyridin-3-yl]propanoic acid

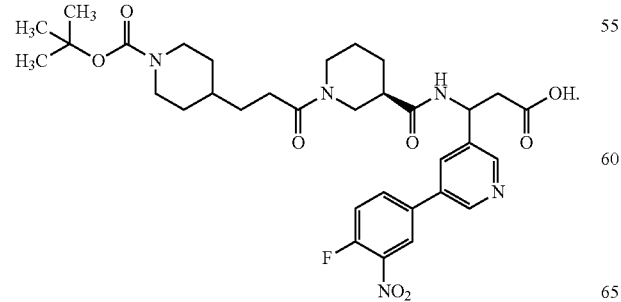

Another preferred compound of Formula II is Example 12a tert-butyl 4-{3-[(3R)-3-{[(1S)-1-{5-[(3-cyano-4-fluorobenzyl)oxy]pyridin-3-yl}-3-methoxy-3-oxo-propyl]carbamoyl}piperidin-1-yl]-3-oxopropyl}piperidine-1-carboxylate

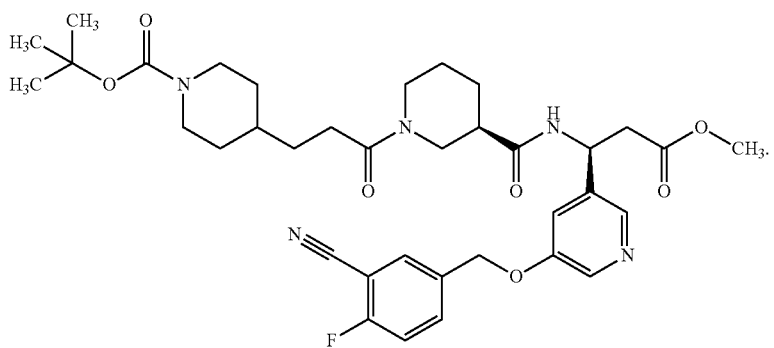 [SMILES: COC(=O)C[C@H](NC(=O)[C@@H]1CCCN(C(=O)CCC2CCN(C(=O)OC(C)(C)C)CC2)C1)c1cncc(OCc2ccc(F)c(C#N)c2)c1]

Another preferred compound of Formula II is Example 13a tert-butyl 4-{3-[(3R)-3-{[(1S)-1-{5-[(4-cyano-3-fluorobenzyl)oxy]pyridin-3-yl}-3-methoxy-3-oxo-propyl]carbamoyl}piperidin-1-yl]-3-oxopropyl}piperidine-1-carboxylate

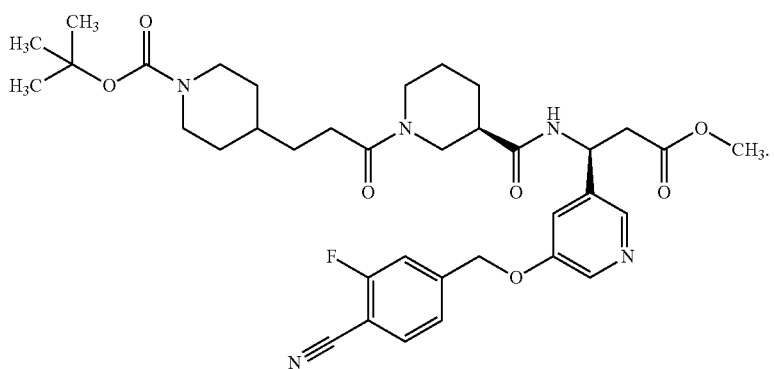 [SMILES: COC(=O)C[C@H](NC(=O)[C@@H]1CCCN(C(=O)CCC2CCN(C(=O)OC(C)(C)C)CC2)C1)c1cncc(OCc2ccc(C#N)c(F)c2)c1]

Another preferred compound of Formula II is Example 15a tert-butyl 4-{3-[(3R)-3-{[(1S)-3-tert-butoxy-1-(5-{[4-(2-fluoroethoxy)phenyl]ethynyl}pyridine-3-yl)-3-oxopropyl]carbamoyl}piperidin-1-yl]-3-oxopropyl}piperidine-1-carboxylate

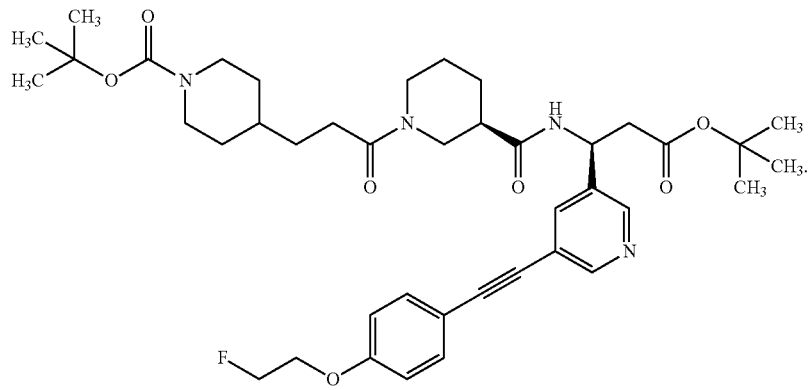 [SMILES: CC(C)(C)OC(=O)C[C@H](NC(=O)[C@@H]1CCCN(C(=O)CCC2CCN(C(=O)OC(C)(C)C)CC2)C1)c1cncc(C#Cc2ccc(OCCF)cc2)c1]

Another preferred compound of Formula II is Example 16a tert-butyl 4-{3-[(3R)-3-{[(1S)-3-tert-butoxy-1-(5-{[3-(2-fluoroethoxy)phenyl]ethynyl}pyridin-3-yl)-3-oxopropyl]carbamoyl}piperidin-1-yl]-3-oxopropyl}piperidine-1-carboxylate

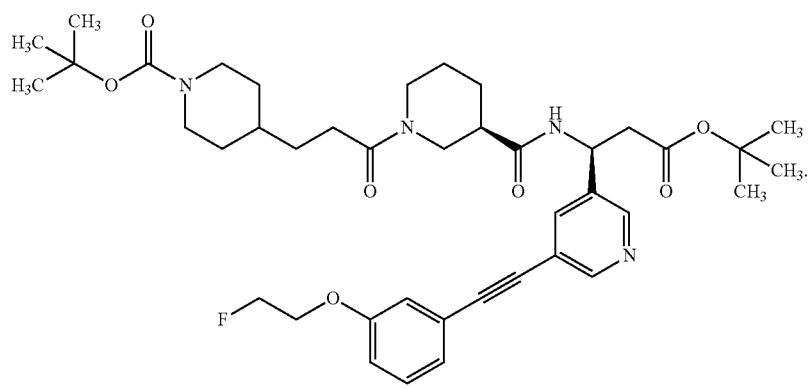 [SMILES: CC(C)(C)OC(=O)C[C@H](NC(=O)[C@@H]1CCCN(C(=O)CCC2CCN(C(=O)OC(C)(C)C)CC2)C1)c1cncc(C#Cc2cccc(OCCF)c2)c1]

Another preferred compound of Formula II is Example 17e tert-butyl 4-{3-[(3R)-3-({1-[5-fluoro-4'-(2-fluoroethoxy)biphenyl-3-yl]-3-methoxy-3-oxopropyl}carbamoyl)piperidin-1-yl]-3-oxopropyl}piperidine-1-carboxylate

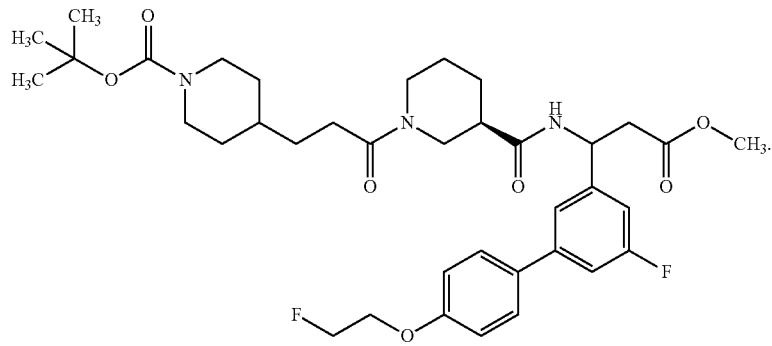 [SMILES: COC(=O)CC(NC(=O)[C@@H]1CCCN(C(=O)CCC2CCN(C(=O)OC(C)(C)C)CC2)C1)c1cc(F)cc(-c2ccc(OCCF)cc2)c1]

Another preferred compound of Formula II is Example 17f 3-({[(3R)-1-{3-[1-(tert-butoxycarbonyl)piperidin-4-yl]propanoyl}piperidin-3-yl]carbonyl}amino)-3-[5-fluoro-4'-(2-fluoroethoxy)biphenyl-3-yl]propanoic acid

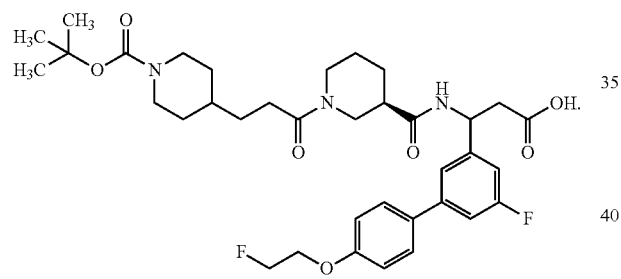

Another preferred compound of Formula II is Example 18a tert-butyl 4-{3-[(3R)-3-{[(1S)-3-tert-butoxy-1-({[4-(2-fluoroethoxy)phenyl]ethyl}pyridin-3-yl)-3-oxopropyl]carbamoyl}piperidin-1-yl]-3-oxopropyl}piperidine-1-carboxylate

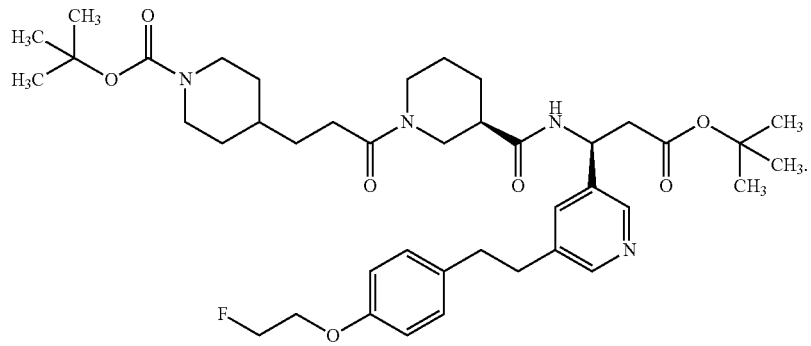 [SMILES: CC(C)(C)OC(=O)C[C@H](NC(=O)[C@@H]1CCCN(C(=O)CCC2CCN(C(=O)OC(C)(C)C)CC2)C1)c1cncc(CCc2ccc(OCCF)cc2)c1]

Another preferred compound of Formula II is Example 19a tert-butyl 4-{3-[(3R)-3-{[(1S)-3-tert-butoxy-1-({[3-(2-fluoroethoxy)phenyl]ethyl}pyridin-3-yl)-3-oxopropyl]carbamoyl}piperidin-1-yl]-3-oxopropyl}piperidine-1-carboxylate

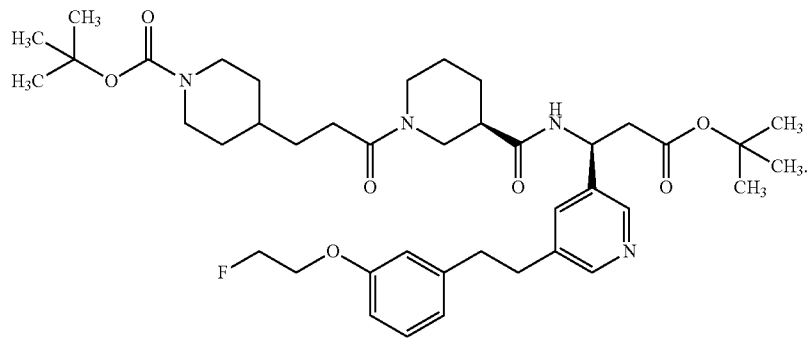 [SMILES: CC(C)(C)OC(=O)C[C@H](NC(=O)[C@@H]1CCCN(C(=O)CCC2CCN(C(=O)OC(C)(C)C)CC2)C1)c1cncc(CCc2cccc(OCCF)c2)c1]

Another preferred compound of Formula II is Example 20

(E/Z) tert-butyl 4-{3-[(3R)-3-{[(1S)-3-tert-butoxy-1-({[3-(2-fluoroethoxy)phenyl]ethenyl}pyridin-3-yl)-3-oxopropyl]carbamoyl}piperidin-1-yl]-3-oxopropyl}piperidine-1-carboxylate

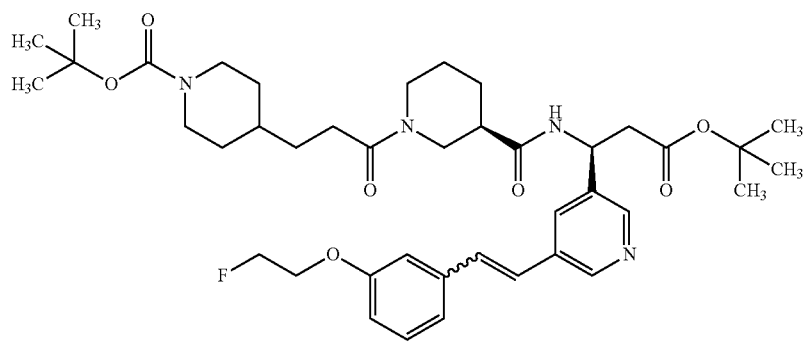 [SMILES: CC(C)(C)OC(=O)C[C@H](NC(=O)[C@@H]1CCCN(C(=O)CCC2CCN(C(=O)OC(C)(C)C)CC2)C1)c1cncc(C=Cc2cccc(OCCF)c2)c1]

Another preferred compound of Formula II is tert-butyl 4-{3-[(3R)-3-{[(1S)-1-{3-[2-[$^{18}$F]fluoroethoxy]phenyl}-3-methoxy-3-oxopropyl]carbamoyl}piperidin-1-yl]-3-oxopropyl}piperidine-1-carboxylate

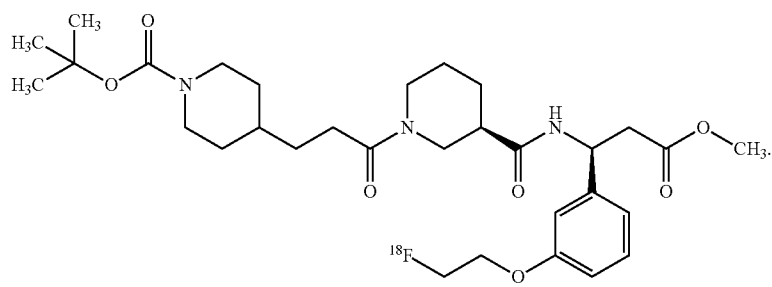 [SMILES: COC(=O)C[C@H](NC(=O)[C@@H]1CCCN(C(=O)CCC2CCN(C(=O)OC(C)(C)C)CC2)C1)c1cccc(OCC[18F])c1]

Another preferred compound of Formula II is (3S)-3-({[(3R)-1-{3-[1-(tert-butoxycarbonyl)piperidin-4-yl]propanoyl}piperidin-3-yl]carbonyl}amino)-3-{3-[2-[$^{18}$F]fluoroethoxy]phenyl}propanoic acid

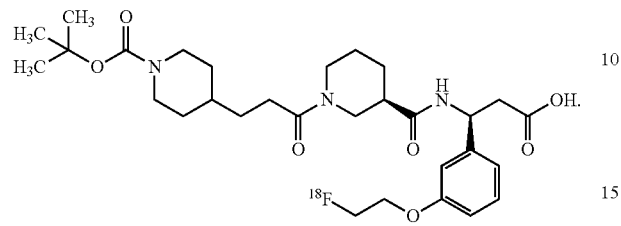

Another preferred compound of Formula II is tert-butyl 4-{3-[(3R)-3-({1-[4-(2-[$^{18}$F]fluoroethoxy)phenyl]-3-methoxy-3-oxopropyl}carbamoyl)-piperidin-1-yl]-3-oxopropyl}piperidine-1-carboxylate

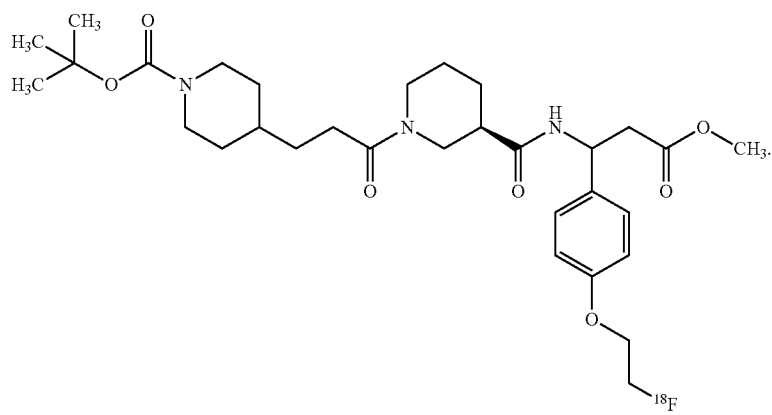 [SMILES: COC(=O)CC(NC(=O)[C@@H]1CCCN(C(=O)CCC2CCN(C(=O)OC(C)(C)C)CC2)C1)c1ccc(OCC[18F])cc1]

Another preferred compound of Formula II is 3-({[(3R)-1-{3-[1-(tert-butoxycarbonyl)piperidin-4-yl]propanoyl}piperidin-3-yl]carbonyl}amino)-3-{4-[2-[$^{18}$F]fluoroethoxy]phenyl}propanoic acid

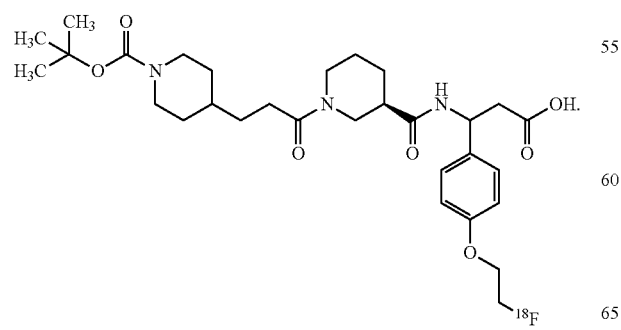

Another preferred compound of Formula II is tert-butyl 4-{3-[(3R)-3-({(1S)-3-tert-butoxy-1-[5-(2-[¹⁸F]fluoroethoxy)pyridin-3-yl]-3-oxopropyl}-carbamoyl)piperidin-1-yl]-3-oxopropyl}piperidine-1-carboxylate

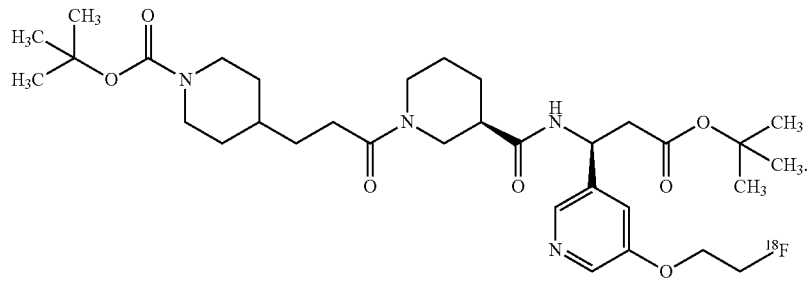 [SMILES: CC(C)(C)OC(=O)C[C@H](NC(=O)[C@@H]1CCCN(C(=O)CCC2CCN(C(=O)OC(C)(C)C)CC2)C1)c1cncc(OCC[18F])c1]

Another preferred compound of Formula II is tert-butyl 4-{3-[(3R)-3-({(1S)-1-[5-(2-[¹⁸F]fluoroethoxy)pyridin-3-yl]-3-methoxy-3-oxopropyl}carbamoyl)piperidin-1-yl]-3-oxopropyl}piperidine-1-carboxylate

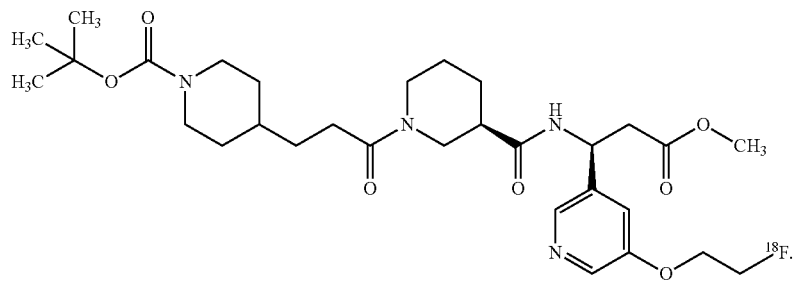

Another preferred compound of Formula II is (3S)-3-({[(3R)-1-{3-[1-(tert-butoxycarbonyl)piperidin-4-yl]propanoyl}piperidin-3-yl]carbonyl}amino)-3-{5-[2-[¹⁸F]fluoroethoxy]pyridin-3-yl}propanoic acid

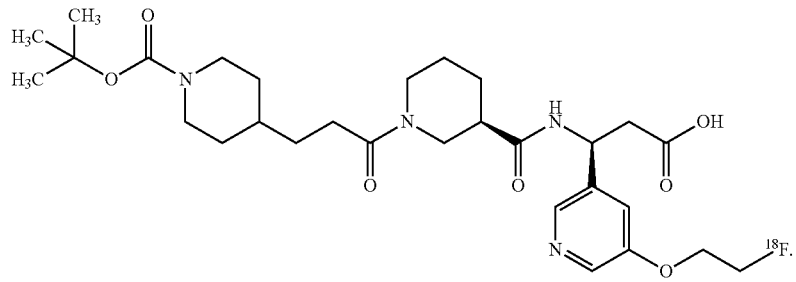

Another preferred compound of Formula II is tert-butyl 4-(3-{(3R)-3-[(1-{5-[2-[¹⁸F]fluoroethoxy]
pyridin-3-yl}-3-methoxy-3-oxopropyl)carbamoyl]
piperidin-1-yl}-3-oxopropyl)piperidine-1-carboxy-
late

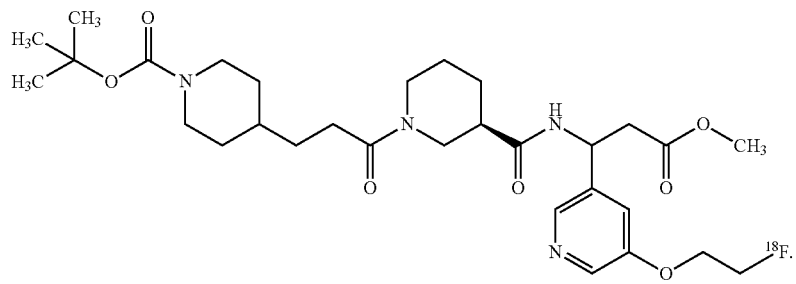

Another preferred compound of Formula II is 3-({[(3R)-1-{3-[1-(tert-butoxycarbonyl)piperidin-4-
yl]propanoyl}piperidin-3-yl]carbonyl}amino)-3-{5-
[2-[¹⁸F]fluoroethoxy]pyridin-3-yl}propanoic acid

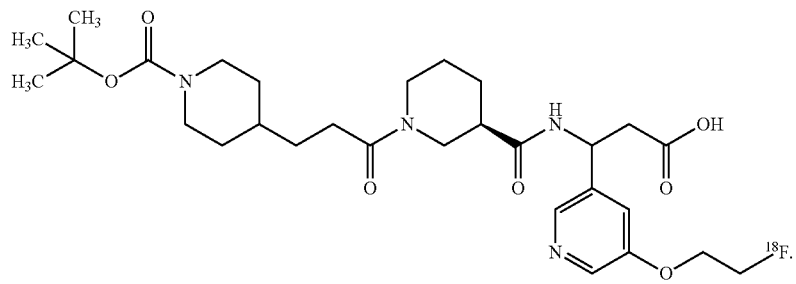

Another preferred compound of Formula II is tert-butyl 4-{3-[(3R)-3-{[(1S)-1-(5-{4-[2-[¹⁸F]fluo-
roethoxy]phenyl}pyridin-3-yl)-3-methoxy-3-oxopro-
pyl]carbamoyl}piperidin-1-yl]-3-
oxopropyl}piperidine-1-carboxylate

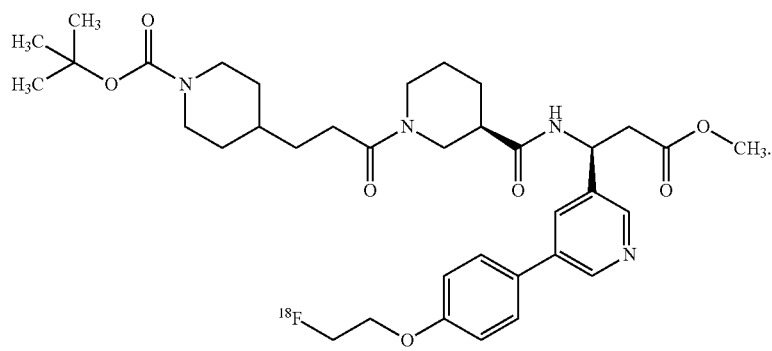 [SMILES: COC(=O)C[C@H](NC(=O)[C@@H]1CCCN(C(=O)CCC2CCN(C(=O)OC(C)(C)C)CC2)C1)c1cncc(-c2ccc(OCC[18F])cc2)c1]

Another preferred compound of Formula II is (3S)-3-({[(3R)-1-{3-[1-(tert-butoxycarbonyl)piperi-
din-4-yl]propanoyl}piperidin-3-yl]-
carbonyl}amino)-3-(5-{4-[2-[$^{18}$F]fluoroethoxy]
phenyl}pyridin-3-yl)propanoic acid

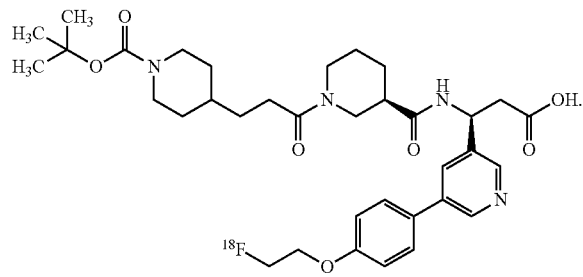 [SMILES: CC(C)(C)OC(=O)N1CCC(CCC(=O)N2CCC[C@@H](C(=O)N[C@@H](CC(=O)O)c3cncc(-c4ccc(OCC[18F])cc4)c3)C2)CC1]

Another preferred compound of Formula II is tert-butyl 4-{3-[(3R)-3-{[(1S)-3-tert-butoxy-1-(5-{4-
[2-[$^{18}$F]fluoroethoxy]phenyl}pyridin-3-yl)-3-oxo-
propyl]carbamoyl}piperidin-1-yl]-3-
oxopropyl}piperidine-1-carboxylate

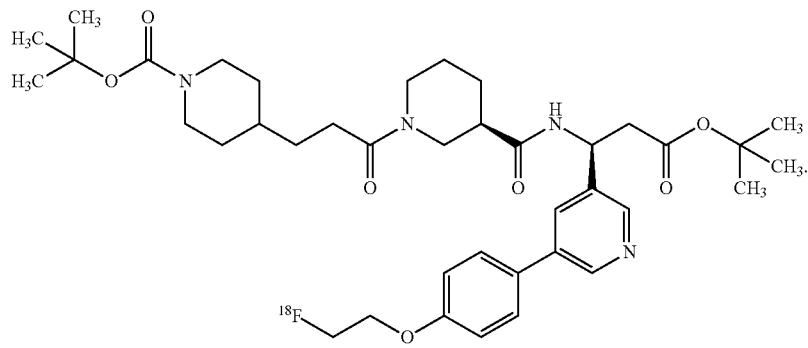 [SMILES: CC(C)(C)OC(=O)C[C@H](NC(=O)[C@@H]1CCCN(C(=O)CCC2CCN(C(=O)OC(C)(C)C)CC2)C1)c1cncc(-c2ccc(OCC[18F])cc2)c1]

Another preferred compound of Formula II is 3-({[(3R)-1-{3-[1-(tert-butoxycarbonyl)piperidin-4-
yl]propanoyl}piperidin-3-yl]carbonyl}amino)-3-[5-
(3-cyano-4-[$^{18}$F]fluorophenyl)pyridin-3-yl]propanoic
acid

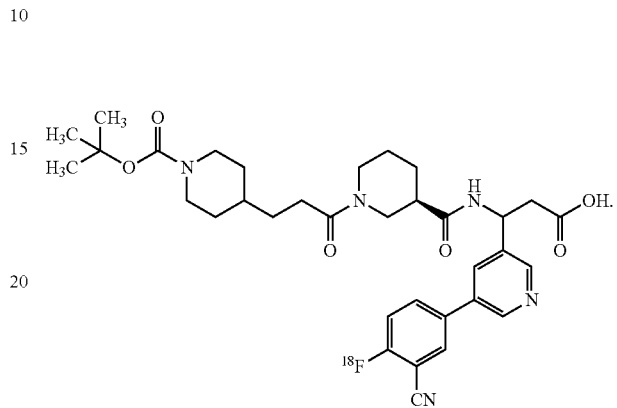

Another preferred compound of Formula II is tert-butyl 4-(3-{(3R)-3-[(1-{5-[3-cyano-4-[$^{18}$F]fluo-
rophenyl]pyridin-3-yl}-3-methoxy-3-oxopropyl)
carbamoyl]piperidin-1-yl}-3-oxopropyl)piperidine-
1-carboxylate

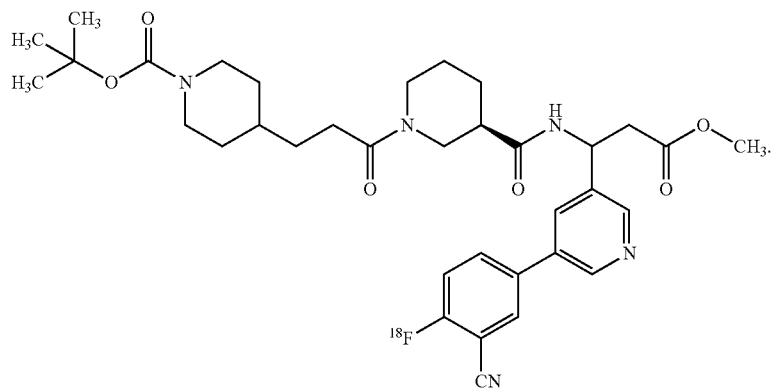

Another preferred compound of Formula II is tert-butyl 4-(3-{(3R)-3-[(1-{5-[4-cyano-3-[$^{18}$F]fluorophenyl]pyridin-3-yl}-3-methoxy-3-oxopropyl)carbamoyl]piperidin-1-yl}-3-oxopropyl)piperidine-1-carboxylate

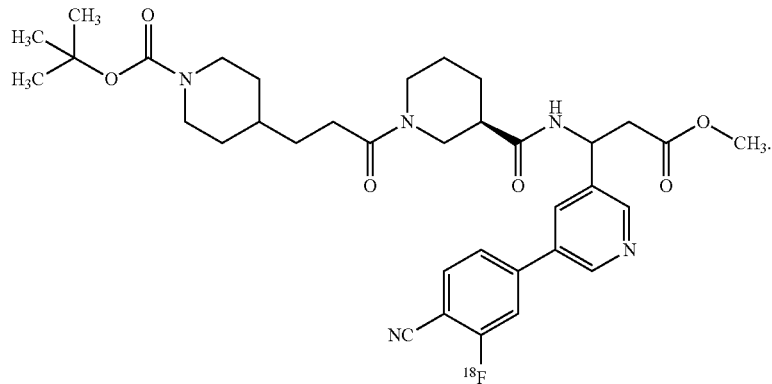 [SMILES: COC(=O)CC(NC(=O)[C@@H]1CCCN(C(=O)CCC2CCN(C(=O)OC(C)(C)C)CC2)C1)c1cncc(-c2ccc(C#N)c([18F])c2)c1]

Another preferred compound of Formula II is 3-({[(3R)-1-{3-[1-(tert-butoxycarbonyl)piperidin-4-yl]propanoyl}piperidin-3-yl]carbonyl}amino)-3-{5-[4-cyano-3-[$^{18}$F]fluorophenyl]pyridin-3-yl}propanoic acid

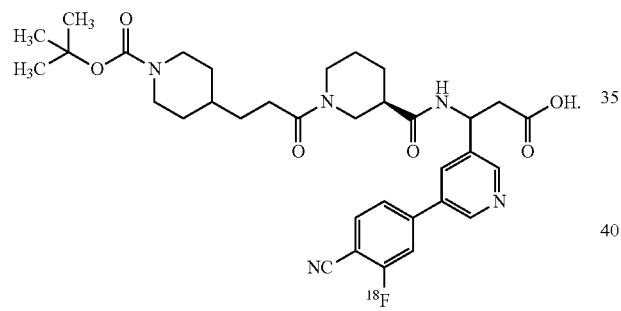

Another preferred compound of Formula II is tert-butyl 4-{3-[(3R)-3-{[(1S)-3-tert-butoxy-1-(5-{[4-(2-[$^{18}$F]fluoroethoxy)phenyl]ethynyl}-pyridine-3-yl)-3-oxopropyl]carbamoyl}piperidin-1-yl]-3-oxopropyl}piperidine-1-carboxylate

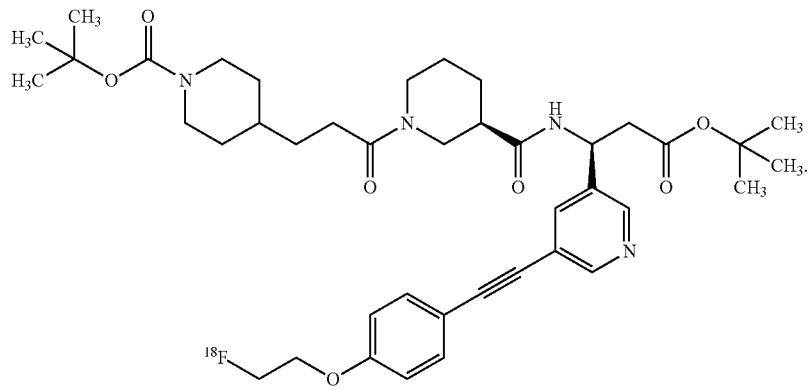

Another preferred compound of Formula II is tert-butyl 4-{3-[(3R)-3-{[(1S)-3-tert-butoxy-1-(5-{[3-(2-[$^{18}$F]fluoroethoxy)phenyl]ethynyl}pyridin-3-yl)-3-oxopropyl]carbamoyl}piperidin-1-yl]-3-oxopropyl}piperidine-1-carboxylate

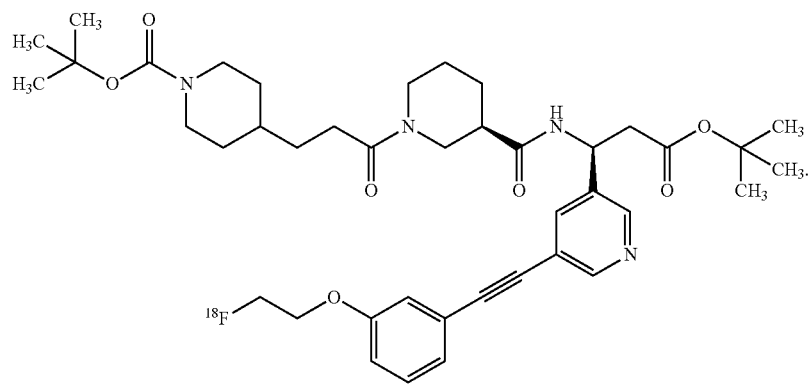

Another preferred compound of Formula II is tert-butyl 4-{3-[(3R)-3-{[(1S)-3-tert-butoxy-1-({[4-(2-[$^{18}$F]fluoroethoxy)phenyl]ethyl}pyridin-3-yl)-3-oxopropyl]carbamoyl}piperidin-1-yl]-3-oxopropyl}piperidine-1-carboxylate

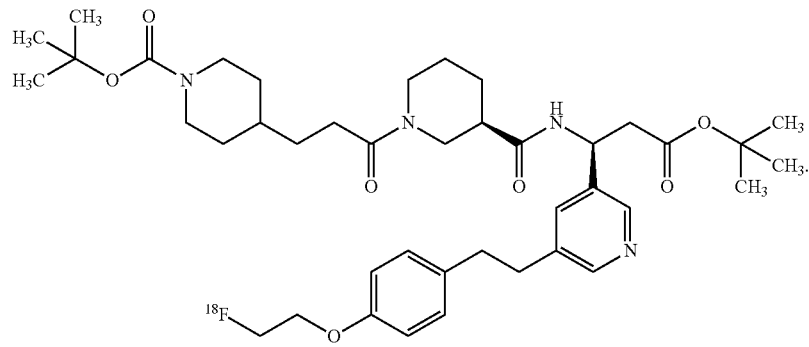

Another preferred compound of Formula II is tert-butyl 4-{3-[(3R)-3-{[(1S)-3-tert-butoxy-1-({[3-(2-[$^{18}$F]fluoroethoxy)phenyl]ethyl}pyridin-3-yl)-3-oxopropyl]carbamoyl}piperidin-1-yl]-3-oxopropyl}piperidine-1-carboxylate

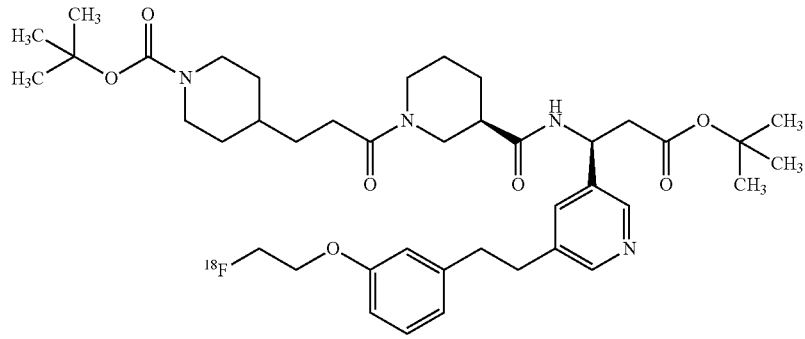

Another preferred compound of Formula II is tert-butyl 4-{3-[(3R)-3-({1-[3-(2-{2-[2-[$^{18}$F]fluoroethoxy]ethoxy}ethoxy)phenyl]-3-methoxy-3-oxopropyl}carbamoyl)piperidin-1-yl]-3-oxopropyl}piperidine-1-carboxylate

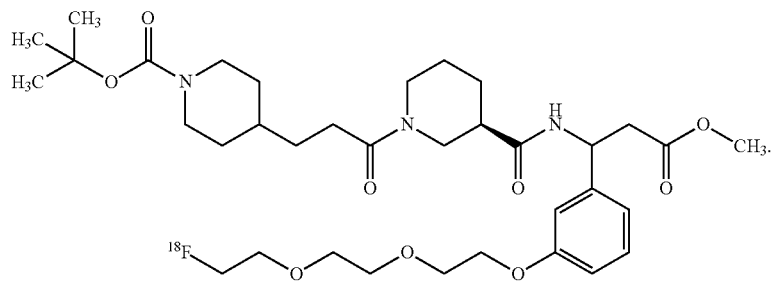 [SMILES: COC(=O)CC(NC(=O)[C@@H]1CCCN(C(=O)CCC2CCN(C(=O)OC(C)(C)C)CC2)C1)c1cccc(OCCOCCOCC[18F])c1]

Another preferred compound of Formula II is 3-({[(3R)-1-{3-[1-(tert-butoxycarbonyl)piperidin-4-yl]propanoyl}piperidin-3-yl]carbonyl}amino)-3-[3-(2-{2-[2-[$^{18}$F]fluoroethoxy]ethoxy}ethoxy)phenyl]propanoic acid

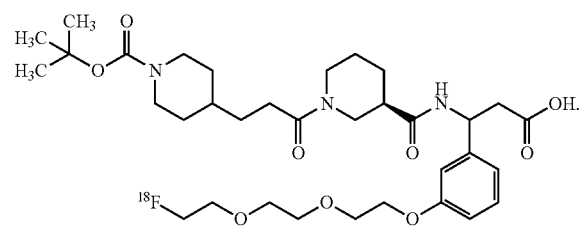 [SMILES: CC(C)(C)OC(=O)N1CCC(CCC(=O)N2CCC[C@@H](C(=O)NC(CC(=O)O)c3cccc(OCCOCCOCC[18F])c3)C2)CC1]

The third aspect of the present invention is directed to compounds of Formula III:

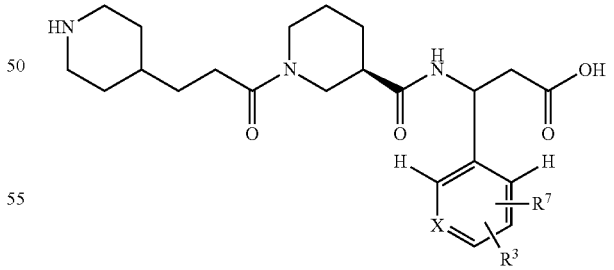

wherein

R$^3$ is selected from the group consisting of H, F, CF$_3$, COR$^9$, COOR$^{10}$, SOR$^{10}$, SO$_2$R$^{10}$, CN and NO$_2$; preferably R$^3$ is selected from the group consisting of H, F, CF$_3$, CN, NO$_2$;

R$^7$ is selected from the group consisting of Y, —O(CH$_2$)$_n$—Y, —(OCH$_2$CH$_2$)$_m$—Y, Z, —OCH$_2$—Z; —CH$_2$—CH$_2$—Z, —CH═CH—Z and —C≡C—Z;

X is selected from CH or N;
Y is selected from $^{18}$F or F;
R$^9$ is hydrogen or (C$_1$-C$_6$)alkyl; preferably hydrogen or (C$_1$-C$_4$)alkyl, more preferably hydrogen, methyl, ethyl or tert-butyl;
R$^{10}$ is (C$_1$-C$_6$)alkyl; preferably (C$_1$-C$_4$)alkyl, more preferably methyl, ethyl or tert-butyl;
Z is a group

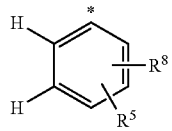

wherein * indicates the atom of connection of Z;
R$^5$ is selected from the group consisting of H, CF$_3$, COR$^9$, COOR$^{10}$, SOR$^{10}$, SO$_2$R$^{10}$, CN and NO$_2$; preferably R$^3$ is selected from the group consisting of H, CF$_3$, CN, NO$_2$;
R$^8$ is selected from the group consisting of Y, —O(CH$_2$)$_n$—Y and —(OCH$_2$CH$_2$)$_m$—Y;
n is 1-3;
and m is 2-3;
with the proviso that if R$^7$ has the meaning of Y, R$^3$ has the meaning of CF$_3$, COR$^9$, COOR$^{10}$, SOR$^{10}$, SO$_2$R$^{10}$, CN or NO$_2$ and
with the proviso that if R$^8$ has the meaning of Y, R$^5$ has the meaning of CF$_3$, COR$^9$, COOR$^{10}$, SOR$^{10}$, SO$_2$R$^{10}$, CN or NO$_2$;
including E and Z-isomers and diastereomers, mixtures thereof, and any pharmaceutically acceptable salt or complex thereof.
Preferably, X is N.
Preferably, Y is $^{18}$F.
Preferably, Y is F.
In a preferred embodiment, X is N and R$^3$ is H and R$^7$ is —O(CH2)$_n$—F.
In a preferred embodiment, X is N and R$^3$ is H and R$^7$ is —O(CH2)$_n$-$^{18}$F.

Compounds of Formula III are defined by the general formula and/or the combination of the preferred features as defined above.

In a first embodiment, compounds of the Formula III are defined as single diastereomers of Formula III-A, see structure in table C.

In a second embodiment, compounds of the Formula III are defined as mixture of the two diastereomers of Formula III-A and Formula III-B, see structure in table C.

Preferred features as disclosed above are incorporated herein for all embodiments.

TABLE C

Formula III diastereomers

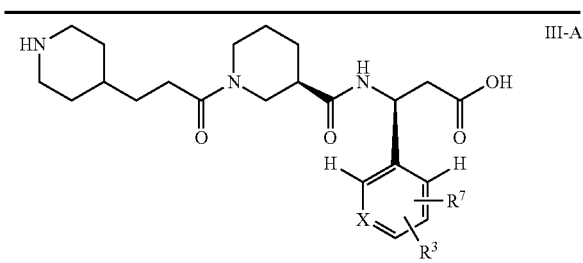

III-A

TABLE C-continued

Formula III diastereomers

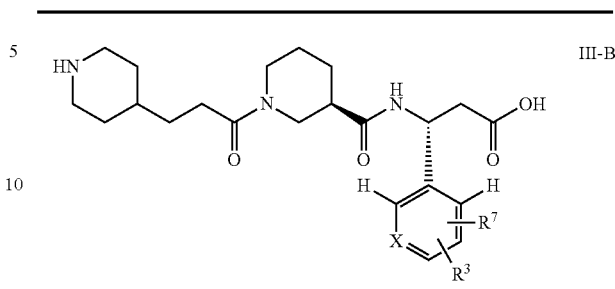

III-B

The compounds of Formula III-A and Formula III-B furthermore encompass pharmaceutically acceptable salts of an inorganic or organic acid or base thereof, hydrates, complexes, and solvates thereof and optionally a pharmaceutically acceptable carrier, diluent, adjuvant or excipients.

The compounds of Formula III may exist as zwitterions. All forms of the compounds, including free acid, free-base and zwitterions, are contemplated to be within the scope of the present invention. It is well known in the art that compounds containing both amino and carboxyl groups often exist in equilibrium with their zwitterionic forms. Thus, any of the compounds described herein throughout that contain, for example, both amino and carboxyl groups, also include reference to their corresponding zwitterions.

A preferred compound of Formula III is Example 1

(3S)-3-[3-(2-fluoroethoxy)phenyl]-3-[({(3R)-1-[3-(piperidin-4-yl)propanoyl]piperidin-3-yl}-carbonyl)amino]propanoic acid

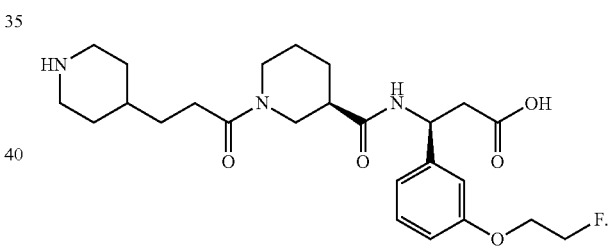

Another preferred compound of Formula III is Example 2

(3S)-3-[4-(2-fluoroethoxy)phenyl]-3-[({(3R)-1-[3-(piperidin-4-yl)propanoyl]piperidin-3-yl}carbonyl)amino]propanoic acid

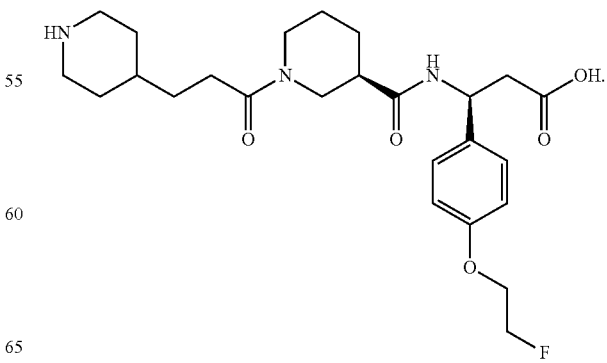

Another preferred compound of Formula III is Example 3

(3S)-3-[5-(2-fluoroethoxy)pyridin-3-yl]-3-[({(3R)-1-[3-(piperidin-4-yl)propanoyl]piperidin-3-yl}carbonyl)amino]propanoic acid

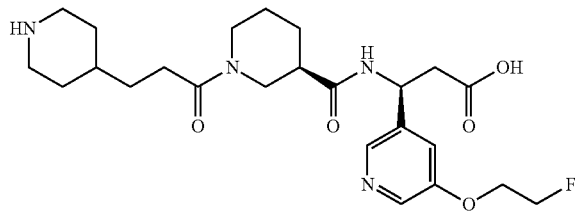 [SMILES: O=C(O)C[C@H](NC(=O)[C@@H]1CCCN(C(=O)CCC2CCNCC2)C1)c1cncc(OCCF)c1]

Another preferred compound of Formula III is Example 4

(3S)-3-(3-{2-[2-(2-fluoroethoxy)ethoxy]ethoxy}phenyl)-3-[({(3R)-1-[3-(piperidin-4-yl)-propanoyl]piperidin-3-yl}carbonyl)amino]propanoic acid

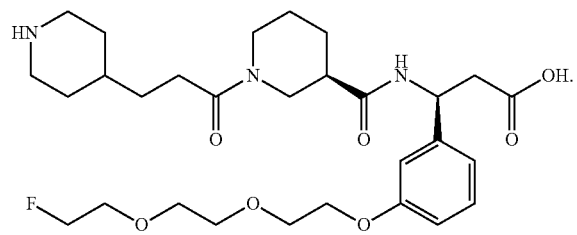

Another preferred compound of Formula III is Example 5

(3S)-3-(5-{2-[2-(2-fluoroethoxy)ethoxy]ethoxy}pyridine-3-yl)-3-[({(3R)-1-[3-(piperidin-4-yl)-propanoyl]piperidin-3-yl}carbonyl)amino]propanoic acid

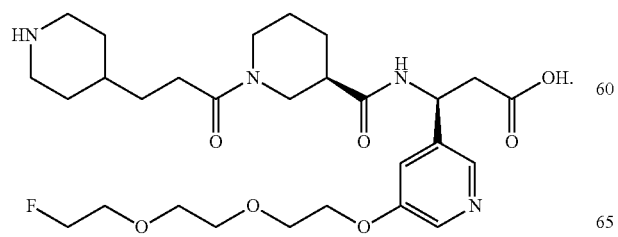

Another preferred compound of Formula III is Example 6

(3S)-3-{5-[3-(2-fluoroethoxy)phenyl]pyridin-3-yl}-3-[({(3R)-1-[3-(piperidin-4-yl)propanoyl]-piperidin-3-yl}carbonyl)amino]propanoic acid

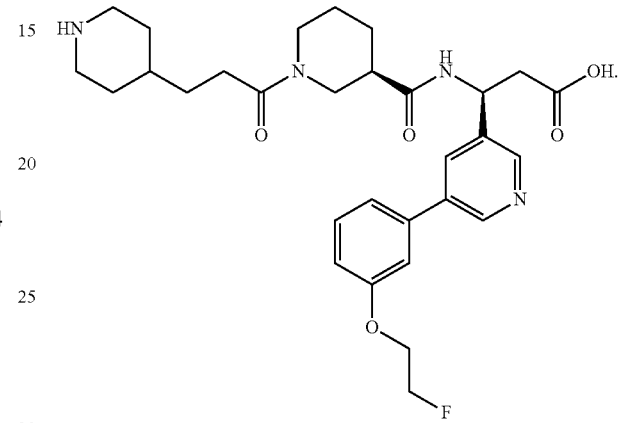

Another preferred compound of Formula III is Example 7

(3S)-3-{5-[4-(2-fluoroethoxy)phenyl]pyridin-3-yl}-3-[({(3R)-1-[3-(piperidin-4-yl)propanoyl]-piperidin-3-yl}carbonyl)amino]propanoic acid

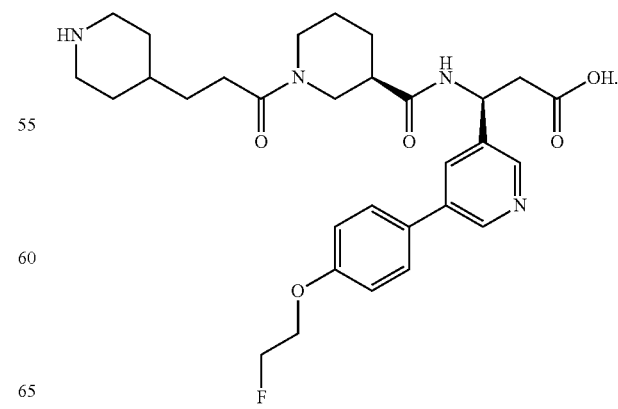

Another preferred compound of Formula III is Example 8

(3S)-3-{5-[2-(2-fluoroethoxy)phenyl]pyridin-3-yl}-3-[({(3R)-1-[3-(piperidin-4-yl)propanoyl]-piperidin-3-yl}carbonyl)amino]propanoic acid

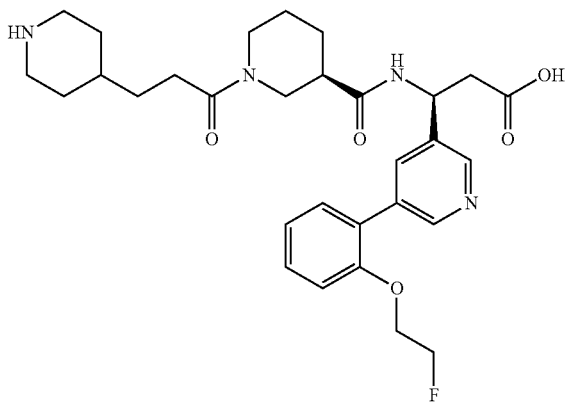 [SMILES: O=C(O)C[C@H](NC(=O)[C@@H]1CCCN(C(=O)CCC2CCNCC2)C1)c1cncc(-c2ccccc2OCCF)c1]

Another preferred compound of Formula III is Example 9

(3S)-3-[5-(3-cyano-4-fluorophenyl)pyridin-3-yl]-3-[({(3R)-1-[3-(piperidin-4-yl)propanoyl]-piperidin-3-yl}carbonyl)amino]propanoic acid

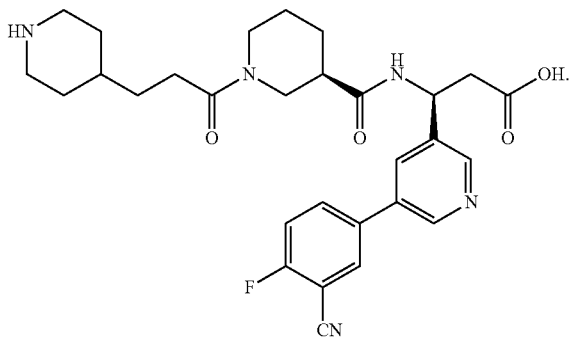

Another preferred compound of Formula III is Example 10

(3S)-3-[5-(4-cyano-3-fluorophenyl)pyridin-3-yl]-3-[({(3R)-1-[3-(piperidin-4-yl)propanoyl]-piperidin-3-yl}carbonyl)amino]propanoic acid

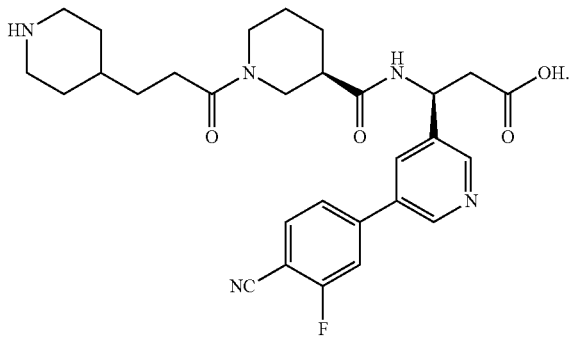

Another preferred compound of Formula III is Example 11

(3S)-3-[5-(4-fluoro-3-nitrophenyl)pyridin-3-yl]-3-[({(3R)-1-[3-(piperidin-4-yl)propanoyl]-piperidin-3-yl}carbonyl)amino]propanoic acid

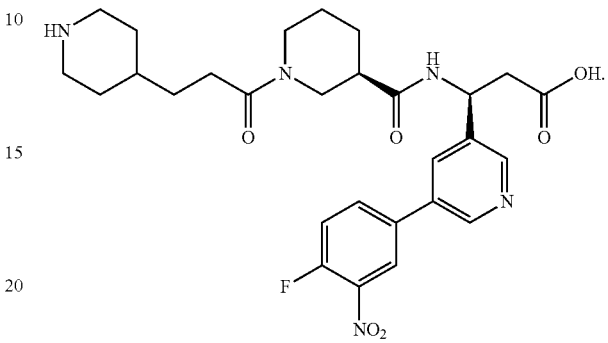

Another preferred compound of Formula III is Example 12

(3R)-3-{5-[(3-cyano-4-fluorobenzyl)oxy]pyridin-3-yl}-3-[({(3S)-1-[3-(piperidin-4-yl)propanoyl]-piperidin-3-yl}carbonyl)amino]propanoic acid

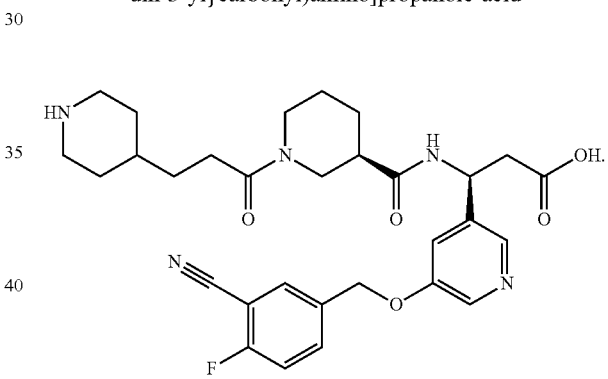

Another preferred compound of Formula III is Example 13

(3S)-3-{5-[(4-cyano-3-fluorobenzyl)oxy]pyridin-3-yl}-3-[({(3R)-1-[3-(piperidin-4-yl)propanoyl]-piperidin-3-yl}carbonyl)amino]propanoic acid

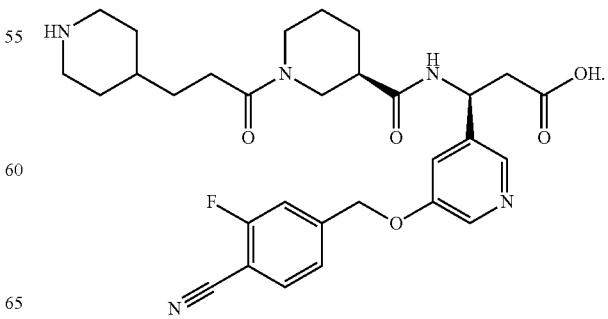

Another preferred compound of Formula III is Example 14

(3S)-3-(4-cyano-3-fluorophenyl)-3-[({(3R)-1-[3-(piperidin-4-yl)propanoyl]piperidin-3-yl}-carbonyl)amino]propanoic acid

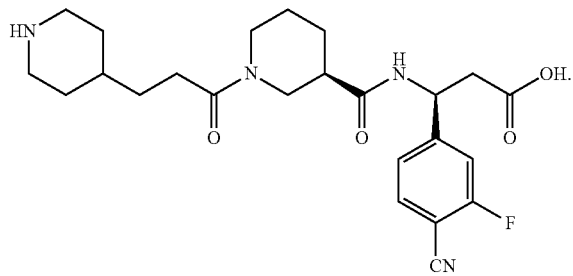 [SMILES: N#Cc1ccc([C@H](CC(=O)O)NC(=O)[C@@H]2CCCN(C(=O)CCC3CCNCC3)C2)cc1F]

Another preferred compound of Formula III is Example 15

(3S)-3-(5-{[4-(2-fluoroethoxy)phenyl]ethynyl}pyridin-3-yl)-3-[({(3R)-1-[3-(piperidin-4-yl)propanoyl]piperidin-3-yl}carbonyl)amino]propanoic acid

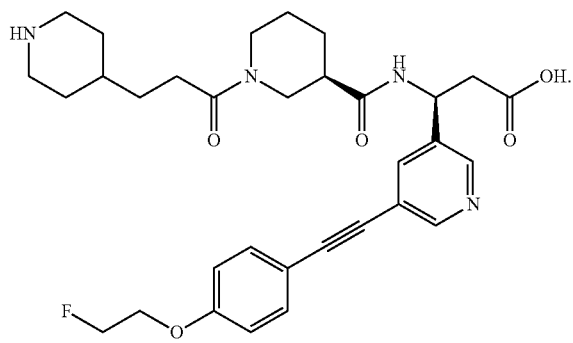 [SMILES: O=C(O)C[C@H](NC(=O)[C@@H]1CCCN(C(=O)CCC2CCNCC2)C1)c1cncc(C#Cc2ccc(OCCF)cc2)c1]

Another preferred compound of Formula III is Example 16

(3S)-3-(5-{[3-(2-fluoroethoxy)phenyl]ethynyl}pyridin-3-yl)-3-[({(3R)-1-[3-(piperidin-4-yl)-propanoyl]piperidin-3-yl}carbonyl)amino]propanoic acid

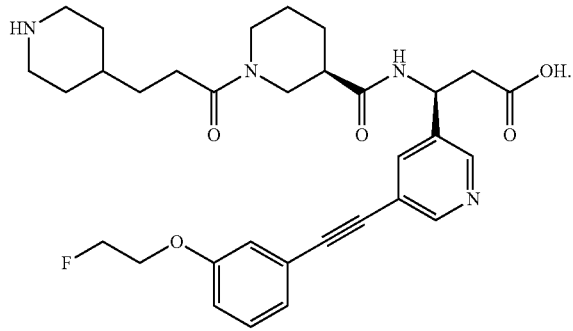 [SMILES: O=C(O)C[C@H](NC(=O)[C@@H]1CCCN(C(=O)CCC2CCNCC2)C1)c1cncc(C#Cc2cccc(OCCF)c2)c1]

Another preferred compound of Formula III is Example 17

(3S)-3-[5-fluoro-4'-(2-fluoroethoxy)biphenyl-3-yl]-3-[({(3R)-1-[3-(piperidin-4-yl)propanoyl]-piperidin-3-yl}carbonyl)amino]propanoic acid

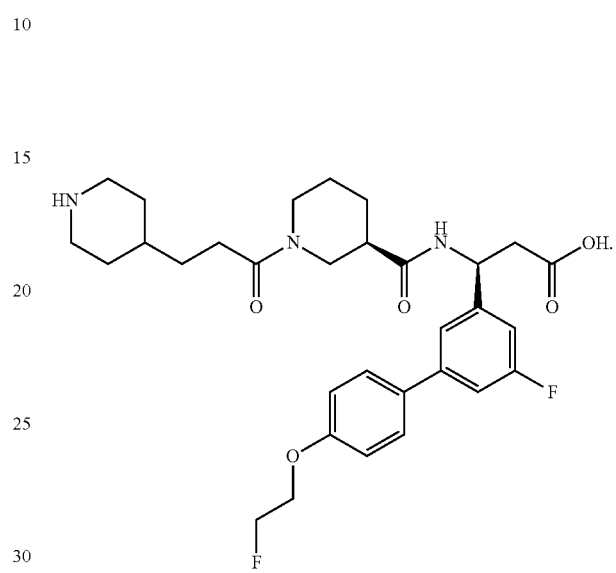

Another preferred compound of Formula III is Example 18

(3S)-3-(5-{2-[4-(2-fluoroethoxy)phenyl]ethyl}pyridin-3-yl)-3-[({(3R)-1-[3-(piperidin-4-yl)-propanoyl]piperidin-3-yl}carbonyl)amino]propanoic acid

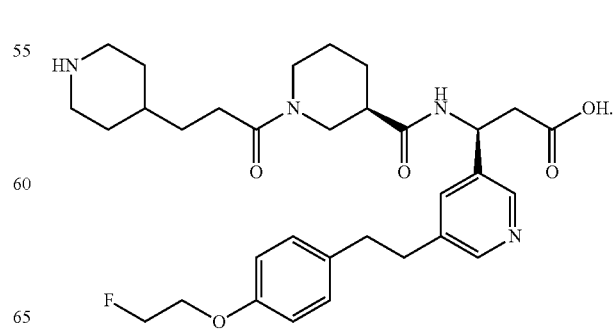

Another preferred compound of Formula III is Example 19

(3S)-3-(5-{2-[3-(2-fluoroethoxy)phenyl]ethyl}pyridin-3-yl)-3-[({(3R)-1-[3-(piperidin-4-yl)propanoyl]piperidin-3-yl}carbonyl)amino]propanoic acid

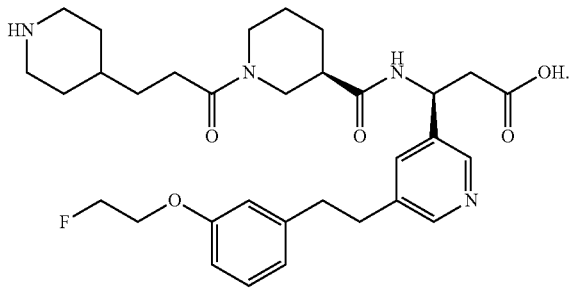

Another preferred compound of Formula III is Example 20

(E/Z)(3S)-3-(5-{[3-(2-fluoroethoxy)phenyl]ethenyl}yridin-3-yl)-3-[({(3R)-1-[3-(piperidin-4-yl)propanoyl]piperidin-3-yl}carbonyl)amino]propanoic acid

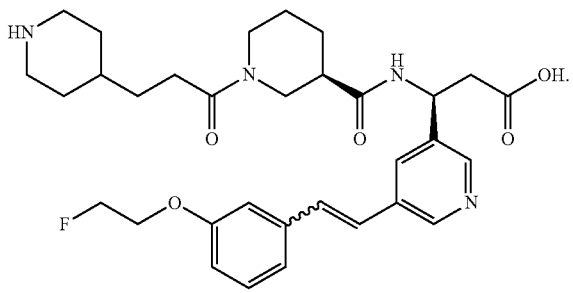

Another preferred compound of Formula III is Example 38

(3S)-3-[3-(2-[$^{18}$F]fluoroethoxy)phenyl]-3-[({(3R)-1-[3-(piperidin-4-yl)propanoyl]piperidin-3-yl}carbonyl)amino]propanoic acid

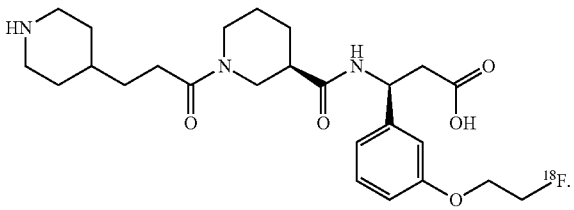

Another preferred compound of Formula III is Example 39

(3S)-3-[4-(2-[$^{18}$F]fluoroethoxy)phenyl]-3-[({(3R)-1-[3-(piperidin-4-yl)propanoyl]piperidin-3-yl}carbonyl)amino]propanoic acid

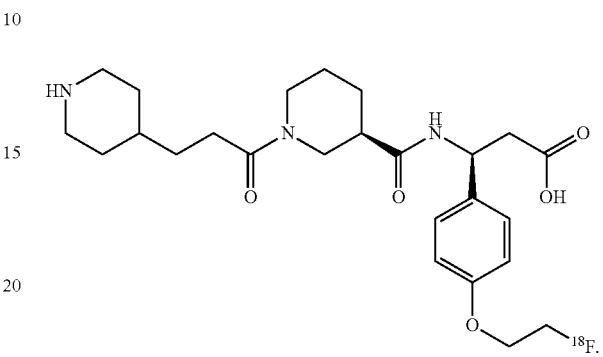

Another preferred compound of Formula III is Example 40

(3S)-3-[5-(2-[$^{18}$F]fluoroethoxy)pyridin-3-yl]-3-[({(3R)-1-[3-(piperidin-4-yl)propanoyl]piperidin-3-yl}carbonyl)amino]propanoic acid

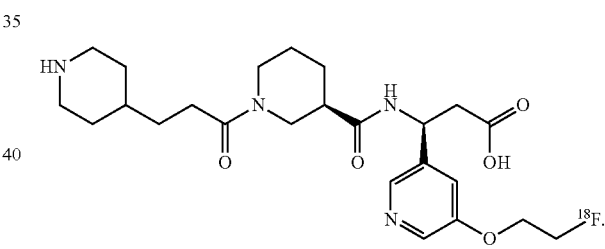

Another preferred compound of Formula III is Example 41

(3S)-3-{5-[4-(2-[$^{18}$F]fluoroethoxy)phenyl]pyridin-3-yl}-3-[({(3R)-1-[3-(piperidin-4-yl)propanoyl]piperidin-3-yl}carbonyl)amino]propanoic acid

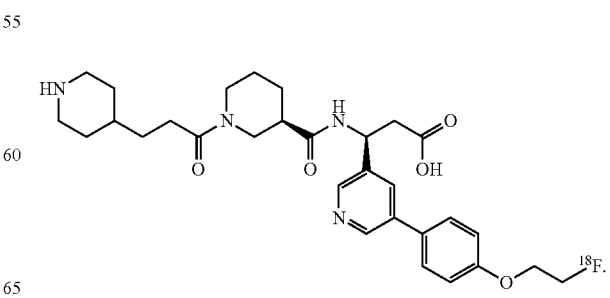

Another preferred compound of Formula III is Example 42

(3S)-3-[5-(3-cyano-4-[$^{18}$F]fluorophenyl)pyridin-3-yl]-3-[({(3R)-1-[3-(piperidin-4-yl)propanoyl]-piperidin-3-yl}carbonyl)amino]propanoic acid

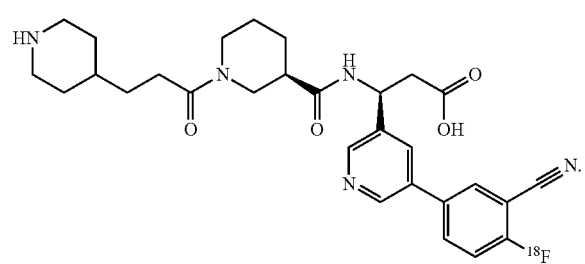 [SMILES: N#Cc1cc(-c2cncc([C@H](CC(=O)O)NC(=O)[C@@H]3CCCN(C(=O)CCC4CCNCC4)C3)c2)ccc1[18F]]

Another preferred compound of Formula III is Example 43

(3S)-3-[5-(4-cyano-3-[$^{18}$F]fluorophenyl)pyridin-3-yl]-3-[({(3R)-1-[3-(piperidin-4-yl)-propanoyl]piperidin-3-yl}carbonyl)amino]propanoic acid

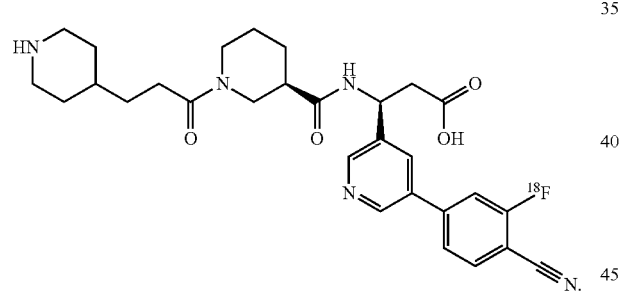

Another preferred compound of Formula III is Example 44

(3S)-3-(5-{[4-(2-[$^{18}$F]fluoroethoxy)phenyl]ethynyl}pyridin-3-yl)-3-[({(3R)-1-[3-(piperidin-4-yl)-propanoyl]piperidin-3-yl}carbonyl)amino]propanoic acid

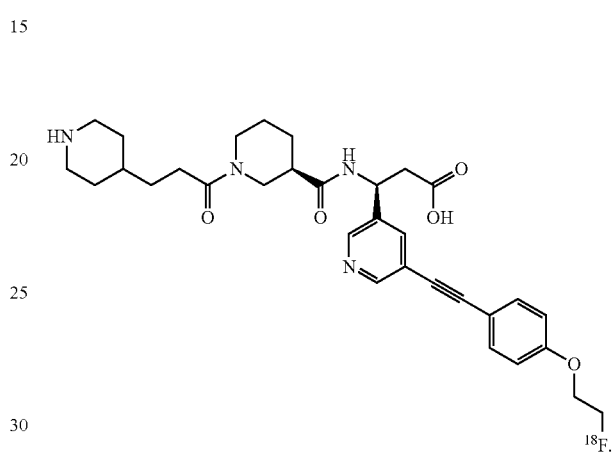

Another preferred compound of Formula III is Example 45

(3S)-3-(5-{[3-(2-[$^{18}$F]fluoroethoxy)phenyl]ethynyl}pyridin-3-yl)-3-[({(3R)-1-[3-(piperidin-4-yl)-propanoyl]piperidin-3-yl}carbonyl)amino]propanoic acid

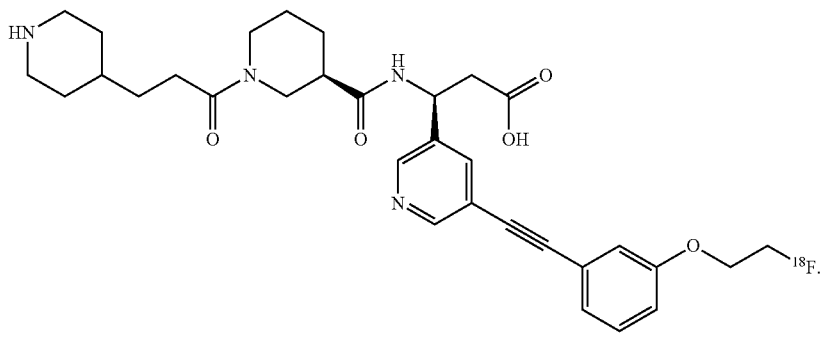

Another preferred compound of Formula III is Example 46

(3S)-3-(5-{2-[4-(2-[$^{18}$F]fluoroethoxy)phenyl]ethyl}pyridin-3-yl)-3-[({(3R)-1-[3-(piperidin-4-yl)-propanoyl]piperidin-3-yl}carbonyl)amino]propanoic acid

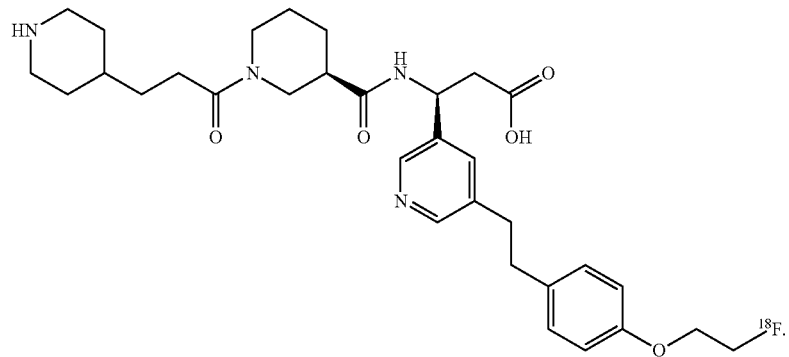

Another preferred compound of Formula III is Example 47

(3S)-3-(5-{2-[3-(2-[$^{18}$F]fluoroethoxy)phenyl]ethyl}pyridin-3-yl)-3-[({(3R)-1-[3-(piperidin-4-yl)-propanoyl]piperidin-3-yl}carbonyl)amino]propanoic acid

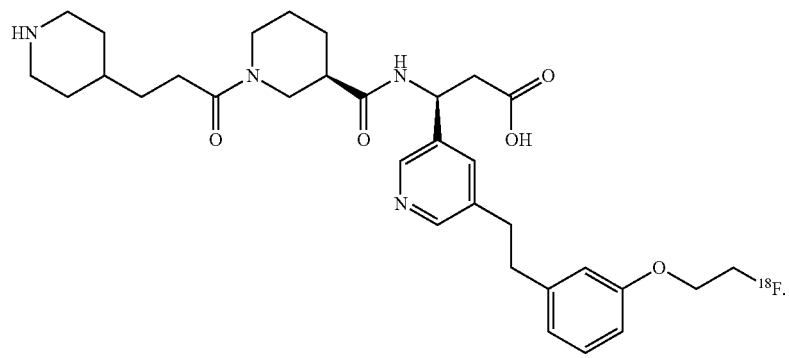

Another preferred compound of Formula III is Example 48

(3S)-3-(3-{2-[2-(2-[$^{18}$F]fluoroethoxy)ethoxy]ethoxy}phenyl)-3-[({(3R)-1-[3-(piperidin-4-yl)-propanoyl]piperidin-3-yl}carbonyl)amino]propanoic acid

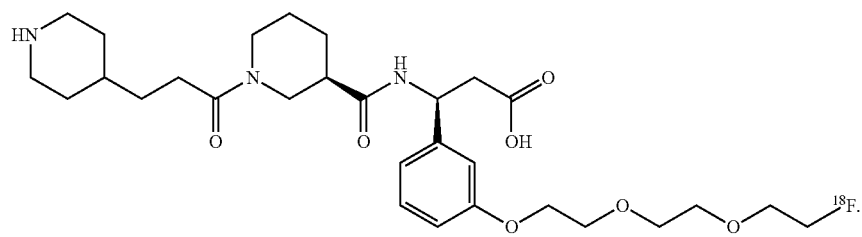

The fourth aspect of the present invention is directed to methods for preparation of compounds of Formula III

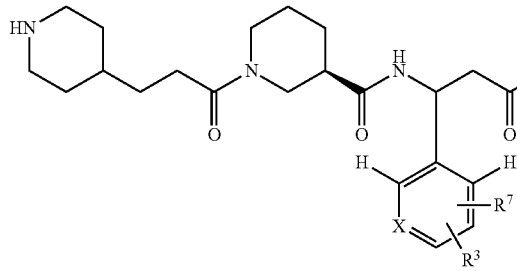

starting with compounds of Formula I,

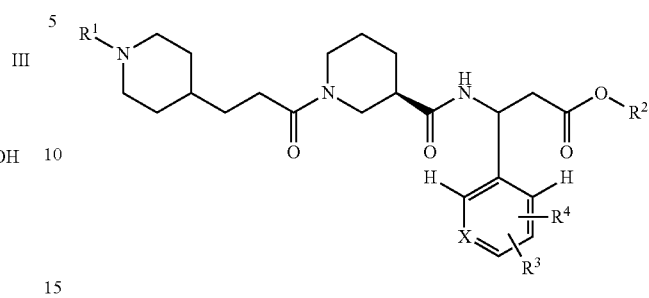

wherein
- R¹ is hydrogen or an amine-protecting group;
- R² is hydrogen or a carboxyl-protecting group;
- wherein at least one of R¹ and R² is not H;
- R³ is selected from the group consisting of H, F, CF₃, COR⁹, COOR¹⁰, SOR¹⁰, SO₂R¹⁰, CN and NO₂; preferably R³ is selected from the group consisting of H, F, CF₃, CN, and NO₂;
- R⁴ is selected from the group consisting of OH, Halogen, —NO₂, —N⁺(Me)₃(W⁻), —I⁺R¹¹(W⁻)—O(CH₂)ₙ-LG, —(OCH₂CH₂)ₘ-LG, Q, —OCH₂-Q; —CH₂—CH₂-Q, —CH═CH-Q and —C≡C-Q; preferably R⁴ is selected from the group consisting of OH, Halogen, —N⁺(Me)₃(W⁻), —O(CH₂)ₙ-LG, —(OCH₂CH₂)ₘ-LG, Q, —OCH₂-Q; —CH₂—CH₂-Q, —CH═CH-Q and —C≡C-Q;
- X is selected from CH or N;
- LG is a leaving group;
- R⁹ is hydrogen or (C₁-C₆)alkyl; preferably hydrogen or (C₁-C₄)alkyl, more preferably hydrogen, methyl, ethyl or tert-butyl;
- R¹⁰ is (C₁-C₆)alkyl; preferably (C₁-C₄)alkyl, more preferably methyl, ethyl or tert-butyl;
- R¹¹ is selected from the group consisting of phenyl, (4-methyl)phenyl, (4-methoxy)phenyl, 2-furanyl and 2-thienyl; preferably R¹ is selected from the group consisting of (4-methoxy)phenyl and 2-thienyl;
- W⁻ is selected from the group comprising CF₃(S(O)₂O⁻, iodide anion, bromide anion and CF₃C(O)O⁻; preferably W⁻ is selected from the group CF₃(S(O)₂O⁻, bromide anion and CF₃C(O)O⁻;
- Q is a group

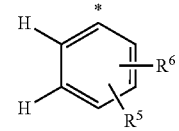

wherein * indicates the atom of connection of Q;
- R⁵ is selected from the group consisting of H, CF₃, COR⁹, COOR¹⁰, SOR¹⁰, SO₂R¹⁰, CN and NO₂; preferably R⁵ is selected from the group consisting of H, CF₃, CN, and NO₂
- R⁶ is selected from the group consisting of OH, Halogen, —NO₂, —N⁺(Me)₃(W⁻), —I⁺R¹¹(W⁻), —O(CH₂)ₙ-LG and —(OCH₂CH₂)ₘ-LG; preferably R⁶ is selected from the group consisting of OH, Halogen, —N⁺(Me)₃(W⁻), —O(CH₂)ₙ-LG and —(OCH₂CH₂)ₘ-LG; n is 1-3;
- and m is 2-3;

wherein
- R³ is selected from the group consisting of H, F, CF₃, COR⁹, COOR¹⁰, SOR¹⁰, SO₂R¹⁰, CN and NO₂; preferably R³ is selected from the group consisting of H, F, CF₃, CN, NO₂;
- R⁷ is selected from the group consisting of Y, —O(CH₂)ₙ—Y, —(OCH₂CH₂)ₘ—Y, Z, —OCH₂—Z; —CH₂—CH₂—Z, —CH═CH—Z and —C≡C—Z;
- X is selected from CH or N;
- Y is selected from ¹⁸F or F;
- R⁹ is hydrogen or (C₁-C₆)alkyl; preferably hydrogen or (C₁-C₄)alkyl, more preferably hydrogen, methyl, ethyl or tert-butyl;
- R¹⁰ is (C₁-C₆)alkyl; preferably (C₁-C₄)alkyl, more preferably methyl, ethyl or tert-butyl;
- Z is a group

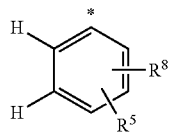

wherein * indicates the atom of connection of Z;
- R⁵ is selected from the group consisting of H, CF₃, COR⁹, COOR¹⁰, SOR¹⁰, SO₂R¹⁰, CN and NO₂; preferably R³ is selected from the group consisting of H, CF₃, CN, NO₂;
- R⁸ is selected from the group consisting of Y, —O(CH₂)ₙ—Y and —(OCH₂CH₂)ₘ—Y;
- n is 1-3;
- and m is 2-3;
- with the proviso that if R⁷ has the meaning of Y, R³ has the meaning of CF₃, COR⁹, COOR¹⁰, SOR¹⁰, SO₂R¹⁰, CN or NO₂ and
- with the proviso that if R⁸ has the meaning of Y, R⁵ has the meaning of CF₃, COR⁹, COOR¹⁰, SOR¹⁰, SO₂R¹⁰, CN or NO₂;

with the proviso that if $R^4$ has the meaning of Halogen, —$NO_2$, —$N^+(Me)_3(W^-)$ or —$I^+R^{11}(W^-)$, $R^3$ has the meaning of $CF_3$, $COR^9$, $COOR^{10}$, $SOR^{10}$, $SO_2R^{10}$, CN or $NO_2$ and with the proviso that if $R^6$ has the meaning of Halogen, —$NO_2$, —$N^+(Me)_3(W^-)$ or —$I^+R^{11}(W^-)$, $R^5$ has the meaning of $CF_3$, $COR^9$, $COOR^{10}$, $SOR^{10}$, $SO_2R^{10}$, CN or $NO_2$;

and a fluorination reaction to obtain compounds of Formula II,

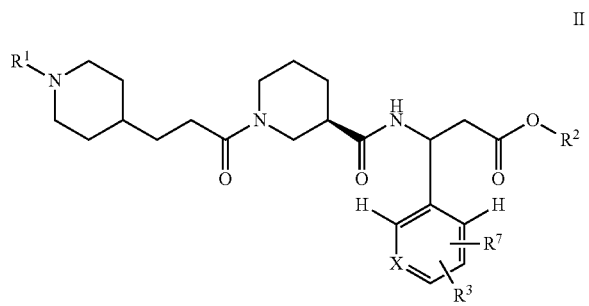

wherein $R^1$ is hydrogen or an amine-protecting group;

$R^2$ is hydrogen or a carboxyl-protecting group;

wherein at least one of $R^1$ and $R^2$ is not hydrogen;

$R^3$ is selected from the group consisting of H, F, $CF_3$, $COR^9$, $COOR^{10}$, $SOR^{10}$, $SO_2R^{10}$, CN and $NO_2$; preferably $R^3$ is selected from the group consisting of H, F, $CF_3$, CN, $NO_2$;

$R^7$ is selected from the group consisting of Y, —$O(CH_2)_n$—Y, —$(OCH_2CH_2)_m$—Y, Z, —$OCH_2$—Z; —$CH_2$—$CH_2$—Z, —CH=CH—Z and —C≡C—Z;

X is selected from CH or N;

Y is selected from $^{18}F$ or F;

$R^9$ is hydrogen or $(C_1-C_6)$alkyl; preferably hydrogen or $(C_1-C_4)$alkyl, more preferably hydrogen, methyl, ethyl or tert-butyl;

$R^{10}$ is $(C_1-C_6)$alkyl; preferably $(C_1-C_4)$alkyl, more preferably methyl, ethyl or tert-butyl;

Z is a group

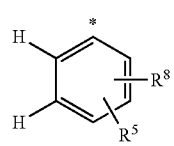

wherein * indicates the atom of connection of Z;

$R^5$ is selected from the group consisting of H, $CF_3$, $COR^9$, $COOR^{10}$, $SOR^{10}$, $SO_2R^{10}$, CN and $NO_2$; preferably $R^5$ is selected from the group consisting of H, $CF_3$, CN, $NO_2$ $R^8$ is selected from the group consisting of Y, —$O(CH_2)_n$—Y and —$(OCH_2CH_2)_m$—Y;

n is 1-3;

and m is 2-3;

with the proviso that if $R^7$ has the meaning Y, $R^3$ has the meaning of $CF_3$, $COR^9$, $COOR^{10}$, $SOR^{10}$, $SO_2R^{10}$, CN or $NO_2$ and with the proviso that if $R^8$ has the meaning Y, $R^5$ has the meaning of $CF_3$, $COR^9$, $COOR^{10}$, $SOR^{10}$, $SO_2R^{10}$, CN or $NO_2$;

and cleavage of the protecting group(s)

or reaction of compounds of Formula I with a $^{18}F$ or F reagent or $^{18}F$ or F building block and cleavage of protecting groups to obtain compounds of Formula III.

Further, the fourth aspect of the present invention is directed to methods for preparation of compounds of Formula III

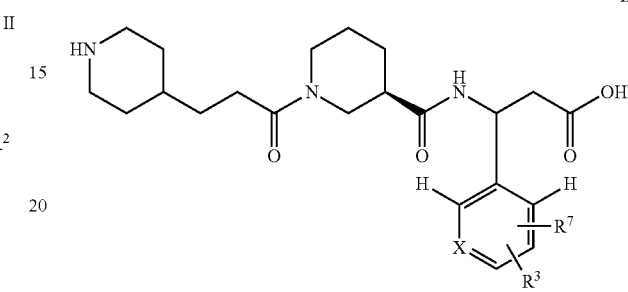

wherein $R^3$ is H, F, $CF_3$, CN or $NO_2$;

$R^7$ is Y, —$O(CH_2)_n$—Y, —$(OCH_2CH_2)_m$—Y, Z, —$OCH_2$—Z; —$CH_2$—$CH_2$—Z, —CH=CH—Z or —C≡C—Z;

X is selected from CH or N;

Y is $^{18}F$ or F;

Z is a group

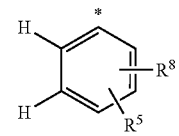

wherein * indicates the atom of connection of Z;

$R^5$ is H, $CF_3$, CN or $NO_2$;

$R^8$ is Y, —$O(CH_2)_n$—Y or —$(OCH_2CH_2)_m$—Y;

n is 1-3;

and m is 2-3, starting with compounds of Formula I,

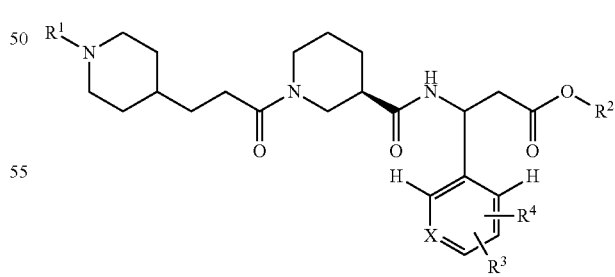

wherein $R^2$ is hydrogen or a carboxyl-protecting group;

wherein at least one of $R^1$ and $R^2$ is not H;

$R^3$ is H, F, $CF_3$, CN and $NO_2$;

$R^4$ is OH, Halogen, —$N^+(Me)_3(W^-)$, —$O(CH_2)_n$-LG, —$(OCH_2CH_2)_m$-LG, Q, —$OCH_2$-Q; —$CH_2$—$CH_2$-Q, —CH=CH-Q and —C≡C-Q;

X is selected from CH or N;
LG is a leaving group;
W⁻ is CF$_3$(S(O)$_2$O—, bromide anion and CF$_3$C(O)O⁻;
Q is a group

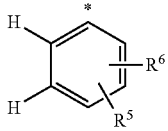

wherein * indicates the atom of connection of Q;
R$^5$ is H, CF$_3$, CN and NO$_2$;
R$^6$ is OH, Halogen, —N⁺(Me)$_3$(W⁻), —O(CH$_2$)$_n$-LG and —(OCH$_2$CH$_2$)$_m$-LG;
n is 1-3;
and m is 2-3;
with the proviso that if R$^4$ has the meaning of Halogen or —N⁺(Me)$_3$(W⁻), R$^3$ has the meaning of CF$_3$, CN or NO$_2$ and
with the proviso that if R$^6$ has the meaning of Halogen or —N⁺(Me)$_3$(W⁻), R$^5$ has the meaning of CF$_3$, CN or NO$_2$;
and a fluorination reaction to obtain compounds of Formula II,

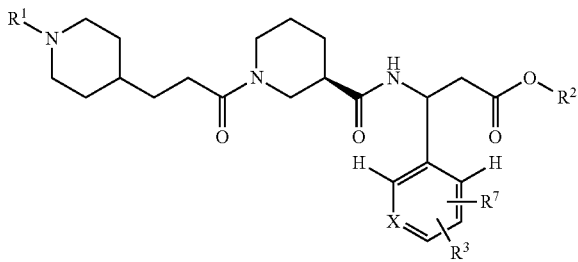

wherein
R$^1$ is hydrogen or an amine-protecting group;
R$^2$ is hydrogen or a carboxyl-protecting group;
wherein at least one of R$^1$ and R$^2$ is not hydrogen;
R$^3$ is H, F, CF$_3$, CN and NO$_2$;
R$^7$ is Y, —O(CH$_2$)$_n$—Y, —(OCH$_2$CH$_2$)$_m$—Y, Z, —OCH$_2$—Z; —CH$_2$—CH$_2$—Z, —CH=CH—Z or —C≡C—Z;
X is selected from CH or N;
Y is selected from $^{18}$F or F;
Z is a group

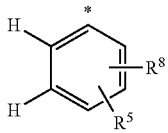

wherein * indicates the atom of connection of Z;
R$^5$ is H, CF$_3$, CN and NO$_2$;
R$^8$ is Y, —O(CH$_2$)$_n$—Y or —(OCH$_2$CH$_2$)$_m$—Y;
n is 1-3;
and m is 2-3;
with the proviso that if R$^7$ has the meaning of Y, R$^3$ has the meaning of CF$_3$, CN or NO$_2$ and with the proviso that if R$^8$ has the meaning of Y, R$^5$ has the meaning of CF$_3$, CN or NO$_2$;
and cleavage of the protecting group(s)
or
reaction of compounds of Formula I with a $^{18}$F or F reagent or $^{18}$F or F building block and cleavage of protecting groups to obtain compounds of Formula III.

In a first embodiment, the invention is directed to a method for preparation of compounds of Formula III comprising the steps of:
$^{18}$F-radiofluorination of a compound of Formula I, wherein R$^4$ is different from OH, or $^{18}$F-radiofluorination of a compound of Formula I, wherein R$^6$ is different from OH, to obtain a compound of Formula II, and subsequent
Cleavage of protecting groups from a compound of Formula II to obtain a compound of Formula III.

Optionally the method is followed by the purification of a compound of Formula III by solid phase extraction or by semi-preparative HPLC. Preferred HPLC columns are reversed phase columns such as ACE 5μ C18-HL (10×250 mm), Phenomenex Gemini 5μ C18 110A (10×250 mm) or Zorbax Bonus RP 5 μm C18-HL (9.4×250 mm). Mixtures of buffer solution, acids, bases, water etc. with organic solvents such as acetonitrile, methanol, ethanol etc. can be used as mobile phase. The collected peak from the HPLC purification optionally can be trapped on a solid-phase-extraction cartridge, preferably via a C18 separation cartridge. Pure organic solvents such as acetonitrile, methanol, ethanol etc. or aqueous buffer solutions, acids, bases, water etc. or mixtures of organic solvents and cited aqueous solutions can be used to elute the purified F-18 labeled product from the cartridge. Preferably the F-18 labeled product is eluted with pure ethanol or mixtures with water.

The preferred features and embodiments disclosed for compounds of general formula I, II and III are herein incorporated.

Methods for $^{18}$F-fluorination are well known to the person skilled in the art. For example, the $^{18}$F reagent can be K$^{18}$F, KH$^{18}$F$_2$, H$^{18}$F, Rb$^{18}$F, Cs$^{18}$F, Na$^{18}$F.

Optionally, the $^{18}$F reagent comprises a chelating agent such as a cryptand (e.g.: 4,7,13,16,21,24-Hexaoxa-1,10-diazabicyclo[8.8.8]-hexacosane—Kryptofix®) or a crown ether (e.g.: 18-crown-6).

The $^{18}$F reagent can also be a tetraalkylammonium salt of $^{18}$F or a tetraalkylphosphonium salt of $^{18}$F, known to those skilled in the art, e.g.: tetrabutylammonium [$^{18}$F]fluoride, tetrabutylphosphonium [$^{18}$F]fluoride.

Preferably, the $^{18}$F reagent is Cs$^{18}$F, K$^{18}$F, KH$^{18}$F$_2$, tetrabutylammonium [$^{18}$F]fluoride and contains Kryptofix®.

The reagents, solvents and conditions which can be used for this fluorination are common and well-known to the skilled person in the field. See, e.g., *J. Fluorine Chem.*, 27 (1985):177-191; Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50). Preferably, the solvents used in the present method are DMF, DMSO, acetonitrile, DMA, or mixtures thereof, preferably the solvent is acetonitrile, DMSO.

Precursors for alkyl-$^{18}$F compounds of general formula I (wherein R$^4$ or R$^6$ has not the meaning OH, -Halogen, —NO$_2$, —N⁺(Me)$_3$(W⁻), —I⁺R$^{11}$(W⁻)) are e.g. halogenides or sulfonates like methylsulfonyloxy, (4-methylphenyl)sulfonyloxy, trifluormethylsulfonyloxy, nonafluorobutylsulfonyloxy, (4-bromophenyl)sulfonyloxy, (4-nitrophenyl)sulfonyloxy etc. (formula I with $R^4$ or $R^6$ containing a leaving group (LG)) which can be synthesized from the respective hydroxy compounds according to methods known in the art (J. March, Advanced Organic Chemistry, $4^{th}$ ed. 1992, John Wiley & Sons, pp 352ff).

Precursors for alkyl-$^{18}$F compounds of general formula I (wherein $R^4$ or $R^6$ has the meaning of —OH) can be coupled to under basic conditions to prosthetic groups containing both an F-18 labeling and a good leaving group like a halogenide or a sulfonate like methylsulfonyloxy, (4-methylphenyl)sulfonyloxy, trifluormethylsulfonyloxy, nonafluorobutylsulfonyloxy, (4-bromophenyl)sulfonyloxy, (4-nitrophenyl)sulfonyloxy etc. These indirect labelings described in this invention can be performed according to methods known in the art (in: Schubiger P. A., Friebe M., Lehmann L., (eds), PET-Chemistry—The Driving Force in Molecular Imaging. Springer, Berlin Heidelberg, pp. 15-50).

Precursors for aryl-$^{18}$F compounds of general formula I (wherein $R^4$ or $R^6$ has the meaning of -Halogen, $—NO_2$, $—N^+(Me)_3(W^-)$, $—I^+R^{11}(W^-)$) are e.g. aryl halogenides, nitro compounds, trimethyl ammonium compounds, aryliodonium compounds etc. which can be converted to the respective $^{18}$F compounds of this invention by methods known in the art (L. Cai, S. Lu, V. Pike, Eur. J. Org. Chem. 2008, 2853-2873). Starting materials for these precursors can be synthesized by methods known in the art (R. C. Larock, Comprehensive Organic Transformations, VCH Publishers 1989).

Optionally the method is followed by the purification of a compound of Formula III by solid phase extraction or by semi-preparative HPLC. Preferred HPLC columns are reversed phase columns such as ACE 5μ C18-HL (10×250 mm), Phenomenex Gemini 5μ C18 110A (10×250 mm) or Zorbax Bonus RP 5 μm C18-HL (9.4×250 mm). Mixtures of buffer solution, acids, bases, water etc. with organic solvents such as acetonitrile, methanol, ethanol etc. can be used as mobile phase. The collected peak from the HPLC purification optionally can be trapped on a solid-phase-extraction cartridge, preferably via a C18 separation cartridge. Pure organic solvents such as acetonitrile, methanol, ethanol etc. or aqueous buffer solutions, acids, bases, water etc. or mixtures of organic solvents and cited aqueous solutions can be used to elute the purified F-18 labeled product from the cartridge. Preferably the F-18 labeled product is eluted with pure ethanol or mixtures with water.

In a second embodiment, the invention is directed to a method for preparation of compounds of Formula III, comprising the steps of:
  Reacting of a compound of Formula I, wherein $R^4$ is OH, or reacting a compound of Formula I, wherein $R^6$ is OH, with an $^{18}$F labeled building block, and subsequent
  Cleaving of protecting groups from a compound of Formula II to obtain a compound of Formula III.

Optionally the method is followed by the purification of a compound of Formula III by solid phase extraction or by semi-preparative HPLC. Preferred HPLC columns are reversed phase columns such as ACE 5 μ C18-HL (10×250 mm), Phenomenex Gemini 5μ C18 110A (10×250 mm) or Zorbax Bonus RP 5μm C18-HL (9.4×250 mm). Mixtures of buffer solution, acids, bases, water etc. with organic solvents such as acetonitrile, methanol, ethanol etc. can be used as mobile phase. The collected peak from the HPLC purification optionally can be trapped on a solid-phase-extraction cartridge, preferably via a C18 separation cartridge. Pure organic solvents such as acetonitrile, methanol, ethanol etc. or aqueous buffer solutions, acids, bases, water etc. or mixtures of organic solvents and cited aqueous solutions can be used to elute the purified F-18 labeled product from the cartridge. Preferably the F-18 labeled product is eluted with pure ethanol or mixtures with water.

In a third embodiment, the invention is directed to a method for preparation of compounds of Formula III, comprising the steps of:
  Reacting of a compound of Formula I, wherein $R^4$ is OH, or reacting a compound of Formula I, wherein $R^6$ is OH, with a building block containing a leaving group LG and subsequent
  $^{18}$F-radiofluorination of the obtained compound of Formula I, to obtain a compound of Formula II, and subsequent
  Cleaving of protecting groups to obtain a compound of Formula III.

Optionally the method is followed by the purification of a compound of Formula III by solid phase extraction or by semi-preparative HPLC. Preferred HPLC columns are reversed phase columns such as ACE 5 μ C18-HL (10×250 mm), Phenomenex Gemini 5μ C18 110A (10×250 mm) or Zorbax Bonus RP 5μm C18-HL (9.4×250 mm). Mixtures of buffer solution, acids, bases, water etc. with organic solvents such as acetonitrile, methanol, ethanol etc. can be used as mobile phase. The collected peak from the HPLC purification optionally can be trapped on a solid-phase-extraction cartridge, preferably via a C18 separation cartridge. Pure organic solvents such as acetonitrile, methanol, ethanol etc. or aqueous buffer solutions, acids, bases, water etc. or mixtures of organic solvents and cited aqueous solutions can be used to elute the purified F-18 labeled product from the cartridge. Preferably the F-18 labeled product is eluted with pure ethanol or mixtures with water.

The fifth aspect of the present invention is directed to methods for preparation of compounds of Formula III (cold standard).

In a first embodiment, the invention is directed to a method for preparation of compounds of Formula III comprising the steps of:
  Fluorination of a compound of Formula I to obtain a compound of Formula II, and subsequent
  Cleavage of protecting groups from a compound of Formula II to obtain a compound of Formula III.

Optionally the method is followed by the purification of a compound of Formula III. Suitable purification methods are chromatography methods (e.g. HPLC, flash-chromatography).

The preferred features and embodiments disclosed for compounds of general formula I, II and III are herein incorporated.

In a second embodiment, the invention is directed to a method for preparation of compound of Formula III comprising the steps of
  Reacting of a compound of Formula I, wherein $R^4$ is OH, or reacting a compound of Formula I, wherein $R^6$ is OH, with an fluorine containing building block, and subsequent
  Cleaving of protecting groups to obtain a compound of Formula III.

Optionally the method is followed by the purification of a compound of Formula III. Suitable purification methods are chromatography methods (e.g. HPLC, flash-chromatography).

The preferred features and embodiments disclosed for compounds of general formula I and III are herein incorporated.

In a third embodiment, the invention is directed to a method for preparation of compounds of Formula III, comprising the steps of:

Reacting of a compound of Formula I, wherein $R^4$ is OH, or reacting a compound of Formula I, wherein $R^6$ is OH, with a building block containing a leaving group LG and subsequent Fluorination of the obtained compound of Formula I, to obtain a compound of Formula II, and subsequent Cleaving of protecting groups to obtain a compound of Formula III.

Optionally the method is followed by the purification of a compound of Formula III. Suitable purification methods are chromatography methods (e.g. HPLC, flash-chromatography).

The invention relates also to the use of compound of Formula III for the manufacture of medicament or pharmaceutical for treatment.

In a sixth aspect of the invention, the invention is directed to $^{18}F$ labeled compounds according to Formula III for the manufacture of an imaging tracer or radiopharmaceutical agent for imaging thrombi. The imaging agent or radiopharmaceutical agent is preferably suitable as imaging agent for PET applications.

In other words, the invention is directed to $^{18}F$ labeled compounds of general formula III as imaging tracer or radiopharmaceutical agent.

The invention is directed to $^{18}F$ labeled compounds of general formula III for use in the imaging of thrombi.

The invention is also directed to a method for imaging or diagnosing of thrombi comprising the steps:

Administering to a mammal an effective amount of a $^{18}F$ labeled compound of formula III, Obtaining images of the mammal and Assessing images.

The present invention is also directed to a method of imaging comprising the step of introducing into a patient a detectable quantity of an $^{18}F$ labeled compound of Formula III and imaging said patient.

Another aspect of the invention is the use of a compound of Formula III as described above and herein for diagnosing thrombi in a patient, in particular in a mammal, such as a human.

Preferably, the use of a compound of the invention in the diagnosis is performed using positron emission tomography (PET).

Another aspect of the invention is directed to a method of imaging thrombi. Such a method comprises a) administering to a mammal a compound as described above and herein containing a detectable label, and b) detecting the signal stemming from the compound that is specifically taken up by thrombi.

In a further aspect, the invention is directed to a method of diagnosing a patient with a thromboembolic disease, such as myocardial infarction, pulmonary embolism, stroke and transient ischemic attacks. This method comprises a) administering to a human in need of such diagnosis a compound of the invention with a detectable label for detecting the compound in the human as described above and herein, and b) measuring the signal from the detectable label arising from the administration of the compound to the human, preferably by positron emission tomography (PET).

In a further aspect, the invention is directed to a method of diagnosing a patient with a life threatening disease, such as aortic aneurism, chronic thromboembolic pulmonary hypertension (CETPH), arterial fibrillation and coronary thrombosis. This method comprises a) administering to a human in need of such diagnosis a compound of the invention with a detectable label for detecting the compound in the human as described above and herein, and b) measuring the signal from the detectable label arising from the administration of the compound to the human, preferably by positron emission tomography (PET).

In a further aspect, the invention is directed to a method of diagnosing and health monitoring of cardiovascular risk patients. This method comprises a) administering to a human in need of such diagnosis a compound of the invention with a detectable label for detecting the compound in the human as described above and herein, and b) measuring the signal from the detectable label arising from the administration of the compound to the human, preferably by positron emission tomography (PET).

Methods of diagnosing and use for PET imaging of thrombi involve administration of one of the preferred compounds listed below:

(3S)-3-[3-(2-[$^{18}F$]Fluoroethoxy)phenyl]-3-[({(3R)-1-[3-(piperidin-4-yl)propanoyl]piperidin-3-yl}-carbonyl)amino]propanoic acid

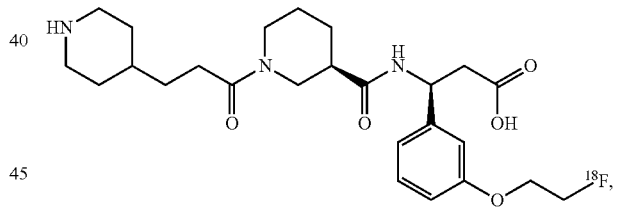

(3S)-3-[4-(2-[$^{18}F$]Fluoroethoxy)phenyl]-3-[({(3R)-1-[3-(piperidin-4-yl)propanoyl]piperidin-3-yl}carbonyl)amino]propanoic acid

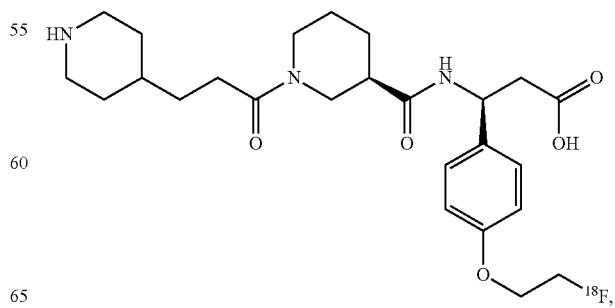

(3S)-3-[5-(2-[$^{18}$F]Fluoroethoxy)pyridin-3-yl]-3-
[({(3R)-1-[3-(piperidin-4-yl)propanoyl]piperidin-3-
yl}carbonyl)amino]propanoic acid

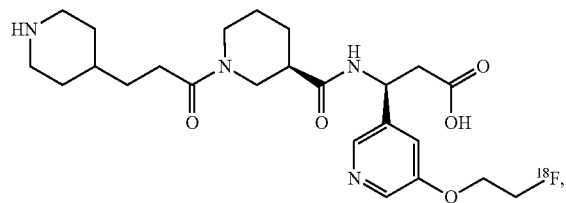

(3S)-3-{5-[4-(2-[$^{18}$F]Fluoroethoxy)phenyl]pyridin-
3-yl}-3-[({(3R)-1-[3-(piperidin-4-yl)propanoyl]piperidin-3-yl}carbonyl)amino]propanoic acid

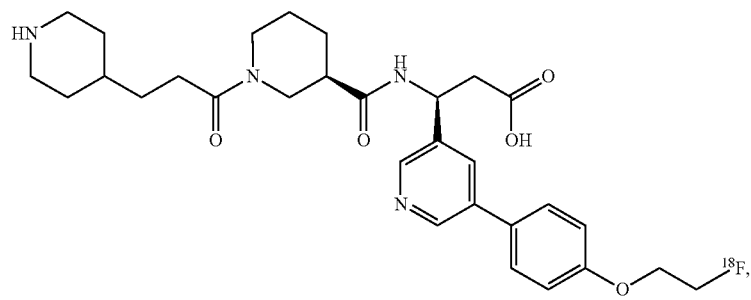

(3S)-3-[5-(3-Cyano-4-[$^{18}$F]fluorophenyl)pyridin-3-
yl]-3-[({(3R)-1-[3-(piperidin-4-yl)propanoyl]-piperidin-3-yl}carbonyl)amino]propanoic acid (3S)-3-[5-(4-Cyano-3-[$^{18}$F]fluorophenyl)pyridin-3-
yl]-3-[({(3R)-1-[3-(piperidin-4-yl)-propanoyl]piperidin-3-yl}carbonyl)amino]propanoic acid

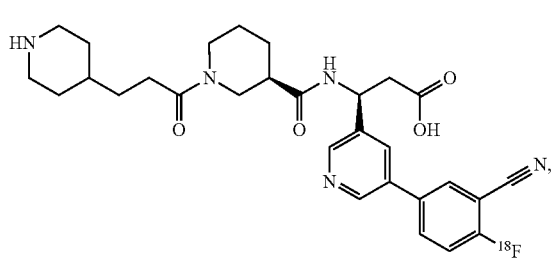 [SMILES: N#Cc1cc(-c2cncc([C@H](CC(=O)O)NC(=O)[C@@H]3CCCN(C(=O)CCC4CCNCC4)C3)c2)ccc1[18F]]

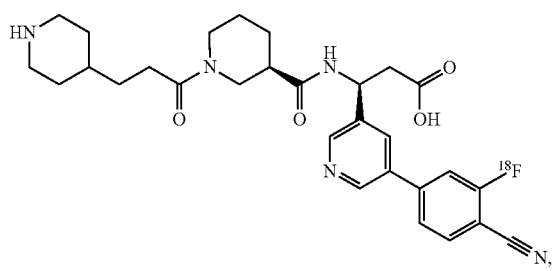 [SMILES: N#Cc1ccc(-c2cncc([C@H](CC(=O)O)NC(=O)[C@@H]3CCCN(C(=O)CCC4CCNCC4)C3)c2)cc1[18F]]

(3S)-3-(5-{[4-(2-[$^{18}$F]Fluoroethoxy)phenyl]
ethynyl}pyridin-3-yl)-3-[({(3R)-1-[3-(piperidin-4-
yl)-propanoyl]piperidin-3-yl}carbonyl)amino]pro-
panoic acid
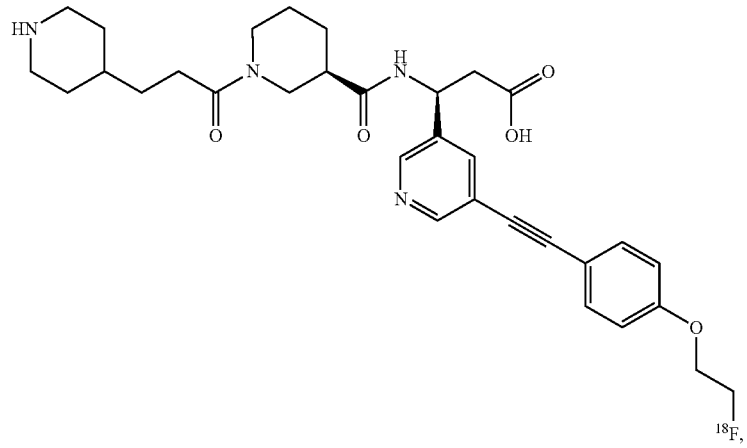
25
(3S)-3-(5-{[3-(2-[$^{18}$F]Fluoroethoxy)phenyl]
ethynyl}pyridin-3-yl)-3-[({(3R)-1-[3-(piperidin-4-
yl)-propanoyl]piperidin-3-yl}carbonyl)amino]pro-
panoic acid
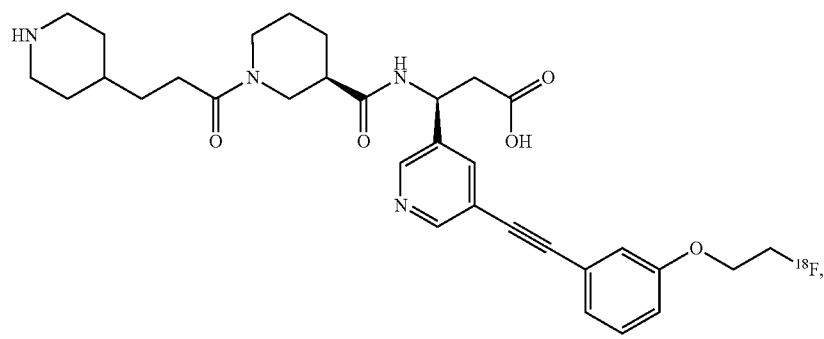
(3S)-3-(5-{2-[4-(2-[$^{18}$F]Fluoroethoxy)phenyl]
ethyl}pyridin-3-yl)-3-[({(3R)-1-[3-(piperidin-4-yl)-
propanoyl]piperidin-3-yl}carbonyl)amino]propanoic
acid
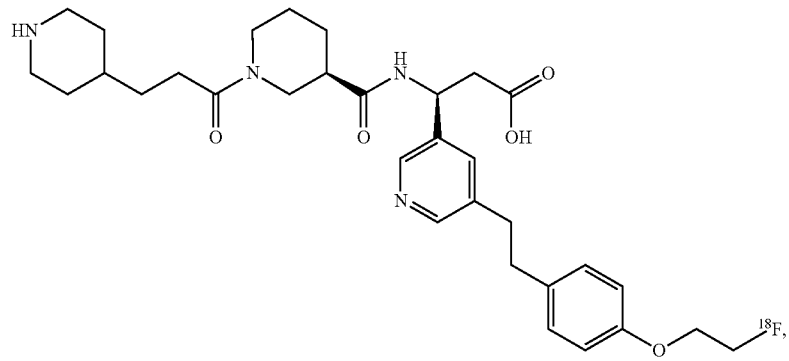

(3S)-3-(5-{2-[3-(2-[¹⁸F]Fluoroethoxy)phenyl]
ethyl}pyridin-3-yl)-3-[({(3R)-1-[3-(piperidin-4-yl)-
propanoyl]piperidin-3-yl}carbonyl)amino]propanoic
acid

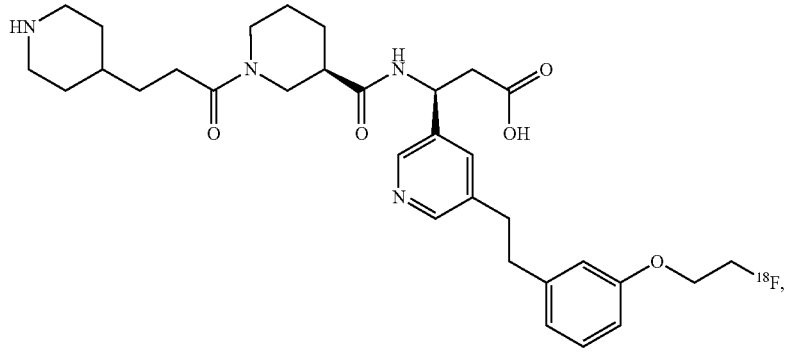

(3S)-3-(3-{2-[2-(2-[¹⁸F]Fluoroethoxy)ethoxy]
ethoxy}phenyl)-3-[({(3R)-1-[3-(piperidin-4-yl)-pro-
panoyl]piperidin-3-yl}carbonyl)amino]propanoic
acid

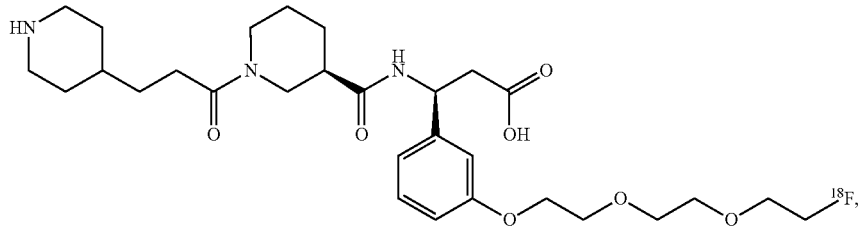

including diastereomers, mixtures thereof, and suitable salts thereof, and pharmaceutically acceptable carriers or diluents as described above.

In a seventh aspect, the invention is directed to a kit comprising one vial or more than one vial comprising a predetermined quantity of:
a) compounds of Formula I, or
b) ¹⁹F labeled compounds of Formula III.

Further, according to this aspect of the present invention the kit comprises a compound having a general chemical Formula as disclosed above along with an acceptable carrier, diluent, excipient or adjuvant or mixture thereof.

Preferably, the Kit comprises a physiologically acceptable vehicle or carrier and optional adjuvants and preservatives, reagents suitable to perform the herein disclosed reactions and/or to generate the ¹⁸F labeling reagents. Furthermore, the kit may contain instructions for its use.

In an eighth aspect, the invention is directed to the use of compounds of general formula III for conducting biological assays and chromatographic identification. More preferably, the use relates to ¹⁹F labeled compounds of general formula III.

¹⁹F labeled compounds of general formula III are useful as references and/or measurement agents.

The compounds of general formula III are herein defined as above and encompass all embodiments and preferred features.

In a ninth aspect, the invention is directed to a composition comprising compounds of formula I, II or III as defined in the above aspects and included embodiments.

In a first embodiment, the invention is directed to a composition comprising ¹⁸F labeled compound of formula III and pharmaceutically suitable adjuvants. These adjuvants include, inter alia, carriers, solvents, or stabilizers.

The person skilled in the art is familiar with adjuvants which are suitable for the desired pharmaceutical formulations, preparations or compositions on account of his/her expert knowledge.

The administration of the compounds, pharmaceutical compositions or combinations according to the invention is performed in any of the generally accepted modes of administration available in the art. Parenteral administration may be used to circumvent a bioabsorption step. Intravenous deliveries are preferred.

Preferably, the compositions according to the invention are administered such that the dose of the active compound for imaging is in the range of 3.7 MBq (0.1 mCi) to 740 MBq (20 mCi) per patient.

More preferably, a dose in the range from 3.7 MBq to 400 MBq per patient will be used.

Preferably, the composition comprises one of the compounds disclosed below:

(3S)-3-[3-(2-[¹⁸F]Fluoroethoxy)phenyl]-3-[({(3R)-1-
[3-(piperidin-4-yl)propanoyl]piperidin-3-yl}-carbo-
nyl)amino]propanoic acid

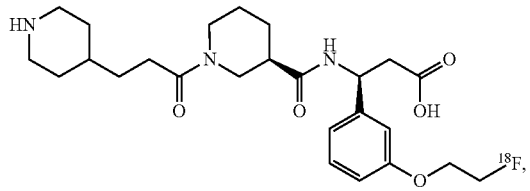

93

(3S)-3-[4-(2-[$^{18}$F]Fluoroethoxy)phenyl]-3-[({(3R)-1-[3-(piperidin-4-yl)propanoyl]piperidin-3-yl}carbonyl)amino]propanoic acid

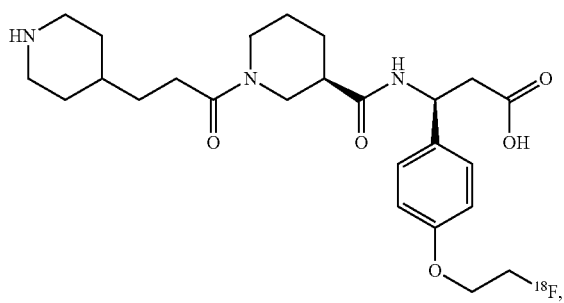

(3S)-3-[5-(2-[$^{18}$F]Fluoroethoxy)pyridin-3-yl]-3-[({(3R)-1-[3-(piperidin-4-yl)propanoyl]piperidin-3-yl}carbonyl)amino]propanoic acid

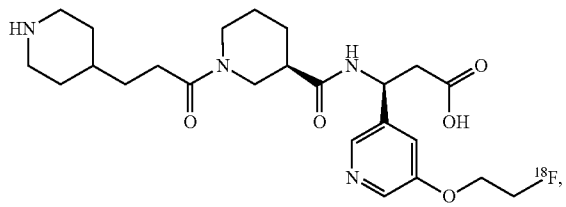

(3S)-3-{5-[4-(2-[$^{18}$F]Fluoroethoxy)phenyl]pyridin-3-yl}-3-[({(3R)-1-[3-(piperidin-4-yl)propanoyl]piperidin-3-yl}carbonyl)amino]propanoic acid

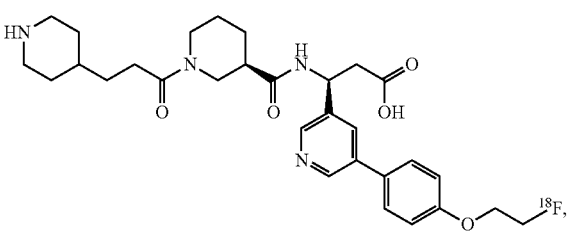

94

(3S)-3-[5-(3-Cyano-4-[$^{18}$F]fluorophenyl)pyridin-3-yl]-3-[({(3R)-1-[3-(piperidin-4-yl)propanoyl]-piperidin-3-yl}carbonyl)amino]propanoic acid

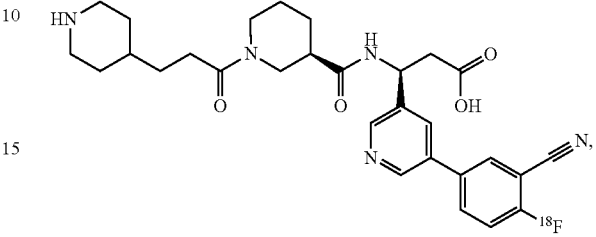

(3S)-3-[5-(4-Cyano-3-[$^{18}$F]fluorophenyl)pyridin-3-yl]-3-[({(3R)-1-[3-(piperidin-4-yl)-propanoyl]piperidin-3-yl}carbonyl)amino]propanoic acid

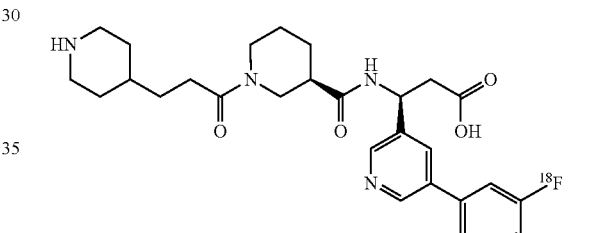

(3S)-3-(5-{[4-(2-[$^{18}$F]Fluoroethoxy)phenyl]ethynyl}pyridin-3-yl)-3-[({(3R)-1-[3-(piperidin-4-yl)-propanoyl]piperidin-3-yl}carbonyl)amino]propanoic acid

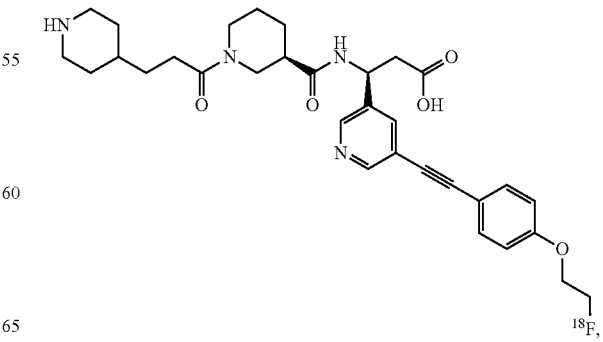

(3S)-3-(5-{[3-(2-[$^{18}$F]Fluoroethoxy)phenyl]ethynyl}pyridin-3-yl)-3-[({(3R)-1-[3-(piperidin-4-yl)-propanoyl]piperidin-3-yl}carbonyl)amino]propanoic acid
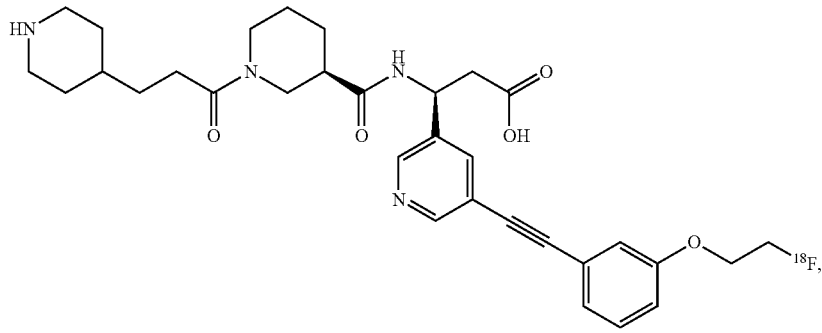
(3S)-3-(5-{2-[4-(2-[$^{18}$F]Fluoroethoxy)phenyl]ethyl}pyridin-3-yl)-3-[({(3R)-1-[3-(piperidin-4-yl)-propanoyl]piperidin-3-yl}carbonyl)amino]propanoic acid
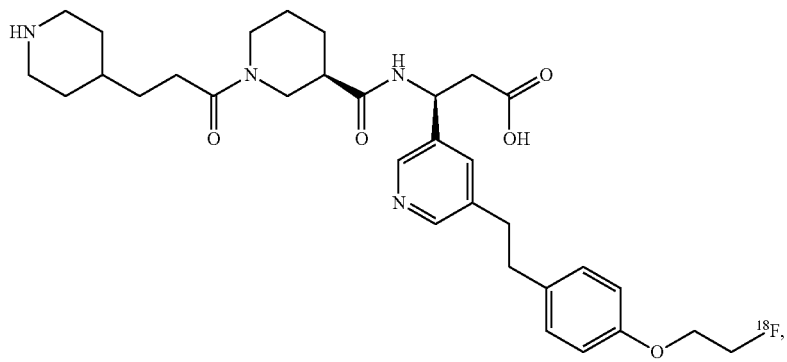
(3S)-3-(5-{2-[3-(2-[$^{18}$F]Fluoroethoxy)phenyl]ethyl}pyridin-3-yl)-3-[({(3R)-1-[3-(piperidin-4-yl)-propanoyl]piperidin-3-yl}carbonyl)amino]propanoic acid
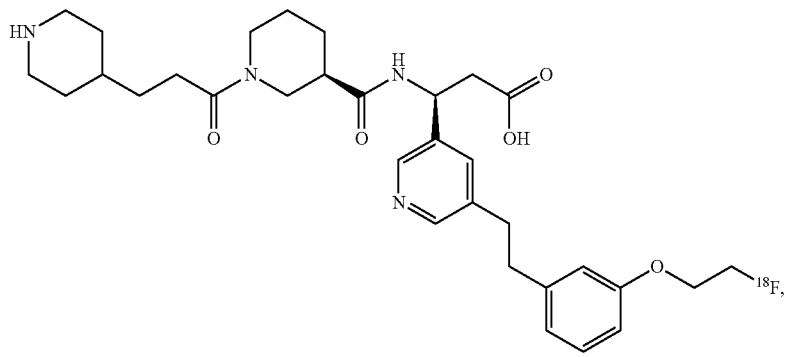

(3S)-3-(3-{2-[2-(2-[¹⁸F]Fluoroethoxy)ethoxy]
ethoxy}phenyl)-3-[({(3R)-1-[3-(piperidin-4-yl)-pro-
panoyl]piperidin-3-yl}carbonyl)amino]propanoic
acid

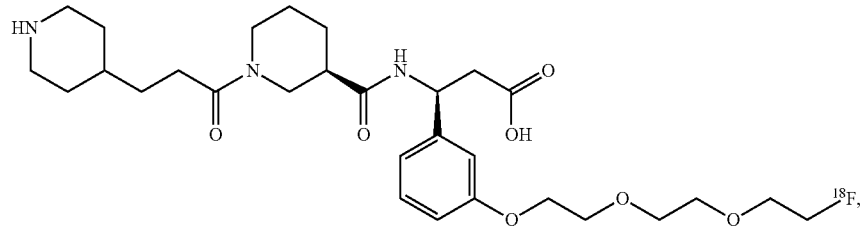

including diastereomers, mixtures thereof, and suitable salts thereof, and pharmaceutically acceptable carriers or diluents as described above.

In a second embodiment, the invention is directed to a composition comprising ¹⁹F labeled compounds of formula III. Such composition can be used for analytical purposes.

Preferably, the composition comprises one of the compounds disclosed below:

(3S)-3-[3-(2-Fluoroethoxy)phenyl]-3-[({(3R)-1-[3-
(piperidin-4-yl)propanoyl]piperidin-3-yl}-carbonyl)
amino]propanoic acid

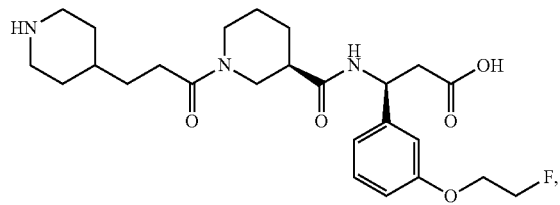

(3S)-3-[4-(2-Fluoroethoxy)phenyl]-3-[({(3R)-1-[3-
(piperidin-4-yl)propanoyl]piperidin-3-yl}carbonyl)
amino]propanoic acid

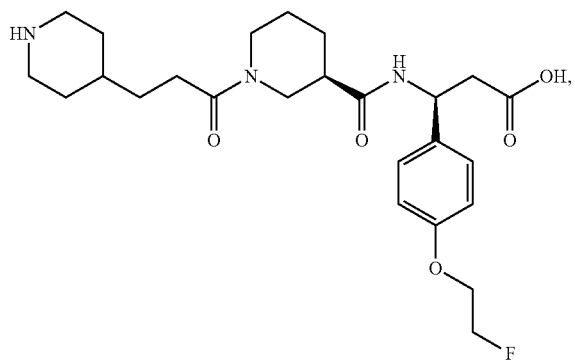 [SMILES: O=C(O)C[C@H](NC(=O)[C@@H]1CCCN(C(=O)CCC2CCNCC2)C1)c1ccc(OCCF)cc1]

(3S)-3-[5-(2-Fluoroethoxy)pyridin-3-yl]-3-[({(3R)-
1-[3-(piperidin-4-yl)propanoyl]piperidin-3-yl}-car-
bonyl)amino]propanoic acid

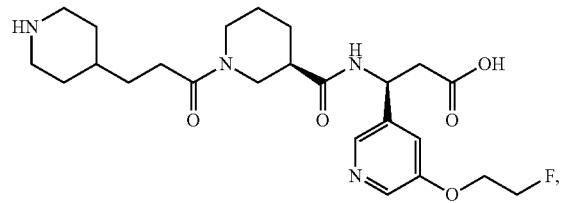 [SMILES: O=C(O)C[C@H](NC(=O)[C@@H]1CCCN(C(=O)CCC2CCNCC2)C1)c1cncc(OCCF)c1]

(3S)-3-(3-{2-[2-(2-Fluoroethoxy)ethoxy]
ethoxy}phenyl)-3-[({(3R)-1-[3-(piperidin-4-yl)-pro-
panoyl]piperidin-3-yl}carbonyl)amino]propanoic
acid

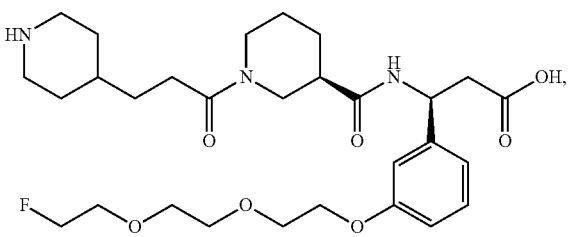 [SMILES: O=C(O)C[C@H](NC(=O)[C@@H]1CCCN(C(=O)CCC2CCNCC2)C1)c1cccc(OCCOCCOCCF)c1]

(3S)-3-(5-{2-[2-(2-Fluoroethoxy)ethoxy]
ethoxy}pyridine-3-yl)-3-[({(3R)-1-[3-(piperidin-4-
yl)-propanoyl]piperidin-3-yl}carbonyl)amino]pro-
panoic acid

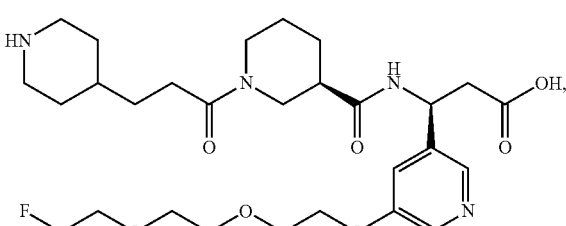

99

(3S)-3-{5-[3-(2-Fluoroethoxy)phenyl]pyridin-3-yl}-
3-[({(3R)-1-[3-(piperidin-4-yl)propanoyl]-piperidin-
3-yl}carbonyl)amino]propanoic acid

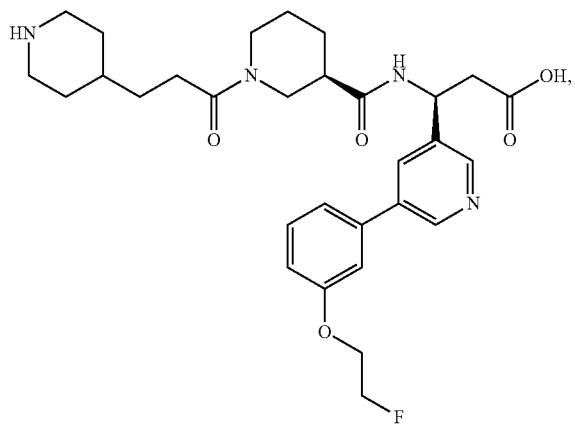 [SMILES: O=C(O)C[C@H](NC(=O)[C@@H]1CCCN(C(=O)CCC2CCNCC2)C1)c1cncc(-c2cccc(OCCF)c2)c1]

(3S)-3-{5-[4-(2-Fluoroethoxy)phenyl]pyridin-3-yl}-
3-[({(3R)-1-[3-(piperidin-4-yl)propanoyl]-piperidin-
3-yl}carbonyl)amino]propanoic acid

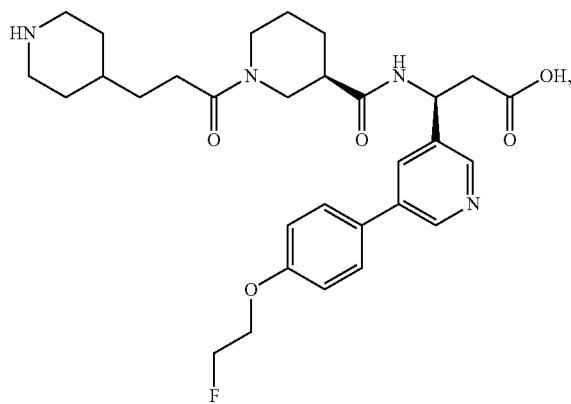 [SMILES: O=C(O)C[C@H](NC(=O)[C@@H]1CCCN(C(=O)CCC2CCNCC2)C1)c1cncc(-c2ccc(OCCF)cc2)c1]

100

(3S)-3-{5-[2-(2-Fluoroethoxy)phenyl]pyridin-3-yl}-
3-[({(3R)-1-[3-(piperidin-4-yl)propanoyl]-piperidin-
3-yl}carbonyl)amino]propanoic acid

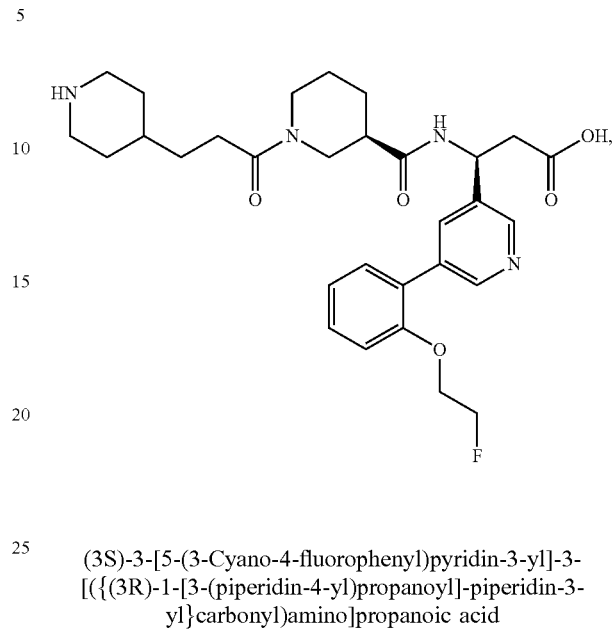

(3S)-3-[5-(3-Cyano-4-fluorophenyl)pyridin-3-yl]-3-
[({(3R)-1-[3-(piperidin-4-yl)propanoyl]-piperidin-3-
yl}carbonyl)amino]propanoic acid

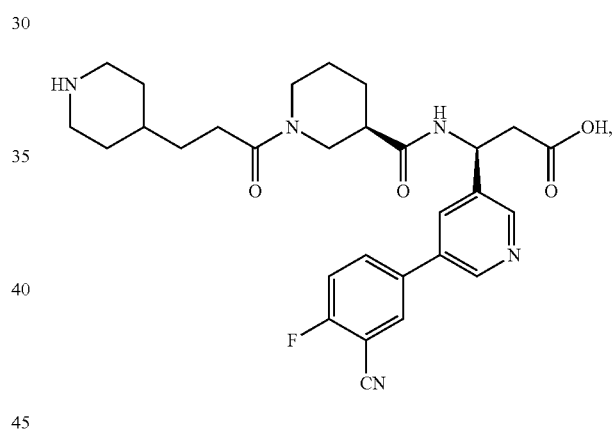

(3S)-3-[5-(4-Cyano-3-fluorophenyl)pyridin-3-yl]-3-
[({(3R)-1-[3-(piperidin-4-yl)propanoyl]-piperidin-3-
yl}carbonyl)amino]propanoic acid

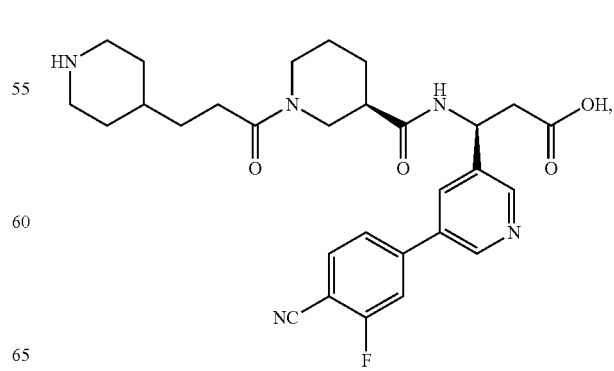

| 101 | 102 |
|---|---|
| (3S)-3-[5-(4-Fluoro-3-nitrophenyl)pyridin-3-yl]-3-[({(3R)-1-[3-(piperidin-4-yl)propanoyl]-piperidin-3-yl}carbonyl)amino]propanoic acid | (3S)-3-(4-Cyano-3-fluorophenyl)-3-[({(3R)-1-[3-(piperidin-4-yl)propanoyl]piperidin-3-yl}-carbonyl)amino]propanoic acid |

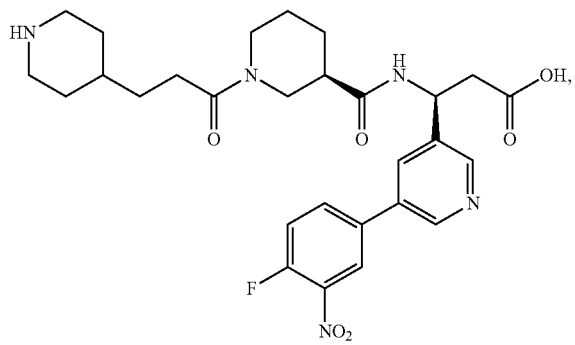 [SMILES: O=C(O)C[C@H](NC(=O)[C@@H]1CCCN(C(=O)CCC2CCNCC2)C1)c1cncc(-c2ccc(F)c([N+](=O)[O-])c2)c1]

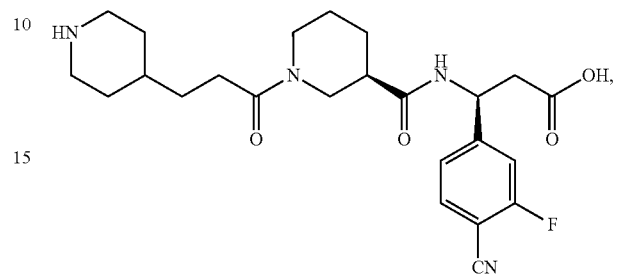

(3R)-3-{5-[(3-Cyano-4-fluorobenzyl)oxy]pyridin-3-yl}-3-[({(3S)-1-[3-(piperidin-4-yl)propanoyl]-piperidin-3-yl}carbonyl)amino]propanoic acid (3S)-3-(5-{[4-(2-Fluoroethoxy)phenyl]ethynyl}pyridin-3-yl)-3-[({(3R)-1-[3-(piperidin-4-yl)propanoyl]piperidin-3-yl}carbonyl)amino]propanoic acid

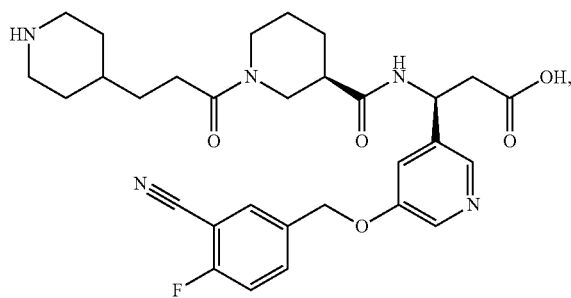 [SMILES: N#Cc1cc(COc2cncc([C@H](CC(=O)O)NC(=O)[C@@H]3CCCN(C(=O)CCC4CCNCC4)C3)c2)ccc1F]

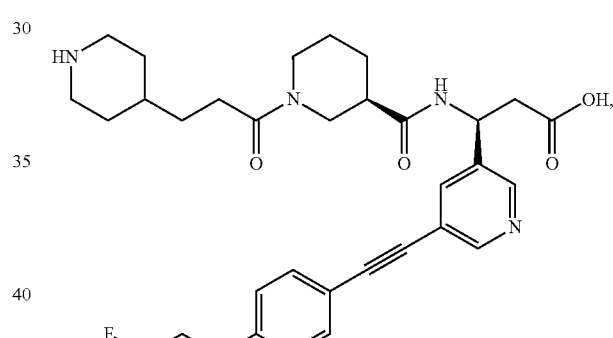

(3S)-3-{5-[(4-Cyano-3-fluorobenzyl)oxy]pyridin-3-yl}-3-[({(3R)-1-[3-(piperidin-4-yl)propanoyl]-piperidin-3-yl}carbonyl)amino]propanoic acid (3S)-3-(5-{[3-(2-Fluoroethoxy)phenyl]ethynyl}pyridin-3-yl)-3-[({(3R)-1-[3-(piperidin-4-yl)-propanoyl]piperidin-3-yl}carbonyl)amino]propanoic acid

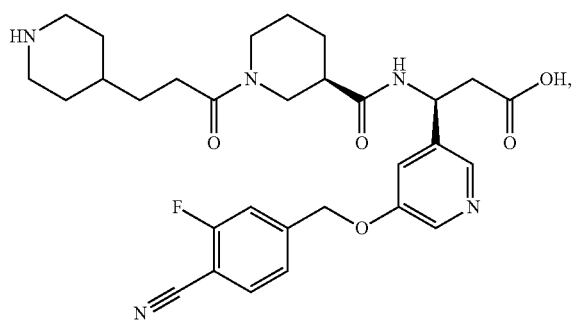 [SMILES: N#Cc1ccc(COc2cncc([C@H](CC(=O)O)NC(=O)[C@@H]3CCCN(C(=O)CCC4CCNCC4)C3)c2)cc1F]

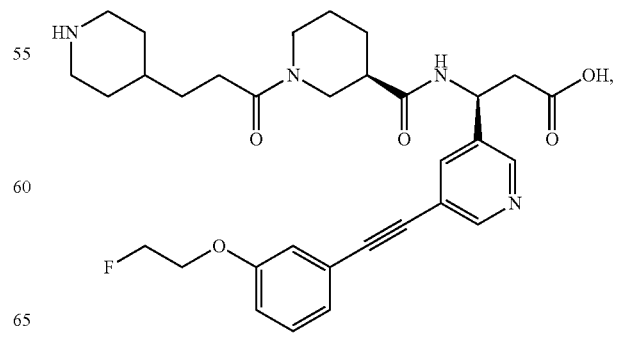

103

(3S)-3-[5-Fluoro-4'-(2-fluoroethoxy)biphenyl-3-yl]-3-[({(3R)-1-[3-(piperidin-4-yl)propanoyl]-piperidin-3-yl}carbonyl)amino]propanoic acid

104

(3S)-3-(5-{2-[3-(2-Fluoroethoxy)phenyl]ethyl}pyridin-3-yl)-3-[({(3R)-1-[3-(piperidin-4-yl)propanoyl]piperidin-3-yl}carbonyl)amino]propanoic acid

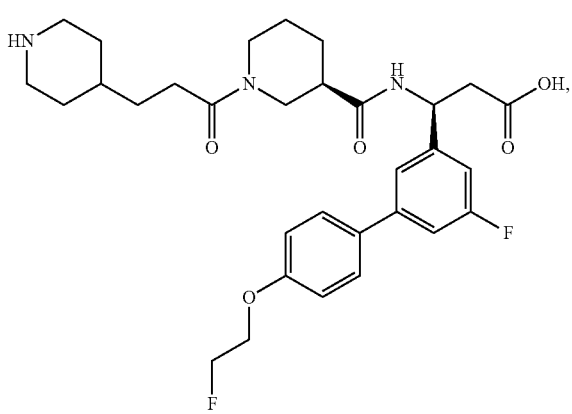 [SMILES: O=C(O)C[C@H](NC(=O)[C@@H]1CCCN(C(=O)CCC2CCNCC2)C1)c1cc(F)cc(-c2ccc(OCCF)cc2)c1]

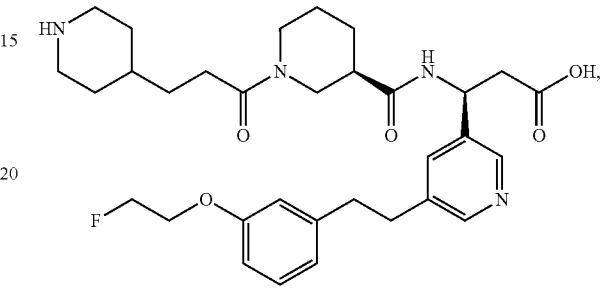

(E/Z)(3S)-3-(5-{[3-(2-Fluoroethoxy)phenyl]ethenyl}pyridin-3-yl)-3-[({(3R)-1-[3-(piperidin-4-yl)propanoyl]piperidin-3-yl}carbonyl)amino]propanoic acid (3S)-3-(5-{2-[4-(2-Fluoroethoxy)phenyl]ethyl}pyridin-3-yl)-3-[({(3R)-1-[3-(piperidin-4-yl)propanoyl]piperidin-3-yl}carbonyl)amino]propanoic acid

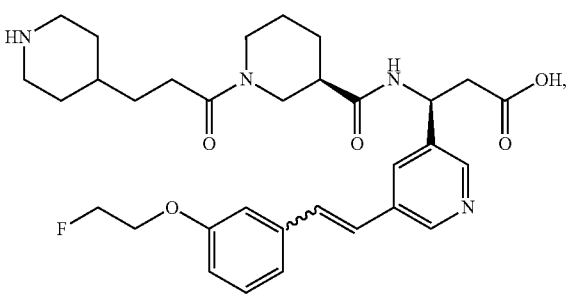

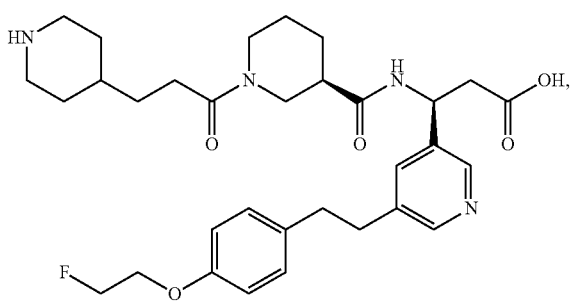 [SMILES: O=C(O)C[C@H](NC(=O)[C@@H]1CCCN(C(=O)CCC2CCNCC2)C1)c1cncc(CCc2ccc(OCCF)cc2)c1]

including E and Z-isomers and diastereomers, mixtures thereof, and suitable salts thereof.

In a third embodiment, the invention is directed to a composition comprising compound of formula I. Such composition can be used for manufacturing of $^{18}F$ labeled compounds of formula III (radiopharmaceutical) and $^{19}F$ labeled compounds of formula III (cold standard).

Preferably, the composition comprises one of the compounds disclosed below:

tert-Butyl 4-{3-[(3R)-3-({(1S)-3-methoxy-1-[3-(2-{[(4-methylphenyl)sulfonyl]oxy}ethoxy)-phenyl]-3-oxopropyl}carbamoyl)piperidin-1-yl]-3-oxopropyl}piperidine-1-carboxylate

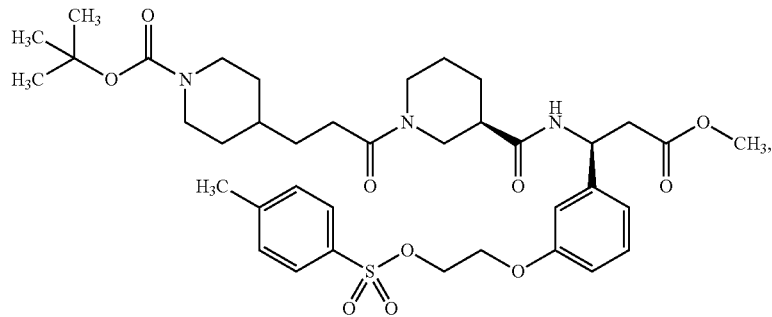

tert-Butyl 4-{3-[(3R)-3-({3-methoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate

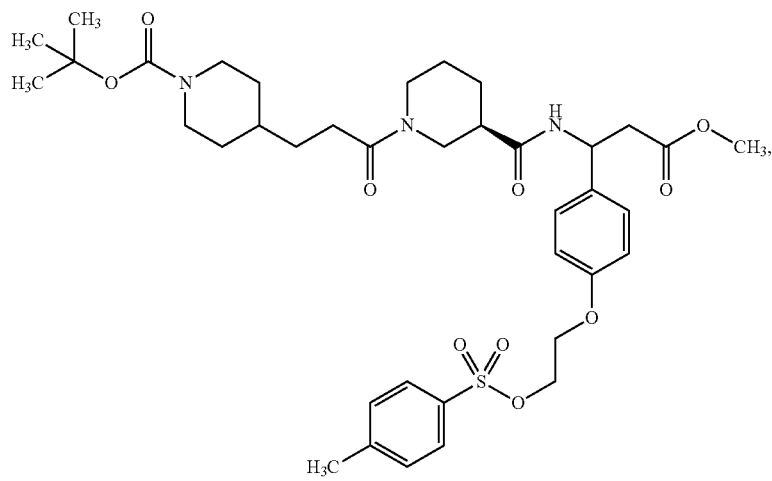 [SMILES: COC(=O)CC(NC(=O)[C@@H]1CCCN(C(=O)CCC2CCN(C(=O)OC(C)(C)C)CC2)C1)c1ccc(OCCOS(=O)(=O)c2ccc(C)cc2)cc1]

tert-Butyl 4-{3-[(3R)-3-({(1S)-3-tert-butoxy-1-[4-(2-{[(4-methylphenyl)sulfonyl]oxy}ethoxy)-phenyl]-3-oxopropyl}carbamoyl)piperidin-1-yl]-3-oxopropyl}piperidine-1-carboxylate

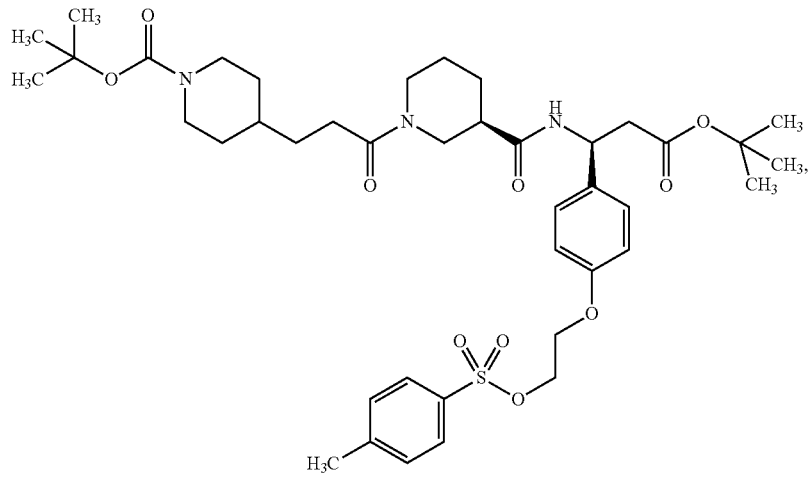 [SMILES: Cc1ccc(S(=O)(=O)OCCOc2ccc([C@H](CC(=O)OC(C)(C)C)NC(=O)[C@@H]3CCCN(C(=O)CCC4CCN(C(=O)OC(C)(C)C)CC4)C3)cc2)cc1]

tert-Butyl 4-{3-[(3R)-3-({(1S)-3-methoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylat

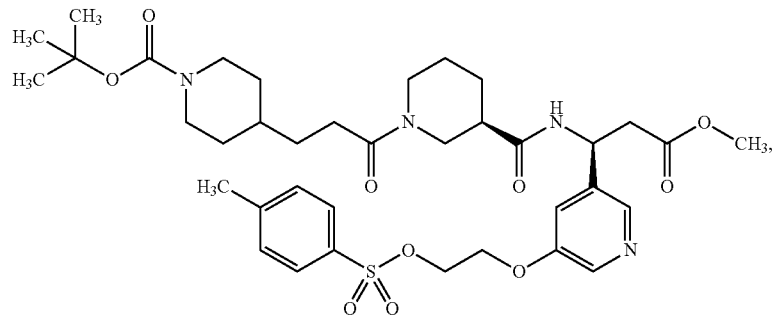 [SMILES: COC(=O)C[C@H](NC(=O)[C@@H]1CCCN(C(=O)CCC2CCN(C(=O)OC(C)(C)C)CC2)C1)c1cncc(OCCOS(=O)(=O)c2ccc(C)cc2)c1]

tert-Butyl 4-{3-[(3R)-3-({(1S)-3-tert-butoxy-1-[5-(2-{[(4-methylphenyl)sulfonyl]oxy}ethoxy)-pyridin-3-yl]-3-oxopropyl}carbamoyl)piperidin-1-yl]-3-oxopropyl}piperidine-1-carboxylate

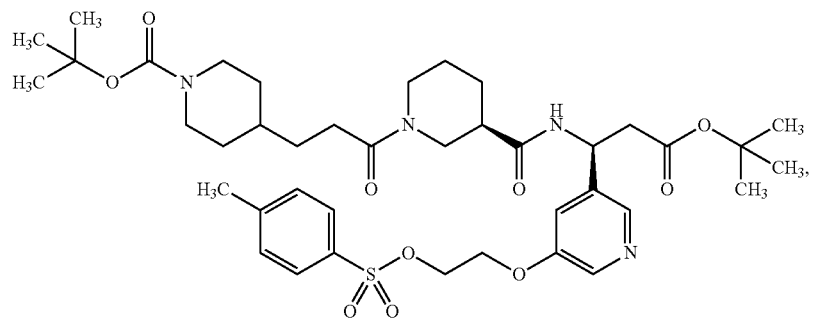 [SMILES: Cc1ccc(S(=O)(=O)OCCOc2cncc([C@H](CC(=O)OC(C)(C)C)NC(=O)[C@@H]3CCCN(C(=O)CCC4CCN(C(=O)OC(C)(C)C)CC4)C3)c2)cc1]

tert-Butyl 4-{3-[(3R)-3-{[3-methoxy-1-{5-[4-(2-{[(4-methylphenyl)sulfonyl]oxy}ethoxy)phenyl]-pyridin-3-yl}-3-oxopropyl]carbamoyl}piperidin-1-yl]-3-oxopropyl}piperidine-1-carboxylate

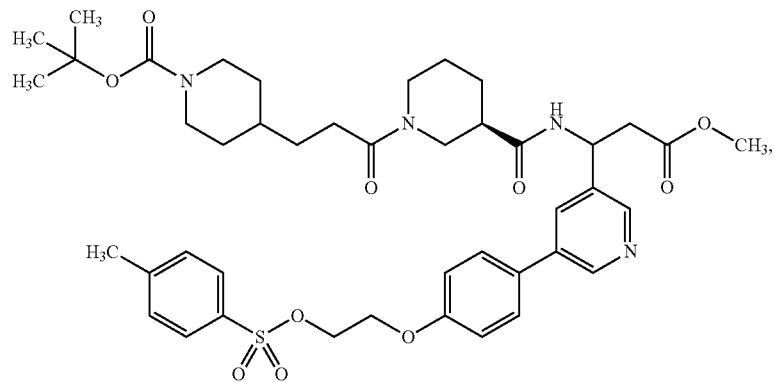

tert-Butyl 4-{3-[(3R)-3-{[(1S)-3-tert-butoxy-1-{5-[4-(2-{[(4-methylphenyl)sulfonyl]oxy}ethoxy)-phenyl]pyridin-3-yl}-3-oxopropyl]carbamoyl}piperidin-1-yl]-3-oxopropyl}piperidine-1-carboxylate

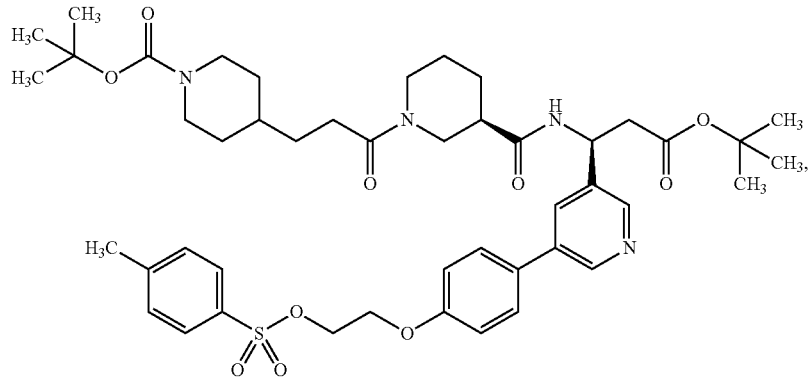 [SMILES: Cc1ccc(S(=O)(=O)OCCOc2ccc(-c3cncc([C@H](CC(=O)OC(C)(C)C)NC(=O)[C@@H]4CCCN(C(=O)CCC5CCN(C(=O)OC(C)(C)C)CC5)C4)c3)cc2)cc1]

tert-Butyl 4-{3-[(3R)-3-({1-[5-(4-chloro-3-cyanophenyl)pyridin-3-yl]-3-methoxy-3-oxopropyl}-carbamoyl)piperidin-1-yl]-3-oxopropyl}piperidine-1-carboxylate

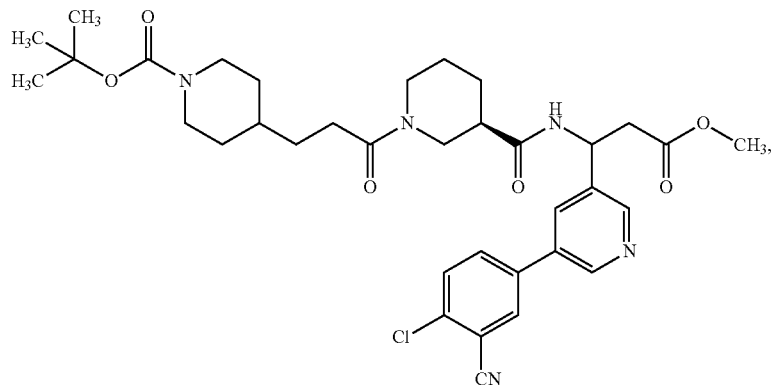

tert-Butyl-4-{3-[(3R)-3-{[(1S)-1-{5-[(3-bromo-4-cyanobenzyl)oxy]pyridin-3-yl}-3-methoxy-3-oxopropyl]carbamoyl}piperidin-1-yl]-3-oxopropyl}piperidine-1-carboxylate

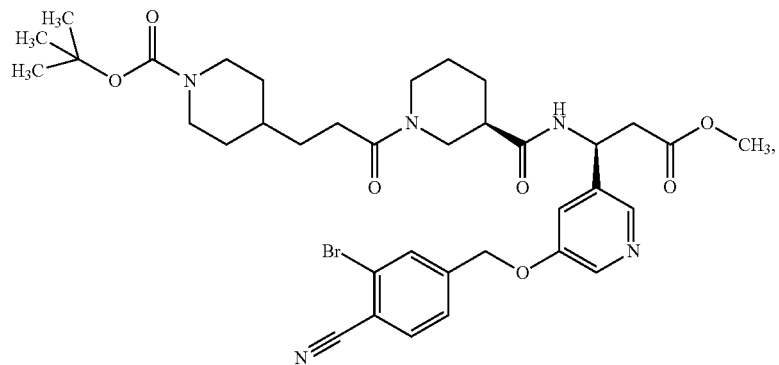 [SMILES: COC(=O)C[C@H](NC(=O)[C@@H]1CCCN(C(=O)CCC2CCN(C(=O)OC(C)(C)C)CC2)C1)c1cncc(OCc2ccc(C#N)c(Br)c2)c1]

tert-Butyl 4-{3-[(3R)-3-{[3-methoxy-1-{5-[3-(2-{[(4-methylphenyl)sulfonyl]oxy}ethoxy)phenyl]-pyridin-3-yl}-3-oxopropyl]carbamoyl}piperidin-1-yl]-3-oxopropyl}piperidine-1-carboxylate

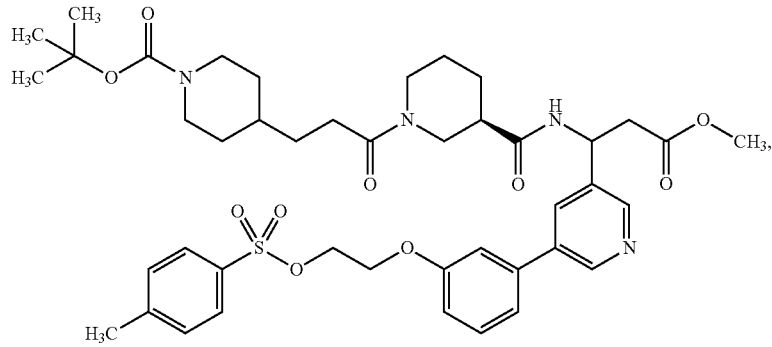 [SMILES: COC(=O)CC(NC(=O)[C@@H]1CCCN(C(=O)CCC2CCN(C(=O)OC(C)(C)C)CC2)C1)c1cncc(-c2cccc(OCCOS(=O)(=O)c3ccc(C)cc3)c2)c1]

tert-Butyl 4-{3-[(3R)-3-{[3-methoxy-1-{5-[2-(2-{[(4-methylphenyl)sulfonyl]oxy}ethoxy)-phenyl]pyridin-3-yl}-3-oxopropyl]carbamoyl}piperidin-1-yl]-3-oxopropyl}piperidine-1-carboxylate

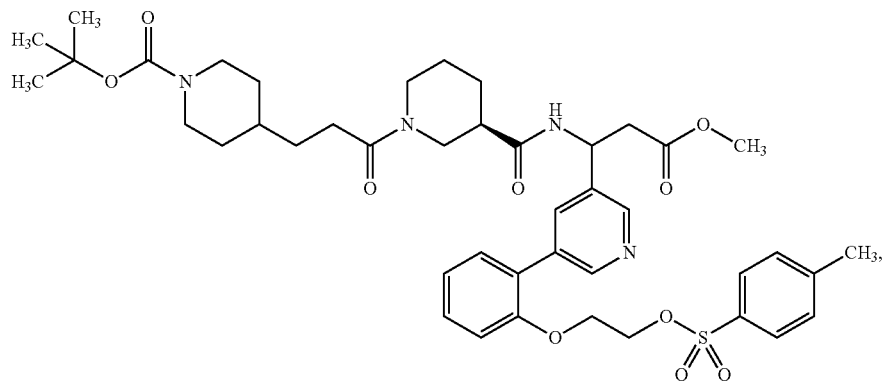 [SMILES: COC(=O)CC(NC(=O)[C@@H]1CCCN(C(=O)CCC2CCN(C(=O)OC(C)(C)C)CC2)C1)c1cncc(-c2ccccc2OCCOS(=O)(=O)c2ccc(C)cc2)c1]

tert-Butyl 4-{3-[(3R)-3-({1-[5-(4-chloro-3-nitrophenyl)pyridin-3-yl]-3-methoxy-3-oxopropyl}-carbamoyl)piperidin-1-yl]-3-oxopropyl}piperidine-1-carboxylate

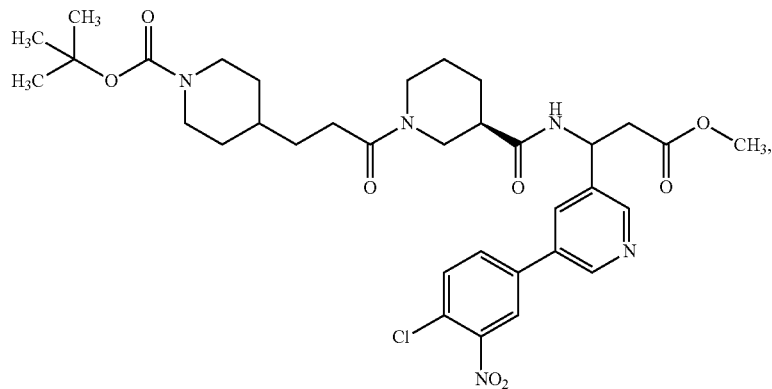

tert-Butyl 4-{3-[(3R)-3-({1-[5-fluoro-4'-(2-{[(4-methylphenyl)sulfonyl]oxy}ethoxy)biphenyl-3-yl]-3-methoxy-3-oxopropyl}carbamoyl)piperidin-1-yl]-3-oxopropyl}piperidine-1-carboxylate

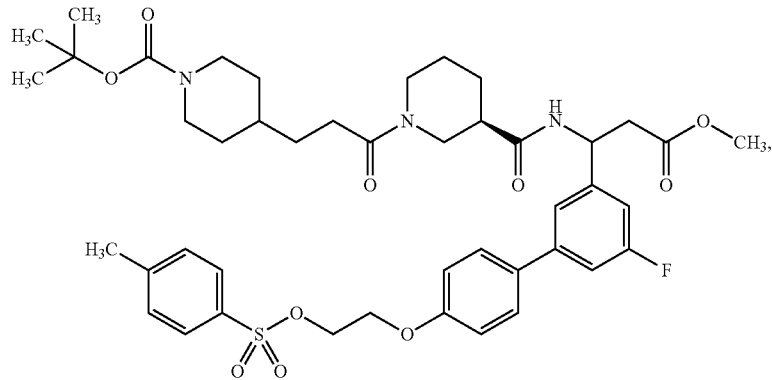 [SMILES: COC(=O)CC(NC(=O)[C@@H]1CCCN(C(=O)CCC2CCN(C(=O)OC(C)(C)C)CC2)C1)c1cc(F)cc(-c2ccc(OCCOS(=O)(=O)c3ccc(C)cc3)cc2)c1]

tert-Butyl 4-{3-[(3R)-3-{[(1S)-3-tert-butoxy-1-(5-{[4-(2-{[(4-methylphenyl)sulfonyl]oxy}-ethoxy)phenyl]ethynyl}pyridin-3-yl)-3-oxopropyl]carbamoyl}piperidin-1-yl]-3-oxopropyl}-piperidine-1-carboxylate

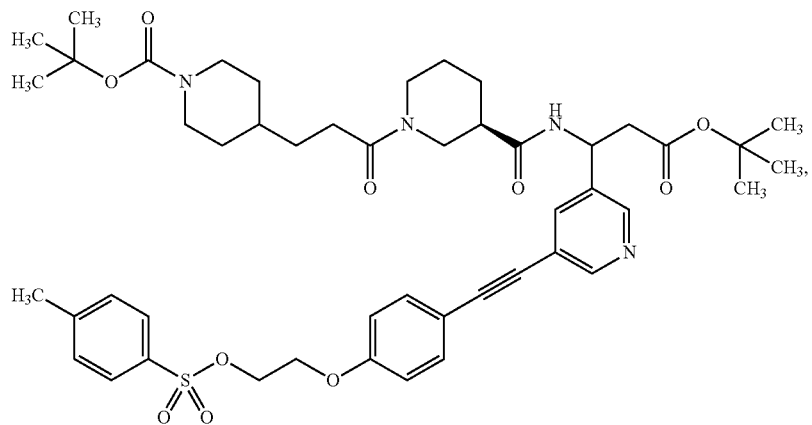 [SMILES: Cc1ccc(S(=O)(=O)OCCOc2ccc(C#Cc3cncc(C(CC(=O)OC(C)(C)C)NC(=O)[C@@H]4CCCN(C(=O)CCC5CCN(C(=O)OC(C)(C)C)CC5)C4)c3)cc2)cc1]

45 tert-Butyl 4-{3-[(3R)-3-{[(1S)-3-tert-butoxy-1-(5-{[3-(2-{[(4-methylphenyl)sulfonyl]oxy}-ethoxy)phenyl]ethynyl}pyridin-3-yl)-3-oxopropyl]carbamoyl}piperidin-1-yl]-3-oxopropyl}-piperidine-1-carboxylate

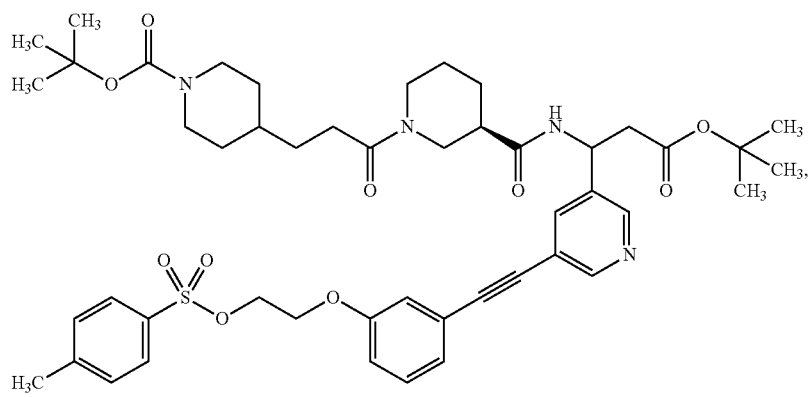 [SMILES: Cc1ccc(S(=O)(=O)OCCOc2cccc(C#Cc3cncc(C(CC(=O)OC(C)(C)C)NC(=O)[C@@H]4CCCN(C(=O)CCC5CCN(C(=O)OC(C)(C)C)CC5)C4)c3)c2)cc1]

tert-Butyl 4-{3-[(3R)-3-{[(1S)-3-tert-butoxy-1-(5-{2-[4-(2-{[(4-methylphenyl)sulfonyl]oxy}-ethoxy)phenyl]ethyl}pyridin-3-yl)-3-oxopropyl]carbamoyl}piperidin-1-yl]-3-oxopropyl}-piperidine-1-carboxylate

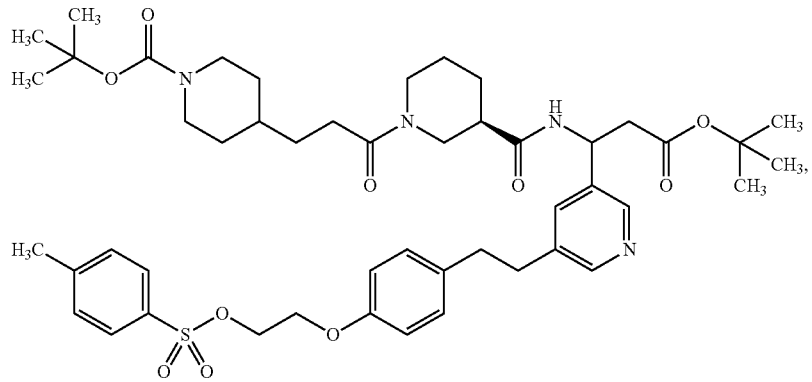 [SMILES: Cc1ccc(S(=O)(=O)OCCOc2ccc(CCc3cncc(C(CC(=O)OC(C)(C)C)NC(=O)[C@@H]4CCCN(C(=O)CCC5CCN(C(=O)OC(C)(C)C)CC5)C4)c3)cc2)cc1]

tert-Butyl 4-{3-[(3R)-3-{[(1S)-3-tert-butoxy-1-(5-{2-[3-(2-{[(4-methylphenyl)sulfonyl]oxy}-ethoxy)phenyl]ethyl}pyridin-3-yl)-3-oxopropyl]carbamoyl}piperidin-1-yl]-3-oxopropyl}-piperidine-1-carboxylate

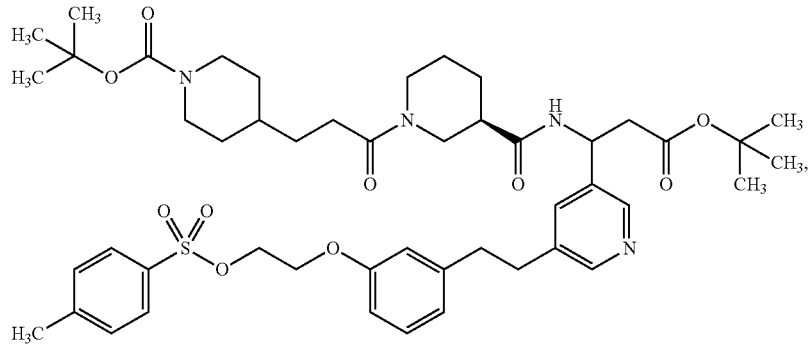 [SMILES: Cc1ccc(S(=O)(=O)OCCOc2cccc(CCc3cncc(C(CC(=O)OC(C)(C)C)NC(=O)[C@@H]4CCCN(C(=O)CCC5CCN(C(=O)OC(C)(C)C)CC5)C4)c3)c2)cc1]

including diastereomers, mixtures thereof, and suitable salts thereof.

DEFINITIONS

The following terms describe generic and specific structural elements of the chemical scaffold of the compounds of the present invention, as well as functional groups and substituents attached thereto. They can be combined in a way resulting in structures in line with the chemical valency rules and of suitable chemical stability, that is, compounds that are sufficiently robust to survive isolation to a useful degree of purity from a reaction mixture, and for their intended use, such as formulation into a pharmaceutical composition.

For the purposes of the present invention, the terms have the following meaning, unless otherwise specified:

The term "amine-protecting group" as employed herein by itself or as part of another group is known or obvious to someone skilled in the art, which is chosen from but not limited to a class of protecting groups namely carbamates, amides, imides, N-alkyl amines, N-aryl amines, imines, enamines, boranes, N—P protecting groups, N-sulfenyl, N-sulfonyl and N-silyl, and which is chosen from but not limited to those described in the textbook Greene and Wuts, Protecting groups in Organic Synthesis, third edition, page 494-653, included herewith by reference. The "amine-protecting group" is preferably carbobenzyloxy (Cbz), p-methoxybenzyl carbonyl (Moz or MeOZ), tert-butyloxycarbonyl (BOC), 9-fluorenylmethyloxycarbonyl (FMOC), benzyl (Bn), p-methoxybenzyl (PMB), 3,4-dimethoxybenzyl (DMPM), p-methoxyphenyl (PMP), triphenylmethyl (Trityl), methoxyphenyl diphenylmethyl (MMT) or the protected amino group is a 1,3-dioxo-1,3-dihydro-2H-isoindol-2-yl (phthalimido) or an azido group.

The term "carboxyl-protecting group" as employed herein by itself or as part of another group is known or obvious to someone skilled in the art, which is chosen from but not limited to a class of protecting groups namely esters, amides and hydrazides, and which is chosen from but not limited to those described in the textbook Greene and Wuts, Protecting groups in Organic Synthesis, third edition, page 369-453, included herewith by reference. The "carboxyl-protecting group" is preferably methyl, ethyl, propyl, butyl, tert-butyl, allyl, benzyl, 4-methoxybenzyl or 4-methoxyphenyl.

The term "alkyl", by itself or as part of another group, refers to a straight chain or branched chain alkyl group with 1 to 6 carbon atoms such as, for example methyl, ethyl, propyl isopropyl, butyl, isobutyl, tert-butyl, pentyl, isopentyl, neopentyl, hexyl.

The term "halogen" represents fluorine, chlorine and bromine.

The term "leaving group" as employed herein by itself or as part of another group is known or obvious to someone skilled in the art, and means that an atom or group of atoms is detachable from a chemical substance by a nucleophilic agent. Examples are given e.g. in P. Stang et al. *Synthesis* (1982), p. 85-125, table 2 (p. 86; (the last entry of this table 2 needs to be corrected: "n-$C_4F_9S(O)_2$—O— nonaflat" instead of "n-$C_4H_9S(O)_2$—O— nonaflat"), Carey and Sundberg, Organische Synthese, (1995), page 279-281, table 5.8; or Netscher, *Recent Res. Dev. Org. Chem.*, 2003, 7, 71-83, scheme 1, 2, 10 and 15 and others). (Coenen, Fluorine-18 Labeling Methods: Features and Possibilities of Basic Reactions, (2006), in: Schubiger P. A., Friebe M., Lehmann L., (eds), PET-Chemistry—The Driving Force in Molecular Imaging. Springer, Berlin Heidelberg, pp. 15-50, explicitly: scheme 4 pp. 25, scheme 5 pp 28, table 4 pp 30, Figure 7 pp 33).

Preferably, the "leaving group" is fluoride, chloride, bromide, iodide or a sulfonate leaving group including but not limited to methylsulfonyloxy, (4-methylphenyl)sulfonyloxy, trifluormethylsulfonyloxy, nonafluorobutylsulfonyloxy, (4-bromophenyl)sulfonyloxy, (4-nitrophenyl)sulfonyloxy, (2-nitrophenyl)sulfonyloxy, (4-isopropylphenyl)sulfonyloxy, (2,4,6-tri-isopropyl-phenyl)sulfonyloxy, (2,4,6-trimethylphenyl)sulfonyloxy, (4-tertbutylphenyl)-sulfonyloxy, (4-methoxyphenyl)sulfonyloxy.

The term "$^{18}F$ building block" as employed herein by itself or as part of another group is known or obvious to someone skilled in the art, which is chosen from a class of compounds used for an indirect method of $^{18}F$ fluorination via a prosthetic group. This means that a primary $^{18}F$-labeled compound contains a further functional group suitable for coupling of this prosthetic group to a second molecule. This functional group can be a leaving group including but not limited to a halogen or a sulfonate leaving group. Examples are given e.g. for $^{18}F$-fluoroalkylation in Block et al. *J. Label. Compd. Radiopharm.* (1988), p. 201-216 and for $^{18}F$-fluoroacylation in Block et al. *J. Label. Compd. Radiopharm.* (1988), p. 185-200. The functional can also be another electrophilic moiety like an aldehyde used e.g. for a coupling via reductive amination to the second molecule (Wilson et al. *J. Label. Compd. Radiopharm.* (1990), p. 1189-1199). Alternatively the functional group can also be a nucleophilic moiety e.g. an amine used for $^{18}F$-fluoroamidation like in Shia et al. *Biochem.* (1989), p. 4801-4806.

Preferably the "$^{18}F$ building block" is taken from the group of prosthetic groups used for $^{18}F$-fluoroalkylation like n-[$^{18}F$]fluoroalkyl-1-aryl sulfonates, like n-[$^{18}F$]fluoroalkoxyalkyl-1-aryl sulfonates and n-[$^{18}F$]fluoroalkyl-1-halogenides. More preferably the "$^{18}F$ building block" is bromo-[$^{18}F$]fluoromethane, 1-bromo-2-[$^{18}F$]fluoroethane, 1-bromo-2-[$^{18}F$]fluoropropane, 2-[$^{18}F$]fluoroethyl methanesulfonate, 2-[$^{18}F$]fluoroethyl 4-methylbenzenesulfonate, 2-[$^{18}F$]fluoroethyl 4-nitrobenzenesulfonate, 2-[$^{18}F$]fluoropropyl methanesulfonate, 2-[$^{18}F$]fluoropropyl 4-methylbenzenesulfonate, 2-[18F]fluoropropyl 4-nitrobenzenesulfonate, 2-[2-(2-[18F]fluoroethoxy)ethoxy]ethyl methanesulfonate, 2-[2-(2-[$^{18}F$]fluoroethoxy)ethoxy]-ethyl 4-methylbenzenesulfonate and 2-[2-(2-[$^{18}F$]fluoroethoxy) ethoxy]ethyl 4-nitrobenzenesulfonate.

If chiral centers or other forms of isomeric centers are not otherwise defined in a compound according to the present invention, all forms of such stereoisomers, including E- and Z-isomers and diastereomers, are intended to be covered herein. Compounds containing chiral centers may be used as a diastereomeric mixture or as a diastereomerically enriched mixture, or these isomeric mixtures may be separated using well-known techniques, and an individual stereoisomer maybe used alone. In cases wherein compounds may exist in tautomeric forms, each tautomeric form is contemplated as being included within this invention whether existing in equilibrium or predominantly in one form.

Suitable salts of the compounds according to the invention include salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalene disulfonic acid, acetic acid, trifluoroacetic acid, propionic acid, lactic acid, tartaric acid, malic acid, citric acid, fumaric acid, maleic acid and benzoic acid.

Suitable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and by way of preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

The term "thrombus (thrombi)" describes all kinds of blood clots (venous and arterial thrombi). The term "thrombus (thrombi)" includes also any terms of phrases like "thrombotic deposits" and "thrombus formation sites". Thrombi usually arise as a result of the blood coagulation step in hemostasis or pathologically as the result of different causes like thrombotic disorders. In this investigation all platelet containing thrombi are included as well as circulating thrombi (embolus), which get stuck somewhere in the vascular tree.

The term "purification" as employed herein has the objective to eliminate the excess of side product such as $^{18}F$-Fluoride and to concentrate and trap the reaction product. Purification is carried out by any method known to those in the art, suitable for radiotracer e.g. chromatography, HPLC, solid-phase-extraction cartridges or column.

General Synthesis

In general the synthesis of these compounds is documented in the literature:

1) *J. Med. Chem.* 1999, 42, 5254-5265
2) *Organic Progress Research & Development* 2003, 7, 866-872

Modifications and improvements of these methods are described in detail in the experimental part. The principal path to compounds of Formula I is exemplified in Scheme 1:

Scheme 1

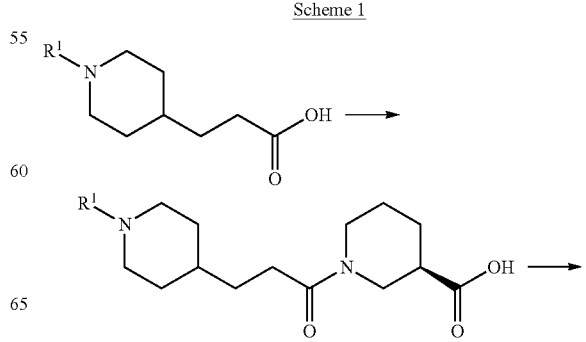

119
-continued

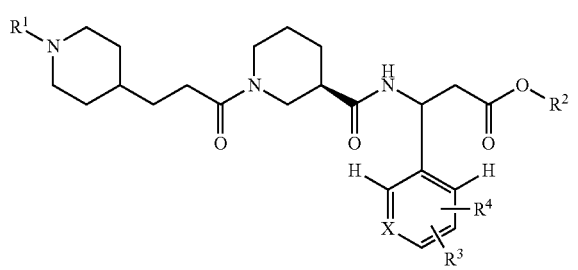

120

Stereochemistry

The compounds of Formula I obtained in the synthesis outlined in Scheme 1 are mixtures of two diastereomers. These were separated at the end of the synthesis by preparative HPLC. It was possible (examples 4, 5, 8, 25 and 27) to realize a stereoselective approach to the protected 3-amino-3-arylpropanoic acids (Scheme 2 to 4). In general, stereoselective methods for the synthesis of B-amino acids are applicable (M. Liu, M. P. Sibi, *Tetrahedron* 2002 58, 7991-8035 or E. Juaristi, V. Soloshonok Eds. of *Enantioselective Synthesis of Beta-Amino Acids*, second edition, Wiley-Interscience, ISBN 0-471-46738-3).

Scheme 2

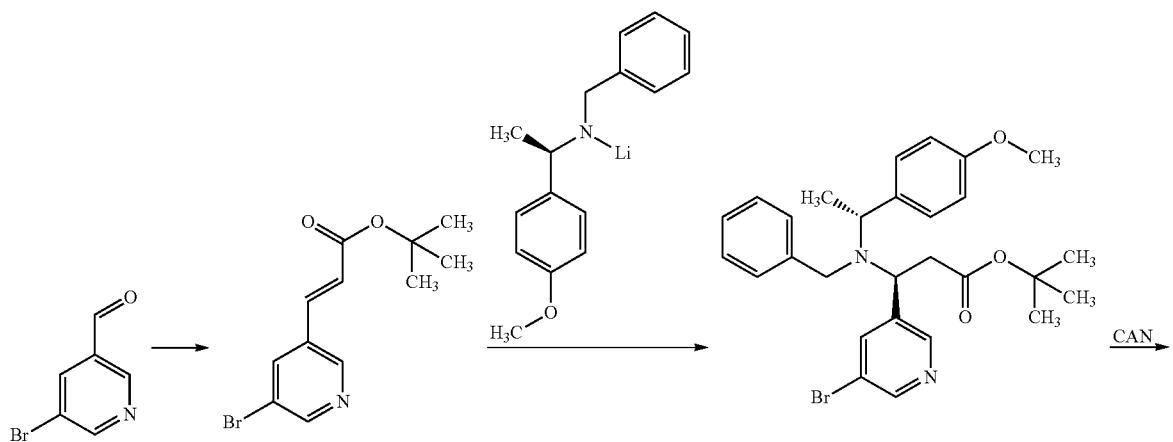

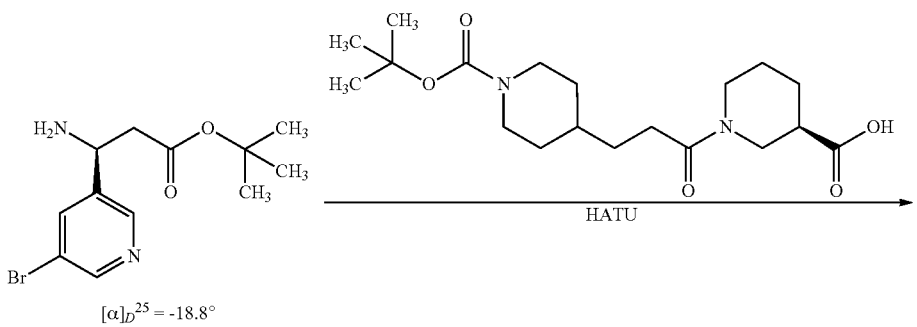

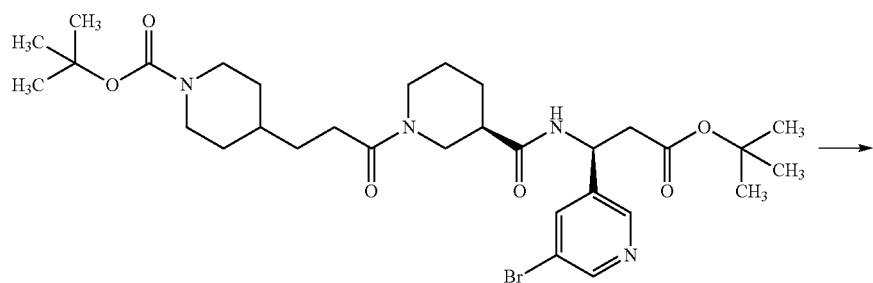

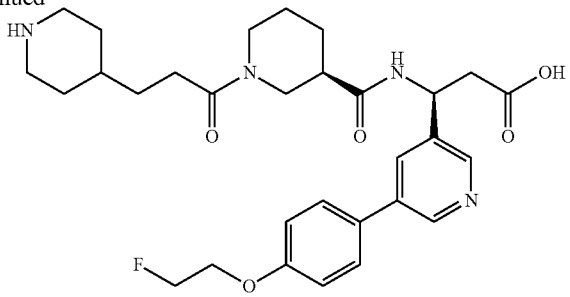

(E)-3-(5-Bromo-pyridin-3-yl)acrylic acid tert-butyl ester was synthesized as described in WO 2010/038081, page 143. The preparation of (S)-3-amino-3-(5-bromo-pyridin-3-yl)-propionic acid tert-butyl ester was accomplished as described in J. Chem. Soc., Perkin Trans. 1, 2002, 1858-1868 for (S)-3-amino-3-(pyridin-3-yl)propionic acid tert-butyl ester 14. For this compound an optical rotation $[\alpha]_D$ −17.6° is specified, whereas the bromo-derivative obtained gave $[\alpha]_D$ −18.8°. The final product of the synthesis using this pure enantiomeric intermediate gave the active diastereomer with an enantiomeric excess of 53% (scheme 2).

In a second approach (scheme 3) the 3-pyridyl nitrile could be transformed to the aryl enamine which was stereoselectively reduced (Yi Hsiao et. al. J. Am. Chem. Soc. 2004 126, 9918-9919) to the enantiomerically enriched 3-amino-3-arylpropanoic acid tert.-butyl ester. The ester was coupled to the piperidine fragment via an activated ester. Further standard transformations of protective groups or palladium catalyzed transformations like Suzuki or Sonogashira reaction delivered the exemplified compounds.

Scheme 3

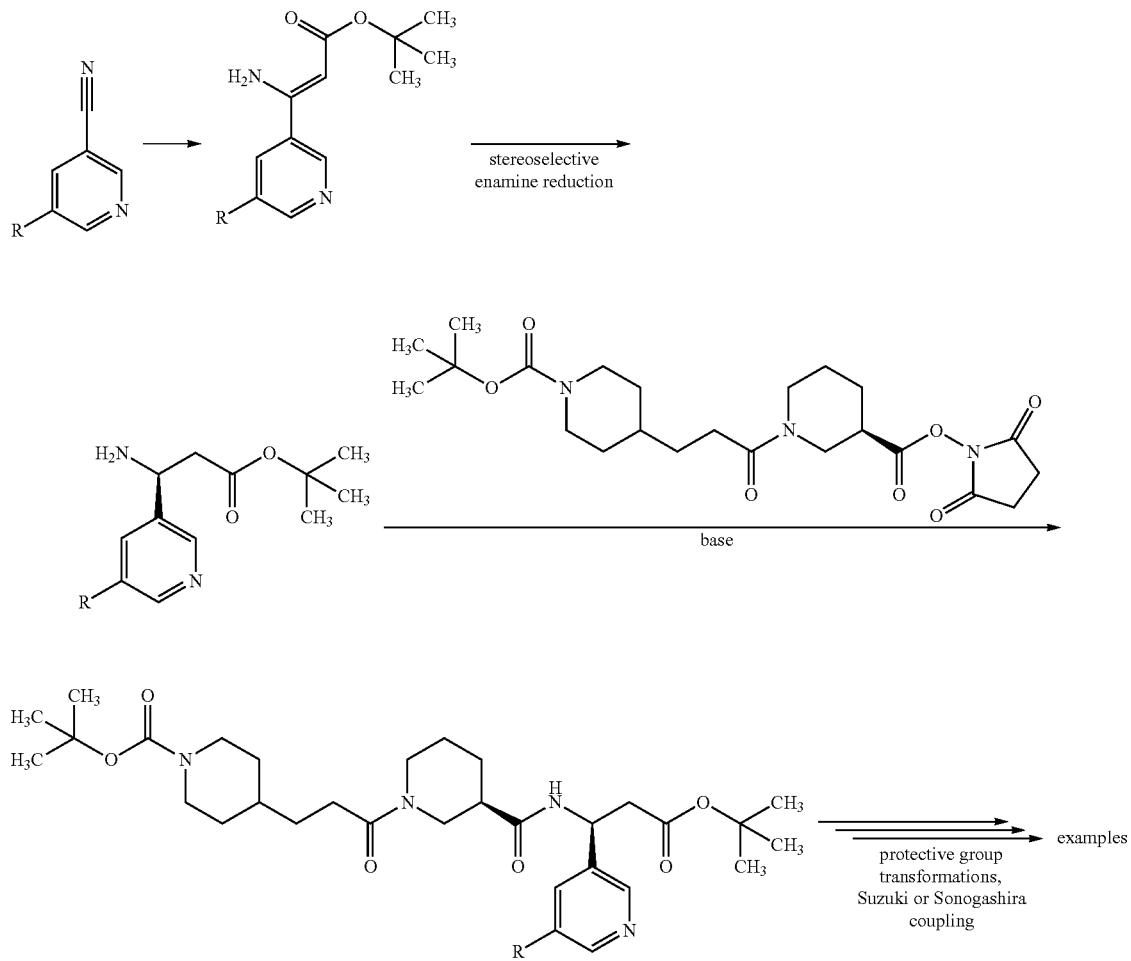

In a third approach (scheme 4) the mixed malonic diester was coupled in a stereoselective Mannich reaction with the in situ generated BOC imine (J. Song et al., *Org. Lett.* 2007, 9, 603-606) derived from the corresponding N-BOC amido sulfone in presence of a chiral thiourea catalyst (Y. Yamaoka et al., *Synthesis* 2007, 16, 2571-2575). Further standard transformations of protective groups including the decarboxylation of the substituted mono malonic ester delivered the exemplified compounds.

100-110° C. for 10-20 min to effect labeling. The crude reaction mixture was analyzed by HPLC. The product peak was confirmed by co-injection of the reaction mixture with the F-19 cold standards of general formula II.

Depending on the protection groups of the F-18 intermediate of general formula II a one-step or two-step hydrolysis was performed. In the case of methyl ester compounds of general formula II 0.5 M NaOH (100 µl) was added to the reaction mixture and after stirring for 5-10 min at 25° C., 1

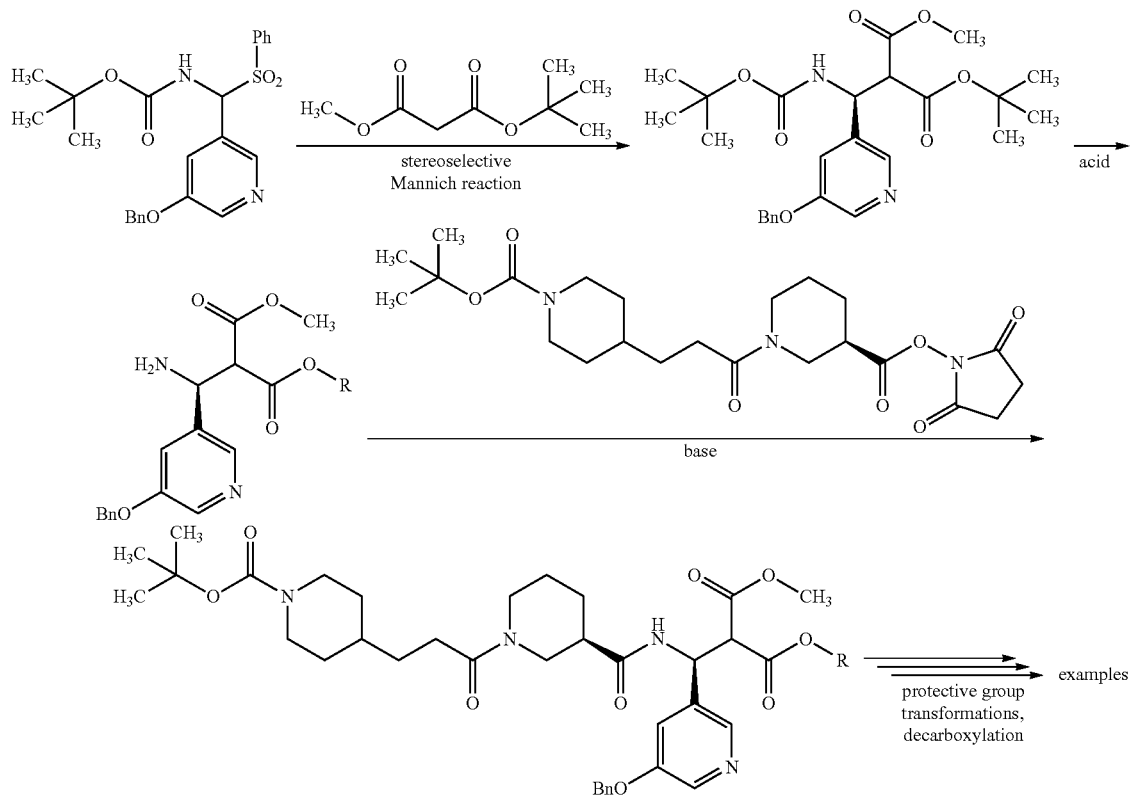

Scheme 4

Radiochemistry

The compounds of formula II and III containing an F-18 labeling were obtained according to one of the three general synthesis procedures outlined below.

General Synthesis of Alkyl-F-18 Compounds Via Direct Labeling

[$^{18}$F]Fluoride was produced by proton bombardment in a cyclotron using a silver target (1 mL) filled with [$^{18}$O] water for the $^{18}$O (p,n)$^{18}$F reaction. The aqueous [$^{18}$F]fluoride was passed through a cartridge (e.g. QMA-resin cartridge Waters, Sep Pak Light QMA Part. No.: WAT023525). The trapped [$^{18}$F]fluoride was then eluted from the cartridge using a mixture of Kryptofix® (Kryptofix® is 4,7,13,16,21,24-Hexaoxa-1,10-diazabicyclo[8.8.8]hexacosane) (5.27 mg in 1.5 ml acetonitrile) and potassium carbonate (1.0 mg in 0.5 ml water). Alternatively cesium carbonate (2.3 mg in 0.5 ml water) was used as base. This $^{18}$F-fluoride (up to 10 GBq) solution was azeotropically dried by heating under a stream of nitrogen at 110-120° C. for 20-30 minutes. During this time 3×1 ml acetonitrile were added and evaporated. After drying a solution of the precursor (2-4 mg in 200-300 µL acetonitrile) was added. The reaction vessel was heated at M HCL (200 µl) was added and stirring was continued for 5-15 min at 100-110° C. In the case of tert-butyl ester compounds of general formula II 1 M HCl (150-400 µL) was added to the reaction mixture and stirring was continued for 5-15 min at 100-110° C.

After complete hydrolysis the reaction mixture was optionally neutralized with 1 M NaOH or directly diluted with water (4 mL) and transferred to a semi preparative HPLC for purification. The collected product peak was diluted with water (15-40 ml) and immobilized on a C18 separation cartridge. The pure F-18 labeled product was eluted from the cartridge with pure ethanol (1-2 ml). After complete evaporation of the ethanol at 80-90° C. the final F-18 product was taken up in water (100-300 µl).

General Synthesis of Aryl-F-18 Compounds Via Direct Labeling

[$^{18}$F]Fluoride was produced by proton bombardment in a cyclotron using a silver target (1 mL) filled with [$^{18}$O] water for the $^{18}$O (p, n)$^{18}$F reaction. The aqueous [$^{18}$F]fluoride was passed through a cartridge (e.g. QMA-resin cartridge Waters, Sep Pak Light QMA Part. No.: WAT023525). The trapped [$^{18}$F]fluoride was then eluted from the cartridge using a mixture of Kryptofix® (10.4 mg in 1.5 ml Acetonitrile) and potassium bicarbonate (2.8 mg in 0.5 ml water). This $^{18}$F-fluoride (up to 5 GBq) solution was azeotropically dried by heating under a stream of nitrogen at 110-120° C. for 20-30 minutes. During this time 3×1 ml Acetonitrile were added and evaporated. After drying a solution of the precursor (1-2 mg in 200-300 µL DMSO) was added. The reaction vessel was heated at 150-160° C. for 10-15 min to effect labeling. The crude reaction mixture was analyzed by HPLC. The product peak was confirmed by co-injection of the reaction mixture with the F-19 cold standards of general formula II. This F-18 intermediate of general formula II was hydrolysed in a two-step procedure. 0.5 M NaOH (100 µl) was added to the reaction mixture and after stirring for 5-10 min at 25° C., 1 M HCl (200 µl) was added and stirring was continued for 5-10 min at 70-80° C.

After complete hydrolysis the reaction mixture was optionally neutralized with 1 M NaOH or directly diluted with water (4 mL) and transferred to a semi preparative HPLC for purification. The collected product peak was diluted with water (15-40 ml) and immobilized on a C18 separation cartridge. The pure F-18 labeled product was eluted from the cartridge with pure ethanol (1-2 ml). After complete evaporation of the ethanol at 80-90° C. the final F-18 product was taken up in water (100-300 µl).

General Synthesis of Alkyl-F18 Compounds Via Indirect Labeling with a Prosthetic Group of General Formula $^{18}$F—O(CH$_2$)$_n$-LG, $^{18}$F—(OCH$_2$CH$_2$)$_m$-LG, Wherein LG Stands for a Suitable Leaving Group for Coupling

[$^{18}$F]Fluoride was produced by proton bombardment in a cyclotron using a silver target (1 mL) filled with [$^{18}$O] water for the $^{18}$O (p, n)$^{18}$F reaction. The aqueous [$^{18}$F]fluoride was passed through a cartridge (e.g. QMA-resin cartridge Waters, Sep Pak Light QMA Part. No.: WAT023525). The trapped [$^{18}$F]fluoride was then eluted from the cartridge using a mixture of Kryptofix® (5.27 mg in 1.5 ml Acetonitrile) and potassium carbonate (1.0 mg in 0.5 ml water). This $^{18}$F-fluoride (up to 5 GBq) solution was azeotropically dried by heating under a stream of nitrogen at 110-120° C. for 20-30 minutes. During this time 3×1 ml Acetonitrile were added and evaporated. After drying a solution of the precursor of the prosthetic group (10 mg) in DMF or orthodichlorobenzene (500 µl) was added. The reaction vessel was heated at 100-130° C. for 10-15 min to effect labeling. The resulting prosthetic group of the general formula $^{18}$F—O(CH$_2$)$_n$-LG or $^{18}$F—(OCH$_2$CH$_2$)$_m$-LG was either purified via a distillation (15-25 min at 100-110° C.) under a slow nitrogen stream (e.g. for 2-[$^{18}$F]fluoroethyl bromide) or via a semi preparative HPLC after dilution with water (4 mL) (e.g. toluene-4-sulfonic acid 2-[2-(2-[$^{18}$F]fluoroethoxy) ethoxy]ethyl ester). In case of purification via semi preparative HPLC the collected peak was diluted with water (15-20 ml) and immobilized on a C18 separation cartridge. The pure F-18 labeled product was eluted from the cartridge with acetonitrile (1-2 ml). The acetonitrile was evaporated at 90-100° C.

The precursor (2.5 mg) to be coupled to the prosthetic group is dissolved in DMF (100-300 µl) and 2 M NaOH (20 µl) is added for deprotonation. This mixture is added to the vial containing the prosthetic group $^{18}$F—O(CH$_2$)$_n$-LG or $^{18}$F—(OCH$_2$CH$_2$)$_m$-LG. After heating at 100-110° C. for 20-25 min the recooled reaction mixture was treated with 1-2 M NaOH (100 µl). The solution was stirred for additional 10-15 min before 2-4 M HCl (200 µl) was added. The mixture was heated for 10 min at 100-110° C.

After complete hydrolysis the reaction mixture was optionally neutralized with 1 M NaOH or directly diluted with water (4 mL) and transferred to a semi preparative HPLC for purification. The collected product peak was diluted with water (15-40 ml) and immobilized on a C18 separation cartridge. The pure F-18 labeled product was eluted from the cartridge with pure ethanol (1-2 ml). After complete evaporation of the ethanol at 80-90° C. the final F-18 product was taken up in water (100-300 µl).

PET-imaging was performed continuously from shortly before up to 60 minutes post injection. Venous blood samples were taken at 3, 10, 30 and 60 minutes p.i. and were measured in a gamma-counter (Automatic Gamma Counter Wizard$^2$ 3, Perkin Elmer) and expressed as cpm/mg blood. Additionally, the blood-concentration of the compound was measured from the PET-Image over the whole imaging period and expressed as % ID/g. As already shown in mice, the compound was rapidly eliminated from the blood.

Figure 5:
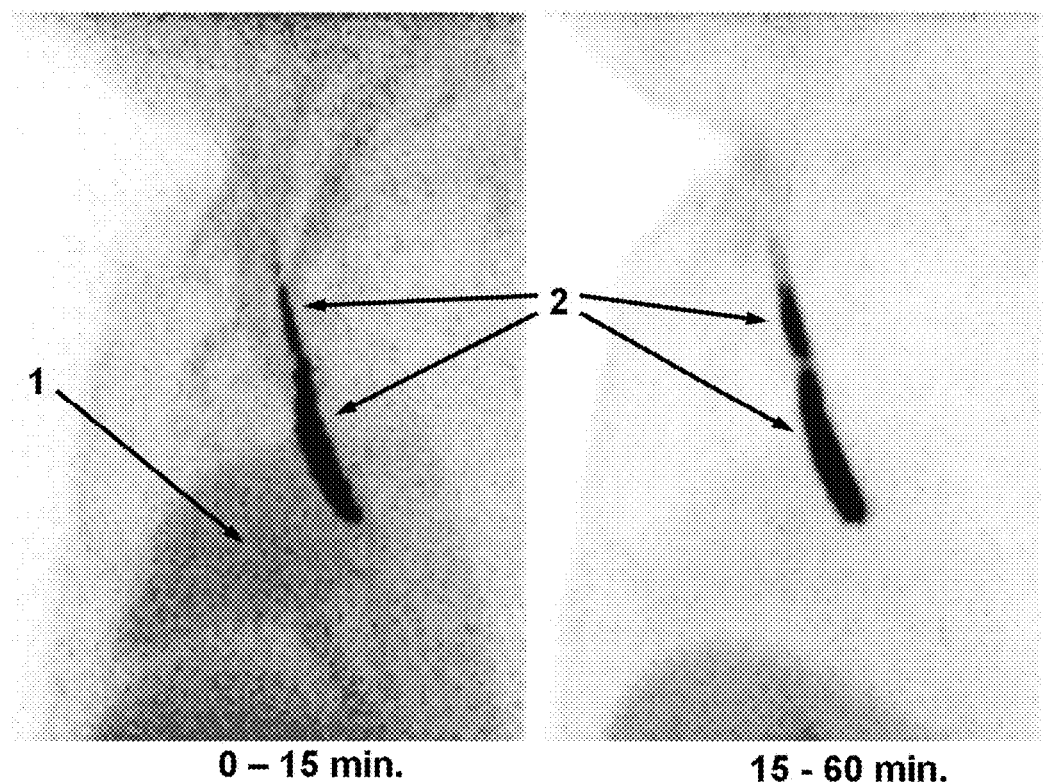

FIG. 5: PET-Imaging of an arterial thrombus in a cynomolgus monkey: The Figure shows an arterial thrombus (arrow 2) which had developed on the surface of a roughened polyethylene catheter tube (PE50). The thrombus is already visible inside the descending Aorta nearby the heart (arrow 1) within the first 15 minutes (left image). There is no signal loss up to 60 minutes (right image). The compound is quickly eliminated from the blood and there is no background in adjacent tissue and organs after 15 minutes (right image).

Figure 6:
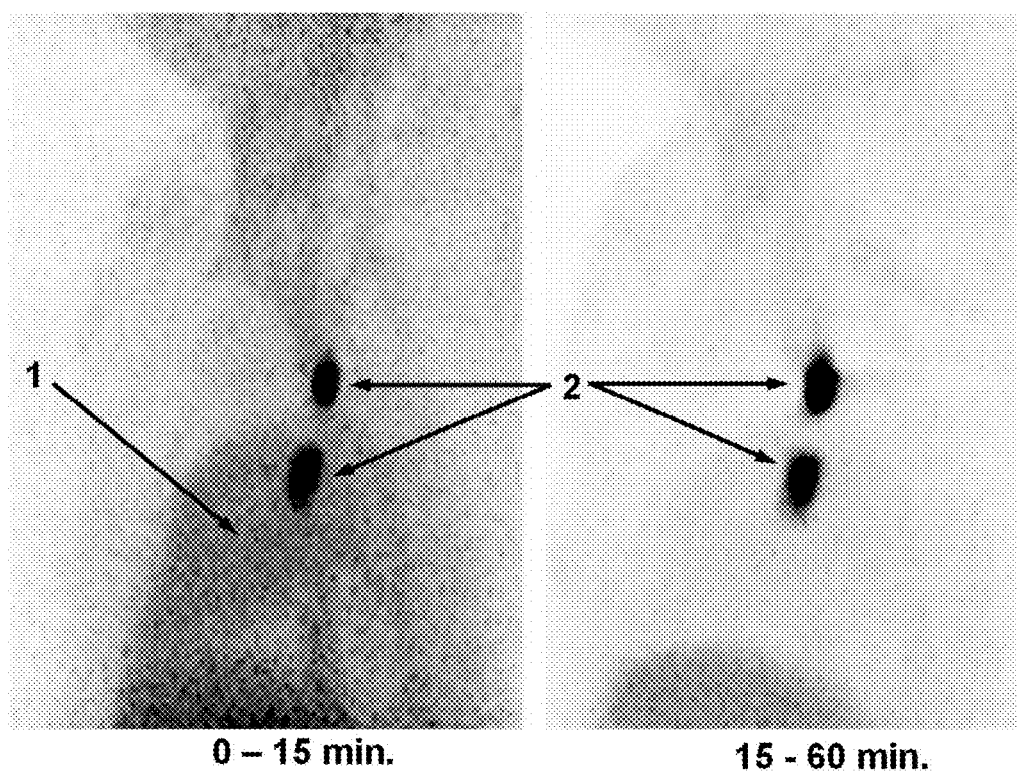

FIG. 6: PET-Imaging of an arterial thrombus in a cynomolgus monkey: The Figure shows two arterial thrombi (arrow 2) which had developed on the surface of a polyethylene catheter tube (PE50) which was roughened at two parts with a gap in between. There is no signal visible between the thrombi proving that the compound solely binds to thrombus and not to the polymeric tube alone. The thrombus is already visible inside the descending Aorta nearby the heart (arrow 1) within the first 15 minutes (left image). There is no signal loss up to 60 minutes (right image). The compound is quickly eliminated from the blood and there is no background in adjacent tissue or organs after 15 minutes (right image).

Figure 7:
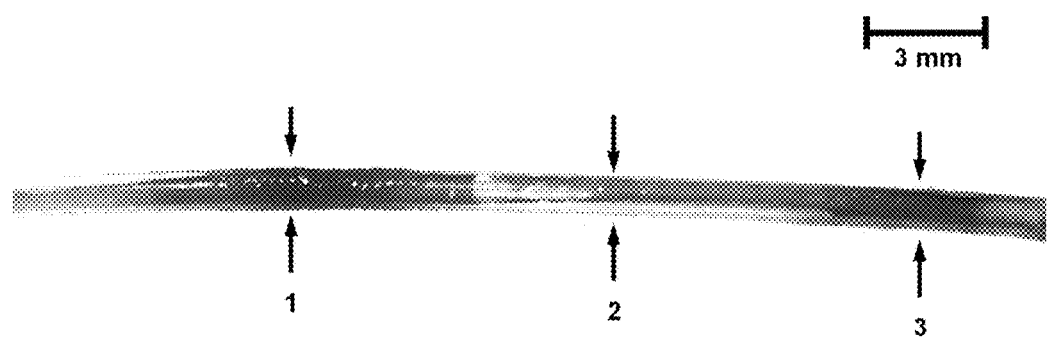

FIG. 7: Arterial thrombi removed from monkey 2: The image shows the polyethylene catheter tube (PE50, outer diameter: 1 mm) which was roughened at two parts (⅓) with a gap (2) in between. The thrombus had only developed on the rough parts of the tube-surface and was extremely thin (approximately ¹/₁₀th mm [arrow 1] or even less [arrow 3]). This shows that even tiniest thrombi can be detected anywhere in the body.

Figure 8:
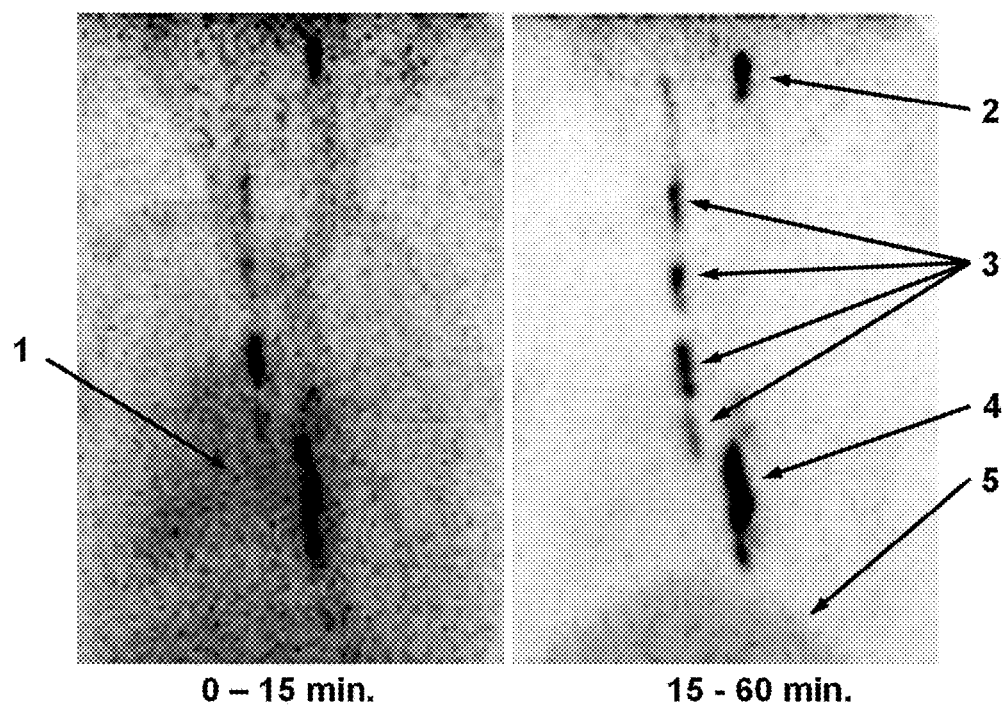

FIG. 8: PET-Imaging of arterial and venous thrombi in a cynomolgus monkey with the reduced tracer-dosage of 15 MBq per animal: The Figure shows several arterial (arrow 3) and venous (arrow 4) thrombi which had developed on the surface of polyethylene catheter tubes (PE50) which were roughened at some parts with gaps in between. All thrombi could be seen already in the first 15 minutes. However, the contrast was much better after 15 minutes because of the low background. Apart from the thrombogenic catheters another arterial thrombus showed up in the image, which was found in the right carotid artery later on and had most probably developed as a result of vessel damage while the preparation. The heart (left image, arrow 1) is only visible within the first 15 minutes, while the liver (right image, arrow 5) can still be seen up to 60 minutes.

EXPERIMENTAL PART

Abbreviations

| | |
|---|---|
| ACN | acetonitrile |
| Boc | tert-butoxycarbonyl |
| br | broad signal (in NMR data) |
| CAN | ceric ammonium nitrate |
| CI | chemical ionisation |
| d | doublet |
| DAD | diode array detector |
| dd | doublet of doublet |
| ddd | doublet of doublet of doublet |
| dt | doublet of triplet |
| DMF | N,N-dimethylformamide |
| DMSO | dimethylsulfoxide |
| EI | electron ionisation |
| ELSD | evaporative light scattering detector |
| ESI | electrospray ionisation |
| EtOAc | ethyl acetate |
| EtOH | ethanol |
| Fmoc | fluorenylmethyloxycarbonyl |
| Fu | Fraction unbound |
| Hal | halogenide |
| HATU | N-[(dimethylamino)(3H-[1,2,3]triazolo[4,5-b]pyridin-3-yloxy)-methylidene]-N-methylmethanaminium hexafluorophosphate |
| HPLC | high performance liquid chromatography |
| HT | High throughput |
| GBq | Giga Bequerel |
| $K_{2.2.2}$ | 4, 7, 13, 16, 21, 24-hexaoxa-1,10-diazabicyclo[8.8.8]hexacosane |
| $K_2CO_3$ | potassium carbonate |
| MBq | Mega Bequerel |
| LCMS | Liquid chromatography-mass spectroscopy |
| MWCO | Molecular weight cut off |
| MeCN | acetonitrile |
| MeOH | methanol |
| MS | mass spectrometry |
| MTB | methyl tert-butyl ether |
| m | multiplet |
| mc | centred multiplet |
| $NH_4Cl$ | ammonium chloride |
| NMR | nuclear magnetic resonance spectroscopy: chemical shifts (δ) are given in ppm. |
| q | quadruplett (quartet) |
| PMB | para-methoxybenzyl |
| Rt | Retention time |
| RT | room temperature |
| s | singlet |
| t | triplet |
| TBAF | tetrabutylammonium fluoride |
| TEE | Transesophageal Echocardiography |
| THF | tetrahydrofuran |

-continued

| | |
|---|---|
| THP | tetrahydropyran |
| TIA | transient ischemic attack |
| UPLC | ultra performance liquid chromatography |

Examples were analyzed and characterized by the following analytical methods to determine characteristic retention time and mass spectrum:

| | |
|---|---|
| System: | Waters Acquity UPLC-MS: Binary Solvent Manager, Sample Manager/Organizer, Column Manager, PDA, ELSD, SQD 3001 |
| Column: | Acquity UPLC BEH C18 1.7 50 × 2.1 mm |
| Solvent: | A1 = H2O + 0.1% HCOOH |
| | A2 = H2O + 0.2% NH3 |
| | B1 = Acetonitrile |
| Gradient: | 0-1.6 min 1-99% B, 1.6-2.0 min 99% B |
| Flow: | 0.8 mL/min |
| Temperature: | 60° C. |
| Injection: | 2.0 μl |
| Detection: | DAD scan range 210-400 nm –> Peak table ELSD |
| Method: | MS ESI+, ESI– Switch –> diverse scan ranges possible |

Method 1: UPLC (ACN-HCOOH)

Instrument: Waters Acquity UPLC-MS SQD 3001; column: Acquity UPLC BEH C18 1.7 50×2.1 mm; eluent A: water+0.1% formic acid, eluent B: acetonitril; gradient: 0-1.6 min 1-99% B, 1.6-2.0 min 99% B; flow 0.8 ml/min; temperature: 60° C.; injection: 2 μl; DAD scan: 210-400 nm; ELSD Method 2: UPLC (ACN-NH3)

Instrument: Waters Acquity UPLC-MS SQD 3001; column: Acquity UPLC BEH C18 1.7 50×2.1 mm; eluent A: water+0.2% ammonia Eluent B: acetonitrile; gradient: 0-1.6 min 1-99% B, 1.6-2.0 min 99% B; flow 0.8 ml/min; temperature: 60° C.; injection: 2 μl; DAD scan: 210-400 nm; ELSD

EXAMPLES

Example 1

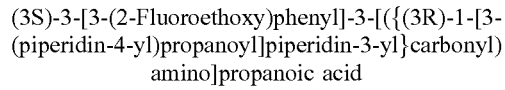

(3S)-3-[3-(2-Fluoroethoxy)phenyl]-3-[({(3R)-1-[3-(piperidin-4-yl)propanoyl]piperidin-3-yl}carbonyl)amino]propanoic acid

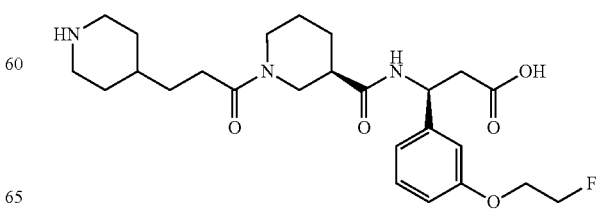

Example 1a

Methyl 3-[(tert-butoxycarbonyl)amino]-3-(3-hydroxyphenyl)propanoate

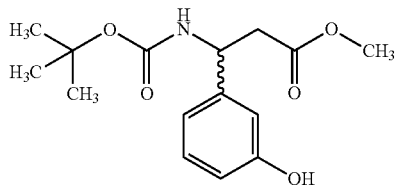 [SMILES: COC(=O)CC(NC(=O)OC(C)(C)C)c1cccc(O)c1]

Methyl 3-amino-3-(3-hydroxyphenyl)propanoate (2.78 g, 14.2 mmol) in THF (70 mL) and triethylamine (3 mL, 21.3 mmol) were added to a solution of di tert.-butyldicarbonate (4.66 g, 21.3 mmol) in THF (70 mL) and the mixture was stirred for 72 hours. Saturated ammonium chloride solution was added and the mixture extracted with dichloromethane. The organic layer was washed with brine, dried over sodium sulfate and concentrated in vacuum. The residue was purified by chromatography on silica gel (ethyl acetate in hexane 0 to 30%) to yield 3.24 g methyl 3-[(tert-butoxycarbonyl)amino]-3-(3-hydroxyphenyl)propanoate.

$^1$H-NMR (400 MHz, DMSO$_{d6}$): δ=1.35 (s, 9 H), 2.56-2.75 (m, 2 H), 3.55 (s, 3 H), 4.81 (m, 1 H), 6.60 (ddd, 1 H), 6.69 (m, 2 H), 7.08 (dd, 1 H), 7.42 (d, 1 H), 9.37 (s, 1 H) ppm.

Example 1b

Methyl 3-[(tert-butoxycarbonyl)amino]-3-[3-(2-fluoroethoxy)phenyl]propanoate

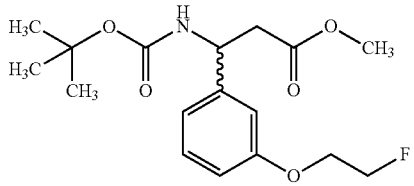 [SMILES: COC(=O)CC(NC(=O)OC(C)(C)C)c1cccc(OCCF)c1]

To methyl 3-[(tert-butoxycarbonyl)amino]-3-(3-hydroxyphenyl)propanoate (4.46 g, 20 mmol) in THF was added cesium carbonate (9.84 g, 30 mmol) and 1-fluoro-2-iodoethane (5 g, 30 mmol) and the mixture was stirred for 9 hours. After filtration the filtrate was concentrated in vacuum to yield 5.0 g of methyl 3-[(tert-butoxycarbonyl)amino]-3-[3-(2-fluoroethoxy)phenyl]propanoate.

$^1$H-NMR (400 MHz, CDCl$_3$): δ=1.43 (br. s, 9 H), 2.83 (m, 2 H), 3.63 (s, 3 H), 4.23 (ddd, 2 H), 4.76 (ddd, 2 H), 5.08 (br., 1 H), 5.48 (br., 1H), 6.82 (dd, 1 H), 6.88 (s, 1 H), 6.91 (d, 1 H), 7.26 (t, 1 H) ppm.

Example 1c

Methyl 3-amino-3-[3-(2-fluoroethoxy)phenyl]propanoate

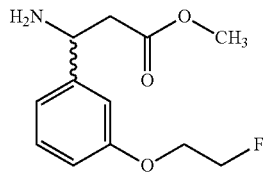 [SMILES: COC(=O)CC(N)c1cccc(OCCF)c1]

To methyl 3-[(tert-butoxycarbonyl)amino]-3-[3-(2-fluoroethoxy)phenyl]propanoate (5.0 g, 20 mmol) in dichloromethane was added trifluoro acetic acid (5.64 mL, 73 mmol). After stirring for 24 hours at room temperature additional trifluoro acetic acid (1.13 mL) was added and stirring was continued for 20 hours. The mixture was concentrated under reduced pressure and the residue was purified by chromatography on silica gel (methanol in dichloromethane 0% to 40%)) to yield 4.9 g methyl 3-amino-3-[3-(2-fluoroethoxy)phenyl]propanoate.

$^1$H-NMR (300 MHz, DMSO$_{d6}$): δ=2.86-3.12 (m, 2 H), 4.13-4.24 (m, 1 H), 4.24-4.34 (m, 1 H), 4.52-4.75 (m, 2 H), 4.75-4.95 (m, 1 H), 7.00 (dd, 1 H), 7.06 (d, 1 H), 7.12 (d, 1 H), 7.28-7.42 (m, 1 H), 8.44 (br. s., 2H) ppm.

Example 1d

Tert-butyl 4-{3-[(3R)-3-({(1-[3-(2-fluoroethoxy)phenyl]-3-methoxy-3-oxopropyl}carbamoyl)piperidin-1-yl]-3-oxopropyl}piperidine-1-carboxylate

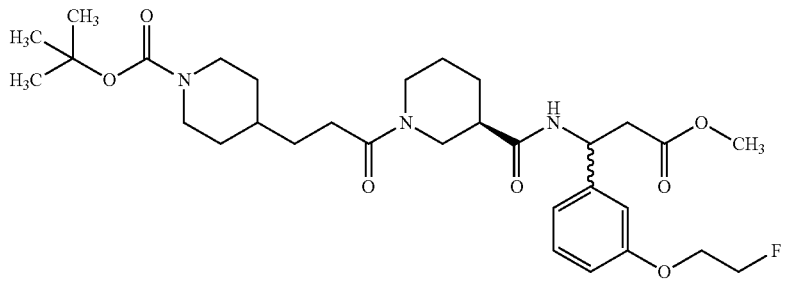 [SMILES: COC(=O)CC(NC(=O)[C@@H]1CCCN(C(=O)CCC2CCN(C(=O)OC(C)(C)C)CC2)C1)c1cccc(OCCF)c1]

(3R)-1-{3-[1-(Tert-butoxycarbonyl)piperidin-4-yl]propanoyl}piperidine-3-carboxylic acid (105 mg, 286 μmol, Bioorg. Med. Chem. 13 (2005) 4343-4352, Compound 10) were suspended in 2 ml N,N-dimethylformamide and cooled to 0° C. HATU (117 mg, 308 µmol), a solution of methyl 3-amino-3-[3-(2-fluoroethoxy)phenyl]propanoate (53 mg, 220 µmol) in 3.4 ml N,N-dimethylformamide and N-ethyl-diisopropylamine (0.11 ml, 660 µmol) were added. The mixture was stirred at 0° C. for 5 minutes and at room temperature for 24 hours. Water was added and the mixture extracted with dichloromethane, washed with saturated sodium chloride solution and dried over sodium sulfate. The solution was concentrated under reduced pressure and the residue was purified by chromatography on an amino phase column (Separtis® Flash-NH2, ethyl acetate in dichloromethane 0% to 100%) to yield 88 mg of tert-butyl 4-{3-[(3R)-3-({(1-[3-(2-fluoroethoxy)phenyl]-3-methoxy-3-oxopropyl}carbamoyl)piperidin-1-yl]-3-oxopropyl}piperidine-1-carboxylate.

UPLC (ACN-HCOOH): Rt.=1.22/1.23 min
MS (ES$^+$): m/e=592.44 (M+H$^+$)

Example 1e 3-({[(3R)-1-{3-[1-(tert-butoxycarbonyl)piperidin-4-yl]propanoyl}piperidin-3-yl]carbonyl}amino)-3-[3-(2-fluoroethoxy)phenyl]propanoic acid

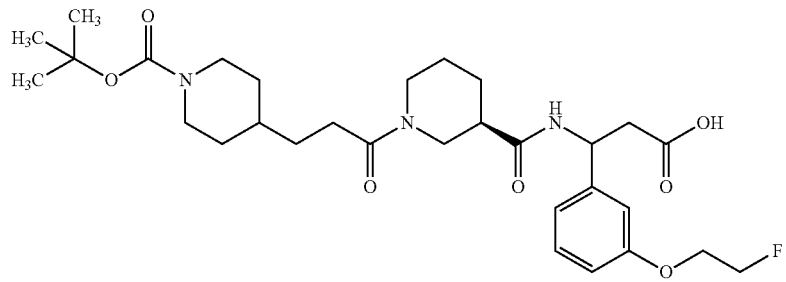 [SMILES: CC(C)(C)OC(=O)N1CCC(CCC(=O)N2CCC[C@@H](C(=O)NC(CC(=O)O)c3cccc(OCCF)c3)C2)CC1]

Tert-butyl 4-{3-[(3R)-3-({(1-[3-(2-fluoroethoxy)phenyl]-3-methoxy-3-oxopropyl}carbamoyl)piperidin-1-yl]-3-oxopropyl}piperidine-1-carboxylate (67 mg, 102 µmol) was dissolved in methanol (12.4 mL) and barium hydroxide octahydrate (2.2 g, 7.1 mmol) was added. The mixture was stirred at room temperature for one hour and then diluted with brine and diethyl ether. The mixture was acidified with 1 M hydrochloric acid and phases were separated. Concentration of the organic phase gave 70 mg 3-({[(3R)-1-{3-[1-(tert-butoxycarbonyl)piperidin-4-yl]propanoyl}piperidin-3-yl]carbonyl}amino)-3-[3-(2-fluoroethoxy)phenyl]propanoic acid UPLC (ACN-HCOOH): Rt.=1.12/1.14 min
MS (ES$^+$): m/e=578.3 (M+H$^+$)
$^1$H-NMR (500 MHz, DMSO$_{d6}$, at 80° C.): δ=0.82-1.05 (m, 2 H), 1.05-1.51 (m, 6 H), 1.40(s, 9 H), 1.56-1.70 (m, 4 H), 2.29-2.41 (m, 3 H), 2.58-2.80 (m, 5 H), 3.20 (br., 3H), 3.91 (d, 2 H), 4.25 (ddd, 2 H), 4.73 (ddd, 2 H), 5.19 (m, 1 H), 6.85 (m, 1 H), 6.94 (m, 2 H), 7.23 (td, 1 H), 8.15 (d, 1 H) ppm.

Example 1f (3S)-3-[3-(2-Fluoroethoxy)phenyl]-3-[({(3R)-1-[3-(piperidin-4-yl)propanoyl]piperidin-3-yl}carbonyl)amino]propanoic acid To 3-({[(3R)-1-{3-[1-(tert-butoxycarbonyl)piperidin-4-yl]propanoyl}piperidin-3-yl]carbonyl}amino)-3-[3-(2-fluoro-roethoxy)phenyl]propanoic acid (65 mg, 90 µmol) in dioxane was added a 4 M solution of hydrochloric acid in dioxane (0.23 ml, 900 µmol) and stirred for 3 hours at room temperature. The solution was concentrated under reduced pressure and the residue was purified by preparative HPLC to yield 8.7 mg of (3S)-3-[5-(2-fluoroethoxy)phenyl]-3-[({(3R)-1-[3-(piperidin-4-yl)propanoyl]piperidin-3-yl}carbonyl)amino]propanoic acid.

| | |
|---|---|
| Column: | C18 YMC-ODS AQ 10 µm 170 × 25 mm |
| Solvent: | A = H2O + 0.1% HCOOH |
| | B = acetonitrile |
| Gradient: | 0-0.25 min 10% B, 0.25-10 min 10-50% B |
| Flow: | 60 mL/min |
| Temperature: | RT |
| Detection: | 261 nm |
| Rt.: | 4.84-5.73 min |

UPLC (ACN-HCOOH): Rt.=0.76 min
MS (ES$^+$): m/e=478.29 (M+H$^+$)
$^1$H-NMR (500 MHz, DMSO$_{d6}$, 80° C.): δ=1.20-1.70 (m, 8 H), 1.80 (m, 2 H), 2.17 (br. 1H), 2.25-2.50 (m, 4 H), 2.60-2.71 (m, 3 H), 3.05-3.25 (m, 3 H), 3.72 (br., 3 H), 4.23 (ddd, 2 H), 4.73 (ddd, 2 H), 5.10 (m, 1 H), 6.80 (m, 1 H), 6.91 (m, 2 H), 7.21 (t, 1 H), 8.28 (br., 1 H) ppm.

Example 2

(3S)-3-[4-(2-Fluoroethoxy)phenyl]-3-[({(3R)-1-[3-(piperidin-4-yl)propanoyl]piperidin-3-yl}carbonyl)amino]propanoic acid

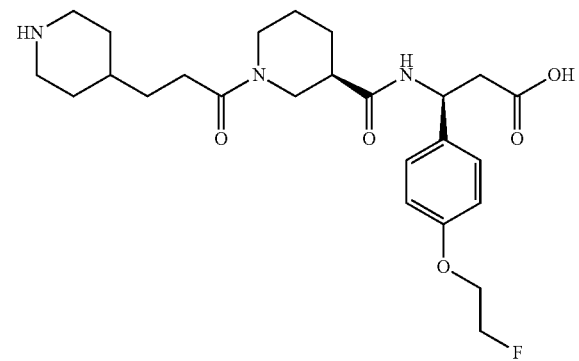 [SMILES: O=C(O)C[C@H](NC(=O)[C@@H]1CCCN(C(=O)CCC2CCNCC2)C1)c1ccc(OCCF)cc1]

Example 2a

3-Amino-3-(4-hydroxyphenyl)propionic acid methyl ester

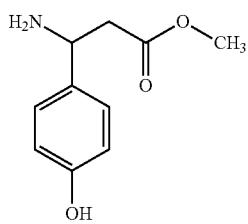

5.298 g (29.24 mmol) commercial 3-amino-3-(4-hydroxyphenyl)propionic acid were suspended in 136 ml methanol, the mixture cooled to 0° C. and 3.20 ml (43.86 mmol) thionyl chloride were slowly added. The mixture was stirred at room temperature for 20 hours and concentrated. The residue was treated with saturated sodium hydrogen carbonate solution and extracted with dichloromethane and dichloromethane/2-propanol 8:2. The organic part was concentrated to give 5.09 g (80%) 3-amino-3-(4-hydroxyphenyl)propionic acid methyl ester.

UPLC (ACN-HCOOH): Rt.=0.45 min
MS (ES$^+$): m/e=179.07 (M+H$^+$—NH$_3$)
MS (ES$^-$): m/e=240.30 (M+HCOO$^-$)

Example 2b

Tert-butyl 4-[3-((3R)-3-{[1-(4-hydroxyphenyl)-3-methoxy-3-oxopropyl]Carbamoyl}piperidin-1-yl)-3-oxopropyl]piperidine-1-carboxylate

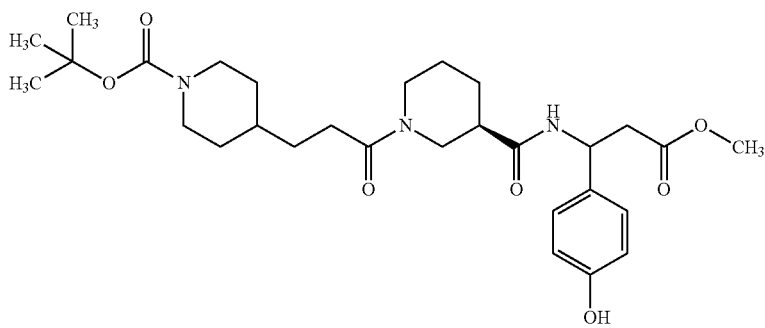 [SMILES: COC(=O)CC(NC(=O)[C@@H]1CCCN(C(=O)CCC2CCN(C(=O)OC(C)(C)C)CC2)C1)c1ccc(O)cc1]

490.75 mg (1.33 mmol) (3R)-1-{3-[1-(tert-butoxycarbonyl)piperidin-4-yl]propanoyl}piperidine-3-carboxylic acid (Bioorg. Med. Chem. 13 (2005) 4343-4352, Compound 10) were suspended in 8 ml N,N-dimethylformamide and cooled to 0° C. 0.545 g (1.43 mmol) HATU, a solution of 200.0 mg (1.0 mmol) 3-amino-3-(4-hydroxy-phenyl)-propionic acid methyl ester in 12 ml N,N-dimethylformamide and 0.53 ml (3.07 mmol) N-ethyl-diisopropylamine were added. The mixture was stirred at 0° C. for 5 minutes and at room temperature for 24 hours. 20 ml water were added and the mixture extracted with dichloromethane, washed with saturated sodium chloride solution, dried over sodium sulfate and concentrated in vacuum. Chromatography over 28 g basic silica gel (dichloromethane/ethanol 100/0-95/5-90/10-80/20) gave 465 mg (83%) tert-butyl 4-[3-((3R)-3-{[1-(4-hydroxyphenyl)-3-methoxy-3-oxopropyl]carbamoyl}piperidin-1-yl)-3-oxopropyl]piperidine-1-carboxylate.

UPLC (ACN-HCOOH): Rt.=1.11 min
MS (ES$^+$): m/e=546.31 (M+H$^+$)
MS (ES$^-$): m/e=590.23 (M+HCOO$^-$)

Example 2c

Tert-butyl 4-{3-[(3R)-3-({1-[4-(2-fluoroethoxy)phenyl]-3-methoxy-3-oxopropyl}carbamoyl)piperidin-1-yl]-3-oxopropyl}piperidine-1-carboxylate

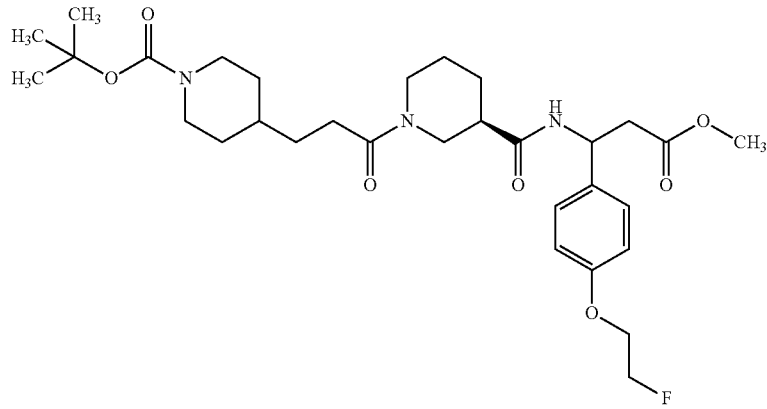 [SMILES: COC(=O)CC(NC(=O)[C@@H]1CCCN(C(=O)CCC2CCN(C(=O)OC(C)(C)C)CC2)C1)c1ccc(OCCF)cc1]

150 mg (0.28 mmol) 4-(3-{(R)-3-[1-(4-hydroxy-phenyl)-2-methoxycarbonyl-ethylcarbamoyl]-piperidin-1-yl}-3-oxo-propyl)-piperidine-1-carboxylic acid tert-butyl ester were dissolved in 3 ml tetrahydrofurane. 179 mg (0.55 mmol) cesium carbonate and 91 mg (0.52 mmol) 1-iodo-2-fluoroethane were added. The mixture was stirred at room temperature for 60 hours and filtrated. The filtrate was concentrated. Chromatography over 10 g silica gel (dichloromethane/ethanol 100/0-90/10) gave 90 mg (50%) tert-butyl 4-{3-[(3R)-3-({1-[4-(2-fluoroethoxy)phenyl]-3-methoxy-3-oxopropyl}carbamoyl)piperidin-1-yl]-3-oxopropyl}piperidine-1-carboxylate and 40 mg starting material.

UPLC (ACN-HCOOH): Rt.=1.24-1.25 min
MS (ES$^+$): m/e=592.31 (M+H$^+$)
MS (ES$^-$): m/e=590.29 (M−H), 636.26 (M+HCOO$^-$)

Example 2d 3-({[(3R)-1-{3-[1-(Tert-butoxycarbonyl)piperidin-4-yl]propanoyl}piperidin-3-yl]carbonyl}amino)-3-[4-(2-fluoroethoxy)phenyl]propanoic acid

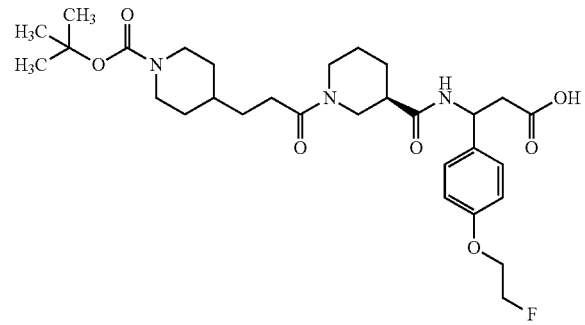 [SMILES: CC(C)(C)OC(=O)N1CCC(CCC(=O)N2CCC[C@@H](C(=O)NC(CC(=O)O)c3ccc(OCCF)cc3)C2)CC1]

96 mg (0.16 mmol) tert-butyl 4-{3-[(3R)-3-({1-[4-(2-fluoroethoxy)phenyl]-3-methoxy-3-oxopropyl}carbamoyl)piperidin-1-yl]-3-oxopropyl}piperidine-1-carboxylate were dissolved in 20 ml methanol. 512 mg (1.62 mmol) barium hydroxide octahydrate were added. The mixture was stirred at room temperature for 70 hours and then diluted with 20 ml water. The mixture was acidified with 1 N hydrochloric acid to pH 4 and extracted with 2×40 ml dichloromethane. Concentration of the organic phase gave 93 mg (99%) 3-({[(3R)-1-{3-[1-(tert-butoxycarbonyl)piperidin-4-yl]propanoyl}piperidin-3-yl]carbonyl}amino)-3-[4-(2-fluoroethoxy)phenyl]propanoic acid.

UPLC (ACN-HCOOH): Rt.=1.14-1.16 min
MS (ES$^+$): m/e=578.30 (M+H$^+$)
MS (ES$^-$): m/e=576.30 (M−H), 622.16 (M+HCOO$^-$)

Example 2e (3S)-3-[4-(2-Fluoroethoxy)phenyl]-3-[({(3R)-1-[3-(piperidin-4-yl)propanoyl]piperidin-3-yl}carbonyl)amino]propanoic acid

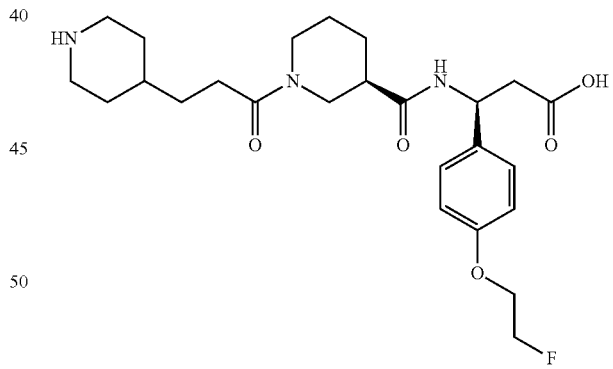

93 mg (0.16 mmol) 3-({[(3R)-1-{3-[1-(Tert-butoxycarbonyl)piperidin-4-yl]propanoyl}piperidin-3-yl]carbonyl}amino)-3-[4-(2-fluoroethoxy)phenyl]propanoic acid ester were dissolved in 3.3 ml dioxane. 0.4 ml (1.6 mmol) 4 N hydrochloric acid were added. The mixture was stirred at room temperature for 48 hours and then concentrated to give 131 mg which were purified by HPLC:

| | |
|---|---|
| System: | Waters Autopurificationsystem: Pump 254, Sample Manager 2767, CFO, DAD 2996, ELSD 2424, SQD 3001 |
| Column: | XBrigde C18 5 μm 100 × 30 mm |

-continued

| Solvent: | A = H2O + 0.2% NH3 |
| --- | --- |
| | B = Methanol |
| Gradient: | 0-1 min 10% B, 1-8 min 10-70% B |
| Flow: | 50 mL/min |
| Temperature: | RT |
| Solution: | 131 mg/2 mL DMSO/MeOH 1:1 |
| Injection: | 2 × 1 mL |
| Detection: | DAD scan range 210-400 nm |
| | MS ESI+, ESI−, scan range 160-1000 m/z |
| | ELSD |

| Fractions: | Rt. in min | DAD TAC | Amount |
| --- | --- | --- | --- |
| −11 | 5.0-5.4 | >99% | 19 mg |
| −12 | 5.7-6.0 | 90.2% | 16 mg |

The fractions were concentrated, mixed with tert.-butanol and lyophilized.

Fraction 12 contained the desired isomer.
UPLC (ACN-HCOOH): Rt.=0.65 min
MS (ES$^+$): m/e=478.37 (M+H$^+$)
MS (ES$^-$): m/e=476.43 (M−H)

Example 3

(3S)-3-[5-(2-Fluoroethoxy)pyridin-3-yl]-3-[({(3R)-1-[3-(piperidin-4-yl)propanoyl]-piperidin-3-yl}carbonyl)amino]propanoic acid

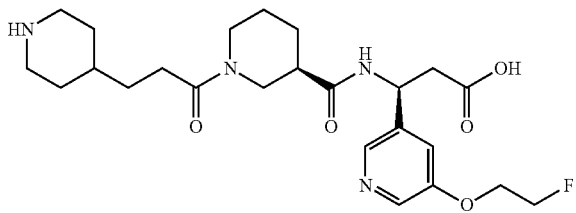 [SMILES: O=C(O)C[C@H](NC(=O)[C@@H]1CCCN(C(=O)CCC2CCNCC2)C1)c1cncc(OCCF)c1]

Example 3a

Tert-butyl 4-{3-[(3R)-3-({(1S)-3-tert-butoxy-1-[5-(2-fluoroethoxy)pyridin-3-yl]-3-oxopropyl}carbamoyl)piperidin-1-yl]-3-oxopropyl}piperidine-1-carboxylate

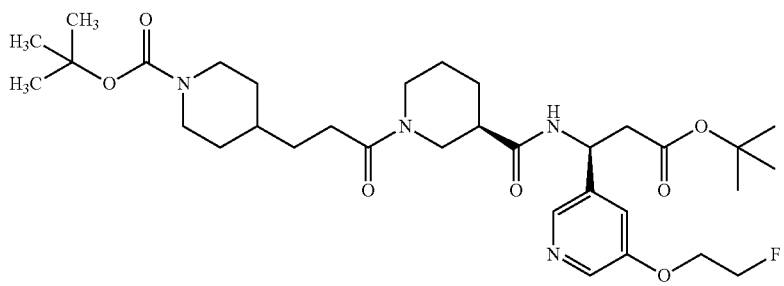 [SMILES: CC(C)(C)OC(=O)C[C@H](NC(=O)[C@@H]1CCCN(C(=O)CCC2CCN(C(=O)OC(C)(C)C)CC2)C1)c1cncc(OCCF)c1]

Tert-butyl 4-{3-[(3R)-3-{[(1S)-3-tert-butoxy-1-(5-hydroxypyridin-3-yl)-3-oxopropyl]carbamoyl}piperidin-1-yl]-3-oxopropyl}piperidine-1-carboxylate (example 25e, 800 mg, 1.36 mmol) was dissolved in N,N-dimethylformamide (52 mL). Cesium carbonate (1.1 g, 3.4 mmol) and 2-fluoroethyltosylate (445 mg, 2.04 mmol) were added. The mixture was stirred at room temperature for 3.5 hours, additional cesium carbonate (70 mg, 0.21 mmol) and 2-fluoroethyltosylate (28 mg, 0.13 mmol) were added and stirring was continued for 2.5 hours at room temperature and 17 hours at 5° C. The mixture was quenched by addition of saturated aqueous ammonium chloride solution and extracted with diethyl ether and ethyl acetate. The combined extracts were washed with brine and dried over sodium sulfate. The solution was concentrated under reduced pressure and the residue was purified by chromatography on silica gel (ethyl acetate in hexane 20 to 100% followed by dioxane in ethyl acetate 0 to 50%) to yield 670 mg of tert-butyl 4-{3-[(3R)-3-({(1S)-3-tert-butoxy-1-[5-(2-fluoroethoxy)pyridin-3-yl]-3-oxopropyl}carbamoyl)piperidin-1-yl]-3-oxopropyl}piperidine-1-carboxylat.
UPLC (ACN-HCOOH): Rt.=1.24 min
MS (ES$^+$): m/e=633.5 (M+H$^+$)

Example 3b (3S)-3-[5-(2-Fluoroethoxy)pyridin-3-yl]-3-[({(3R)-1-[3-(piperidin-4-yl)propanoyl]-piperidin-3-yl}carbonyl)amino]propanoic acid Tert-butyl 4-{3-[(3R)-3-({(1S)-3-tert-butoxy-1-[5-(2-fluoroethoxy)pyridin-3-yl]-3-oxopropyl}carbamoyl)piperidin-1-yl]-3-oxopropyl}piperidine-1-carboxylat (660 mg, 1.06 mmol) in formic acid (12 mL) was heated for 30 minutes to 60° C. and 10 minutes to 100° C. The solution was concentrated under reduced pressure and the residue was purified by preparative HPLC to yield 311 mg of (3S)-3-[5-(2-fluoroethoxy)pyridin-3-yl]-3-[({(3R)-1-[3-(piperidin-4-yl)propanoyl]piperidin-3-yl}carbonyl)amino]propanoic acid.

| Column: | C18 YMC-ODS AQ 10 μm 200 × 51 mm |
| --- | --- |
| Solvent: | A = H2O + 0.1% HCOOH |
| | B = acetonitrile |
| Gradient: | 0-1 min 1% B, 1-10 min 1-25% B, |
| Flow: | 240 mL/min |
| Temperature: | RT |
| Detection: | 277 nm |
| Rt.: | 5.21-7.05 min |

UPLC (ACN-HCOOH): Rt.=0.50 min
MS (ES$^+$): m/e=479.4 (M+H$^+$)

$^1$H-NMR (400 MHz, DMSO$_{d6}$): δ=1.13-1.29 (m, 2 H), 1.35-1.77 (m, 7 H), 1.88 (d, 1 H), 2.00 (m, 1 H), 2.21-2.43 (m, 4 H), 2.50-2.78 (m, 3 H), 2.96-3.11 (m, 1 H), 3.15 (d, 1 H), 3.28 (d, 1 H), 3.64 (br., 4 H), 4.30 (ddd, 2 H), 4.75 (ddd, 2 H), 5.09 (m, 1 H), 7.27 (s, 1 H), 8.10 (s, 1 H), 8.16 (s, 1 H), 8.53 (d, 1 H) ppm.

Example 4

(3S)-3-(3-{2-[2-(2-Fluoroethoxy)ethoxy]ethoxy}phenyl)-3-[({(3R)-1-[3-(piperidin-4-yl)propanoyl]piperidin-3-yl}carbonyl)amino]propanoic acid

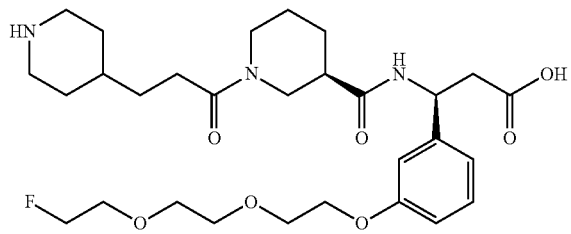

Example 4a

Tert-butyl {[3-(benzyloxy)phenyl](phenylsulfonyl)methyl}carbamate

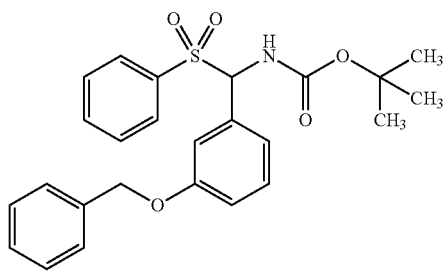 [SMILES: CC(C)(C)OC(=O)NC(c1cccc(OCc2ccccc2)c1)S(=O)(=O)c1ccccc1]

To 3-(benzyloxy)benzaldehyde (5 g, 23.6 mmol) and benzenesulfinic acid sodium salt (3.9 g, 23.6 mmol) in THF (23 mL) was added water (51.5 mL), tert-butyl carbamate (2.76 g, 23.6 mmol) and formic acid (2.66 mL, 70 mmol). The mixture was stirred for 4 day and filtrated. The precipitate was washed with water and triturated in hexane containing 9% dichloromethane. After filtration the solids were dried in vacuum to yield 7.24 g of tert-butyl {[3-(benzyloxy)phenyl](phenylsulfonyl)methyl}carbamate.

$^1$H-NMR (400 MHz, CDCl$_3$): δ=1.27 (s, 9 H), 5.07 (s, 2 H), 5.73 (d, 1 H), 5.90 (d, 1 H), 6.94-7.14 (m, 3 H), 7.30-7.49 (m, 6 H), 7.55 (t, 2 H), 7.65 (t, 1 H), 7.92 (d, 2 H) ppm.

Example 4b

Tert-butyl methyl 2-{(S)-[3-(benzyloxy)phenyl][(tert-butoxycarbonyl)amino]methyl}propanedioate

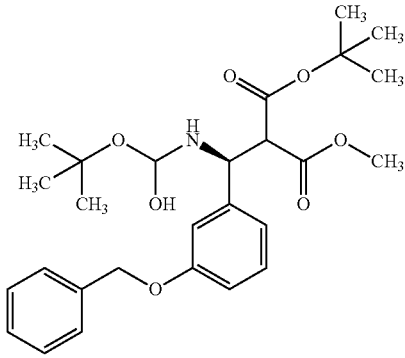 [SMILES: COC(=O)C(C(=O)OC(C)(C)C)[C@H](NC(O)OC(C)(C)C)c1cccc(OCc2ccccc2)c1]

Tert-butyl {[3-(benzyloxy)phenyl](phenylsulfonyl)methyl}carbamate (3.0 g, 5.93 mmol) was suspended in a toluene (21.6 mL) water (16 mL) mixture. At 0° C. tert-butyl methyl malonate (1.2 mL, 7.1 mmol), cesium carbonate (1.94 g, 5.9 mmol) and 1-[3,5-bis(trifluoromethyl)phenyl]-3-[(1R,2R)-(−)-2-(dimethylamino)cyclohexyl]thiourea (246 mg, 0.59 mmol) was added and the mixture was stirred for 72 hours at 0° C. After storage at −20° C. for 72 hours the mixture was diluted with water and ethyl acetate, after filtration the phases were separated and the aqueous phase extracted with ethyl acetate. The combined extracts were dried over sodium sulfate and concentrated. The residue was purified by chromatography on silica gel (ethyl acetate in hexane 0 to 35%) to yield 2.17 g of enantiomerically enriched tert-butyl methyl 2-{(S)-[3-(benzyloxy)phenyl][(tert-butoxycarbonyl)amino]methyl}propanedioate.

$^1$H-NMR (400 MHz, CDCl$_3$): δ=1.20 (s, 4.5 H), 1.36 (s, 9 H), 1.41 (s, 4.5 H), 3.04 (br., 3 H), 3.47 (s, 1.5 H), 3.66 (s, 1.5 H), 3.88 (m, 1 H), 5.09 (s, 2 H), 5.06-5.11 (m, 1H), 6.85-6.93 (m, 2 H), 7.02 (m, 1 H), 7.21 (m, 1 H), 7.28-7.46 (m, 5 H) ppm.

Example 4c

Tert-butyl methyl 2-[(S)-[3-(benzyloxy)phenyl]({[(3R)-1-{3-[1-(tert-butoxycarbonyl)piperidin-4-yl]propanoyl}piperidin-3-yl]carbonyl}amino)methyl]propanedioate

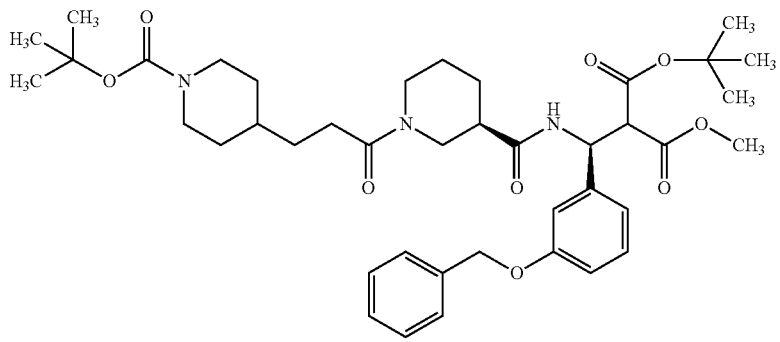 [SMILES: COC(=O)C(C(=O)OC(C)(C)C)[C@H](NC(=O)[C@@H]1CCCN(C(=O)CCC2CCN(C(=O)OC(C)(C)C)CC2)C1)c1cccc(OCc2ccccc2)c1]

To tert-butyl methyl 2-{(S)-[3-(benzyloxy)phenyl][(tert-butoxycarbonyl)amino]methyl}propanedioate (600 mg, 1.24 mmol) was added 0° C. cold formic acid (13.8 mL) and the solution was stored at 5° C. for 20 hours. Ice was added and pH was adjusted to 8 by addition of aqueous sodium hydrogen carbonate solution. The aqueous phase was extracted with ethyl acetate. The combined extracts were washed with aqueous sodium hydrogen carbonate solution and brine and dried over sodium sulfate. Concentration under reduced pressure yields 390 mg of raw tert-butyl methyl 2-{(S)-amino[3-(benzyloxy)phenyl]methyl}propanedioate. (3R)-1-{3-[1-(Tert-butoxycarbonyl)piperidin-4-yl]propanoyl}piperidine-3-carboxylic acid (447 mg, 1.21 mmol) were suspended in N,N-dimethylformamide (14 mL) and cooled to 0° C. HATU (646 mg, 1.7 mmol), a solution of the raw tert-butyl methyl 2-{(S)-amino[3-(benzyloxy)phenyl]methyl}propanedioate (780 mg, 1.21 mmol) in N,N-dimethylformamide (14 mL) and N-ethyl-diisopropylamine (350 µL, 3.64 mmol) were added. The mixture was stirred at 0° C. for 2 hours. Ice water and saturated ammonium chloride solution was added, the mixture extracted with ethyl acetate and dried over sodium sulfate. The solution was concentrated under reduced pressure and the residue was purified by chromatography on an amino phase column (Separtis® Flash-NH2, ethyl acetate in hexane 0 to 100%) to yield 700 mg of tert-butyl methyl-[(S)-[3-(benzyloxy)phenyl]({[(3R)-1-{3-[1-(tert-butoxycarbonyl)piperidin-4-yl]propanoyl}piperidin-3-yl]carbonyl}amino)methyl]propanedioate.

UPLC (ACN-HCOOH): Rt.=1.53 min
MS (ES$^+$): m/e=736.68 (M+H$^+$)
MS (ES$^-$): m/e=780.82 (M+HCOO$^-$)

Example 4d

Tert-butyl 4-{3-[(3R)-3-({(1S)-1-[3-(benzyloxy)phenyl]-3-methoxy-3-oxopropyl}carbamoyl)piperidin-1-yl]-3-oxopropyl}piperidine-1-carboxylate

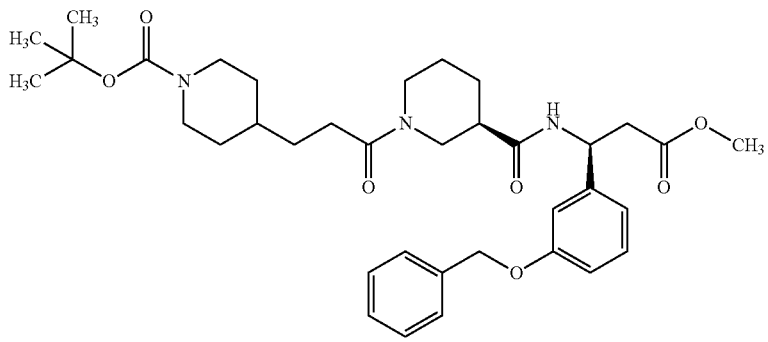 [SMILES: COC(=O)C[C@H](NC(=O)[C@@H]1CCCN(C(=O)CCC2CCN(C(=O)OC(C)(C)C)CC2)C1)c1cccc(OCc2ccccc2)c1]

Tert-butyl methyl 2-[(S)-[3-(benzyloxy)phenyl]({[(3R)-1-{3-[1-(tert-butoxycarbonyl)piperidin-4-yl]propanoyl}piperidin-3-yl]carbonyl}amino)methyl]propanedioate (700 mg, 0.95 mmol) was solved in formic acid (5.4 mL) and stored for 5 days at room temperature. The mixture was concentrated under reduced pressure to yield 640 g of raw (3S)-3-[3-(benzyloxy)phenyl]-2-(methoxycarbonyl)-3-[({(3R)-1-[3-(piperidin-4-yl)propanoyl]piperidin-3-yl}carbonyl)amino]propanoic acid. The methyl ester in THF (65 mL) and triethylamine (2.5 mL, 18 mmol) was heated to 60° C. for 4 hours. After concentration under reduced pressure the residue was purified by preparative HPLC to yield 147 mg of methyl (3S)-3-[3-(benzyloxy)phenyl]-3-[({(3R)-1-[3-(piperidin-4-yl)propanoyl]piperidin-3-yl}carbonyl)amino]propanoate.

| | |
|---|---|
| Column: | C18 Chromatorex 10 µm 30 × 125 mm |
| Solvent: | A = H2O + 0.1% HCOOH |
| | B = acetonitrile |
| Gradient: | 0-0.5 min 1% B, 0.5-10 min 1-60% B, |
| Flow: | 65 mL/min |
| Temperature: | RT |
| Detection: | 277 nm |
| Rt.: | 7.09-7.40 min |

To the free piperidine in dichloromethane (1.5 mL) and triethylamine (0.11 mL) was added di-tert-butyl dicarbonate (90 µL, 0.38 mmol) and the mixture was stirred for 2 hours to yield 159 mg of tert-butyl 4-{3-[(3R)-3-({(1S)-1-[3-(benzyloxy)phenyl]-3-methoxy-3-oxopropyl}carbamoyl)piperidin-1-yl]-3-oxopropyl}piperidine-1-carboxylate after concentration in vacuum.

UPLC (ACN-HCOOH): Rt.=1.41 min
MS (ES$^+$): m/e=636.59 (M+H$^+$)
MS (ES$^-$): m/e=680.44 (M+HCOO$^-$)

Example 4e

Tert-butyl 4-{3-[(3R)-3-({(1S)-1-[3-hydroxyphenyl]-3-methoxy-3-oxopropyl}carbamoyl)piperidin-1-yl]-3-oxopropyl}piperidine-1-carboxylate

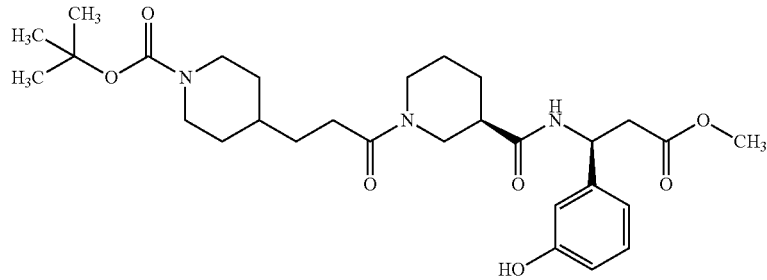 [SMILES: COC(=O)C[C@H](NC(=O)[C@@H]1CCCN(C(=O)CCC2CCN(C(=O)OC(C)(C)C)CC2)C1)c1cccc(O)c1]

Tert-butyl 4-{3-[(3R)-3-({(1S)-1-[3-(benzyloxy)phenyl]-3-methoxy-3-oxopropyl}carbamoyl)piperidin-1-yl]-3-oxopropyl}piperidine-1-carboxylate (650 mg, 1.02 mmol) was dissolved in ethyl acetate (45 mL) and methanol (7.4 mL) and palladium on charcoal (65 mg, 10%) was added. The mixture was shaken under a hydrogen atmosphere for 16 hours filtrated through celite which were washed with methanol. The filtrate was concentrated and purified by chromatography on silica gel (methanol in ethyl acetate 0% to 25%) to yield 422 mg of tert-butyl-4-{3-[(3R)-3-{[(1S)-1-(3-hydroxyphenyl)-3-methoxy-3-oxopropyl]carbamoyl}piperidin-1-yl]-3-oxopropyl}piperidine-1-carboxylate.

$^1$H-NMR (400 MHz, DMSO$_{d6}$, at 80° C.): δ=1.01 (m, 2 H), 1.26-1.53 (m, 4 H), 1.41 (s, 9 H), 1.65 (m, 4 H), 1.83 (m, 1 H), 2.23-2.38 (m, 3 H), 2.65-2.76 (m, 5 H), 3.57 (s, 3 H), 3.92 (m, 3 H), 5.19 (q, 1 H), 6.64 (d, 1 H), 6.72 (m, 2 H), 7.09 (t, 1 H), 8.05 (d, 1 H), 9.04 (br., 1 H) ppm UPLC (ACN-HCOOH): Rt.=1.14 min
MS (ES$^+$): m/e=546.53 (M+H$^+$)
MS (ES$^-$): m/e=590.43 (M+HCOO$^-$)

Example 4f

Tert-butyl-4-{3-[(3R)-3-{[(1S)-1-(3-{2-[2-(2-fluoroethoxy)ethoxy]ethoxy}phenyl)-3-methoxy-3-oxopropyl]carbamoyl}piperidin-1-yl]-3-oxopropyl}piperidine-1-carboxylate

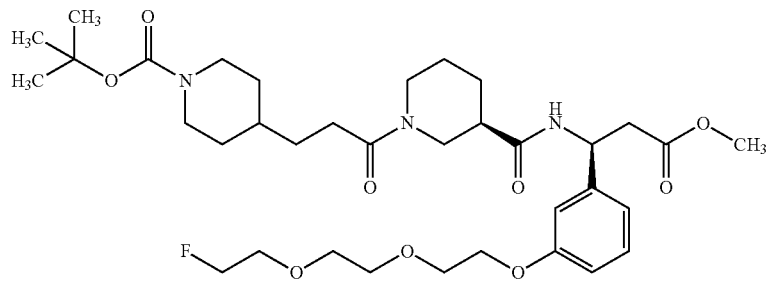 [SMILES: COC(=O)C[C@H](NC(=O)[C@@H]1CCCN(C(=O)CCC2CCN(C(=O)OC(C)(C)C)CC2)C1)c1cccc(OCCOCCOCCF)c1]

To tert-butyl-4-{3-[(3R)-3-{[(1S)-1-(3-hydroxyphenyl)-3-methoxy-3-oxopropyl]carbamoyl}piperidin-1-yl]-3-oxopropyl}piperidine-1-carboxylate (26 mg, 50 μmol) in DMF (6.6 mL) was added cesium carbonate (38.8 mg, 120 μmol) and 2-[2-(2-fluoroethoxy)ethoxy]ethyl 4-methylbenzenesulfonate (22 mg, 70 μmol) while stirring at room temperature. After 5 hours toluene was added and the mixture was concentrated in vacuum. The DMF free residue was purified by preparative thin layer chromatography on silica gel (dichloromethane in ethyl acetate 30%) to yield 21 mg of tert-butyl 4-{3-[(3R)-3-{[(1S)-1-(3-{2-[2-(2-fluoroethoxy)ethoxy]ethoxy}phenyl)-3-methoxy-3-oxopropyl]carbamoyl}piperidin-1-yl]-3-oxopropyl}piperidine-1-carboxylate.

$^1$H-NMR (400 MHz, DMSO$_{d6}$, at 80° C.): δ=1.02 (m, 2 H), 1.25-1.51 (m, 5 H), 1.41 (s, 9 H), 1.55-1.70 (m, 4 H), 1.82 (m, 1 H), 2.26-2.38 (m, 3 H), 2.73-2.81 (m, 4 H), 3.40 (m, 1 H), 3.56-3.65 (m, 5 H), 3.58 (s, 3 H), 3.69-3.74 (m, 1 H), 3.74-3.81 (m, 2 H), 3.91 (br., 2 H), 4.06-4.14 (m, 2 H) 4.50 (ddd, 2 H), 5.21 (q, 1 H), 6.82 (dd, 1 H), 6.85-6.96 (m, 2 H), 7.21 (t, 1 H), 8.08 (d, 1 H) ppm.

UPLC (ACN-HCOOH): Rt.=1.26 min
MS (ES$^+$): m/e=680.54 (M+H$^+$)
MS (ES$^-$): m/e=724.50 (M+HCOO$^-$)

Example 4 g (3S)-3-(3-{2-[2-(2-Fluoroethoxy)ethoxy]ethoxy}phenyl)-3-[({(3R)-1-[3-(piperidin-4-yl)propanoyl]piperidin-3-yl}carbonyl)amino]propanoic acid Tert-butyl 4-{3-[(3R)-3-{[(1S)-1-(3-{2-[2-(2-fluoroethoxy)ethoxy]ethoxy}phenyl)-3-methoxy-3-oxopropyl]carbamoyl}piperidin-1-yl]-3-oxopropyl}piperidine-1-carboxylate (20.3 mg, 27 μmol) was solved in tert.-butanol (0.77 mL) and methanol (0.76 mL) and barium hydroxide octahydrate (42 mg, 0.13 mmol) was added. After stirring for 60 minutes room temperature the solvent was distilled off at 0° C. by high vacuum. The residue was solved in water (1 mL) and acidified by formic acid (2 mL). After 18 hours at 5° C. additional formic acid (2 mL) was added. After 3 hours at room temperature the solvent was distilled off at 0° C. by high vacuum and the residue was purified by preparative HPLC to yield 8.4 mg of (3S)-3-(3-{2-[2-(2-fluoroethoxy)ethoxy]ethoxy}phenyl)-3-[({(3R)-1-[3-(piperidin-4-yl)propanoyl]piperidin-3-yl}carbonyl)amino]propanoic acid.

| Column: | C18 Chromatorex 10 μm 30 × 125 mm |
|---|---|
| Solvent: | A = H2O + 0.1% HCOOH |
| | B = acetonitrile |
| Gradient: | 0-0.5 min 15% B, 0.5-10 min 15-70% B, |
| Flow: | 65 mL/min |
| Temperature: | RT |
| Detection: | 285 nm |
| Rt.: | 3.48-4.19 min |

UPLC (ACN-HCOOH): Rt.=0.69 min
MS (ES$^+$): m/e=566.41 (M+H$^+$)
MS (ES$^-$): m/e=564.37 (M–H)

Example 5

(3S)-3-(5-{2-[2-(2-Fluoroethoxy)ethoxy]ethoxy}pyridine-3-yl)-3-[({(3R)-1-[3-(piperidin-4-yl)propanoyl]piperidin-3-yl}carbonyl)amino]propanoic acid

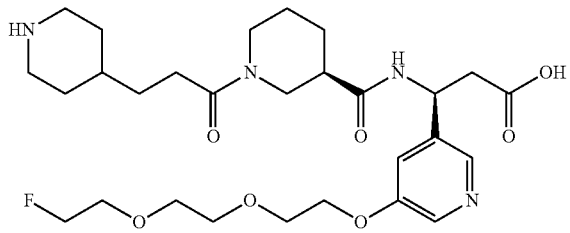

Example 5a

Tert-butyl {[5-(benzyloxy)pyridin-3-yl](phenylsulfonyl)methyl}carbamate

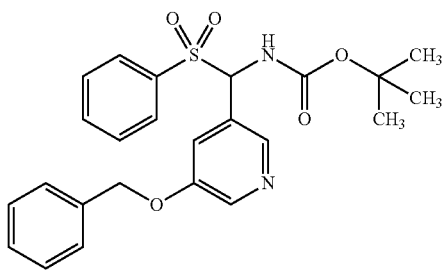 [SMILES: CC(C)(C)OC(=O)NC(c1cncc(OCc2ccccc2)c1)S(=O)(=O)c1ccccc1]

To 5-(Benzyloxy)pyridine-3-carbaldehyde (3.61 g, 16.9 mmol, Harrowven, D. C. et al *Tetrahedron*, 2001 57 p. 4447-4454) and benzenesulfinic acid sodium salt (2.7 g, 16.6 mmol) in THF (16.3 mL) was added water (36.3 mL), tert-butyl carbamate (1.94 g, 16.6 mmol) and formic acid (1.9 mL, 49 mmol). The mixture was stirred for 4 day and filtrated. The filtrate was stirred for 2 additional days and filtrated again. The formed precipitates were washed with water and triturated in hexane containing 9% dichloromethane. After filtration the solids were dried in vacuum to yield 3.17 g of tert-butyl {[5-(benzyloxy)pyridin-3-yl](phenylsulfonyl)methyl}carbamate.
$^1$H-NMR (400 MHz, CDCl$_3$): δ=1.27 (s, 9 H), 5.13 (s, 2 H), 5.83 (d, 1 H), 5.97 (d, 1 H), 7.32-7.50 (m, 6 H), 7.53-7.63 (m, 2 H), 7.68 (t, 1 H), 7.93 (d, 2 H), 8.27 (s, 1 H), 8.44 (d, 1 H) ppm.

Example 5b

Tert-butyl methyl 2-{(S)-[5-(benzyloxy)pyridin-3-yl][(tert-butoxycarbonyl)amino]methyl}propanedioate

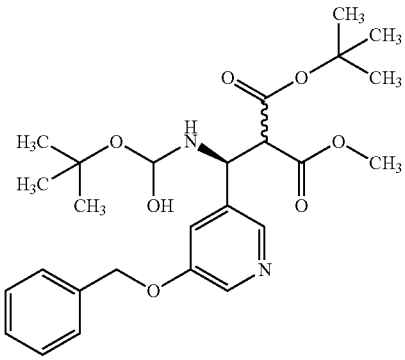 [SMILES: COC(=O)C(C(=O)OC(C)(C)C)[C@H](NC(O)OC(C)(C)C)c1cncc(OCc2ccccc2)c1]

Tert-butyl {[5-(benzyloxy)pyridin-3-yl](phenylsulfonyl)methyl}carbamate (2.2 g, 4.84 mmol) was suspended in a toluene (16.5 ML) water (13 mL) mixture. At 0° C. tert-butyl methyl malonate (1.0 mL, 5.8 mmol), cesium carbonate (1.58 g, 4.84 mmol) and 1-[3,5-bis(trifluoromethy)phenyl]-3-[(1R,2R)-(–)-2-(dimethylamino)cyclohexyl]thiourea (200 mg, 0.48 mmol) was added and the mixture was stirred for 48 hours at 0° C. After storage at 5° C. for 72 hours the mixture was diluted with water and ethyl acetate, the phases were separated and the aqueous phase extracted with ethyl acetate. The combined extracts were dried over sodium sulfate and concentrated. The residue was purified by chromatography on silica gel (ethyl acetate in hexane 0% to 60%) to yield 1.54 g of enantiomerically enriched tert-butyl methyl 2-{(S)-[5-(benzyloxy)pyridin-3-yl][(tert-butoxycarbonyl)amino]methyl}propanedioate.
$^1$H-NMR (300 MHz, CDCl$_3$): δ=1.36 (s, 4.5 H), 1.43 (s, 9 H), 1.48 (s, 4.5 H), 3.65 (s, 1.5 H), 3.76-3.87 (m, 1H), 3.77 (s, 1.5 H), 5.10 (s, 2 H), 5.48 (br., 1 H), 6.27 (br., 1 H), 7.26 (s, 1 H), 7.35-7.44 (m, 5 H), 8.21 (d, 1 H), 8.28 (s, 1 H) ppm.

Example 5c

Tert-butyl 4-{3-[(3R)-3-{[(2,5-dioxopyrrolidin-1-yl)oxy]carbonyl}piperidin-1-yl]-3-oxopropyl}piperidine-1-carboxylate

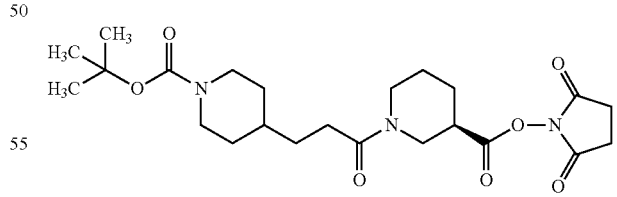

To (3R)-1-{3-[1-(tert-butoxycarbonyl)piperidin-4-yl]propanoyl}piperidine-3-carboxylic acid (1.91 g, 5.18 mmol) in 1,2-dimethoxyethane (13.5 mL) was added N-hydroxysuccinimide (0.60 g, 5.18 mmol) and 1,3-dicyclohexyl carbodiimide (1.18 g, 5.7 mmol). The solution was stirred for 4 hours at room temperature while a precipitate formed. The mixture was then cooled to 0° C. filtrated and the solid washed with diethyl ether. The filtrate and the diethyl ether wash were combined and concentrated to yield 2.61 g of raw tert-butyl 4-{3-[(3R)-3-{[(2,5-dioxopyrrolidin-1-yl)oxy]carbonyl}piperidin-1-yl]-3-oxopropyl}piperidine-1-carboxylate.
UPLC (ACN-HCOOH): Rt.=1.13 min
MS (ES$^+$): m/e=466.31 (M+H$^+$)

Example 5d

Tert-butyl 4-{3-[(3R)-3-({(1S)-1-[5-(benzyloxy)pyridin-3-yl]-3-methoxy-3-oxopropyl}carbamoyl)piperidin-1-yl]-3-oxopropyl}piperidine-1-carboxylate

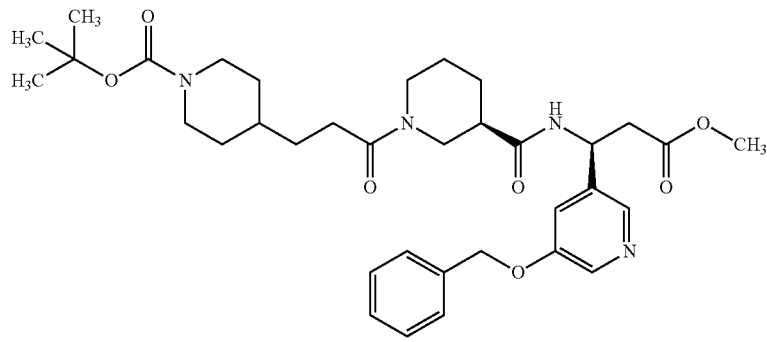 [SMILES: COC(=O)C[C@H](NC(=O)[C@@H]1CCCN(C(=O)CCC2CCN(C(=O)OC(C)(C)C)CC2)C1)c1cncc(OCc2ccccc2)c1]

To tert-butyl methyl 2-{(S)-[5-(benzyloxy)pyridin-3-yl][(tert-butoxycarbonyl)amino]methyl}propanedioate in dioxane (15 mL) was added a 4 M solution of hydrochloric acid in dioxane (11.2 mL, 45 mmol) and stirred for 20 hours. The mixture was diluted with dioxane and toluene and concentrated under reduced pressure. The dilution and concentration procedure was repeated with toluene and dichloromethane to yield 1.64 g of raw 2-[(S)-amino-(5-benzyloxy)pyridin-3-yl)methyl]malonic acid monomethyl ester. The monomethyl ester was cooled to 0° C. in DMF (18 mL) and a solution of tert-butyl 4-{3-[(3R)-3-{[(2,5-dioxopyrrolidin-1-yl)oxy]carbonyl}piperidin-1-yl]-3-oxopropyl}piperidine-1-carboxylate (3.0 g, 5.15 mmol) and triethylamine (1.94 mL, 13.9 mmol) in dichloromethane (18 mL). The mixture was stirred at 0° C. for 21 hours and then heated to 60° C. for one hour. After cooling to room temperature saturated aqueous ammonium chloride solution was added. Phases were separated and the aqueous phase was extracted with diethyl ether and ethyl acetate. The combined extracts were dried over sodium sulfate and concentrated in vacuum. The residue was purified by chromatography on silica gel (methanol in ethyl acetate 0% to 15%) to yield 1.4 g of tert-butyl 4-{3-[(3R)-3-({(1S)-1-[5-(benzyloxy)pyridin-3-yl]-3-methoxy-3-oxopropyl}carbamoyl)piperidin-1-yl]-3-oxopropyl}piperidine-1-carboxylate.

UPLC (ACN-HCOOH): Rt.=1.25 min

MS (ES$^+$): m/e=637.6 (M+H$^+$)
MS (ES$^-$): m/e=681.5 (M+HCOO$^-$)

Example 5e

Tert-butyl 4-{3-[(3R)-3-({(1S)-1-[5-(hydroxy)pyridin-3-yl]-3-methoxy-3-oxopropyl}carbamoyl)piperidin-1-yl]-3-oxopropyl}piperidine-1-carboxylate

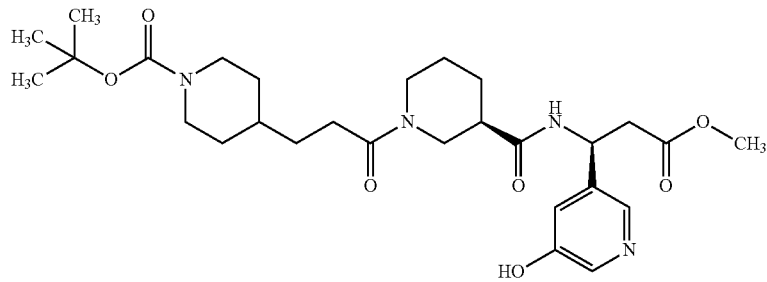

Tert-butyl 4-{3-[(3R)-3-({(1S)-1-[5-(benzyloxy)pyridin-3-yl]-3-methoxy-3-oxopropyl}carbamoyl)piperidin-1-yl]-3-oxopropyl}piperidine-1-carboxylate (650 mg, 1.02 mmol) was dissolved in ethyl acetate (45 mL) and methanol (7.4 mL) and palladium on charcoal (65 mg, 10%) was added. The mixture was shaken under a hydrogen atmosphere for 16 hours filtrated through celite which were washed with methanol. The filtrate was concentrated and purified by chromatography on silica gel (methanol in ethyl acetate 0% to 25%) to yield 422 mg of tert-butyl-4-{3-[(3R)-3-{[(1S)-1-(5-hydroxypyridin-3-yl)-3-methoxy-3-oxopropyl]carbamoyl}piperidin-1-yl]-3-oxopropyl}piperidine-1-carboxylate.

$^1$H-NMR (400 MHz, DMSO$_{d6}$, at 80° C.): δ=1.00 (m, 2 H), 1.26-1.55 (m, 4 H), 1.40 (s, 9 H), 1.65 (m, 4 H), 1.83 (m, 1 H), 2.17-2.40 (m, 3 H), 2.63-2.74 (m, 2 H), 2.75-2.90 (m,

3 H), 3.58 (s, 3 H), 3.90 (m, 3 H), 5.19 (m, 1 H), 7.08 (d, 1 H), 7.94-8.07 (m, 2 H), 8.16 (d, 1 H), 9.57 (br., 1 H) ppm.
UPLC (ACN-HCOOH): Rt.=0.95 min
MS (ES+): m/e=547.4 (M+H+)

Example 5f

Tert-butyl-4-{3-[(3R)-3-{[(1S)-1-(5-{2-[2-(2-fluoroethoxy)ethoxy]ethoxy}pyridin-3-yl)-3-methoxy-3-oxopropyl]carbamoyl}piperidin-1-yl]-3-oxopropyl}piperidine-1-carboxylate

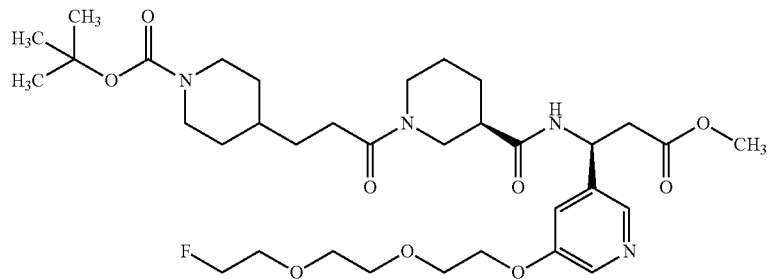 [SMILES: COC(=O)C[C@H](NC(=O)[C@@H]1CCCN(C(=O)CCC2CCN(C(=O)OC(C)(C)C)CC2)C1)c1cncc(OCCOCCOCCF)c1]

To tert-butyl-4-{3-[(3R)-3-{[(1S)-1-(5-hydroxypyridin-3-yl)-3-methoxy-3-oxopropyl]carbamoyl}piperidin-1-yl]-3-oxopropyl}piperidine-1-carboxylate (30 mg, 60 µmol) in DMF (7.6 mL) was added cesium carbonate (44.7 mg, 140 µmol) and 2-[2-(2-fluoroethoxy)ethoxy]ethyl 4-methylbenzenesulfonate (25 mg, 80 µmol) while stirring at room temperature. After 5 hours toluene was added and the mixture was concentrated in vacuum. The DMF free residue was purified by preparative thin layer chromatography on silica gel (ethyl acetate) to yield 16.7 mg of tert-butyl 4-{3-[(3R)-3-{[(1S)-1-(5-{2-[2-(2-fluoroethoxy)ethoxy]ethoxy}pyridin-3-yl)-3-methoxy-3-oxopropyl]carbamoyl}piperidin-1-yl]-3-oxopropyl}piperidine-1-carboxylate.
1H-NMR (400 MHz, MeOD): δ=1.00-1.19 (m, 2 H), 1.40-1.60 (m, 5 H), 1.45 (s, 9 H), 1.73 (m, 4 H), 1.94 (m, 1 H), 2.27-2.54 (m, 3 H), 2.73 (br., 2 H), 2.91 (m, 3 H), 3.66 (s, 3 H), 3.64-3.72 (m, 7 H), 3.87 (m, 2 H), 4.06 (br., 3 H), 4.23 (m, 2 H), 4.50 (ddd, 2 H), 5.36 (t, 1 H), 7.41 (dd, 1 H), 8.17 (d, 1 H), 8.13 (d, 1 H) ppm.
UPLC (ACN-HCOOH): Rt.=1.10 min
MS (ES+): m/e=681.3 (M+H+)
MS (ES−): m/e=725.5 (M+HCOO−)

Example 5 g (3S)-3-(5-{2-[2-(2-fluoroethoxy)ethoxy]ethoxy}pyridin-3-yl)-3-[({(3R)-1-[3-(piperidin-4-yl)propanoyl]piperidin-3-yl}carbonyl)amino]propanoic acid Tert-butyl 4-{3-[(3R)-3-{[(1S)-1-(5-{2-[2-(2-fluoroethoxy)ethoxy]ethoxy}pyridin-3-yl)-3-methoxy-3-oxopropyl]carbamoyl}piperidin-1-yl]-3-oxopropyl}piperidine-1-carboxylate (16.5 mg, 22 µmol) as solved in tert.-butanol (0.62 mL) and methanol (0.6 mL) and barium hydroxide octahydrate (34 mg, 315 µmol) was added. After stirring for 45 minutes room temperature the solvent was distilled off at 0° C. by high vacuum. The residue was solved in water (0.3 mL) and acidified by formic acid (0.9 mL). After 18 hours at 5° C. the solvent was distilled off at 0° C. by high vacuum and the residue was purified by preparative HPLC to yield 1.6 mg of (3R)-3-(5-{2-[2-(2-fluoroethoxy)ethoxy]ethoxy}pyridin-3-yl)-3-[({(3S)-1-[3-(piperidin-4-yl)propanoyl]piperidin-3-yl}carbonyl)amino]propanoic acid.

| Column: | C18 Chromatorex 10 µm 30 × 125 mm |
|---|---|
| Solvent: | A = H2O + 0.1% HCOOH |
| | B = acetonitrile |
| Gradient: | 0-0.5 min 5% B, 0.5-6 min 5-40% B, |
| Flow: | 150 mL/min |

-continued

| Temperature: | RT |
|---|---|
| Detection: | 285 nm |
| Rt: | 2.36-2.45 min |

UPLC (ACN-HCOOH): Rt.=0.55 min
MS (ES+): m/e=567.4 (M+H+)
MS (ES−): m/e=565.4 (M−H),

Example 6

(3S)-3-{5-[3-(2-Fluoroethoxy)phenyl]pyridin-3-yl}-3-[({(3R)-1-[3-(piperidin-4-yl)propanoyl]piperidin-3-yl}carbonyl)amino]propanoic acid

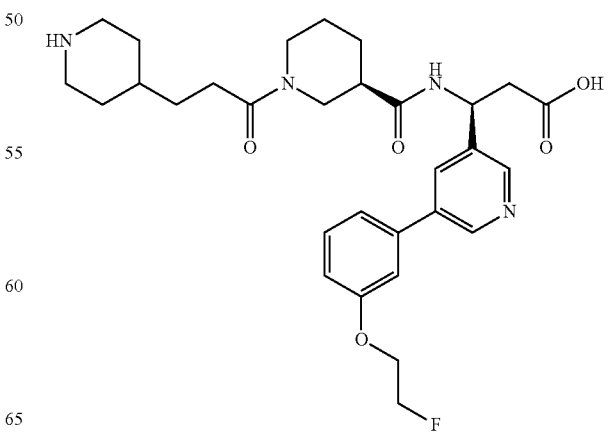

Example 6a

Tert-butyl 4-{3-[(3R)-3-({1-[5-(3-hydroxyphenyl)pyridin-3-yl]-3-methoxy-3-oxopropyl}carbamoyl)piperidin-1-yl]-3-oxopropyl}piperidine-1-carboxylate

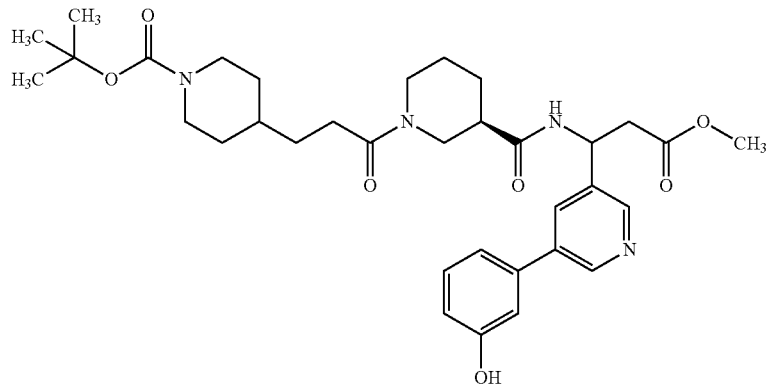 [SMILES: COC(=O)CC(NC(=O)[C@@H]1CCCN(C(=O)CCC2CCN(C(=O)OC(C)(C)C)CC2)C1)c1cncc(-c2cccc(O)c2)c1]

To 400.0 mg (0.66 mmol) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate (example 8c) in 16 ml toluene were added 15.17 mg (0.01 mmol) tetrakis(triphenylphosphine)palladium(0), 108.6 mg (0.79 mmol) (3-hydroxyphenyl)boronic acid in 4.0 ml ethanol and 118.3 mg (2.04 mmol) potassium fluoride in 4.0 ml water. The mixture was stirred at 100° C. for 26 hours, diluted with water and extracted with ethyl acetate. The organic phase was dried over sodium sulfate and concentrated in vacuum. Chromatography over 10 g silica gel (dichloromethane/ethanol 100/0-95/5-90/10) gave 236 mg (58%) tert-butyl 4-{3-[(3R)-3-({1-[5-(3-hydroxyphenyl)pyridin-3-yl]-3-m ethoxy-3-oxopropyl}carbamoyl)piperidin-1-yl]-3-oxopropyl}piperidine-1-carboxylate.

UPLC (ACN-HCOOH): Rt=1.10 min
MS (ES$^+$): m/e=624.70 (M+H$^+$)
MS (ES$^-$): m/e=621.46 (M−H), 667.57 (M+HCOO$^-$)

Example 6b

Tert-butyl 4-{3-[(3R)-3-{[1-{5-[3-(2-fluoroethoxy)phenyl]pyridin-3-yl}-3-methoxy-3-oxopropyl]carbamoyl}piperidin-1-yl]-3-oxopropyl}piperidine-1-carboxylate

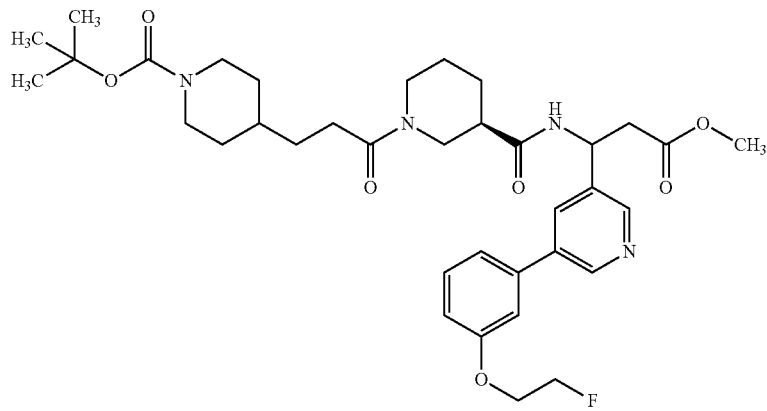 [SMILES: COC(=O)CC(NC(=O)[C@@H]1CCCN(C(=O)CCC2CCN(C(=O)OC(C)(C)C)CC2)C1)c1cncc(-c2cccc(OCCF)c2)c1]

128 mg (0.21 mmol) tert-butyl 4-{3-[(3R)-3-({1-[5-(3-hydroxyphenyl)pyridin-3-yl]-3-methoxy-3-oxopropyl}carbamoyl)piperidin-1-yl]-3-oxopropyl}piperidine-1-carboxylate were dissolved in 2.25 ml tetrahydrofurane. 134 mg (0.41 mmol) cesium carbonate and 68 mg (0.39 mmol) 1-iodo-2-fluoroethane were added. The mixture was stirred at room temperature for 70 hours. 68 mg (0.39 mmol) 1-iodo-2-fluoroethane were added and the mixture stirred at room temperature for 48 hours. 68 mg (0.39 mmol) 1-iodo-2-fluoroethane were added and the mixture stirred at room temperature for 70 hours. 68 mg (0.39 mmol) 1-iodo-2-fluoroethane were added and the mixture stirred at room temperature for 24 hours. 68 mg (0.39 mmol) 1-iodo-2-fluoroethane, 2 ml tetrahydrofurane and 134 mg (0.41 mmol) cesium carbonate were added and the mixture stirred at room temperature for 24 hours. 68 mg (0.39 mmol) 1-iodo-2-fluoroethane were added and the mixture stirred at room temperature for 24 hours. 68 mg (0.39 mmol) 1-iodo-2-fluoroethane were added and the mixture stirred at room temperature for 24 hours. 68 mg (0.39 mmol) 1-iodo-2-fluoroethane were added and the mixture stirred at room temperature for 70 hours, diluted with water and extracted with ethyl acetate. The organic phase was dried over sodium sulfate and concentrated in vacuum. Chromatography over 10 g silica gel (dichloromethane/ethanol 100/0-90/10) gave 100 mg (65%) tert-butyl 4-{3-[(3R)-3-{[1-{5-[3-(2-fluoroethoxy)phenyl]pyridin-3-yl}-3-methoxy-3-oxopropyl]carbamoyl}piperidin-1-yl]-3-oxopropyl}piperidine-1-carboxylate.

UPLC (ACN-HCOOH): Rt.=1.20 min
MS (ES+): m/e=669.3 (M+H+)
MS (ES−): m/e=713.5 (M+HCOO−)

Example 6c 3-({[(3R)-1-{3-[1-(Tert-butoxycarbonyl)piperidin-4-yl]propanoyl}piperidin-3-yl]carbonyl}amino)-3-{5-[3-(2-fluoroethoxy)phenyl]pyridin-3-yl}propanoic acid

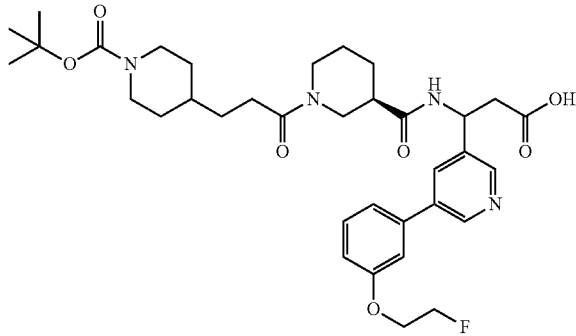 [SMILES: CC(C)(C)OC(=O)N1CCC(CCC(=O)N2CCC[C@@H](C(=O)NC(CC(=O)O)c3cncc(-c4cccc(OCCF)c4)c3)C2)CC1]

95 mg (0.14 mmol) Tert-butyl 4-{3-[(3R)-3-{[1-{5-[3-(2-fluoroethoxy)phenyl]pyridin-3-yl}-3-methoxy-3-oxopropyl]carbamoyl}piperidin-1-yl]-3-oxopropyl}piperidine-1-carboxylate were dissolved in 17 ml methanol. 448 mg (1.42 mmol) barium hydroxide octahydrate were added. The mixture was stirred at room temperature for 20 hours and then concentrated to give 3-({[(3R)-1-{3-[1-(tert-butoxycarbonyl)piperidin-4-yl]propanoyl}piperidin-3-yl]carbonyl}amino)-3-{5-[3-(2-fluoroethoxy)phenyl]pyridin-3-yl}propanoic acid.

UPLC (ACN-HCOOH): Rt.=1.12 min
MS (ES+): m/e=655.5 (M+H+)
MS (ES−): m/e=653.6 (M−H)

Example 6d (3S)-3-{5-[3-(2-Fluoroethoxy)phenyl]pyridin-3-yl}-3-{[(3R)-1-(3-piperidin-4-yl-propionyl)piperidine-3-carbonyl]amino}propionic acid

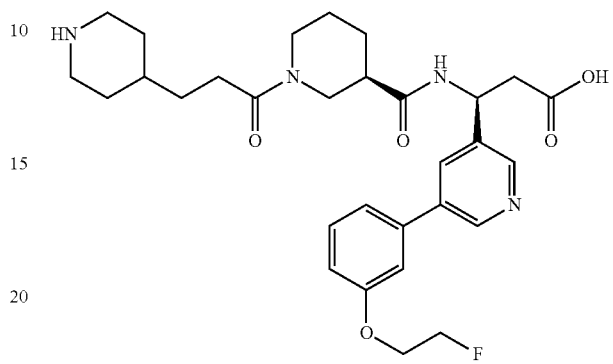

The mixture obtained in example 9c containing 93 mg (0.14 mmol) 4-{3-[(R)-3-(2-carboxy-1-{5-[3-(2-fluoroethoxy)-phenyl]-pyridin-3-yl}-ethylcarbamoyl)-piperidin-1-yl]-3-oxo-propyl}-piperidine-1-carboxylic acid tert-butyl ester was dissolved in 8.7 ml dioxane. 1.07 ml (4.26 mmol) 4 N hydrochloric acid were added. The mixture was stirred at room temperature for 20 hours. 0.178 ml (0.71 mmol) 4 N hydrochloric acid were added. The mixture was stirred at room temperature for 24 hours. 8.0 ml dioxane and 0.178 ml (0.71 mmol) 4 N hydrochloric acid were added. The mixture was stirred at room temperature for 72 hours and then concentrated. To the residue was added a little amount of water and saturated sodium hydrogen carbonate solution to get a pH=6. The mixture was concentrated and extracted with ethyl acetate/ethanol 9:1 and with dichloromethane/methanol 9:1. The organic solutions were filtered, combined and concentrated to give 55 mg which were purified by HPLC:

| System: | Waters Autopurificationsystem: Pump 254, Sample Manager 2767, CFO, DAD 2996, ELSD 2424, SQD 3001 |
|---|---|
| Column: | XBrigde C18 5 μm 100 × 30 mm |
| Solvent: | A = H2O + 0.1% HCOOH |
| | B = Methanol |
| Gradient: | 0-1 min 15% B, 1-8 min 15-70% B |
| Flow: | 50 mL/min |
| Temperature: | RT |
| Solution: | 55 mg/2 mL DMSO/MeOH 1:1 |
| Injection: | 2 × 1 mL |
| Detection: | DAD scan range 210-400 nm |
| | MS ESI+, ESI−, scan range 160-1000 m/z |
| | ELSD |

| Fractions: | Rt. in min | DAD TAC | Amount |
|---|---|---|---|
| 11 | 7.2-7.8 | 78.7% | 8 mg |
| 12 | 7.8-7.2 | 74.2% | 2 mg |
| 13 | 8.2-9.0 | 97.3% | 9 mg |

The fractions were concentrated.

Fraction 13 contained the desired isomer.

UPLC (ACN-HCOOH): Rt.=0.95 min
MS (ES+): m/e=555.12 (M+H+)
MS (ES−): m/e=553.17 (M−H)

Example 7

(3S)-3-{5-[4-(2-Fluoroethoxy)phenyl]pyridin-3-yl}-3-[({(3R)-1-[3-(piperidin-4-yl)propanoyl]piperidin-3-yl}carbonyl)amino]propanoic acid

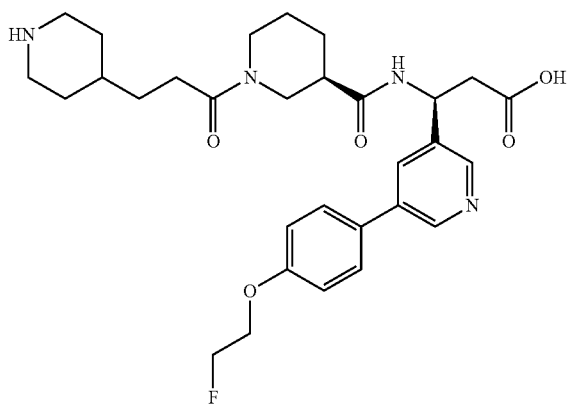 [SMILES: O=C(O)C[C@H](NC(=O)[C@@H]1CCCN(C(=O)CCC2CCNCC2)C1)c1cncc(-c2ccc(OCCF)cc2)c1]

Example 7a

Tert-butyl 4-{3-[(3R)-3-({1-[5-(4-hydroxyphenyl)pyridin-3-yl]-3-methoxy-3-oxopropyl}carbamoyl)piperidin-1-yl]-3-oxopropyl}piperidine-1-carboxylate

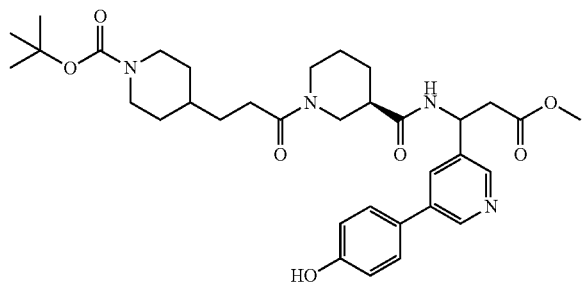 [SMILES: COC(=O)CC(NC(=O)[C@@H]1CCCN(C(=O)CCC2CCN(C(=O)OC(C)(C)C)CC2)C1)c1cncc(-c2ccc(O)cc2)c1]

To 300.0 mg (0.49 mmol) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate (example 8c) in 12 ml toluene were added 11.4 mg (0.01 mmol) tetrakis(triphenylphosphine)palladium(0), 81.5 mg (0.59 mmol) (4-hydroxyphenyl)boronic acid in 3.0 ml ethanol and 88.7 mg (1.53 mmol) potassium fluoride in 3.0 ml water. The mixture was stirred at 100° C. for 4 hours, diluted with water and extracted with ethyl acetate. The organic phase was dried over sodium sulfate and concentrated in vacuum. Chromatography over 10 g silica gel (dichloromethane/ethanol 100/0-95/5-90/10) gave 218 mg (71%) tert-butyl 4-{3-[(3R)-3-({1-[5-(4-hydroxyphenyl)pyridin-3-yl]-3-m ethoxy-3-oxopropyl}carbamoyl)piperidin-1-yl]-3-oxopropyl}piperidine-1-carboxylate.

UPLC (ACN-HCOOH): Rt.=1.02 min

MS (ES$^+$): m/e=624.8 (M+H$^+$)

MS (ES$^-$): m/e=621.5 (M–H), 667.6 (M+HCOO$^-$)

Example 7b

Tert-butyl 4-(3-{(3R)-3-[(1-{5-[4-(2-fluoroethoxy)phenyl]pyridin-3-yl}-3-methoxy-3-oxopropyl)carbamoyl]piperidin-1-yl}-3-oxopropyl)piperidine-1-carboxylate

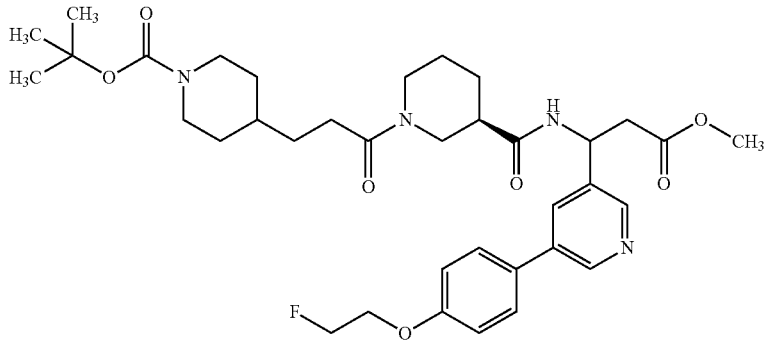 [SMILES: COC(=O)CC(NC(=O)[C@@H]1CCCN(C(=O)CCC2CCN(C(=O)OC(C)(C)C)CC2)C1)c1cncc(-c2ccc(OCCF)cc2)c1]

120 mg (0.19 mmol) tert-butyl 4-{3-[(3R)-3-({1-[5-(4-hydroxyphenyl)pyridin-3-yl]-3-methoxy-3-oxopropyl}carbamoyl)piperidin-1-yl]-3-oxopropyl}piperidine-1-carboxylate were dissolved in 2.11 ml tetrahydrofurane. 126 mg (0.39 mmol) cesium carbonate and 64 mg (0.37 mmol) 1-iodo-2-fluoroethane were added. The mixture was stirred at room temperature for 70 hours. 64 mg (0.37 mmol) 1-iodo-2-fluoroethane were added and the mixture stirred at room temperature for 48 hours. 64 mg (0.37 mmol) 1-iodo-2-fluoroethane were added and the mixture stirred at room temperature for 70 hours. 64 mg (0.37 mmol) 1-iodo-2-fluoroethane were added and the mixture stirred at room temperature for 24 hours. 64 mg (0.37 mmol) 1-iodo-2-fluoroethane, 2 ml tetrahydrofurane and 126 mg (0.39 mmol) cesium carbonate were added and the mixture stirred at room temperature for 24 hours. 64 mg (0.37 mmol) 1-iodo-2-fluoroethane were added and the mixture stirred at room temperature for 24 hours, diluted with water and extracted with ethyl acetate. The organic phase was dried over sodium sulfate and concentrated in vacuum. Chromatography over 10 g silica gel (dichloromethane/ethanol 100/0-90/10) gave 84 mg (62%) tert-butyl 4-(3-{(3R)-3-[(1-{5-[4-(2-fluoroethoxy)phenyl]pyridin-3-yl}-3-methoxy-3-oxopropyl)carbamoyl]piperidin-1-yl}-3-oxopropyl)piperidine-1-carboxylate.

UPLC (ACN-HCOOH): Rt.=1.16 min
MS (ES⁺): m/e=669.3 (M+H⁺)
MS (ES⁻): m/e=713.5 (M+HCOO⁻)

Example 7c 3-({[(3R)-1-{3-[1-(Tert-butoxycarbonyl)piperidin-4-yl]propanoyl}piperidin-3-yl]carbonyl}amino)-3-{5-[4-(2-fluoroethoxy)phenyl]pyridin-3-yl}propanoic acid

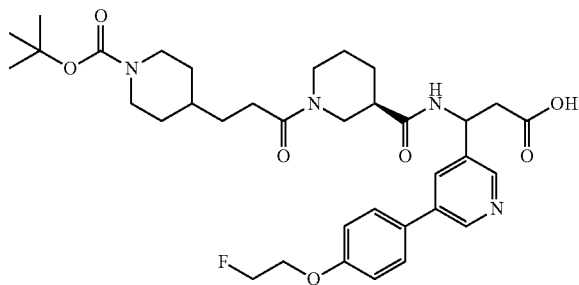 [SMILES: CC(C)(C)OC(=O)N1CCC(CCC(=O)N2CCC[C@@H](C(=O)NC(CC(=O)O)c3cncc(-c4ccc(OCCF)cc4)c3)C2)CC1]

76 mg (0.11 mmol) tert-butyl 4-(3-{(3R)-3-[(1-{5-[4-(2-fluoroethoxy)phenyl]pyridin-3-yl}-3-methoxy-3-oxopropyl)carbamoyl]piperidin-1-yl}-3-oxopropyl)piperidine-1-carboxylate were dissolved in 14 ml methanol. 358.5 mg (1.14 mmol) barium hydroxide octahydrate were added. The mixture was stirred at room temperature for 20 hours and then concentrated to give 3-({[(3R)-1-{3-[1-(tert-butoxycarbonyl)piperidin-4-yl]propanoyl}piperidin-3-yl]carbonyl}amino)-3-{5-[4-(2-fluoroethoxy)phenyl]pyridin-3-yl}propanoic acid.
UPLC (ACN-HCOOH): Rt.=1.08 min
MS (ES⁺): m/e=655.5 (M+H⁺)
MS (ES⁻): m/e=653.5 (M−H)

Example 7d (3S)-3-{5-[4-(2-Fluoroethoxy)phenyl]pyridin-3-yl}-3-[({(3R)-1-[3-(piperidin-4-yl)propanoyl]piperidin-3-yl}carbonyl)amino]propanoic acid

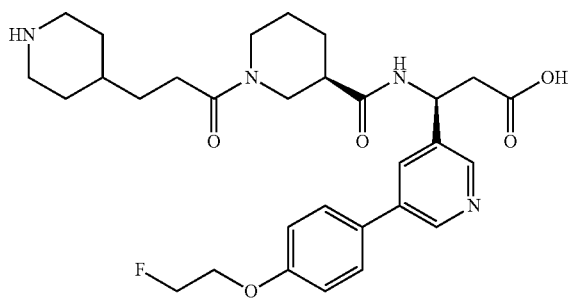 [SMILES: O=C(O)C[C@H](NC(=O)[C@@H]1CCCN(C(=O)CCC2CCNCC2)C1)c1cncc(-c2ccc(OCCF)cc2)c1]

The mixture obtained in example 7c containing 74 mg (0.11 mmol) 3-({[(3R)-1-{3-[1-(tert-butoxycarbonyl)piperidin-4-yl]propanoyl}piperidin-3-yl]carbonyl}amino)-3-{5-[4-(2-fluoroethoxy)phenyl]pyridin-3-yl}propanoic acid was dissolved in 6.9 ml dioxane. 0.85 ml (3.39 mmol) 4 N hydrochloric acid were added. The mixture was stirred at room temperature for 48 hours. 0.141 ml (0.56 mmol) 4 N hydrochloric acid were added. The mixture was stirred at room temperature for 24 hours and then concentrated. To the residue was added a little amount of water and saturated sodium hydrogen carbonate solution to get a pH=6. The mixture was concentrated and extracted with ethyl acetate/ethanol 9:1. The organic solutions were filtered and concentrated to give 49 mg which were purified by HPLC:

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |
| Solvent: | A = H2O + 0.1% HCOOH |
| | B = Methanol |
| Gradient: | 0-1 min 10% B, 1-8 min 10-50% B |
| Flow: | 50 mL/min |
| Temperature: | RT |
| Solution: | 49 mg/2.1 mL DMSO/MeOH 1:1 |
| Injection: | 3 × 0.7 mL |
| Detection: | DAD scan range 210-400 nm |
| | MS ESI+, ESI−, scan range 160-1000 m/z |
| | ELSD |

| Fractions: | Rt. in min | DAD TAC | Amount |
|---|---|---|---|
| 11 | 5.2-5.8 | 91.7% | 11 mg |
| 12 | 6.0-6.9 | 95.5% | 12 mg |
| 13 | 5.8-6.0 | 56.5% | 15 mg |
| | | 35.4% | |

The fractions were concentrated.

Fraction 12 contained the desired isomer.
UPLC (ACN-HCOOH): Rt. =0.89 min
MS (ES⁺): m/e=555.11 (M+H⁺)
MS (ES⁻): m/e=553.16 (M−H)

Example 8

(3S)-3-{5-[2-(2-Fluoroethoxy)phenyl]pyridin-3-yl}-3-[({(3R)-1-[3-(piperidin-4-yl)propanoyl]piperidin-3-yl}carbonyl)amino]propanoic acid

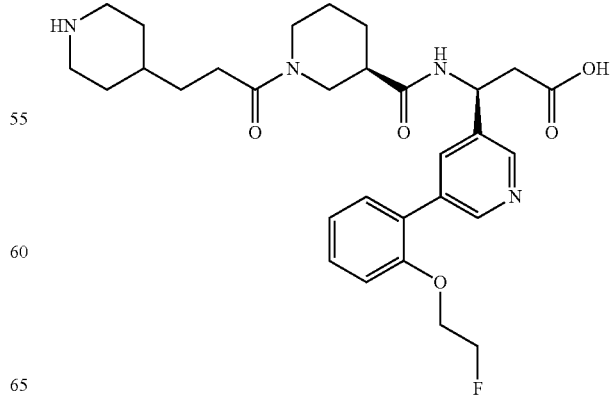

Example 8a

3-Amino-3-(5-bromopyridin-3-yl)propionic acid

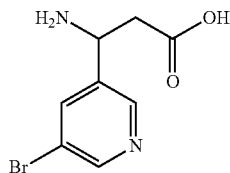 [SMILES: NC(CC(=O)O)c1cncc(Br)c1]

9.50 g (51.07 mmol) 5-bromopyridine-3-carbaldehyde were suspended in 22 ml ethanol. 5.31 g (51.07 mmol) propanedioic acid and 8.27 g (107.25 mmol) ammonium acetate were added. The mixture was refluxed for 4 hours and after cooling to room temperature filtrated. The residue was washed with cold ethanol and dried in vacuum at 45° C. to give 8.69 g (69%) 3-amino-3-(5-bromo-pyridin-3-yl) propionic acid.

$^1$H-NMR (300 MHz, DMSO-d$_6$): δ=3.03 (dd, 2H), 4.71 (br., 1H), 8.24 (t, 1H), 8.68 (d, 1H), 8.75 (d, 1H) ppm.

Example 8b

3-Amino-3-(5-bromopyridin-3-yl)propionic acid methyl ester

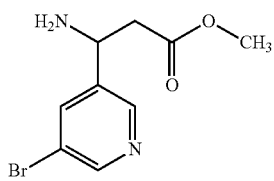

9.54 g (38.93 mmol) 3-amino-3-(5-bromopyridin-3-yl) propionic acid were suspended in 158 ml methanol and the mixture cooled to 0° C. 4.26 ml (58.39 mmol) thionyl chloride were slowly added. The mixture was stirred at room temperature for 20 hours and concentrated. The residue was treated with saturated sodium hydrogen carbonate solution and extracted with dichloromethane. The organic part was dried with sodium sulfate and concentrated. Chromatography over silica gel (dichloromethane/ethanol 100/0-50/50) gave 5.84 g (52%) 3-amino-3-(5-bromopyridin-3-yl)-propionic acid methyl ester.

UPLC (ACN-NH3): Rt.=0.74 min

MS (ES$^+$): m/e=261.2 (M+H$^+$)

$^1$H-NMR (300 MHz, CDCl$_3$): δ=2.68 (d, 2H), 3.71 (s, 3H), 4.48 (t, 1H), 7.91-7.95 (m, 1H), 8.53 (d, 1H), 8.59 (d, 1H) ppm.

Example 8c

Tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate

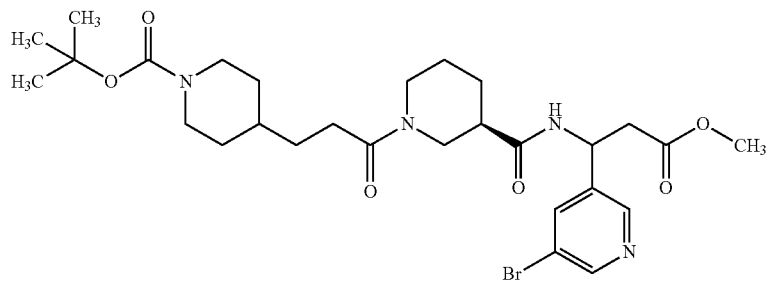 [SMILES: COC(=O)CC(NC(=O)[C@@H]1CCCN(C(=O)CCC2CCN(C(=O)OC(C)(C)C)CC2)C1)c1cncc(Br)c1]

3.324 g (9.02 mmol) (3R)-1-{3-[1-(tert-butoxycarbonyl) piperidin-4-yl]propanoyl}piperidine-3-carboxylic acid (*Bioorg. Med. Chem.* 13 (2005) 4343-4352, Compound 10) were suspended in 52 ml N,N-dimethylformamide and cooled to 0° C. 3.694 g (9.71 mmol) HATU, a solution of 1.798 g (6.94 mmol) 3-amino-3-(5-bromo-pyridin-3-yl)-propionic acid methyl ester in 78 ml N,N-dimethylformamide and 3.56 ml (20.82 mmol) N-ethyl-diisopropylamine were added. The mixture was stirred at 0° C. for 5 minutes and at room temperature for 24 hours. 160 ml water were added and the mixture extracted with 280 ml dichloromethane. The organic phase was washed with water, dried over sodium sulfate and concentrated in vacuum. Chromatography over 55 g basic silica gel (dichloromethane/ethanol 100/0-97/3-94/6) gave 4395 mg (104%) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate.

UPLC (ACN-HCOOH): Rt.=1.18 min

MS (ES$^+$): m/e=511.3 (M+H$^+$-BOC)

MS (ES$^-$): m/e=609.5 (M-H)

Example 8d

Tert-butyl 4-{3-[(3R)-3-({1-[5-(2-hydroxyphenyl)pyridin-3-yl]-3-methoxy-3-oxopropyl}carbamoyl)piperidin-1-yl]-3-oxopropyl}piperidine-1-carboxylate

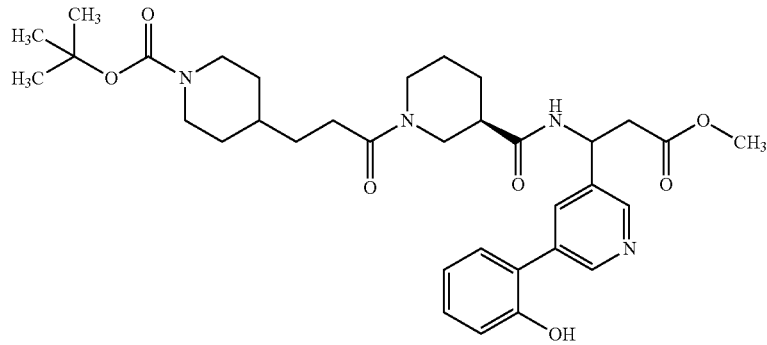 [SMILES: COC(=O)CC(NC(=O)[C@@H]1CCCN(C(=O)CCC2CCN(C(=O)OC(C)(C)C)CC2)C1)c1cncc(-c2ccccc2O)c1]

To 400.0 mg (0.66 mmol) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate in 16 ml toluene were added 15.17 mg (0.01 mmol) tetrakis(triphenylphosphine)palladium(0), 108.6 mg (0.79 mmol) (2-hydroxyphenyl)boronic acid in 4.0 ml ethanol and 118.3 mg (2.04 mmol) potassium fluoride in 4.0 ml water. The mixture was stirred at 100° C. for 20 hours, diluted with water and extracted with ethyl acetate. The organic phase was dried over sodium sulfate and concentrated in vacuum. Chromatography over 10 g silica gel (dichloromethane/ethanol 100/0-95/5-90/10) gave 240 mg (59%) tert-butyl 4-{3-[(3R)-3-({1-[5-(2-hydroxyphenyl)pyridin-3-yl]-3-methoxy-3-oxopropyl}carbamoyl)piperidin-1-yl]-3-oxopropyl}piperidine-1-carboxylate.

UPLC (ACN-HCOOH): Rt.=1.02 min
MS (ES$^+$): m/e=624.58 (M+H$^+$)
MS (ES$^-$): m/e=621.55 (M−H), 667.57 (M+HCOO$^-$)

Example 8e

Tert-butyl 4-(3-{(3R)-3-[(1-{5-[2-(2-fluoroethoxy)phenyl]pyridin-3-yl}-3-methoxy-3-oxopropyl)carbamoyl]piperidin-1-yl}-3-oxopropyl)piperidine-1-carboxylate 124 mg (0.20 mmol) tert-butyl 4-{3-[(3R)-3-({1-[5-(2-hydroxyphenyl)pyridin-3-yl]-3-methoxy-3-oxopropyl}carbamoyl)piperidin-1-yl]-3-oxopropyl}piperidine-1-carboxylate were dissolved in 2.2 ml tetrahydrofurane. 130 mg (0.40 mmol) cesium carbonate and 66 mg (0.38 mmol) 1-iodo-2-fluoroethane were added. The mixture was stirred at room temperature for 90 hours. 66 mg (0.38 mmol) 1-iodo-2-fluoroethane were added and the mixture stirred at room temperature for 20 hours. 66 mg (0.38 mmol) 1-iodo-2-fluoroethane were added and the mixture stirred at room temperature for 60 hours, diluted with water and extracted with ethyl acetate. The organic phase was dried over sodium sulfate and concentrated in vacuum. Chromatography over 10 g silica gel (dichloromethane/ethanol 100/0-90/10) gave 80 mg (54%) tert-butyl 4-(3-{(3R)-3-[(1-{5-[2-(2-fluoroethoxy)phenyl]pyridin-3-yl}-3-methoxy-3-oxopropyl)carbamoyl]piperidin-1-yl}-3-oxopropyl)piperidine-1-carboxylate.

UPLC (ACN-HCOOH): Rt.=1.18 min

MS (ES$^+$): m/e=669.57 (M+H$^+$)

MS (ES$^-$): m/e=667.57 (M−H), 713.62 (M+HCOO$^-$)

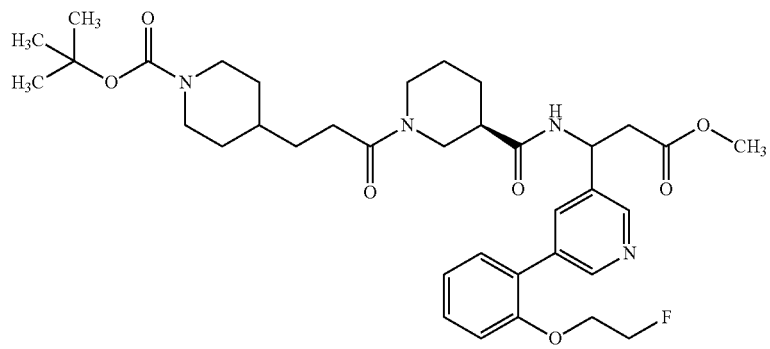 [SMILES: COC(=O)CC(NC(=O)[C@@H]1CCCN(C(=O)CCC2CCN(C(=O)OC(C)(C)C)CC2)C1)c1cncc(-c2ccccc2OCCF)c1]

Example 8f 3-({[(3R)-1-{3-[1-(Tert-butoxycarbonyl)piperidin-4-yl]propanoyl}piperidin-3-yl]carbonyl}amino)-3-{5-[2-(2-fluoroethoxy)phenyl]pyridin-3-yl}propanoic acid

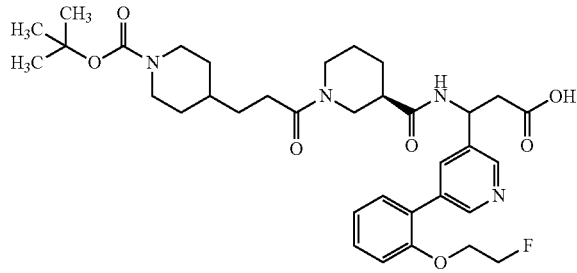 [SMILES: CC(C)(C)OC(=O)N1CCC(CCC(=O)N2CCC[C@@H](C(=O)NC(CC(=O)O)c3cncc(-c4ccccc4OCCF)c3)C2)CC1]

73 mg (0.11 mmol) tert-butyl 4-(3-{(3R)-3-[(1-{5-[2-(2-fluoroethoxy)phenyl]pyridin-3-yl}-3-methoxy-3-oxopropyl)carbamoyl]piperidin-1-yl}-3-oxopropyl)piperidine-1-carboxylate were dissolved in 13 ml methanol. 344 mg (1.09 mmol) barium hydroxide octahydrate were added. The mixture was stirred at room temperature for 20 hours and then concentrated to give 3-({[(3R)-1-{3-[1-(tert-butoxycarbonyl)piperidin-4-yl]propanoyl}piperidin-3-yl]carbonyl}amino)-3-{5-[2-(2-fluoroethoxy)phenyl]pyridin-3-yl}propanoic acid.

UPLC (ACN-HCOOH): Rt.=1.09 min
MS (ES+): m/e=655.5 (M+H+)
MS (ES−): m/e=653.5 (M−H), 622.16 (M+HCOO−)

Example 8 g (3S)-3-{5-[2-(2-Fluoroethoxy)phenyl]pyridin-3-yl}-3-[({(3R)-1-[3-(piperidin-4-yl)propanoyl]piperidin-3-yl}carbonyl)amino]propanoic acid

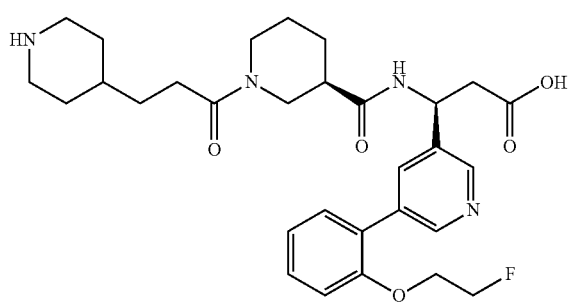 [SMILES: O=C(O)C[C@H](NC(=O)[C@@H]1CCCN(C(=O)CCC2CCNCC2)C1)c1cncc(-c2ccccc2OCCF)c1]

The mixture obtained in example 8f containing 71 mg (0.11 mmol) 3-({[(3R)-1-{3-[1-(tert-butoxycarbonyl)piperidin-4-yl]propanoyl}piperidin-3-yl]carbonyl}amino)-3-{5-[2-(2-fluoroethoxy)phenyl]pyridin-3-yl}propanoic acid was dissolved in 6.6 ml dioxane. 0.81 ml (3.25 mmol) 4 N hydrochloric acid were added. The mixture was stirred at room temperature for 20 hours. 0.136 ml (0.54 mmol) 4 N hydrochloric acid were added. The mixture was stirred at room temperature for 24 hours. 6.0 ml dioxane and 0.136 ml (0.54 mmol) 4 N hydrochloric acid were added. The mixture was stirred at room temperature for 24 hours and then concentrated. To the residue was added a little amount of water and saturated sodium hydrogen carbonate solution to get a pH=6. The mixture was concentrated and extracted with ethyl acetate/ethanol 9:1 and with dichloromethane/methanol 9:1. The organic solutions were filtered, combined and concentrated to give 76 mg which were purified by HPLC:

| System: | Waters Autopurificationsystem: Pump 254, Sample Manager 2767, CFO, DAD 2996, ELSD 2424, SQD 3001 |
|---|---|
| Column: | XBrigde C18 5 μm 100 × 30 mm |
| Solvent: | A = H2O + 0.1% HCOOH |
|  | B = Methanol |
| Gradient: | 0-1 min 15% B, 1-8 min 15-60% B |
| Flow: | 50 mL/min |
| Temperature: | RT |
| Solution: | 76 mg/2.1 mL DMSO/MeOH 1:1 |
| Injection: | 3 × 0.7 mL |
| Detection: | DAD scan range 210-400 nm |
|  | MS ESI+, ESI−, scan range 160-1000 m/z |
|  | ELSD |

| Fractions: | Rt. in min | DAD TAC | Amount |
|---|---|---|---|
| 11 | 6.0-6.6 | 83.0% | 10 mg |
| 12 | 6.6-7.0 | 61.5% | 4 mg |
| 13 | 7.0-7.8 | 98.2% | 11 mg |

The fractions were concentrated.

Fraction 13 contained the desired isomer.

UPLC (ACN-HCOOH): Rt. =0.88 min
MS (ES+): m/e=555.08 (M+H+)
MS (ES−): m/e=553.18 (M−H)

Example 9

(3S)-3-[5-(3-Cyano-4-fluorophenyl)pyridin-3-yl]-3-[({(3R)-1-[3-(piperidin-4-yl)propanoyl]piperidin-3-yl}carbonyl)amino]propanoic acid

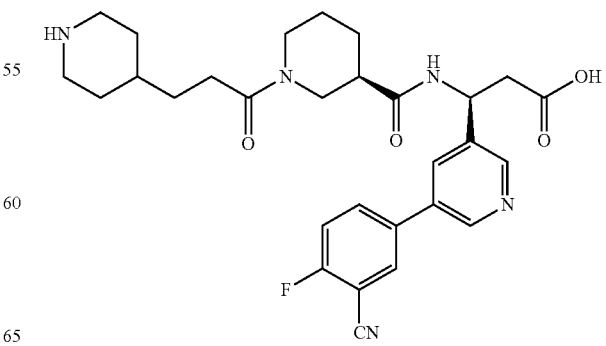

Example 9a

Tert-butyl 4-{3-[(3R)-3-({1-[5-(3-cyano-4-fluorophenyl)pyridin-3-yl]-3-methoxy-3-oxopropyl}carbamoyl)piperidin-1-yl]-3-oxopropyl}piperidine-1-carboxylate

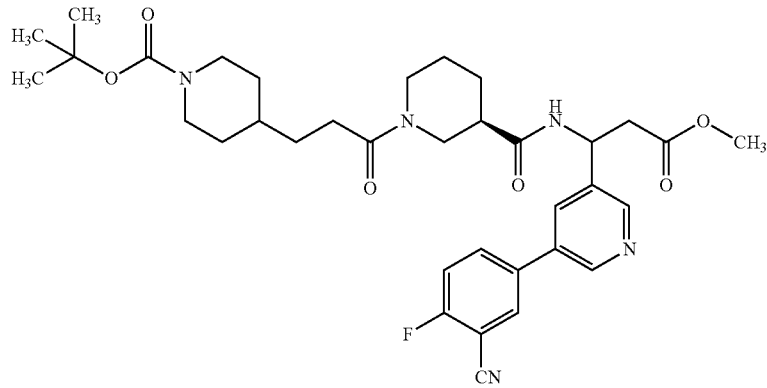 [SMILES: COC(=O)CC(NC(=O)[C@@H]1CCCN(C(=O)CCC2CCN(C(=O)OC(C)(C)C)CC2)C1)c1cncc(-c2ccc(F)c(C#N)c2)c1]

To 300.0 mg (0.49 mmol) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate (example 8c) in 12 ml toluene were added 11.4 mg (0.01 mmol) tetrakis(triphenylphosphine)palladium(0), 97.4 mg (0.59 mmol) (3-cyano-4-fluoro-phenyl)boronic acid in 3.0 ml ethanol and 88.7 mg (1.53 mmol) potassium fluoride in 3.0 ml water. The mixture was stirred at 100° C. for 3 hours, diluted with water and extracted with ethyl acetate. The organic phase was dried over sodium sulfate and concentrated in vacuum. Chromatography over 10 g silica gel (dichloromethane/ethanol 100/0-95/5-90/10) gave 206 mg (58%) tert-butyl 4-{3-[(3R)-3-({1-[5-(3-cyano-4-fluorophenyl)pyridin-3-yl]-3-methoxy-3-oxopropyl}carbamoyl)piperidin-1-yl]-3-oxopropyl}piperidine-1-carboxylate.
UPLC (ACN-HCOOH): Rt.=1.23 min
MS (ES+): m/e=652.3 (M+H+)
MS (ES−): m/e=648.5 (M−H), 694.5 (M+HCOO−)

Example 9b 3-({[(3R)-1-{3-[1-(Tert-butoxycarbonyl)piperidin-4-yl]propanoyl}piperidin-3-yl]carbonyl}amino)-3-[5-(3-cyano-4-fluorophenyl)pyridin-3-yl]propanoic acid

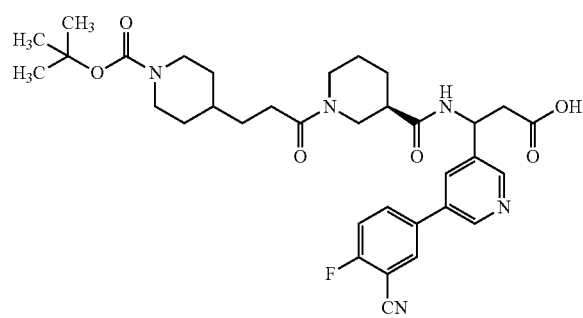 [SMILES: CC(C)(C)OC(=O)N1CCC(CCC(=O)N2CCC[C@@H](C(=O)NC(CC(=O)O)c3cncc(-c4ccc(F)c(C#N)c4)c3)C2)CC1]

100 mg (0.15 mmol) tert-butyl 4-{3-[(3R)-3-({1-[5-(3-cyano-4-fluorophenyl)pyridin-3-yl]-3-methoxy-3-oxopropyl}carbamoyl)piperidin-1-yl]-3-oxopropyl}piperidine-1-carboxylate were dissolved in 5 ml tetrahydrofurane and treated with 2.5 ml 0.1N sodium hydroxide solution. The mixture was stirred for 15 minutes and concentrated to give 97 mg (99%).
UPLC (ACN-HCOOH): Rt.=1.13 min
MS (ES+): m/e=636.5 (M+H+)
MS (ES−): m/e=634.5 (M−H)

Example 9c (3S)-3-[5-(3-Cyano-4-fluorophenyl)pyridin-3-yl]-3-[({(3R)-1-[3-(piperidin-4-yl)propanoyl]piperidin-3-yl}carbonyl)amino]propanoic acid

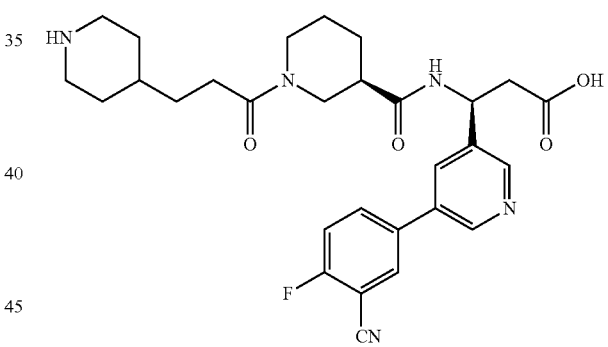

The mixture obtained in example 9b containing 97 mg (0.15 mmol) 3-({[(3R)-1-{3-[1-(tert-butoxycarbonyl)piperidin-4-yl]propanoyl}piperidin-3-yl]carbonyl}amino)-3-[5-(3-cyano-4-fluorophenyl)pyridin-3-yl]propanoic acid was dissolved in 9.6 ml dioxane. 0.39 ml (1.57 mmol) 4 N hydrochloric acid were added. The mixture was stirred at room temperature for 20 hours and then concentrated. To the residue was added a little amount of water and saturated sodium hydrogen carbonate solution to get a pH=6. The mixture was concentrated and extracted with dichloromethane/2-propanol 8:2. The organic solutions were filtered and concentrated to give 44 mg which were purified by HPLC:

| System: | Waters Autopurificationsystem: Pump 254, Sample Manager 2767, CFO, DAD 2996, ELSD 2424, SQD 3001 |
|---|---|
| Column: | XBrigde C18 5 µm 100 × 30 mm |

-continued

| | |
|---|---|
| Solvent: | A = H2O + 0.2% NH3 |
| | B = Methanol |
| Gradient: | 0-1 min 15% B, 1-12 min 15-55% B |
| Flow: | 50 mL/min |
| Temperature: | RT |
| Solution: | 41 mg/2.2 mL DMF/MeOH 1:1 |
| Injection: | 2 × 1.1 mL |
| Detection: | DAD scan range 210-400 nm |
| | MS ESI+, ESI−, scan range 160-1000 m/z |
| | ELSD |

| Fractions: | Rt. in min | DAD TAC | Amount |
|---|---|---|---|
| 11 | 5.52-5.82 | 78% | 7 mg |
| 12 | 6.00-6.34 | 91% | 7.5 mg |

The fractions were concentrated, mixed with tert.-butanol and lyophilized.

Fraction 12 contained the desired isomer.
UPLC (ACN-HCOOH): Rt.=0.95 min
MS (ES+): m/e=536.11 (M+H+)
MS (ES−): m/e=534.11 (M−H)

Example 10

(3S)-3-[5-(4-Cyano-3-fluorophenyl)pyridin-3-yl]-3-[({(3R)-1-[3-(piperidin-4-yl)propanoyl]piperidin-3-yl}carbonyl)amino]propanoic acid

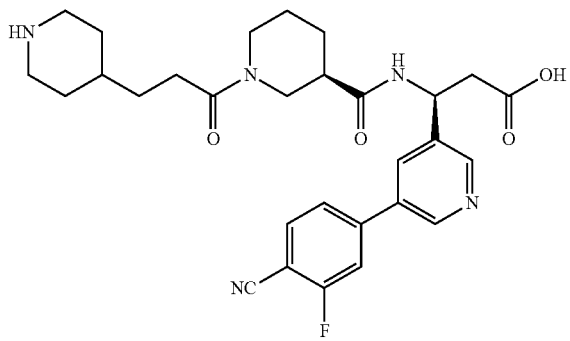

Example 10a

Tert-butyl 4-{3-[(3R)-3-({1-[5-(4-cyano-3-fluorophenyl)pyridin-3-yl]-3-methoxy-3-oxopropyl}carbamoyl)piperidin-1-yl]-3-oxopropyl}piperidine-1-carboxylate

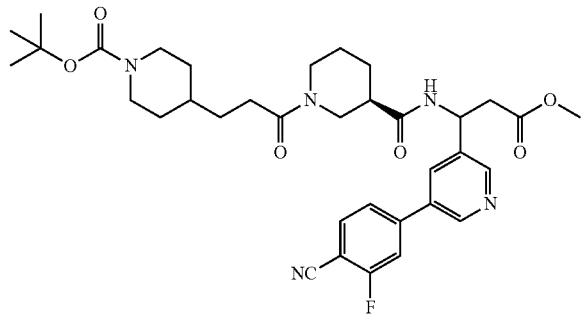 [SMILES: COC(=O)CC(NC(=O)[C@@H]1CCCN(C(=O)CCC2CCN(C(=O)OC(C)(C)C)CC2)C1)c1cncc(-c2ccc(C#N)c(F)c2)c1]

To 300.0 mg (0.49 mmol) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate (example 8c) in 12 ml toluene were added 11.4 mg (0.01 mmol) tetrakis(triphenylphosphine)palladium(0), 97.4 mg (0.59 mmol) (4-cyano-3-fluoro-phenyl)boronic acid in 3.0 ml ethanol and 57.2 mg (0.98 mmol) potassium fluoride in 3.0 ml water. The mixture was stirred at 100° C. for 10 hours and at 60° C. for 20 hours, diluted with water and extracted with ethyl acetate and sodium hydrogen carbonate solution. The organic phase was dried over sodium sulfate and concentrated in vacuum. Chromatography over 10 g silica gel (dichloromethane/ethanol 100/0-95/5-90/10) gave 157 mg (44%) tert-butyl 4-{3-[(3R)-3-({1-[5-(4-cyano-3-fluorophenyl)pyridin-3-yl]-3-methoxy-3-oxopropyl}carbamoyl)piperidin-1-yl]-3-oxopropyl}piperidine-1-carboxylate.

UPLC (ACN-HCOOH): Rt.=1.23 min
MS (ES+): m/e=652.3 (M+H+)
MS (ES−): m/e=648.5 (M−H), 694.6 (M+HCOO−)

Example 10b 3-({[(3R)-1-{3-[1-(Tert-butoxycarbonyl)piperidin-4-yl]propanoyl}piperidin-3-yl]carbonyl}amino)-3-[5-(4-cyano-3-fluorophenyl)pyridin-3-yl]propanoic acid

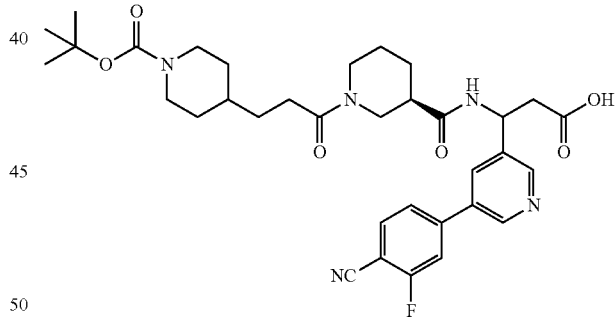

220 mg (0.34 mmol) tert-butyl 4-{3-[(3R)-3-({1-[5-(4-cyano-3-fluorophenyl)pyridin-3-yl]-3-methoxy-3-oxopropyl}carbamoyl)piperidin-1-yl]-3-oxopropyl}piperidine-1-carboxylate were dissolved in 11 ml tetrahydrofurane and treated with 4.1 ml 0.1N sodium hydroxide solution. The mixture was stirred for 15 minutes and concentrated to give 215 mg (100%).

UPLC (ACN-HCOOH): Rt.=1.14 min
MS (ES+): m/e=638.2 (M+H+)
MS (ES−): m/e=634.5 (M−H)

Example 10c (3S)-3-[5-(4-Cyano-3-fluorophenyl)pyridin-3-yl]-3-[({(3R)-1-[3-(piperidin-4-yl)propanoyl]piperidin-3-yl}carbonyl)amino]propanoic acid

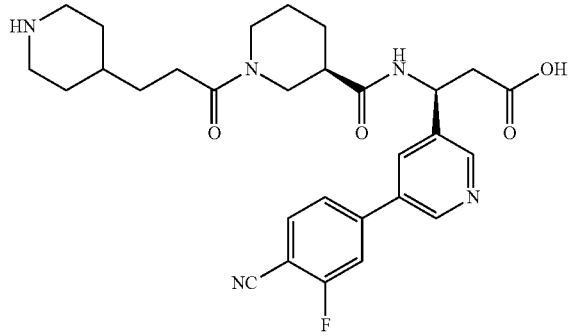

The mixture obtained in example 10b containing 215 mg (0.34 mmol) 3-({[(3R)-1-{3-[1-(tert-butoxycarbonyl)piperidin-4-yl]propanoyl}piperidin-3-yl]carbonyl}amino)-3-[5-(4-cyano-3-fluorophenyl)pyridin-3-yl]propanoic acid was dissolved in 20.6 ml dioxane. 0.85 ml (3.4 mmol) 4 N hydrochloric acid were added. The mixture was stirred at room temperature for 20 hours and then concentrated. To the residue was added a little amount of water and saturated sodium hydrogen carbonate solution to get a pH=6. The mixture was concentrated and extracted with dichloromethane/2-propanol 8:2. The organic solutions were filtered and concentrated to give 205 mg, 203 mg of which were purified by HPLC:

| System: | Dionex: Pump P 580, Gilson: Liquid Handler 215, Knauer: UV-Detektor K-2501 |
|---|---|
| Column: | Chiralcel OZ-H 5 μm 250 × 30 mm |
| Solvent: | Ethanol/Methanol 50:50 |
| Flow: | 30 mL/min |
| Temperature: | RT |
| Solution: | 203 mg/7.6 mL EtOH/MeOH 1:1 |
| Injection: | 4 × 1.9 mL |
| Detection: | UV 254 nm |

| Fractions: | Rt. in min | DAD TAC | Amount |
|---|---|---|---|
| 11 | 5.4-7.1 | >99.9% | 60 mg |
| 12 | 10.4-12.2 | 98.9% | 29 mg |

The fractions were concentrated and dried in the high vacuum.

Fraction 12 contained the desired isomer.

MS (ES⁺): m/e=536.4 (M+H⁺)

MS (ES⁻): m/e=534.4 (M−H), 680.4 (M+HCOO⁻)

Example 11

(3S)-3-[5-(4-Fluoro-3-nitrophenyl)pyridin-3-yl]-3-[({(3R)-1-[3-(piperidin-4-yl)propanoyl]piperidin-3-yl}carbonyl)amino]propanoic acid

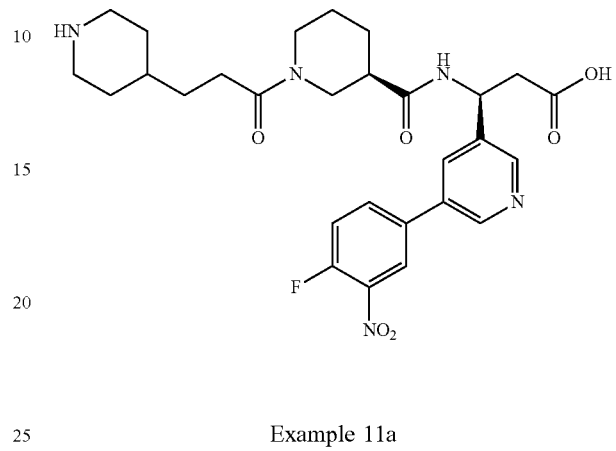

Example 11a

Tert-butyl 4-{3-[(3R)-3-({1-[5-(4-fluoro-3-nitrophenyl)pyridin-3-yl]-3-methoxy-3-oxopropyl}carbamoyl)piperidin-1-yl]-3-oxopropyl}piperidine-1-carboxylate

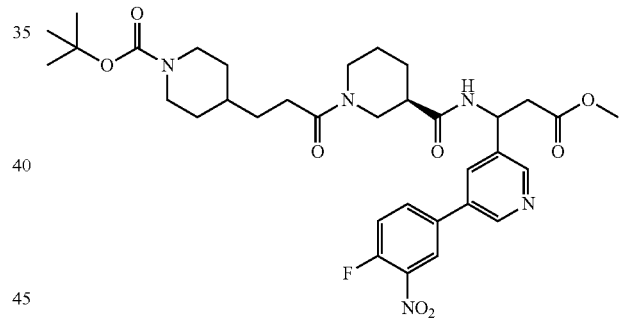

To 300.0 mg (0.49 mmol) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate (example 8c) in 12 ml toluene were added 11.4 mg (0.01 mmol) tetrakis(triphenylphosphine)palladium(0), 109.2 mg (0.59 mmol) (4-fluoro-3-nitro-phenyl)boronic acid in 3.0 ml ethanol and 88.7 mg (1.53 mmol) potassium fluoride in 3.0 ml water. The mixture was stirred at 100° C. for 9 hours and at 60° C. for 20 hours, diluted with water and extracted with ethyl acetate. The organic phase was dried over sodium sulfate and concentrated in vacuum. Chromatography over 10 g silica gel (dichloromethane/ethanol 100/0-95/5-90/10) gave 147 mg (40%) tert-butyl 4-{3-[(3R)-3-({1-[5-(4-fluoro-3-nitrophenyl)pyridin-3-yl]-3-methoxy-3-oxopropyl}carbamoyl)piperidin-1-yl]-3-oxopropyl}piperidine-1-carboxylate.

UPLC (ACN-HCOOH): Rt.=1.23 min

MS (ES⁺): m/e=670.3 (M+H⁺)

MS (ES⁻): m/e=668.5 (M−H), 714.6 (M+HCOO⁻)

Example 11b 3-({[(3R)-1-{3-[1-(Tert-butoxycarbonyl)piperidin-4-yl]propanoyl}piperidin-3-yl]carbonyl}amino)-3-[5-(4-fluoro-3-nitrophenyl)pyridin-3-yl]propanoic acid

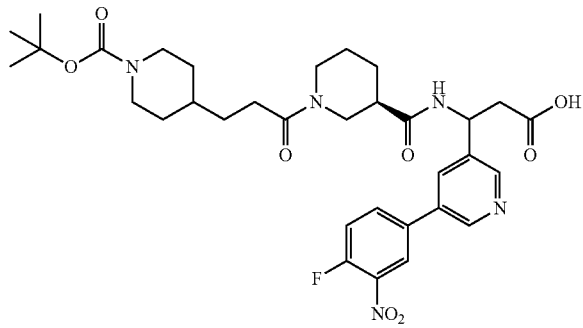 [SMILES: CC(C)(C)OC(=O)N1CCC(CCC(=O)N2CCC[C@@H](C(=O)NC(CC(=O)O)c3cncc(-c4ccc(F)c([N+](=O)[O-])c4)c3)C2)CC1]

225 mg (0.34 mmol) tert-butyl 4-{3-[(3R)-3-({1-[5-(4-fluoro-3-nitrophenyl)pyridin-3-yl]-3-methoxy-3-oxopropyl}carbamoyl)piperidin-1-yl]-3-oxopropyl}piperidine-1-carboxylate were dissolved in 11 ml tetrahydrofurane and treated with 4.0 ml 0.1N sodium hydroxide solution. The mixture was stirred for 15 minutes and concentrated to give 220 mg (100%).

UPLC (ACN-HCOOH): Rt.=1.15 min
MS (ES⁺): m/e=656.4 (M+H⁺)
MS (ES⁻): m/e=654.5 (M−H)

Example 11c (3S)-3-[5-(4-Fluoro-3-nitrophenyl)pyridin-3-yl]-3-[({(3R)-1-[3-(piperidin-4-yl)propanoyl]piperidin-3-yl}carbonyl)amino]propanoic acid

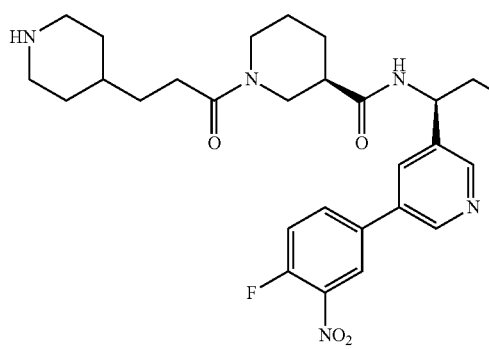

The mixture obtained in example 11b containing 220 mg (0.34 mmol) 3-({[(3R)-1-{3-[1-(tert-butoxycarbonyl)piperidin-4-yl]propanoyl}piperidin-3-yl]carbonyl}amino)-3-[5-(4-fluoro-3-nitrophenyl)pyridin-3-yl]propanoic acid was dissolved in 20.5 ml dioxane. 0.84 ml (3.4 mmol) 4N hydrochloric acid were added. The mixture was stirred at room temperature for 20 hours and then concentrated. To the residue was added a little amount of water and saturated sodium hydrogen carbonate solution to get a pH=6. The mixture was concentrated and extracted with dichloromethane/2-propanol 8:2. The organic solutions were filtered and concentrated to give 213 mg, 211 mg of which were purified by HPLC:

| System: | Dionex: Pump P 580, Gilson: Liquid Handler 215, Knauer: UV-Detektor K-2501 |
| --- | --- |
| Column: | Chiralcel OZ-H 5 μm 250 × 30 mm |
| Solvent: | Ethanol/Methanol 50:50 |
| Flow: | 30 mL/min |
| Temperature: | RT |
| Solution: | 211 mg/3 mL EtOH/MeOH 1:1 |
| Injection: | 4 × 0.75 mL |
| Detection: | UV 254 nm |

| Fractions: | Rt. in min | DAD TAC | Amount |
| --- | --- | --- | --- |
| 11 | 5.4-7.1 | 83.6% | 65 mg |
| 12 | 10.4-12.2 | 90.8% | 35 mg |

The fractions were concentrated and dried in the high vacuum.

Fraction 12 contained the desired isomer.

UPLC (ACN-HCOOH): Rt. =0.78 min
MS (ES⁺): m/e=556.4 (M+H⁺)
MS (ES⁻): m/e=554.4 (M−H)

Example 12

(3R)-3-{5-[(3-Cyano-4-fluorobenzyl)oxy]pyridin-3-yl}-3-[({(3S)-1-[3-(piperidin-4-yl)propanoyl]piperidin-3-yl}carbonyl)amino]propanoic acid

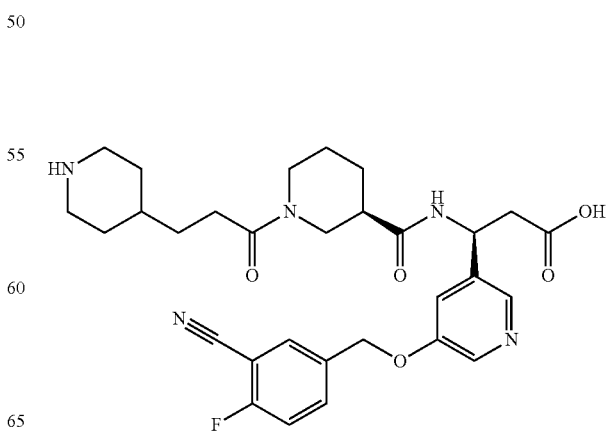

Example 12a

Tert-butyl 4-{3-[(3R)-3-[(1S)-1-{5-[(3-cyano-4-fluorobenzyl)oxy]pyridin-3-yl)-3-methoxy-3-oxopropyl]carbamoyl}piperidin-1-yl]-3-oxopropyl}piperidine-1-carboxylate

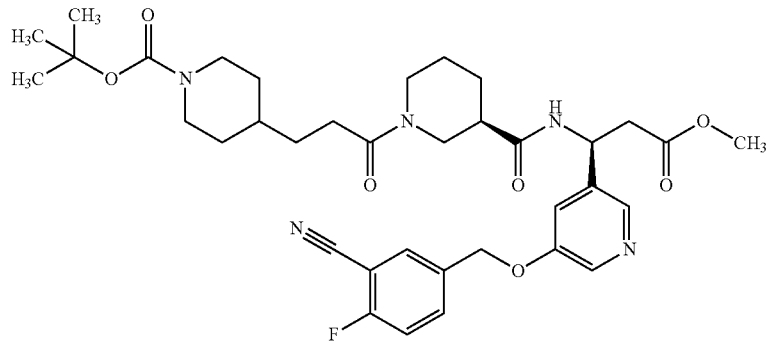 [SMILES: COC(=O)C[C@H](NC(=O)[C@@H]1CCCN(C(=O)CCC2CCN(C(=O)OC(C)(C)C)CC2)C1)c1cncc(OCc2ccc(F)c(C#N)c2)c1]

Polymer bound triphenylphosphine (30 mg) and tert-butyl-4-{3-[(3R)-3-{[(1S)-1-(5-hydroxypyridin-3-yl)-3-methoxy-3-oxopropyl]carbamoyl}piperidin-1-yl]-3-oxopropyl}piperidine-1-carboxylate (example 5e, 30 mg, 60 µmol) were stirred in dichloromethane for 30 minutes. 2-Fluoro-5-(hydroxymethyl)benzonitrile (26 mg, 0.17 mmol) in THF was added and the mixture was cooled to 0° C. Dipropan-2-yl diazene-1,2-dicarboxylate (20 µL, 0.11 mmol) was added, the mixture was stirred for 3 hours at room temperature and then stored for 16 hours at 5° C. After filtration the filtrate was concentrated under reduced pressure and the residue was purified by preparative thin layer chromatography on silica gel (ethyl acetate 100%) to yield 3.2 mg of tert-butyl 4-{3-[(3R)-3-{[(1S)-1-{5-[(3-cyano-4-fluorobenzyl)oxy]pyridin-3-yl}-3-methoxy-3-oxopropyl]carbamoyl}piperidin-1-yl]-3-oxopropyl}piperidine-1-carboxylate.

UPLC (ACN-HCOOH): Rt.=1.24 min
MS (ES$^+$): m/e=680.4 (M+H$^+$)
MS (ES$^-$): m/e=724.5 (M+HCOO$^-$).

Example 12b (3R)-3-{5-[(3-Cyano-4-fluorobenzyl)oxy]pyridin-3-yl}-3-[({(3S)-1-[3-(piperidin-4-yl)propanoyl]piperidin-3-yl}carbonyl)amino]propanoic acid Tert-butyl 4-{3-[(3R)-3-{[(1S)-1-{5-[(3-cyano-4-fluorobenzyl)oxy]pyridin-3-yl}-3-methoxy-3-oxopropyl]carbamoyl}piperidin-1-yl]-3-oxopropyl}piperidine-1-carboxylate (3.2 mg, 10 µmol) as solved in tert.-butanol (0.15 mL) and methanol (0.13 mL) and barium hydroxide octahydrate (7.4 mg, 20 µmol) was added. After stirring for 45 minutes at room temperature the solvent was distilled off at 0° C. by high vacuum. The residue was solved in water (0.3 mL) and acidified by formic acid (0.9 mL). After 3 hours at room temperature the solvent was distilled off at 0° C. by high vacuum and the residue was purified by preparative HPLC to yield 0.8 mg of (3R)-3-{5-[(3-cyano-4-fluorobenzyl)oxy]pyridin-3-yl}-3-[({(3S)-1-[3-(piperidin-4-yl)propanoyl]piperidin-3-yl}carbonyl)amino]propanoic acid.

| | |
|---|---|
| Column: | C18 Chromatorex 10 µm 30 × 125 mm |
| Solvent: | A = H2O + 0.1% HCOOH |
| | B = acetonitrile |
| Gradient: | 0-0.5 min 5% B, 0.5-6 min 5-40% B, |
| Flow: | 150 mL/min |
| Temperature: | RT |
| Detection: | 284 nm |
| Rt.: | 368-4.04 min |

UPLC (ACN-HCOOH): Rt.=0.70 min
MS (ES$^+$): m/e=567.3 (M+H$^+$)
MS (ES$^-$): m/e=565.3 (M–H).

Example 13

(3S)-3-{5-[(4-Cyano-3-fluorobenzyl)oxy]pyridin-3-yl}-3-[({(3R)-1-[3-(piperidin-4-yl)propanoyl]piperidin-3-yl}carbonyl)amino]propanoic acid

Example 13a

Tert-butyl 4-{3-[(3R)-3-{[(1S)-1-{5-[(4-cyano-3-fluorobenzyl)oxy]pyridin-3-yl}-3-methoxy-3-oxopropyl]carbamoyl}piperidin-1-yl]-3-oxopropyl}piperidine-1-carboxylate

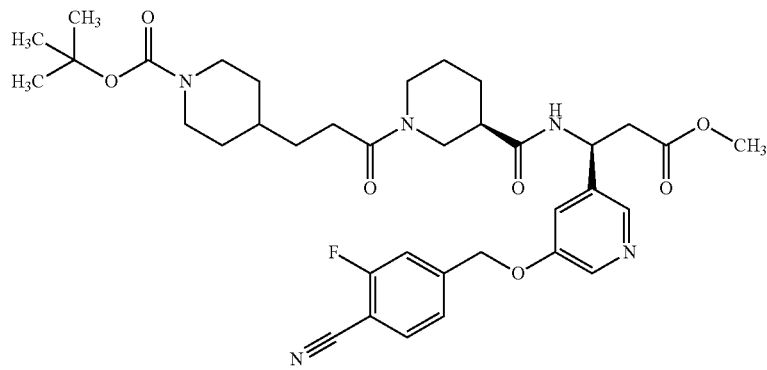 [SMILES: COC(=O)C[C@H](NC(=O)[C@@H]1CCCN(C(=O)CCC2CCN(C(=O)OC(C)(C)C)CC2)C1)c1cncc(OCc2ccc(C#N)c(F)c2)c1]

To tert-butyl-4-{3-[(3R)-3-{[(1S)-1-(5-hydroxypyridin-3-yl)-3-methoxy-3-oxopropyl]carbamoyl}piperidin-1-yl]-3-oxopropyl}piperidine-1-carboxylate (example 5e, 200 mg, 0.37 mmol) in DMF (5 mL) was added sodium hydride (60%, 9.6 mg, 0.24 mmol) and the mixture was cooled to 0° C. 4-(Bromomethyl)-2-fluorobenzonitrile (70.5 mg, 0.33 mmol) in DMF (3 mL) was added while stirring and the mixture was warmed to room temperature. After one hour water, brine and ethyl acetate were added. Phases were separated and the aqueous phase was extracted with ethyl acetate. The combined extracts were dried over sodium sulfate and concentrated in vacuum. The residue was purified by preparative HPLC to yield 10 mg of tert-butyl 4-{3-[(3R)-3-{[(1S)-1-{5-[(4-cyano-3-fluorobenzyl)oxy]pyridin-3-yl}-3-methoxy-3-oxopropyl]carbamoyl}piperidin-1-yl]-3-oxopropyl}piperidine-1-carboxylate.

| | |
|---|---|
| Column: | C18 Chromatorex 10 µm 30 × 125 mm |
| Solvent: | A = H2O + 0.1% HCOOH |
| | B = acetonitrile |
| Gradient: | 0-0.5 min 30% B, 0.5-7 min 30-70% B, |
| Flow: | 120 mL/min |
| Temperature: | RT |
| Detection: | 280 nm |
| Rt.: | 4.61-5.04 min |

UPLC (ACN-HCOOH): Rt.=1.22 min
MS (ES+): m/e=680.4 (M+H+)
MS (ES−): m/e=678.6 (M−H), 724.5 (M+HCOO−).

Example 13b (3S)-3-{5-[(4-Cyano-3-fluorobenzyl)oxy]pyridin-3-yl}-3-[({(3R)-1-[3-(piperidin-4-yl)propanoyl]piperidin-3-yl}carbonyl)amino]propanoic acid Tert-butyl 4-{3-[(3R)-3-{[(1S)-1-(5-(4-cyano-3-fluorobenzyloxy)pyridin-3-yl]-3-methoxy-3-oxopropyl]carbamoyl}piperidin-1-yl]-3-oxopropyl}piperidine-1-carboxylate (10 mg, 15 µmol) as solved in tert.-butanol (0.6 mL) and methanol (0.6 mL) and barium hydroxide octahydrate (23 mg, 74 µmol) was added. After stirring for 45 minutes room temperature the solvent was distilled off at 0° C. by high vacuum. The residue was acidified with formic acid (1 mL). After 18 hours at 5° C. the solvent was distilled off at 0° C. by high vacuum and the residue was purified by preparative HPLC to yield 4 mg of (3R)-3-{5-[(4-cyano-3-fluorobenzyl)oxy]pyridin-3-yl}-3-[({(3S)-1-[3-(piperidin-4-yl)propanoyl]piperidin-3-yl}carbonyl)amino]propanoic acid.

| | |
|---|---|
| Column: | C18 Chromatorex 10 µm 30 × 125 mm |
| Solvent: | A = H2O + 0.1% HCOOH |
| | B = acetonitrile |
| Gradient: | 0-0.5 min 10% B, 0.5-7 min 10-50% B, |
| Flow: | 150 mL/min |
| Temperature: | RT |
| Detection: | 280 nm |
| Rt.: | 2.87-3.15 min |

UPLC (ACN-HCOOH): Rt.=0.71 min
MS (ES+): m/e=566.4 (M+H+)

Example 14

(3S)-3-(4-Cyano-3-fluorophenyl)-3-[({(3R)-1-[3-(piperidin-4-yl)propanoyl]piperidin-3-yl}carbonyl)amino]propanoic acid

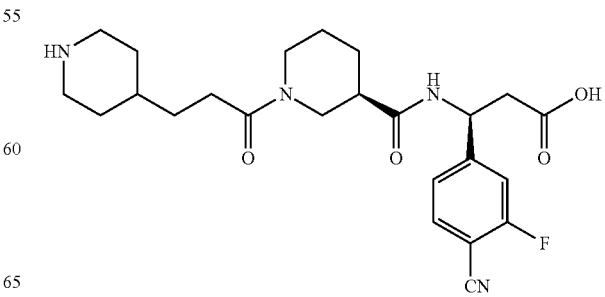

Example 14a

3-Amino-3-(4-cyano-3-fluorophenyl)propionic acid

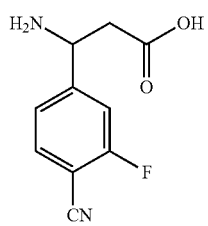 [SMILES: N#Cc1ccc(C(N)CC(=O)O)cc1F]

500 mg (3.35 mmol) 2-fluoro-4-formylbenzonitrile were suspended in 2 ml ethanol. 349 mg (3.35 mmol) propanedioic acid and 0.54 g (7.04 mmol) ammonium acetate were added. The mixture was refluxed for 6 hours and after cooling filtrated. The residue was washed with ethanol and dried in vacuum to give 360 mg (52%) 3-amino-3-(4-cyano-3-fluorophenyl)propionic acid.

Example 14b

3-Amino-3-(4-cyano-3-fluorophenyl)propionic acid methyl ester

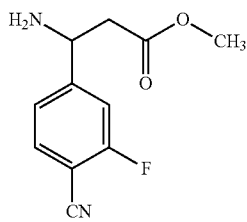 [SMILES: COC(=O)CC(N)c1ccc(C#N)c(F)c1]

436 mg (2.09 mmol) 3-amino-3-(4-cyano-3-fluorophenyl)propionic acid were suspended in 8.5 ml methanol and the mixture cooled to 0° C. 0.23 ml (3.14 mmol) thionyl chloride were slowly added. The mixture was stirred at room temperature for 20 hours and concentrated. The residue was treated with saturated sodium hydrogen carbonate solution and extracted with dichloromethane. The organic part was dried with sodium sulfate and concentrated. Chromatography over silica gel (dichloromethane/ethanol 100/0-97/3-94/ 6) gave 245 mg (47%) 3-amino-3-(4-cyano-3-fluorophenyl)-propionic acid methyl ester.

UPLC (ACN-NH3): Rt.=0.77 min

MS (ES$^+$): m/e=222.74 (M+H$^+$)

Example 14c (3S)-3-(4-Cyano-3-fluorophenyl)-3-[({(3R)-1-[3-(piperidin-4-yl)propanoyl]piperidin-3-yl}carbonyl)amino]propanoic acid

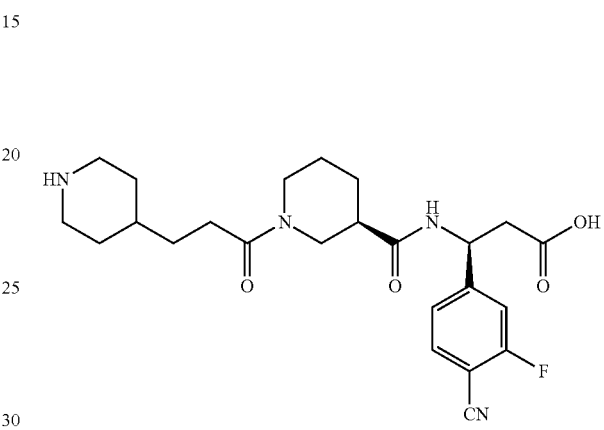

It was produced analogously to examples 2b-2e starting with example 17b to give 254 mg which were purified by HPLC:

| | |
|---|---|
| System: | Waters Autopurificationsystem: Pump 254, Sample Manager 2767, CFO, DAD 2996, ELSD 2424, SQD 3001 |
| Column: | Kromasil C18 5 μm 150 × 30 mm |
| Solvent: | A = H2O + 0.1% HCOOH |
| | B = Methanol |
| Gradient: | 0-1 min 10% B, 1-12 min 10-50% B |
| Flow: | 50 mL/min |
| Temperature: | RT |
| Solution: | 268 mg/3 mL DMSO/MeOH 1:1 |
| Injection: | 4 × 0.75 mL |
| Detection: | DAD scan range 210-400 nm |
| | MS ESI+, ESI−, scan range 160-1000 m/z |
| | ELSD |

| Fractions: | Rt. in min | DAD TAC | Amount |
|---|---|---|---|
| −21 | 6.6-7.4 | 96.7% | 38 mg |
| −23 | 8.2-9.8 | 95.4% | 43 mg |

The fractions were concentrated.

Fraction 23 contained the desired isomer.

UPLC (ACN-HCOOH): Rt.=0.63 min

MS (ES$^+$): m/e=459.1 (M+H$^+$)

MS (ES$^-$): m/e=457.3 (M−H)

Example 15

(3S)-3-(5-{[4-(2-Fluoroethoxy)phenyl]
ethynyl}pyridin-3-yl)-3-[({(3R)-1-[3-(piperidin-4-
yl)propanoyl]piperidin-3-yl}carbonyl)amino]pro-
panoic acid

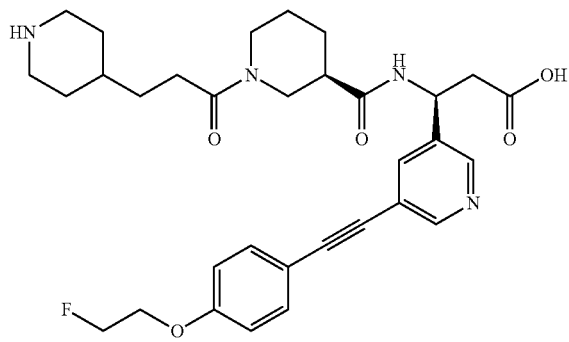 [SMILES: O=C(O)C[C@H](NC(=O)[C@@H]1CCCN(C(=O)CCC2CCNCC2)C1)c1cncc(C#Cc2ccc(OCCF)cc2)c1]

Example 15a

Tert-butyl 4-{3-[(3R)-3-{[(1S)-3-tert-butoxy-1-(5-
{[4-(2-fluoroethoxy)phenyl]ethynyl}pyridine-3-yl)-
3-oxopropyl]carbamoyl}piperidin-1-yl]-
3-oxopropyl}piperidine-1-carboxylate

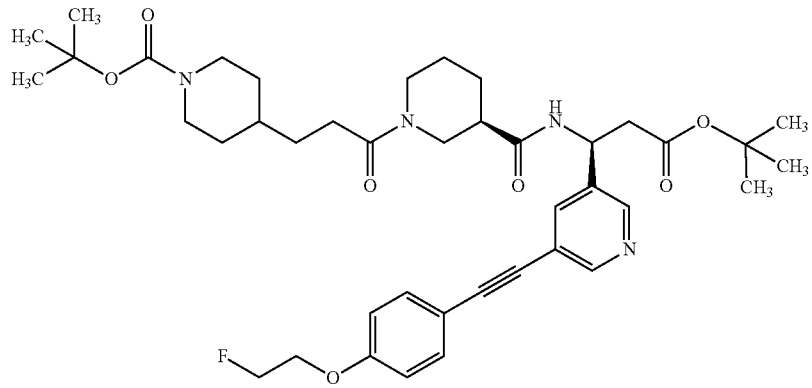 [SMILES: CC(C)(C)OC(=O)C[C@H](NC(=O)[C@@H]1CCCN(C(=O)CCC2CCN(C(=O)OC(C)(C)C)CC2)C1)c1cncc(C#Cc2ccc(OCCF)cc2)c1]

To a degassed solution of tert-butyl 4-[3-((3R)-3-{[(1S)-1-(5-bromopyridin-3-yl)-3-tert-butoxy-3-oxopropyl]carbamoyl}piperidin-1-yl]-3-oxopropyl]piperidine-1-carboxylate (example 27c, 100 mg, 150 µmol), copper iodide (3.5 mg, 20 µmol), tetrakis(triphenylphosphine)palladium (0) (17.7 mg, 20 µmol) and {[4-(2-fluoroethoxy)phenyl]ethynyl}(trimethyl)silane (73 mg, 310 µmol) in 1,2-dimethoxyethan (0.9 mL) and n-butyl amine (0.23 mL) was added a 1 M tetra-n-butyl ammonium fluoride solution in THF (200 µL) over 15 minutes at 80° C. After 20 additional minutes at 80° C. (36 mg, mmol) was added, the mixture was diluted with water after 20 minutes and extracted with ethyl acetate. The organic phase was dried over sodium sulfate and concentrated in vacuum. The residue was purified by preparative HPLC to yield 43 mg of tert-butyl 4-{3-[(3R)-3-{[(1S)-3-tert-butoxy-1-({[4-(2-fluoroethoxy) phenyl]ethynyl}pyridin-3-yl)-3-oxopropyl]carbamoyl}piperidin-1-yl]-3-oxopropyl}piperidine-1-carboxylate.

| Column: | C18 Chromatorex 10 µm 30 × 125 mm |
|---|---|
| Solvent: | A = H₂O + 0.1% HCOOH |
| | B = acetonitrile |
| Gradient: | 0-0.5 min 65% B, 0.5-7 min 65-85% B, |
| Flow: | 120 mL/min |
| Temperature: | RT |
| Detection: | 273 nm |
| Rt.: | 2.50-2.98 min |

UPLC (ACN-HCOOH): Rt.=1.43 min
MS (ES⁺): m/e=735.5 (M+H⁺)
MS (ES⁻): m/e=779.7 (M+HCOO⁻)

Example 15b (3S)-3-(5-{[4-(2-Fluoroethoxy)phenyl]
ethynyl}pyridin-3-yl)-3-[({(3R)-1-[3-(piperidin-4-
yl)propanoyl]piperidin-3-yl}carbonyl)amino]pro-
panoic acid Tert-butyl 4-{3-[(3R)-3-{[(1S)-3-tert-butoxy-1-({[4-(2-fluoroethoxy)phenyl]ethynyl}pyridin-3-yl)-3-oxopropyl]carbamoyl}piperidin-1-yl]-3-oxopropyl}piperidine-1-carboxylate (15.7 mg, 20 µmol) was heated to 60° C. in formic acid for 40 minutes. The solution was then concentrated in vacuum and the residue purified by preparative HPLC to yield 8.9 mg of (3S)-3-(5-{[4-(2-fluoroethoxy)phenyl]ethynyl}pyridin-3-yl)-3-[({(3R)-1-[3-(piperidin-4-yl)propanoyl]piperidin-3-yl}carbonyl)amino]propanoic acid.

| Column: | C18 Chromatorex 10 µm 30 × 125 mm |
|---|---|
| Solvent: | A = H₂O + 0.1% HCOOH |
| | B = acetonitrile |
| Gradient: | 0-0.5 min 20% B, 0.5-7 min 20-40% B, |
| Flow: | 95 mL/min |
| Temperature: | RT |
| Detection: | 271 nm |
| Rt.: | 2.78-4.62 min |

UPLC (ACN-HCOOH): Rt.=0.83 min
MS (ES⁺): m/e=579.3 (M+H⁺)

Example 16

(3S)-3-(5-{[3-(2-Fluoroethoxy)phenyl]ethynyl}pyridin-3-yl)-3-[({(3R)-1-[3-(piperidin-4-yl)propanoyl]piperidin-3-yl}carbonyl)amino]propanoic acid

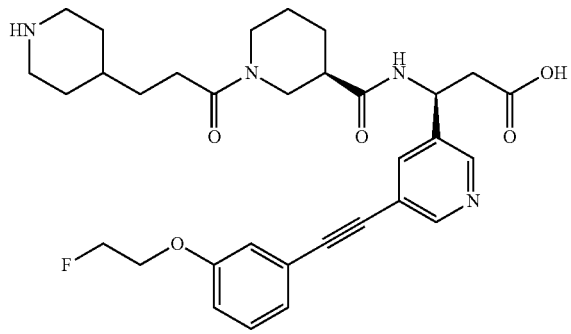 [SMILES: O=C(O)C[C@H](NC(=O)[C@@H]1CCCN(C(=O)CCC2CCNCC2)C1)c1cncc(C#Cc2cccc(OCCF)c2)c1]

Example 16a

Tert-butyl 4-{3-[(3R)-3-{[(1S)-3-tert-butoxy-1-(5-{[3-(2-fluoroethoxy)phenyl]ethynyl}pyridin-3-yl)-3-oxopropyl]carbamoyl}piperidin-1-yl]-3-oxopropyl}piperidine-1-carboxylate

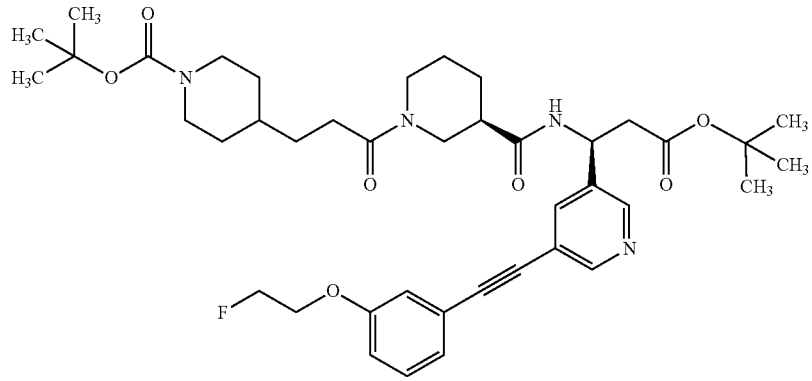 [SMILES: CC(C)(C)OC(=O)C[C@H](NC(=O)[C@@H]1CCCN(C(=O)CCC2CCN(C(=O)OC(C)(C)C)CC2)C1)c1cncc(C#Cc2cccc(OCCF)c2)c1]

To a degassed solution of tert-butyl 4-[3-((3R)-3-{[(1S)-1-(5-bromopyridin-3-yl)-3-tert-butoxy-3-oxopropyl]carbamoyl}piperidin-1-yl)-3-oxopropyl]piperidine-1-carboxylate (example 27c, 100 mg, 15 mmol), copper iodide (4.4 mg, 23 µmol) and tetrakis(triphenylphosphine)palladium(0) (18 mg, 15 µmol) in DMF (0.4 mL) and n-butyl amine (0.23 mL) was added a solution of 1-ethynyl-3-(2-fluoroethoxy)benzene (50 mg, 0.31 mmol) in DMF (0.6 mL) over 60 minutes at 100° C. After additional 20 minutes at 100° C. the mixture was diluted with DMSO and purified by preparative HPLC to yield 90 mg of tert-butyl 4-{3-[(3R)-3-{[(1S)-3-tert-butoxy-1-(5-{[3-(2-fluoroethoxy)phenyl]ethynyl}pyridin-3-yl)-3-oxopropyl]carbamoyl}piperidin-1-yl]-3-oxopropyl}piperidine-1-carboxylate.

| | |
|---|---|
| Column: | C18 Chromatorex 10 µm 30 × 125 mm |
| Solvent: | A = H2O + 0.1% HCOOH |
| | B = acetonitrile |
| Gradient: | 0-0.5 min 65% B, 0.5-7 min 65-90% B, |
| Flow: | 120 mL/min |
| Temperature: | RT |
| Detection: | 277 nm |
| Rt.: | 2.95-3.50 min |

UPLC (ACN-HCOOH): Rt.=1.45 min
MS (ES+): m/e=735.5 (M+H)
MS (ES−): m/e=779.5 (M+HCOO−)

Example 16b (3S)-3-(5-{[3-(2-Fluoroethoxy)phenyl]ethynyl}pyridin-3-yl)-3-[({(3R)-1-[3-(piperidin-4-yl)propanoyl]piperidin-3-yl}carbonyl)amino]propanoic acid Tert-butyl 4-{3-[(3R)-3-{[(1S)-3-tert-butoxy-1-(5-{[3-(2-fluoroethoxy)phenyl]ethynyl}pyridin-3-yl)-3-oxopropyl]carbamoyl}piperidin-1-yl]-3-oxopropyl}piperidine-1-carboxylate (15.7 mg, 20 µmol) was heated to 60° C. in formic acid (1.5 mL) for 40 minutes. The solution was then concentrated in vacuum and the residue purified by preparative HPLC to yield 9.6 mg of (3S)-3-(5-{[3-(2-fluoroethoxy)phenyl]ethynyl}pyridin-3-yl)-3-[({(3R)-1-[3-(piperidin-4-yl)propanoyl]piperidin-3-yl}carbonyl)amino]propanoic acid.

| | |
|---|---|
| Column: | C18 Chromatorex 10 µm 30 × 125 mm |
| Solvent: | A = H2O + 0.1% HCOOH |
| | B = acetonitrile |
| Gradient: | 0-0.5 min 10% B, 0.5-7 min 10-50% B, |
| Flow: | 120 mL/min |
| Temperature: | RT |
| Detection: | 271 nm |
| Rt.: | 4.09-4.38 min |

UPLC (ACN-HCOOH): Rt.=0.91 min
MS (ES+): m/e=579.4 (M+H+)
MS (ES−): m/e=577.4 (M−H)

Example 17

(3S)-3-[5-Fluoro-4'-(2-fluoroethoxy)biphenyl-3-yl]-3-[({(3R)-1-[3-(piperidin-4-yl)propanoyl]piperidin-3-yl}carbonyl)amino]propanoic acid

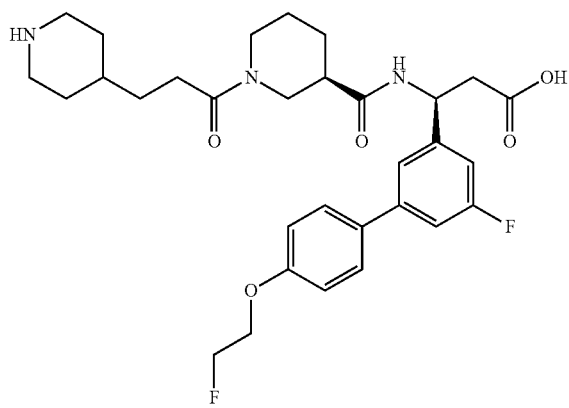 [SMILES: O=C(O)C[C@H](NC(=O)[C@@H]1CCCN(C(=O)CCC2CCNCC2)C1)c1cc(F)cc(-c2ccc(OCCF)cc2)c1]

Example 17a

3-Amino-3-(3-bromo-5-fluorophenyl)propionic acid

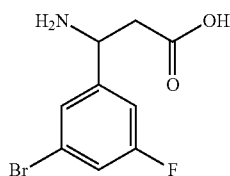

4.72 g (23.25 mmol) 3-bromo-5-fluorobenzaldehyde were suspended in 10 ml ethanol. 2.42 g (23.25 mmol) propanedioic acid and 3.76 g (48.82 mmol) ammonium acetate were added. The mixture was refluxed for 5 hours and after cooling to room temperature filtrated. The residue was washed with cold ethanol and dried in vacuum at 30° C. to give 880 mg (13%) 3-amino-3-(3-bromo-5-fluorophenyl)propionic acid. The filtrate was concentrated and crystallized from ethanol to give further 706 mg (12%) 3-amino-3-(3-bromo-5-fluorophenyl)propionic acid.

UPLC (ACN-HCOOH): Rt.=0.58 min
MS (ES+): m/e=264.1 (M+H+)
MS (ES−): m/e=262.1 (M−H)
$^1$H-NMR (400 MHz, DMSO-d$_6$): δ=2.43 (d, 2H), 4.25 (t, 1H), 7.31 (d, 1H), 7.43 (dt, 1H), 7.50 (s, 1H) ppm.

Example 17b

3-Amino-3-(3-bromo-5-fluorophenyl)propionic acid methyl ester

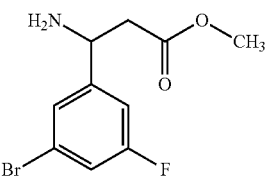

1.59 g (6.05 mmol) 3-amino-3-(3-bromo-5-fluorophenyl) propionic acid were suspended in 24.5 ml methanol and the mixture cooled to 0° C. 0.66 ml (9.08 mmol) thionyl chloride were slowly added. The mixture was stirred at room temperature for 20 hours and concentrated. The residue was treated with saturated sodium hydrogen carbonate solution and extracted with dichloromethane. The organic part was dried with sodium sulfate and concentrated. Chromatography over 10 g silica gel (dichloromethane/ethanol 100/0-95/5-90/10) gave 1.55 g (93%) 3-amino-3-(3-bromo-5-fluorophenyl)propionic acid methyl ester.

UPLC (ACN-NH3): Rt.=1.02 min
MS (ES+): m/e=278.1 (M+H+)
$^1$H-NMR (300 MHz, CHLOROFORM-d): δ=2.55-2.71 (m, 2H), 3.70 (s, 3H), 4.40 (dd, 1H), 7.06 (d, 1H), 7.15 (d, 1H), 7.33 (s, 1H) ppm.

Example 17c

Tert-butyl 4-{3-[(3R)-3-{[1-(3-bromo-5-fluorophenyl)-3-methoxy-3-oxopropyl]carbamoyl}piperidin-1-yl]-3-oxopropyl}piperidine-1-carboxylate

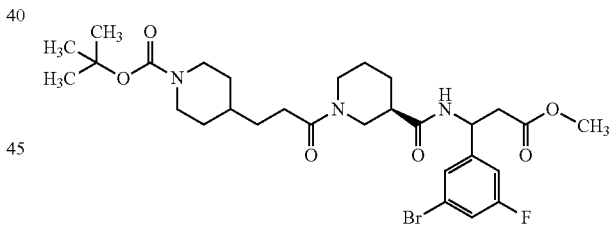

587.2 mg (2.13 mmol) 3-amino-3-(3-bromo-5-fluorophenyl)-propionic acid methyl ester were dissolved in 8.2 ml N,N-dimethylformamide and cooled to 0° C. To this solution was added a solution of 1100 mg (2.36 mmol) tert-butyl 4-{3-[(3R)-3-{[(2,5-dioxopyrrolidin-1-yl)oxy]carbonyl}piperidin-1-yl]-3-oxopropyl}piperidine-1-carboxylate (example 5c) and 0.89 ml (6.38 mmol) triethylamine in 8.2 ml dichloromethane. The mixture was kept at 6° C. for 20 hours. Saturated ammonium chloride solution was added and the mixture extracted with dichloromethane. The organic layer was dried over sodium sulfate and concentrated in vacuum to give 1.66 g (125%) tert-butyl 4-{3-[(3R)-3-{[1-(3-bromo-5-fluorophenyl)-3-methoxy-3-oxopropyl]carbamoyl}piperidin-1-yl]-3-oxopropyl}piperidine-1-carboxylate with 80% purity.

UPLC (ACN-HCOOH): Rt.=1.35 min
MS (ES+): m/e=628.5 (M+H+)
MS (ES−): m/e=626.4 (M−H), 672.4 (M+HCOO−)

Example 17d

Tert-butyl 4-{3-[(3R)-3-{[(1-(5-fluoro-4'-hydroxybiphenyl-3-yl)-3-methoxy-3-oxopropyl]carbamoyl}piperidin-1-yl]-3-oxopropyl}piperidine-1-carboxylate

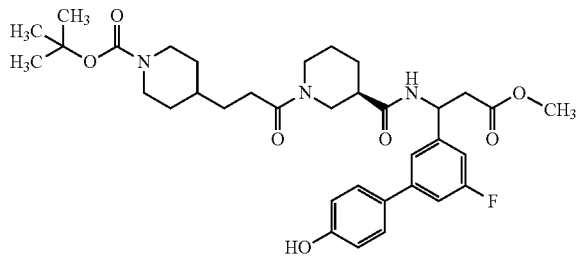 [SMILES: COC(=O)CC(NC(=O)[C@@H]1CCCN(C(=O)CCC2CCN(C(=O)OC(C)(C)C)CC2)C1)c1cc(F)cc(-c2ccc(O)cc2)c1]

To 558.0 mg (0.71 mmol) tert-butyl 4-{3-[(3R)-3-{[1-(3-bromo-5-fluorophenyl)-3-methoxy-3-oxopropyl]carbamoyl}piperidin-1-yl]-3-oxopropyl}piperidine-1-carboxylate in 17.4 ml toluene were added 16.5 mg (0.01 mmol) tetrakis(triphenylphosphine)palladium(0), 117.9 mg (0.85 mmol) (4-hydroxyphenyl)boronic acid in 4.3 ml ethanol and 82.8 mg (1.43 mmol) potassium fluoride in 4.4 ml water. The mixture was stirred at 100° C. for 4 hours, diluted with water and extracted with ethyl acetate. The organic phase was dried over sodium sulfate and concentrated in vacuum. Chromatography over 10 g silica gel (dichloromethane/ethanol 100/0-95/5-90/10) gave 417 mg (92%) tert-butyl 4-{3-[(3R)-3-{[(1-(5-fluoro-4'-hydroxybiphenyl-3-yl)-3-methoxy-3-oxopropyl]carbamoyl}piperidin-1-yl]-3-oxopropyl}piperidine-1-carboxylate.

UPLC (ACN-HCOOH): Rt.=1.24 min
MS (ES$^+$): m/e=640.5 (M+H$^+$)
MS (ES$^-$): m/e=638.5 (M−H), 684.5 (M+HCOO$^-$)

Example 17e

Tert-butyl 4-{3-[(3R)-3-({1-[5-fluoro-4'-(2-fluoroethoxy)biphenyl-3-yl]-3-methoxy-3-oxopropyl}carbamoyl)piperidin-1-yl]-3-oxopropyl}piperidine-1-carboxylate

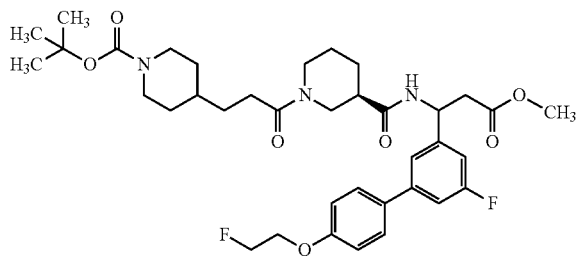 [SMILES: COC(=O)CC(NC(=O)[C@@H]1CCCN(C(=O)CCC2CCN(C(=O)OC(C)(C)C)CC2)C1)c1cc(F)cc(-c2ccc(OCCF)cc2)c1]

234 mg (0.37 mmol) tert-butyl 4-{3-[(3R)-3-{[(1-(5-fluoro-4'-hydroxybiphenyl-3-yl)-3-methoxy-3-oxopropyl]carbamoyl}piperidin-1-yl]-3-oxopropyl}piperidine-1-carboxylate were dissolved in 4.0 ml tetrahydrofurane. 238 mg (0.73 mmol) cesium carbonate and 120.9 mg (0.70 mmol) 1-iodo-2-fluoroethane were added. The mixture was stirred at room temperature for 20 hours. 120.9 mg (0.70 mmol) 1-iodo-2-fluoroethane were added and the mixture stirred at room temperature for 70 hours, diluted with water and extracted with ethyl acetate. The organic phase was dried over sodium sulfate and concentrated in vacuum. Chromatography over 10 g silica gel (dichloromethane/ethanol 100/0-90/10) gave 225 mg (90%) tert-butyl 4-{3-[(3R)-3-({1-[5-fluoro-4'-(2-fluoroethoxy)biphenyl-3-yl]-3-methoxy-3-oxopropyl}carbamoyl)piperidin-1-yl]-3-oxopropyl}piperidine-1-carboxylate.

UPLC (ACN-HCOOH): Rt.=1.38 min
MS (ES$^+$): m/e=686.2 (M+H$^+$)
MS (ES$^-$): m/e=730.5 (M+HCOO$^-$)

Example 17f 3-({[(3R)-1-{3-[1-(Tert-butoxycarbonyl)piperidin-4-yl]propanoyl}piperidin-3-yl]carbonyl}amino)-3-[5-fluoro-4'-(2-fluoroethoxy)biphenyl-3-yl]propanoic acid

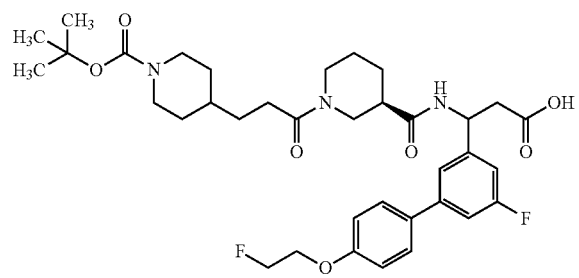 [SMILES: CC(C)(C)OC(=O)N1CCC(CCC(=O)N2CCC[C@@H](C(=O)NC(CC(=O)O)c3cc(F)cc(-c4ccc(OCCF)cc4)c3)C2)CC1]

220 mg (0.32 mmol) tert-butyl 4-{3-[(3R)-3-({1-[5-fluoro-4'-(2-fluoroethoxy)biphenyl-3-yl]-3-methoxy-3-oxopropyl}carbamoyl)piperidin-1-yl]-3-oxopropyl}piperidine-1-carboxylate were dissolved in 10.4 ml tetrahydrofurane. 3.85 ml (0.39 mmol) 0.1N sodium hydroxide solution were added. The mixture was stirred at room temperature for 20 hours, diluted with water and a small amount of 1N sodium hydroxide solution and extracted with ethyl acetate. The aqueous layer was brought to pH=4.5 with 10% aqueous citric acid solution and extracted with dichloromethane and dichloromethane/2-propanol 8/2. The organic layer was dried over sodium sulfate and concentrated in vacuum to give 150 mg (70%) 3-({[(3R)-1-{3-[1-(tert-butoxycarbonyl)piperidin-4-yl]propanoyl}piperidin-3-yl]carbonyl}amino)-3-[5-fluoro-4'-(2-fluoroethoxy)biphenyl-3-yl]propanoic acid.

UPLC (ACN-HCOOH): Rt.=1.32 min
MS (ES$^+$): m/e=672.3 (M+H$^+$)
MS (ES$^-$): m/e=670.4 (M−H)

Example 17 g (3S)-3-[5-Fluoro-4'-(2-fluoroethoxy)biphenyl-3-yl]-3-[({(3R)-1-[3-(piperidin-4-yl)propanoyl]piperidin-3-yl}carbonyl)amino]propanoic acid

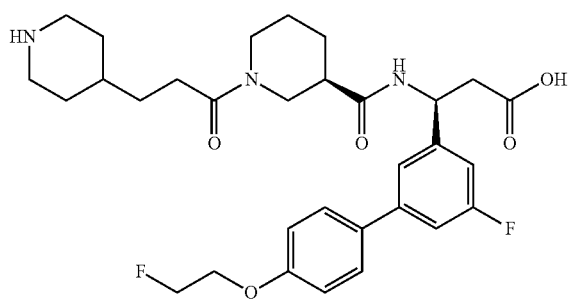 [SMILES: O=C(O)C[C@H](NC(=O)[C@@H]1CCCN(C(=O)CCC2CCNCC2)C1)c1cc(F)cc(-c2ccc(OCCF)cc2)c1]

148 mg (0.22 mmol) 3-({[(3R)-1-{3-[1-(tert-butoxycarbonyl)piperidin-4-yl]propanoyl}piperidin-3-yl]carbonyl}amino)-3-[5-fluoro-4'-(2-fluoroethoxy)biphenyl-3-yl]propanoic acid were suspended in 13.4 ml dioxane. 0.55 ml (2.20 mmol) 4 N hydrochloric acid were added. The mixture was stirred at room temperature for 20 hours and then concentrated to give 150 mg which were purified by HPLC:

| System: | Waters Autopurificationsystem: Pump 254, Sample Manager 2767, CFO, DAD 2996, ELSD 2424, SQD 3001 |
|---|---|
| Column: | XBrigde C18 5 μm 100 × 30 mm |
| Solvent: | A = H2O + 0.2% NH3 |
|  | B = Methanol |
| Gradient: | 0-1 min 10% B, 1-12 min 10-80% B |
| Flow: | 50 mL/min |
| Temperature: | RT |
| Solution: | 150 mg/3 mL DMSO/MeOH 1:1 |
| Injection: | 3 × 1 mL |
| Detection: | DAD scan range 210-400 nm |
|  | MS ESI+, ESI−, scan range 160-1000 m/z |
|  | ELSD |

| Fractions: | Rt. in min | DAD TAC | Amount |
|---|---|---|---|
| 11 | 8.4-8.8 | >99% | 41 mg |
| 12 | 9.3-9.8 | 98.3% | 18 mg |

The fractions were concentrated, mixed with tert.-butanol and lyophilized.

Fraction 12 contained the desired isomer.
UPLC (ACN-HCOOH): Rt.=1.12 min
MS (ES+): m/e=572.19 (M+H+)
MS (ES−): m/e=570.16 (M−H)

Example 18

(3S)-3-(5-{2-[4-(2-Fluoroethoxy)phenyl]ethyl}pyridin-3-yl)-3-[({(3R)-1-[3-(piperidin-4-yl)propanoyl]piperidin-3-yl}carbonyl)amino]propanoic acid

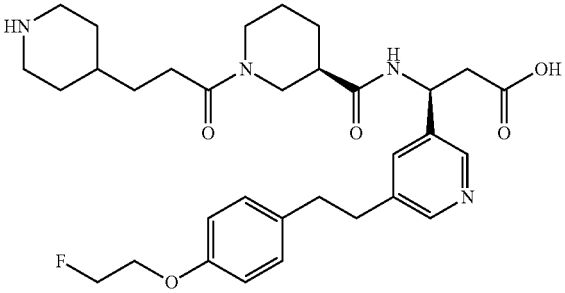 [SMILES: O=C(O)C[C@H](NC(=O)[C@@H]1CCCN(C(=O)CCC2CCNCC2)C1)c1cncc(CCc2ccc(OCCF)cc2)c1]

Example 18a

Tert-butyl 4-{3-[(3R)-3-{[(1S)-3-tert-butoxy-1-(5-{2-[4-(2-fluoroethoxy)phenyl]ethyl}pyridin-3-yl)-3-oxopropyl]carbamoyl}piperidin-1-yl]-3-oxopropyl}piperidine-1-carboxylate

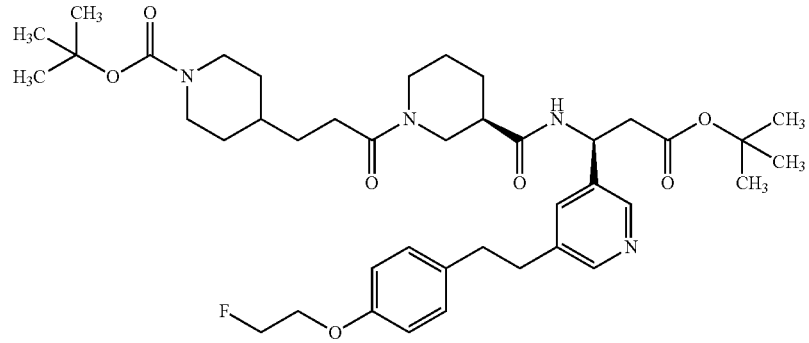 [SMILES: CC(C)(C)OC(=O)C[C@H](NC(=O)[C@@H]1CCCN(C(=O)CCC2CCN(C(=O)OC(C)(C)C)CC2)C1)c1cncc(CCc2ccc(OCCF)cc2)c1]

Tert-butyl 4-{3-[(3R)-3-{[(1S)-3-tert-butoxy-1-(5-{[4-(2-fluoroethoxy)phenyl]ethynyl}pyridin-3-yl)-3-oxopropyl]carbamoyl}piperidin-1-yl]-3-oxopropyl}piperidine-1-carboxylate (20 mg, 30 μmol) in ethyl acetate (0.8 mL) and methanol (013 mL) was stirred for 4.45 hours at room temperature under a hydrogen atmosphere in the presence of palladium on charcoal (10%, 19 mg). The suspension was filtrated through celite, which were washed thoroughly with methanol. The solution was concentrated under reduced pressure and purified by preparative HPLC to yield 13.9 mg of tert-butyl 4-{3-[(3R)-3-{[(1S)-3-tert-butoxy-1-(5-{2-[4-(2-fluoroethoxy)phenyl]ethyl}pyridin-3-yl)-3-oxopropyl]carbamoyl}piperidin-1-yl]-3-oxopropyl}piperidine-1-carboxylate.

| Column: | C18 Chromatorex 10 μm 125 × 30 mm |
|---|---|
| Solvent: | A = H2O + 0.1% HCOOH |
| | B = acetonitrile |
| Gradient: | 0-0.5 min 40% B, 0.5-7 min 40-80% B, |
| Flow: | 120 mL/min |
| Temperature: | RT |
| Detection: | 271 nm |
| Rt.: | 3.48-4.35 min |

UPLC (ACN-HCOOH): Rt.=1.31 min
MS (ES$^+$): m/e=739.5 (M+H$^+$)
MS (ES$^-$): m/e=783.4 (M+HCOO$^-$)

Example 18b (3S)-3-(5-{2-[4-(2-Fluoroethoxy)phenyl]ethyl}pyridin-3-yl)-3-[({(3R)-1-[3-(piperidin-4-yl)propanoyl]piperidin-3-yl}carbonyl)amino]propanoic acid Tert-butyl 4-{3-[(3R)-3-{[(1S)-3-tert-butoxy-1-({[4-(2-fluoroethoxy)phenyl]ethyl}pyridin-3-yl)-3-oxopropyl]carbamoyl}piperidin-1-yl]-3-oxopropyl}piperidine-1-carboxylate (12.5 mg, 20 μmol) was heated to 60° C. in formic acid for 30 minutes. The solution was then concentrated in vacuum and the residue purified by preparative HPLC to yield 9.2 mg of (3S)-3-(5-{2-[4-(2-fluoroethoxy)phenyl]ethyl}pyridin-3-yl)-3-[({(3R)-1-[3-(piperidin-4-yl)propanoyl]piperidin-3-yl}carbonyl)amino]propanoic acid.

| Column: | C18 Chromatorex 10 μm 30 × 125 mm |
|---|---|
| Solvent: | A = H2O + 0.1% HCOOH |
| | B = acetonitrile |
| Gradient: | 0-0.5 min 10% B, 0.5-7 min 10-40% B, |
| Flow: | 120 mL/min |
| Temperature: | RT |
| Detection: | 269 nm |
| Rt.: | 2.31-3.41 min |

UPLC (ACN-HCOOH): Rt.=0.69 min
MS (ES$^+$): m/e=583.5 (M+H$^+$)

Example 19

(3S)-3-(5-{2-[3-(2-Fluoroethoxy)phenyl]ethyl}pyridin-3-yl)-3-[({(3R)-1-[3-(piperidin-4-yl)propanoyl]piperidin-3-yl}carbonyl)amino]propanoic acid

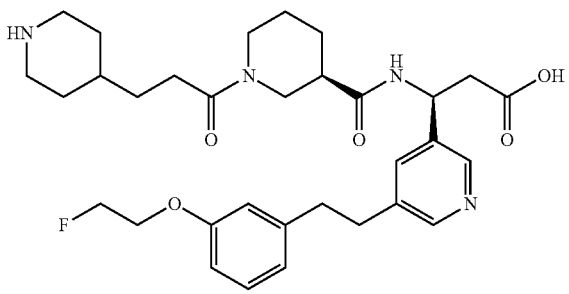 [SMILES: O=C(O)C[C@H](NC(=O)[C@@H]1CCCN(C(=O)CCC2CCNCC2)C1)c1cncc(CCc2cccc(OCCF)c2)c1]

Example 19a

Tert-butyl 4-{3-[(3R)-3-{[(1S)-3-tert-butoxy-1-(5-{2-[3-(2-fluoroethoxy)phenyl]ethyl}pyridin-3-yl)-3-oxopropyl]carbamoyl}piperidin-1-yl]-3-oxopropyl}piperidine-1-carboxylate

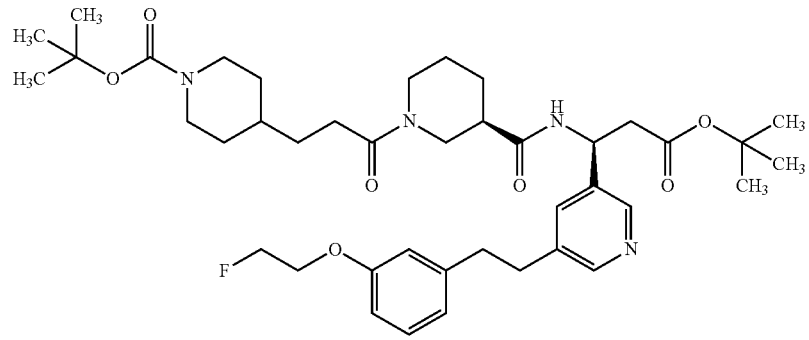 [SMILES: CC(C)(C)OC(=O)C[C@H](NC(=O)[C@@H]1CCCN(C(=O)CCC2CCN(C(=O)OC(C)(C)C)CC2)C1)c1cncc(CCc2cccc(OCCF)c2)c1]

Tert-butyl 4-{3-[(3R)-3-{[(1S)-3-tert-butoxy-1-(5-{[3-(2-fluoroethoxy)phenyl]ethynyl}pyridin-3-yl)-3-oxopropyl]carbamoyl}piperidin-1-yl]-3-oxopropyl}piperidine-1-carboxylate (30 mg, 40 μmol) in ethyl acetate (1.2 mL) and methanol (0.2 mL) was stirred for 2.5 hours at room temperature under a hydrogen atmosphere in the presence of palladium on charcoal (10%, 3 mg). The suspension was filtrated through celite, which were washed thoroughly with methanol. The solution was concentrated under reduced pressure and purified by preparative HPLC to yield 21.9 mg of tert-butyl 4-{3-[(3R)-3-{[(1S)-3-tert-butoxy-1-(5-{2-[3-(2-fluoroethoxy)phenyl]ethyl}pyridin-3-yl)-3-oxopropyl]carbamoyl}piperidin-1-yl]-3-oxopropyl}piperidine-1-carboxylate

| Column: | C18 Chromatorex 10 μm 125 × 30 mm |
|---|---|
| Solvent: | A = H2O + 0.1% HCOOH |
|  | B = acetonitrile |
| Gradient: | 0-0.5 min 40% B, 0.5-7 min 40-80% B, |
| Flow: | 120 mL/min |
| Temperature: | RT |
| Detection: | 271 nm |
| Rt.: | 3.48-4.35 min |

UPLC (ACN-HCOOH): Rt.=1.31 min
MS (ES+): m/e=739.5 (M+H+)
and 2.4 mg of an E/Z mixture of tert-butyl 4-{3-[(3R)-3-{[(1S)-3-tert-butoxy-1-(5-{2-[3-(2-fluoroethoxy)phenyl]ethenyl}pyridin-3-yl)-3-oxopropyl]carbamoyl}piperidin-1-yl]-3-oxopropyl}piperidine-1-carboxylate.
UPLC (ACN-HCOOH): Rt.=1.38 min
MS (ES+): m/e=737.5 (M+H+)

Example 19b (3S)-3-(5-{2-[3-(2-fluoroethoxy)phenyl]ethyl}pyridin-3-yl)-3-[({(3R)-1-[3-(piperidin-4-yl)propanoyl]piperidin-3-yl}carbonyl)amino]propanoic acid Tert-butyl 4-{3-[(3R)-3-{[(1S)-3-tert-butoxy-1-(5-{2-[3-(2-fluoroethoxy)phenyl]ethyl}pyridin-3-yl)-3-oxopropyl]carbamoyl}piperidin-1-yl]-3-oxopropyl}piperidine-1-carboxylate (20 mg, 30 μmol) was heated to 60° C. in formic acid for 50 minutes. The solution was then concentrated in vacuum and the residue purified by preparative HPLC to yield 12 mg of (3S)-3-(5-{2-[3-(2-fluoroethoxy)phenyl]ethyl}pyridin-3-yl)-3-[({(3R)-1-[3-(piperidin-4-yl)propanoyl]piperidin-3-yl}carbonyl)amino]propanoic acid.

| Column: | C18 Chromatorex 10 μm 30 × 125 mm |
|---|---|
| Solvent: | A = H2O + 0.1% HCOOH |
|  | B = acetonitrile |
| Gradient: | 0-0.5 min 10% B, 0.5-7 min 10-40% B, |
| Flow: | 120 mL/min |
| Temperature: | RT |
| Detection: | 269 nm |
| Rt.: | 2.27-3.48 min |

UPLC (ACN-HCOOH): Rt.=0.69 min
MS (ES+): m/e=583.3 (M+H+)

Example 20

(E/Z)(3S)-3-(5-{2-[3-(2-Fluoroethoxy)phenyl]ethenyl}pyridin-3-yl)-3-[({(3R)-1-[3-(piperidin-4-yl)propanoyl]piperidin-3-yl}carbonyl)amino]propanoic acid

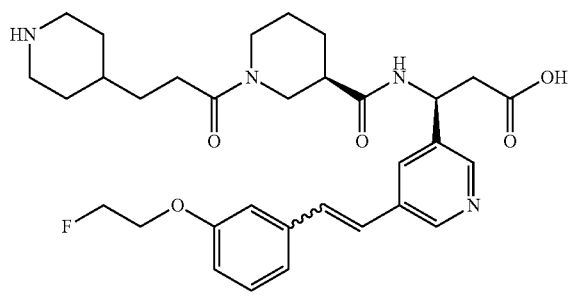 [SMILES: O=C(O)C[C@H](NC(=O)[C@@H]1CCCN(C(=O)CCC2CCNCC2)C1)c1cncc(C=Cc2cccc(OCCF)c2)c1]

Tert-butyl 4-{3-[(3R)-3-{[(1S)-3-tert-butoxy-1-({[3-(2-fluoroethoxy)phenyl]ethenyl}pyridin-3-yl)-3-oxopropyl]carbamoyl}piperidin-1-yl]-3-oxopropyl}piperidine-1-carboxylate (2.4 mg, 3.2 μmol) was heated to 60° C. in formic acid for 40 minutes. The solution was then concentrated in vacuum to yield 1.6 mg of (E/Z)(3S)-3-(5-{2-[3-(2-fluoroethoxy)phenyl]ethenyl}pyridin-3-yl)-3-[({(3R)-1-[3-(piperidin-4-yl)propanoyl]piperidin-3-yl}carbonyl)amino]propanoic acid.
UPLC (ACN-HCOOH): Rt.=0.75/0.77 min
MS (ES+): m/e=581.5 (M+H+)

Example 21

Tert-butyl 4-{3-[(3R)-3-({(1S)-3-methoxy-1-[3-(2-{[(4-methylphenyl)sulfonyl]oxy}ethoxy)phenyl]-3-oxopropyl}carbamoyl)piperidin-1-yl]-3-oxopropyl}piperidine-1-carboxylate

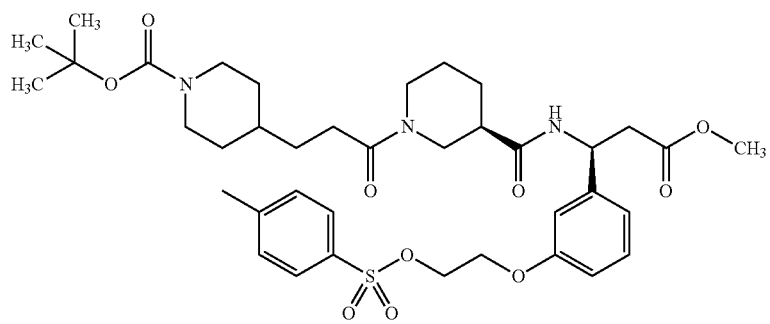 [SMILES: COC(=O)C[C@H](NC(=O)[C@@H]1CCCN(C(=O)CCC2CCN(C(=O)OC(C)(C)C)CC2)C1)c1cccc(OCCOS(=O)(=O)c2ccc(C)cc2)c1]

Tert-butyl-4-{3-[(3R)-3-{[(1S)-1-(5-hydroxypyridin-3-yl)-3-methoxy-3-oxopropyl]carbamoyl}piperidin-1-yl]-3-oxopropyl}piperidine-1-carboxylate (example 4e, 80 mg, 0.15 mmol) was dissolved in N,N-dimethylformamide (20 mL). Cesium carbonate (120 mg, 0.37 mmol) and ethylene glycol bis-p-toluenesulfonate (81 mg, 0.22 mmol) were added. The mixture was stirred at room temperature for 2 hours, quenched by addition of saturated aqueous ammonium chloride solution and extracted with ethyl acetate. The combined extracts were washed with brine and dried over sodium sulfate. The solution was concentrated under reduced pressure and the residue was purified by preparative thin layer chromatography on silica gel (ethyl acetate in dichloromethane 60%) to yield 67 mg of tert-butyl 4-{3-[(3R)-3-({(1S)-3-methoxy-1-[3-(2-{[(4-methylphenyl)sulfonyl]oxy}ethoxy)phenyl]-3-oxopropyl}carbamoyl)piperidin-1-yl]-3-oxopropyl}piperidine-1-carboxylat.

UPLC (ACN-HCOOH): Rt.=1.39 min
MS (ES$^+$): m/e=744.60 (M+H$^+$)
MS (ES$^-$): m/e=788.52 (M+HCOO$^-$)

Example 22

Tert-butyl 4-{3-[(3R)-3-({3-methoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate

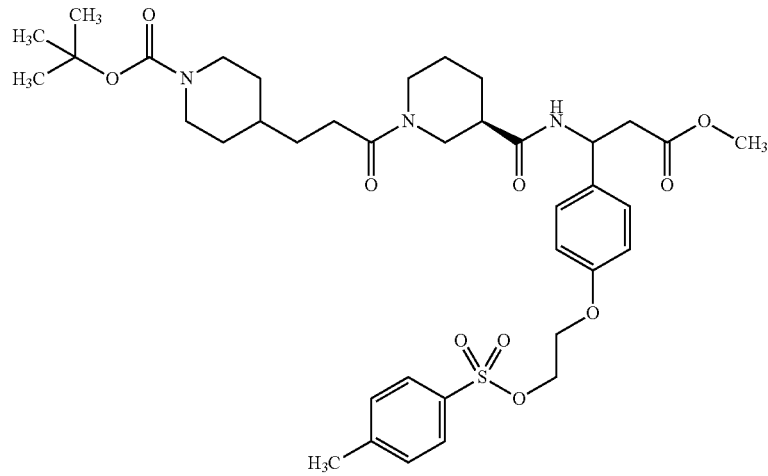 [SMILES: COC(=O)CC(NC(=O)[C@@H]1CCCN(C(=O)CCC2CCN(C(=O)OC(C)(C)C)CC2)C1)c1ccc(OCCOS(=O)(=O)c2ccc(C)cc2)cc1]

100 mg (0.18 mmol) Tert-butyl 4-[3-((3R)-3-{[1-(4-hydroxyphenyl)-3-methoxy-3-oxopropyl]carbamoyl}piperidin-1-yl)-3-oxopropyl]piperidine-1-carboxylate (example 2b) were dissolved in 7 ml N,N-dimethylformamide. 179 mg (0.55 mmol) cesium carbonate and 102 mg (0.28 mmol) ethylene glycol bis-p-toluenesulfonate were added. The mixture was stirred at room temperature for 48 hours and concentrated. The remainder was taken up with saturated ammonium chloride solution and ethyl acetate. The aqueous phase was extracted with 3×20 ml ethyl acetate. The extracts were dried over sodium sulfate and concentrated to yield 195 mg. Chromatography over 5 g silica gel (dichloromethane/ethanol 100/0-95/5) gave 95 mg (63%) tert-butyl 4-{3-[(3R)-3-({3-methoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate.

UPLC (ACN-HCOOH): Rt.=1.37-1.38 min
MS (ES$^+$): m/e=744.37 (M+H$^+$)
MS (ES$^-$): m/e=788.34 (M+HCOO$^-$)

Example 23

Tert-butyl 4-{3-[(3R)-3-({(1S)-3-tert-butoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate

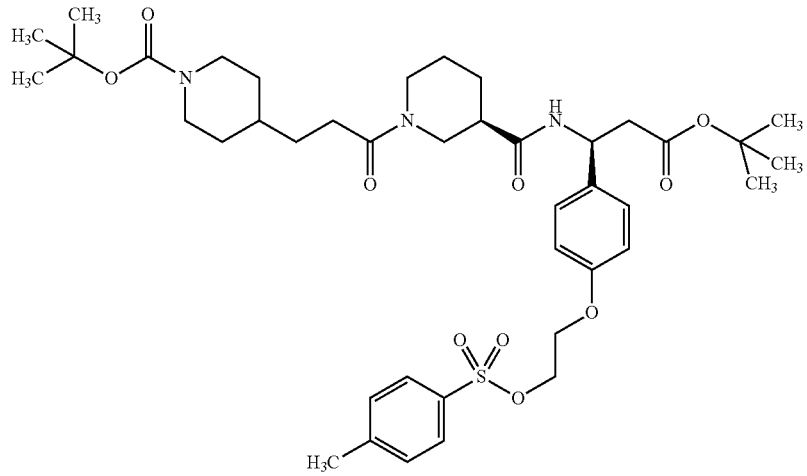 [SMILES: Cc1ccc(S(=O)(=O)OCCOc2ccc([C@H](CC(=O)OC(C)(C)C)NC(=O)[C@@H]3CCCN(C(=O)CCC4CCN(C(=O)OC(C)(C)C)CC4)C3)cc2)cc1]

Example 23a (S)-3-Amino-3-(4-hydroxyphenyl)propionic acid tert-butyl ester

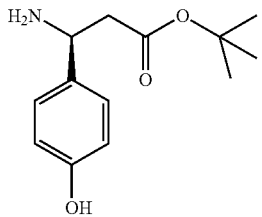 [SMILES: CC(C)(C)OC(=O)C[C@H](N)c1ccc(O)cc1]

1.00 g (5.52 mmol) commercial 3-amino-3-(4-hydroxyphenyl)-propionic acid were suspended in 20 ml tert-butyl acetate and the mixture cooled to 15° C. 0.90 ml (11.10 mmol) perchloric acid were slowly added and the mixture stirred at 20° C. for 1.5 hours. The solution was extracted with saturated sodium hydrogen carbonate solution. The aqueous layer was brought to pH=8 with sodium carbonate and extracted with ethyl acetate. The organic parts were combined, dried over sodium sulfate and concentrated to yield 1.0 g (60%) racemic 3-amino-3-(4-hydroxy-phenyl)-propionic acid tert-butyl ester. This was separated into the enantiomers by HPLC:

| System: | 2x Labomatic Pumpe HD-3000, Labomatic AS-3000, Knauer DAD 2600, Labomatic Labcol Vario 4000 Plus |
| --- | --- |
| Column: | Chiralpak AD-H 5 µm 250 × 50 mm |
| Solvent: | Hexane/IPA 90:10 + 0.1% Diethylamine |
| Flow: | 100 mL/min |
| Temperature: | RT |
| Solution: | 1000 mg/10 mL EtOH |
| Injection: | 4 × 2.5 mL |
| Detection: | UV 230 nm |

| Fractions: | Rt. in min | % | Amount |
| --- | --- | --- | --- |
| 11 | 8.98 | 98.7 | 232.6 mg |
| 12 | 11.07 | 96.4 | 232.7 mg |

The fractions were concentrated.

Fraction 12 contained the desired isomer.
UPLC (ACN-NH3): Rt.=0.81 min
MS (ES+): m/e=239.18 (M+H+)
MS (ES−): m/e=236.18 (M−H), 282.18 (M+HCOO−)
Optical rotation (P2000 Polarimeter, CHCl$_3$): $[\alpha]_D$=−13.6°+/−0.11°

Literature: $[\alpha]_D$=−8.5° (*Tetrahedron: Asymmetry* 18 (2007) 1554-1566, 3.6.72 Compound (S)-46)

Example 23b 4-(3-{(R)-3-[(S)-2-tert-Butoxycarbonyl-1-(4-hydroxy-phenyl)-ethylcarbamoyl]-piperidin-1-yl}-3-oxo-propyl)-piperidine-1-carboxylic acid tert-butyl ester

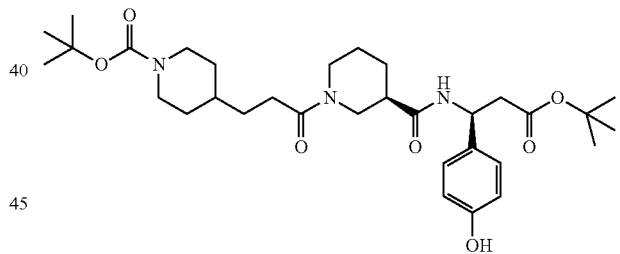

214.0 mg (0.90 mmol) (S)-3-amino-3-(4-hydroxy-phenyl)-propionic acid tert-butyl ester were dissolved in 3.5 ml N,N-dimethylformamide and cooled to 0° C. To this solution was added a solution of 466.4 mg (1.00 mmol) tert-butyl 4-{3-[(3R)-3-{[(2,5-dioxopyrrolidin-1-yl)oxy]carbonyl}piperidin-1-yl]-3-oxopropyl}piperidine-1-carboxylate (example 5c) and 0.38 ml (2.71 mmol) triethylamine in 3.5 ml dichloromethane. The mixture was kept at 6° C. for 20 hours. Saturated ammonium chloride solution was added and the mixture extracted with dichloromethane. The organic layer was dried over sodium sulfate and concentrated in vacuum to give 820 mg. Chromatography over 5 g silica gel (dichloromethane/ethanol 100/0-95/5-90/10) gave 539 mg (102%) 4-(3-{(R)-3-[(S)-2-tert-butoxycarbonyl-1-(4-hydroxy-phenyl)-ethylcarbamoyl]-piperidin-1-yl}-3-oxo-propyl)-piperidine-1-carboxylic acid tert-butyl ester
UPLC (ACN-HCOOH): Rt.=1.24 min
MS (ES+): m/e=588.5 (M+H+)
MS (ES−): m/e=586.6 (M−H), 632.6 (M+HCOO−)

Example 23c

Tert-butyl 4-{3-[(3R)-3-({(1S)-3-tert-butoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate

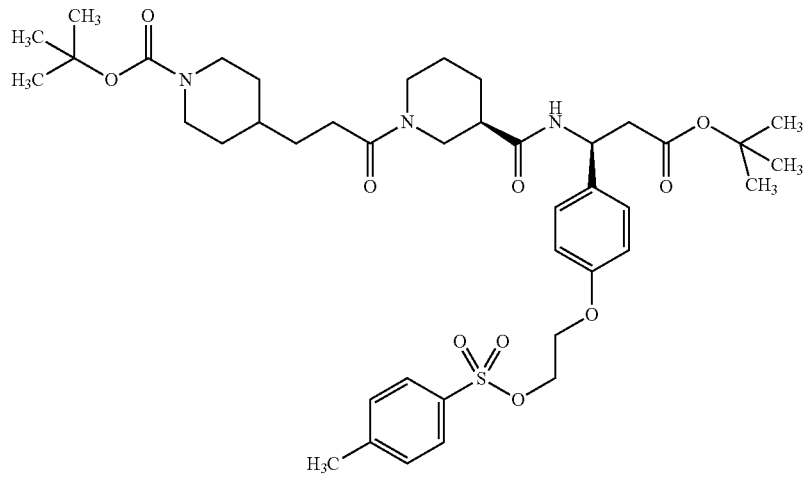 [SMILES: Cc1ccc(S(=O)(=O)OCCOc2ccc([C@H](CC(=O)OC(C)(C)C)NC(=O)[C@@H]3CCCN(C(=O)CCC4CCN(C(=O)OC(C)(C)C)CC4)C3)cc2)cc1]

270.0 mg (0.46 mmol) 4-(3-{(R)-3-[(S)-2-tert-butoxycarbonyl-1-(4-hydroxy-phenyl)-ethylcarbamoyl]-piperidin-1-yl}-3-oxo-propyl)-piperidine-1-carboxylic acid tert-butyl ester were dissolved in 17.7 ml N,N-dimethylformamide. 449 mg (1.38 mmol) cesium carbonate and 255.3 mg (0.69 mmol) ethylene glycol bis-p-toluenesulfonate were added. The mixture was stirred at room temperature for 20 hours and concentrated. The remainder was taken up with saturated ammonium chloride solution and ethyl acetate. The aqueous phase was extracted with 3×20 ml ethyl acetate. The extracts were dried over sodium sulfate and concentrated. Chromatography over 10 g silica gel (dichloromethane/ethanol 100/0-90/10) gave 227 mg (63%) tert-butyl 4-{3-[(3R)-3-({(1S)-3-tert-butoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate which were purified by HPLC:

| System: | Waters Autopurificationsystem: Pump 254, Sample Manager 2767, CFO, DAD 2996, ELSD 2424, SQD 3001 |
|---|---|
| Column: | XBrigde C18 5 μm 100 × 30 mm |
| Solvent: | A = H2O + 0.1% HCOOH |
| | B = Acetonitrile |
| Gradient: | 0-1 min 30% B, 1-8 min 30-100% B |
| Flow: | 50 mL/min |
| Temperature: | RT |
| Solution: | 227 mg/2 mL DMSO/MeOH 1:1 |
| Injection: | 2 × 1 mL |
| Detection: | DAD scan range 210-400 nm |
| | MS ESI+, ESI–, scan range 160-1000 m/z |
| | ELSD |

| Fractions: | Rt. in min | % | Amount |
|---|---|---|---|
| 11 | 6.6-7.0 | >99 | 125 mg |

The fractions were concentrated, mixed with tert.-butanol and lyophilized.

UPLC (ACN-NH3): Rt.=1.48 min
MS (ES+): m/e=787.8 (M+H+)
MS (ES−): m/e=784.6 (M–H), 830.6 (M+HCOO−)

Example 24

Tert-butyl 4-{3-[(3R)-3-({((1S)-3-methoxy-1-[5-(2-{[(4-methyl phenyl)sulfonyl]oxy}ethoxy)pyridin-3-yl]-3-oxopropyl}carbamoyl)piperidin-1-yl]-3-oxopropyl}piperidine-1-carboxylate

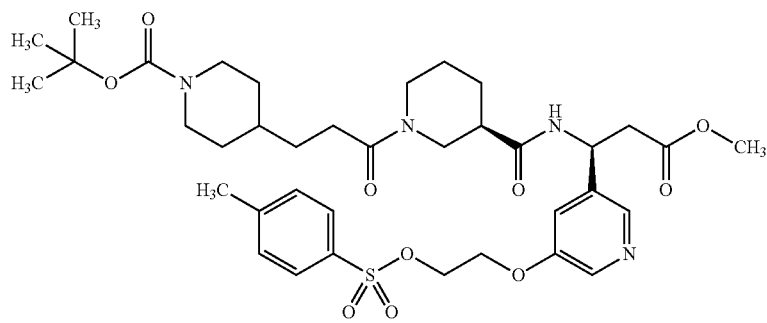

Tert-butyl 4-{3-[(3R)-3-({(1S)-1-[5-(benzyloxy)pyridin-3-yl]-3-methoxy-3-oxopropyl}carbamoyl)piperidin-1-yl]-3-oxopropyl}piperidine-1-carboxylate (example 5e, 200 mg, 0.37 mmol) was dissolved in N,N-dimethylformamide (25.3 mL). Cesium carbonate (298 mg, 0.92 mmol) and ethylene glycol bis-p-toluenesulfonate (203 mg, 0.55 mmol) were added. The mixture was stirred at room temperature for 2 hours and stored at 5° C. for 17 hours. The mixture was quenched by addition of saturated aqueous ammonium chloride solution and extracted with ethyl acetate. The combined extracts were washed with brine and dried over sodium sulfate. The solution was concentrated under reduced pressure and the residue was purified by preparative thin layer chromatography on silica gel (ethyl acetate 100%) to yield 109 mg of tert-butyl 4-{3-[(3R)-3-({(1S)-3-methoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylat.

UPLC (ACN-NH3): Rt.=1.26 min
MS (ES+): m/e=745.6 (M+H+)
MS (ES−): m/e=789.5 (M+HCOO−)

Example 25

Tert-butyl 4-{3-[(3R)-3-({(1S)-3-tert-butoxy-1-[5-(2-{[(4-methyl phenyl)sulfonyl]oxy}ethoxy)pyridin-3-yl]-3-oxopropyl}carbamoyl)piperidin-1-yl]-3-oxopropyl}piperidine-1-carboxylate

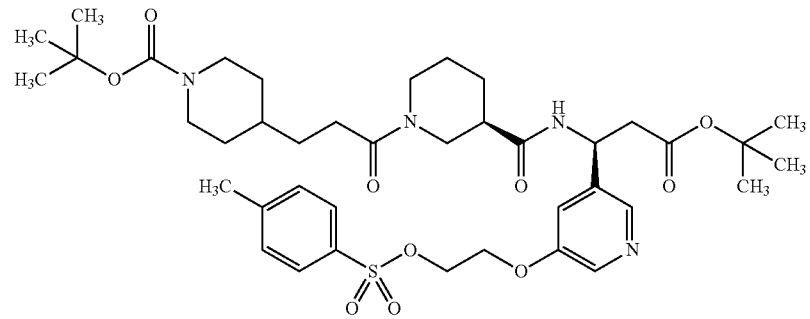 [SMILES: Cc1ccc(S(=O)(=O)OCCOc2cncc([C@H](CC(=O)OC(C)(C)C)NC(=O)[C@@H]3CCCN(C(=O)CCC4CCN(C(=O)OC(C)(C)C)CC4)C3)c2)cc1]

Example 25a 5-(Benzyloxy)pyridine-3-carbonitrile

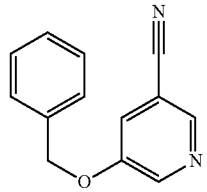 [SMILES: N#Cc1cncc(OCc2ccccc2)c1]

3-(Benzyloxy)-5-bromopyridine (5.38 g, 20.4 mmol, Harrowven et al. *Tetrahedron*, 2001, 57, 4447-4454) in DMF (33 mL) was stirred with copper cyanide (2.9 g, 32.6 mmol) at 160° C. for 7 hours. Saturated aqueous sodium hydrogen carbonate solution and ethyl acetate was added and the formed suspension was stirred at 50° C. for 15 minutes. After filtration the liquid phases were separated. The precipitate was triturated with 10% DMF in ethyl acetate (500 mL) and saturated aqueous sodium hydrogen carbonate solution (100 mL) at 50° C. and filtration and phase separation were performed. The treatment of the precipitate with saturated aqueous sodium hydrogen carbonate solution and 10% DMF in ethyl acetate was repeated two times and the combined organic phases washed with brine and dried over sodium sulfate. The solution was concentrated under reduced pressure and the residue was purified by chromatography on silica gel (ethyl acetate in hexane, 0 to 65%) to yield 3.13 g 5-(benzyloxy)pyridine-3-carbonitrile.

1H-NMR (300 MHz, CDCl3): δ=5.16 (s, 2 H), 7.35-7.55 (m, 6 H), 8.50 (d, 1 H), 8.58 (d, 1 H) ppm.

Example 25 b

Tert-butyl 3-amino-3-[5-(benzyloxy)pyridin-3-yl]prop-2-enoate

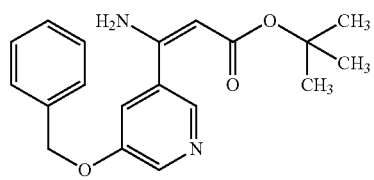 [SMILES: CC(C)(C)OC(=O)/C=C(/N)c1cncc(OCc2ccccc2)c1]

Diisopropylamine (12.8 mL, 91 mmol) was added at 0° C. to a 3M solution of ethyl magnesium bromide in diethyl ether (15 mL, 45 mmol) and additional diethyl ether (40 mL). After one hour at 0° C. t-butyl acetate was added and stirring was continued for 30 minutes. 5-(benzyloxy)pyridine-3-carbonitrile (2.9 g, 13.8 mmol) in diethyl ether (40 mL) was added at 0° C. After 2.5 hours at 0° C. saturated aqueous ammonium chloride solution was added. Phases were separated and the aqueous phase was extracted with diethyl ether. The combined extracts were washed with brine and dried over sodium sulfate. The solution was concentrated under reduced pressure and the residue was purified by chromatography on silica gel (ethyl acetate in hexane, 0 to 45%) to yield 1.95 g tert-butyl 3-amino-3-[5-(benzyloxy)pyridin-3-yl]prop-2-enoate.

1H-NMR (300 MHz, CDCl3): δ=1.53 (s, 9 H), 4.89 (s, 1 H), 5.14 (s, 2 H), 7.33-7.48 (m, 6 H), 8.42 (m, 2 H) ppm.

Example 25c

Tert-butyl (3S)-3-amino-3-[5-(benzyloxy)pyridin-3-yl]propanoate

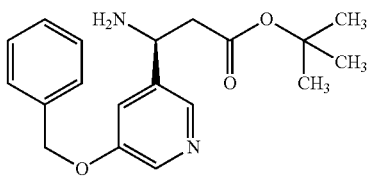 [SMILES: CC(C)(C)OC(=O)C[C@H](N)c1cncc(OCc2ccccc2)c1]

To chloro(1,5-cyclooctadien)rhodium(I) dimer (29 mg, 60 µmol) and (R)-(−)-1-[(S)-2-Di-tert.-butyl-phosphino)ferrocenyl]ethyldi-(4-trifluormethylphenyl)phosphine (81 mg, 120 µmol) under an argon atmosphere was added 2,2,2-trifluoroethanol (4 mL) and the solution was stirred for 40 minutes. To tert-butyl 3-amino-3-[5-(benzyloxy)pyridin-3-yl]prop-2-enoate (1.95 g 5.97 mmol) in degassed 2,2,2-trifluoroethanol (10 mL) in a pressure vessel was added the rhodium catalyst solution and the solution was stirred for 22 hours at 50° C. under hydrogen pressure of 10 bar. The addition of an identically prepared rhodium catalyst solution in 2,2,2-trifluoroethanol (4 mL) was repeated and stirring under 10 bar hydrogen pressure at 50° C. was continued for additional 16 hours. The solution was concentrated under reduced pressure and the residue was purified by chromatography on silica gel (ethyl acetate in hexane, 12 to 100% followed by methanol in ethyl acetate 0 to 15%) to yield 1.16 g of enantiomerically enriched tert-butyl (3S)-3-amino-3-[5-(benzyloxy)pyridin-3-yl]propanoate.

$^1$H-NMR (400 MHz, CDCl$_3$): δ=1.43 (s, 9 H), 2.59 (d, 2 H), 4.42 (t, 1 H), 5.12 (s, 2 H), 7.32-7.50 (m, 6 H), 8.23 (s, 1 H), 8.29 (m, 1 H) ppm.

Optical rotation (P2000 Polarimeter, CHCl$_3$): $[α]_D$= −15.5° (c=1.0 g/100 mL CHCl$_3$)

Example 25d

Tert-butyl 4-{3-[(3R)-3-({(1S)-1-[5-(benzyloxy)pyridin-3-yl]-3-tert-butoxy-3-oxopropyl}carbamoyl)piperidin-1-yl]-3-oxopropyl}piperidine-1-carboxylate

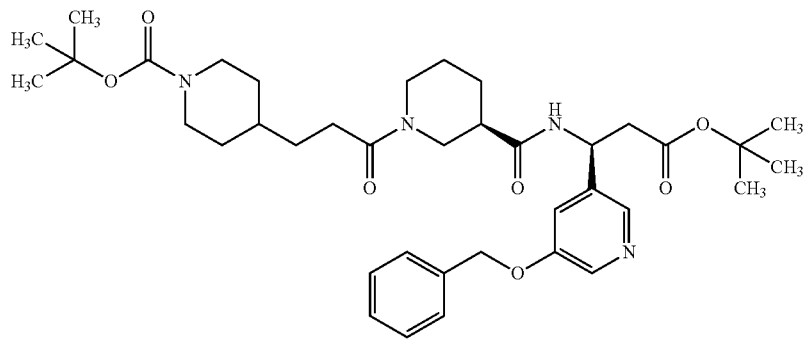 [SMILES: CC(C)(C)OC(=O)C[C@H](NC(=O)[C@@H]1CCCN(C(=O)CCC2CCN(C(=O)OC(C)(C)C)CC2)C1)c1cncc(OCc2ccccc2)c1]

To tert-butyl (3S)-3-amino-3-[5-(benzyloxy)pyridin-3-yl]propanoate (1.15 g, 3.5 mmol) in DMF (13.4 mL) was added tert-butyl 4-{3-[(3R)-3-{[(2,5-dioxopyrrolidin-1-yl)oxy]carbonyl}piperidin-1-yl]-3-oxopropyl}piperidine-1-carboxylate and triethylamine (1.46 mL, 10.5 mmol) in dichloromethane (13.5 mL) at 0° C. After 3 hours the mixture was quenched by addition of saturated aqueous ammonium chloride solution, phases were separated and the aqueous phase was extracted with diethyl ether. Combined organic extracts were dried over sodium sulphate, concentrated under reduced pressure and the residue was purified by chromatography on silica gel (ethyl acetate in hexane, 20 to 100% followed by methanol in ethyl acetate 0 to 20%) to yield 1.76 g tert-butyl 4-{3-[(3R)-3-({(1S)-1-[5-(benzyloxy)pyridin-3-yl]-3-tert-butoxy-3-oxopropyl}carbamoyl)piperidin-1-yl]-3-oxopropyl}piperidine-1-carboxylate.

$^1$H-NMR (300 MHz, DMSO$_{d6}$): δ=0.79-1.08 (m, 3 H), 1.38 (s, 9 H), 1.35 (s, 9 H), 1.49-1.75 (m, 9 H), 2.29 (m, 3 H), 2.59-2.77 (m, 5 H), 2.89-3.13 (m, 1 H), 3.68-3.83 (m, 1 H), 3.83-3.97 (m, 2 H), 5.07-5.27 (m, 1 H), 5.17 (s, 2H), 7.28-7.51 (m, 6 H), 8.12 (br. s, 1 H), 8.24 (br. s, 1 H), 8.39-8.55 (m, 1 H)

Example 25e

Tert-butyl 4-{3-[(3R)-3-{[(1S)-3-tert-butoxy-1-(5-hydroxypyridin-3-yl)-3-oxopropyl]carbamoyl}piperidin-1-yl]-3-oxopropyl}piperidine-1-carboxylate

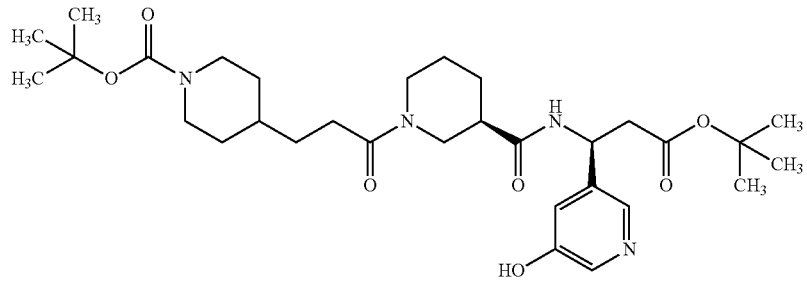 [SMILES: CC(C)(C)OC(=O)C[C@H](NC(=O)[C@@H]1CCCN(C(=O)CCC2CCN(C(=O)OC(C)(C)C)CC2)C1)c1cncc(O)c1]

Tert-butyl 4-{3-[(3R)-3-({(1S)-1-[5-(benzyloxy)pyridin-3-yl]-3-tert-butoxy-3-oxopropyl}carbamoyl)piperidin-1-yl]-3-oxopropyl}piperidine-1-carboxylate (1.69 g, 2.49 mmol) in ethyl acetate (73 mL) and methanol (12 mL) was stirred for 20 hours at room temperature under a hydrogen atmosphere in the presence of palladium on charcoal (10%, 170 mg). The suspension was filtrated through celite, which were washed thoroughly with methanol. The solution was concentrated under reduced pressure and the residue was purified by chromatography on silica gel (methanol in ethyl acetate 0 to 15%) to yield 1.37 g of Tert-butyl 4-{3-[(3R)-3-{[(1S)-3-tert-butoxy-1-(5-hydroxypyridin-3-yl)-3-oxopropyl]carbamoyl}piperidin-1-yl]-3-oxopropyl}piperidine-1-carboxylate.

$^1$H-NMR (400 MHz, DMSO$_{d6}$, 80° C.): δ=0.85-1.09 (m, 2 H), 1.36 (s, 9 H), 1.41 (s, 9 H), 1.30-1.47 (m, 5 H), 1.55-1.72 (m, 4 H), 1.77-1.89 (m, 1 H), 2.29 (m, 3 H), 2.59-2.77 (m, 5 H), 2.89-3.13 (m, 1 H), 3.83-3.97 (m, 3 H), 5.03-5.25 (m, 1 H), 7.09 (t, 1 H), 7.88-8.09 (m, 2 H), 8.14 (d, 1 H), 9.55 (br., 1 H) ppm.

Example 25f

Tert-butyl 4-{3-[(3R)-3-({(1S)-3-tert-butoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylate 4-{3-[(3R)-3-{[(1S)-3-tert-butoxy-1-(5-hydroxypyridin-3-yl)-3-oxopropyl]carbamoyl}piperidin-1-yl]-3-oxopropyl}piperidine-1-carboxylate (200 mg, 0.34 mmol) were dissolved in N,N-dimethylformamide (39 mL). Cesium carbonate (277 mg, 0.85 mmol) and ethylene glycol bis-p-toluenesulfonate (188 mg, 0.51 mmol) were added. The mixture was stirred at room temperature for 4 hours, the addition of cesium carbonate (277 mg, 0.85 mmol) and ethylene glycol bis-p-toluenesulfonate (188 mg, 0.51 mmol) was repeated and stirring at 5° C. was continued for 17 hours. The mixture was quenched by addition of saturated aqueous ammonium chloride solution and extracted with diethyl ether and ethyl acetate. The combined extracts were washed with brine and dried over sodium sulfate. The solution was concentrated under reduced pressure and the residue was purified by chromatography on silica gel (ethyl acetate in hexane 20% to 100% followed by dioxane in ethyl acetate 0 to 60%) to yield 207 mg of tert-butyl 4-{3-[(3R)-3-({(1S)-3-tert-butoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylat.

UPLC (ACN-NH2): Rt.=1.37 min
MS (ES$^+$): m/e=787.5 (M+H$^+$)
MS (ES$^-$): m/e=785.5 (M−H), 831.5 (M+HCOO$^-$)

Example 26

Tert-butyl 4-{3-[(3R)-3-{[3-methoxy-1-{5-[4-(2-{[(4-methyl phenyl)sulfonyl]oxy}ethoxy)phenyl]pyridin-3-yl}-3-oxopropyl]carbamoyl}piperidin-1-yl]-3-oxopropyl}piperidine-1-carboxylate

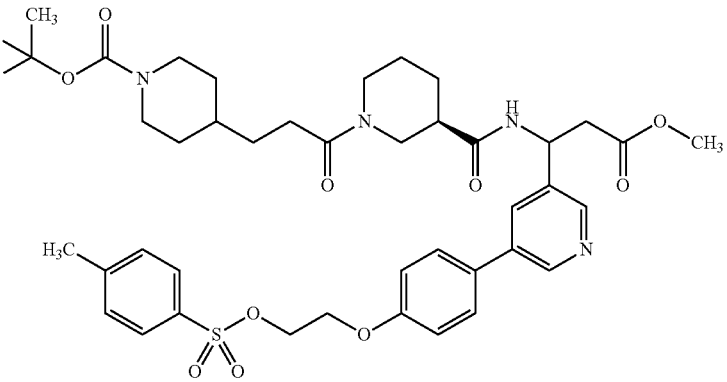

82.0 mg (0.13 mmol) tert-butyl 4-{3-[(3R)-3-({1-[5-(4-hydroxyphenyl)pyridin-3-yl]-3-methoxy-3-oxopropyl}carbamoyl)piperidin-1-yl]-3-oxopropyl}piperidine-1-carboxylate (example 7a) were dissolved in 5.1 ml N,N-dimethylformamide. 129 mg (0.40 mmol) cesium carbonate and 73.2 mg (0.20 mmol) ethylene glycol bis-p-toluenesulfonate were added. The mixture was stirred at room temperature for 20 hours and concentrated. The remainder was taken up with saturated ammonium chloride solution and ethyl acetate. The aqueous phase was extracted with 3×20 ml ethyl acetate. The extracts were dried over sodium sulfate and concentrated. Chromatography over 10 g silica gel (dichloromethane/ethanol 100/0-90/10) gave 64 mg (59%) tert-butyl 4-{3-[(3R)-3-{[3-methoxy-1-{5-[4-(2-{[(4-methylphenyl)sulfonyl]oxy}ethoxy)phenyl]pyridin-3-yl}-3-oxopropyl]carbamoyl}piperidin-1-yl]-3-oxopropyl}piperidine-1-carboxylate.

UPLC (ACN-HCOOH): Rt.=1.30 min
MS (ES$^+$): m/e=821.4 (M+H$^+$)
MS (ES$^-$): m/e=819.6 (M−H), 865.5 (M+HCOO$^-$)

Example 27

Tert-butyl 4-{3-[(3R)-3-{[(1S)-3-tert-butoxy-1-{5-[4-(2-{[(4-methyl phenyl)sulfonyl]oxy}ethoxy)phenyl]pyridin-3-yl}-3-oxopropyl]carbamoyl}piperidin-1-yl]-3-oxopropyl}piperidine-1-carboxylate

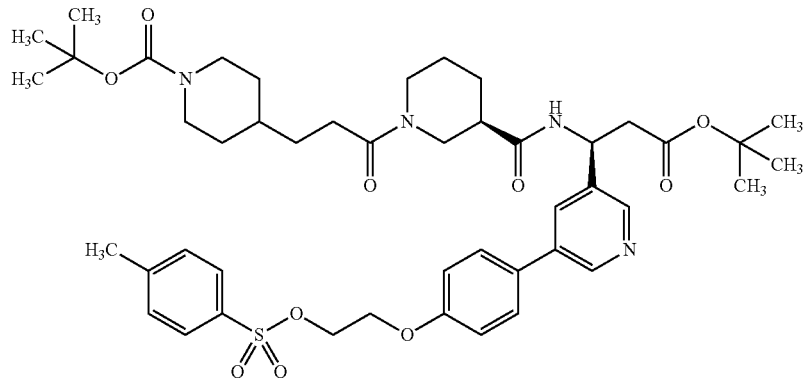 [SMILES: Cc1ccc(S(=O)(=O)OCCOc2ccc(-c3cncc([C@H](CC(=O)OC(C)(C)C)NC(=O)[C@@H]4CCCN(C(=O)CCC5CCN(C(=O)OC(C)(C)C)CC5)C4)c3)cc2)cc1]

Example 27a

Tert-butyl 3-amino-3-[5-bromopyridin-3-yl]prop-2-enoate

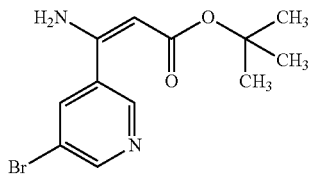 [SMILES: CC(C)(C)OC(=O)/C=C(/N)c1cncc(Br)c1]

Diisopropylamine (9.2 mL, 65 mmol) was added at 0° C. to a 3M solution of ethyl magnesium bromide in diethyl ether (10.9 mL, 32.7 mmol) and additional diethyl ether (20 mL). After one hour at 0° C. tert-butyl acetate (4.3 mL, 32.7 mmol) was added and stirring was continued for 30 minutes. 5-Bromopyridine-3-carbonitrile (2.0 g, 10.9 mmol) in diethyl ether (42 mL) was added at 0° C. After two hours at 0° C. saturated aqueous ammonium chloride solution was added. Phases were separated and the aqueous phase was extracted with diethyl ether. The combined extracts were washed with brine and dried over sodium sulfate. The solution was concentrated under reduced pressure and the residue was purified by chromatography on silica gel (ethyl acetate in hexane, 0 to 60%) to yield 1.12 g tert-butyl 3-amino-3-(5-bromopyridin-3-yl)prop-2-enoate.

$^1$H-NMR (400 MHz, DMSO-d$_6$): δ=1.44 (s, 9 H), 4.77 (s, 1 H), 7.15 (br., 2 H), 8.22 (t, 1 H), 8.75 (d, 1 H), 8.76 (d, 1 H) ppm.

Example 27b

Tert-butyl (3S)-3-amino-3-(5-bromopyridin-3-yl)propanoate

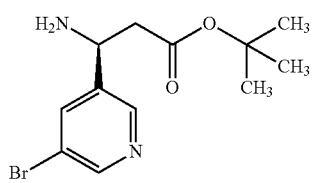 [SMILES: CC(C)(C)OC(=O)C[C@H](N)c1cncc(Br)c1]

To chloro(1,5-cyclooctadien)rhodium(I) dimer (39 mg, 80 µmol) and (R)-(−)-1-[(S)-2-di-tert.-butyl-phosphino)ferrocenyl]ethyldi-(4-trifluormethylphenyl)phosphine (108 mg, 160 µmol) under an argon atmosphere was added 2,2,2-trifluoroethanol (5.8 mL) and the solution was stirred for 40 minutes. To tert-butyl 3-amino-3-(5-bromopyridin-3-yl)prop-2-enoate (1.59 g 5.32 mmol) in degassed 2,2,2-trifluoroethanol (11.6 mL) in a pressure vessel was added the rhodium catalyst solution and the solution was stirred for 22 hours at 50° C. under hydrogen pressure of 11 bar. The solution was concentrated under reduced pressure and the residue was purified by chromatography on silica gel (ethyl acetate in hexane, 12 to 100% followed by methanol in ethyl acetate 0 to 15%) to yield 1.16 g of enantiomerically enriched tert-butyl (3S)-3-amino-3-[5-(benzyloxy)pyridin-3-yl]propanoate.

$^1$H-NMR (300 MHz, CDCl$_3$): δ=1.43 (s, 9 H), 2.59 (d, 2 H), 4.42 (t, 1 H), 7.92 (t, 1 H), 8.58 (d, 1 H), 8.53 (d, 1 H) ppm.

α=−17.6° (c=1.0 g/100 mL, CHCl$_3$)

Example 27c

Tert-butyl 4-{3-[(3R)-3-({(1S)-1-[5-bromopyridin-3-yl]-3-tert-butoxy-3-oxopropyl}carbamoyl)piperidin-1-yl]-3-oxopropyl}piperidine-1-carboxylate

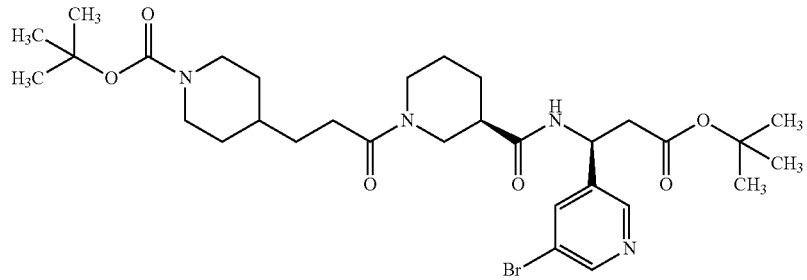 [SMILES: CC(C)(C)OC(=O)C[C@H](NC(=O)[C@@H]1CCCN(C(=O)CCC2CCN(C(=O)OC(C)(C)C)CC2)C1)c1cncc(Br)c1]

To tert-butyl (3S)-3-amino-3-(5-bromopyridin-3-yl)propanoate (1.33 g, 4.42 mmol) in DMF (17 mL) was added tert-butyl 4-{3-[(3R)-3-{[(2,5-dioxopyrrolidin-1-yl)oxy]carbonyl}piperidin-1-yl]-3-oxopropyl}piperidine-1-carboxylate (example 25c 2.54 g, 4.91 mmol) and triethylamine (1.85 mL, 13.2 mmol) in dichloromethane (17 mL) at 0° C. After 3 hours the mixture was quenched by addition of saturated aqueous ammonium chloride solution, phases were separated and the aqueous phase was extracted with diethyl ether. Combined organic extracts were dried over sodium sulphate, concentrated under reduced pressure and the residue was purified by chromatography on silica gel (ethyl acetate in hexane, 12 to 100% followed by methanol in ethyl acetate 0 to 15%) to yield 2.1 g of tert-butyl 4-[3-((3R)-3-{[(1S)-1-(5-bromopyridin-3-yl)-3-tert-butoxy-3-oxopropyl]carbamoyl}piperidin-1-yl)-3-oxopropyl]piperidine-1-carboxylate.

UPLC (ACN-HCOOH): Rt.=1.35 min
MS (ES$^+$): m/e=651.4/653.4 (M+H$^+$)

Example 27d

Tert-butyl 4-{3-[(3R)-3-{[(1S)-3-tert-butoxy-1-{5-[4-(2-{[4-hydroxyphenyl]pyridin-3-yl}-3-oxopropyl]carbamoyl}piperidin-1-yl]-3-oxopropyl}piperidine-1-carboxylate

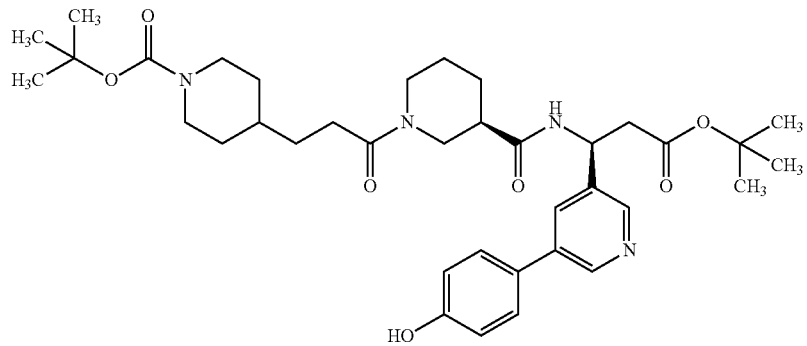 [SMILES: CC(C)(C)OC(=O)C[C@H](NC(=O)[C@@H]1CCCN(C(=O)CCC2CCN(C(=O)OC(C)(C)C)CC2)C1)c1cncc(-c2ccc(O)cc2)c1]

To tert-butyl 4-[3-((3R)-3-{[(1S)-1-(5-bromopyridin-3-yl)-3-tert-butoxy-3-oxopropyl]carbamoyl}piperidin-1-yl)-3-oxopropyl]piperidine-1-carboxylate (200 mg, 307 μmol) in toluene (7.5 mL) was added tetrakis(triphenylphosphine)palladium(0) (14 mg, 0.01 mmol), (4-hydroxyphenyl)boronic acid (55 mg, 399 μmol) in ethanol (1.87 mL) and potassium fluoride (55 mg, 0.61 mmol) in water (1.87 mL). The mixture was stirred at 100° C. for 4 hours, diluted with water and extracted with ethyl acetate. The organic phase was dried over sodium sulfate and concentrated in vacuum. the residue was purified by chromatography on silica gel (ethyl acetate in hexane, 12 to 100% followed by methanol in ethyl acetate 0 to 15%) to yield 156 mg of tert-butyl 4-{3-[(3R)-3-{[(1S)-3-tert-butoxy-1-{5-[4-(2-{[4-hydroxyphenyl]pyridin-3-yl}-3-oxopropyl]carbamoyl}piperidin-1-yl]-3-oxopropyl}piperidine-1-carboxylate.

UPLC (ACN-HCOOH): Rt.=1.17 min
MS (ES$^+$): m/e=665.5 (M+H$^+$)
MS (ES$^-$): m/e=663.5 (M−H), 709.5 (M+HCOO$^-$)

Example 27e

Tert-butyl 4-{3-[(3R)-3-{[(1S)-3-tert-butoxy-1-{5-[4-(2-{[(4-methylphenyl)sulfonyl]oxy}ethoxy)phenyl]pyridin-3-yl}-3-oxopropyl]carbamoyl}piperidin-1-yl]-3-oxopropyl}piperidine-1-carboxylate Tert-butyl 4-{3-[(3R)-3-{[(1S)-3-tert-butoxy-1-{5-[4-(2-{[4-hydroxyphenyl]pyridin-3-yl}-3-oxopropyl]carbamoyl}piperidin-1-yl]-3-oxopropyl}piperidine-1-carboxylate (100 mg, 0.15 mmol) were dissolved in N,N-dimethylformamide (17.4 mL). Cesium carbonate (122 mg, 0.38 mmol) and ethylene glycol bis-p-toluenesulfonate (84 mg, 0.23 mmol) were added. The mixture was stirred at room temperature for 4 hours, the addition of cesium carbonate (122 mg, 0.38 mmol) and ethylene glycol bis-p-toluenesulfonate (84 mg, 0.23 mmol) was repeated and stirring at 5° C. was continued for 17 hours. The mixture was quenched by addition of saturated aqueous ammonium chloride solution and extracted with diethyl ether and ethyl acetate. The combined extracts were washed with brine and dried over sodium sulfate. The solution was concentrated under reduced pressure and the residue was purified by chromatography on silica gel (ethyl acetate in hexane 20 to 100% followed by dioxane in ethyl acetate 0 to 60%) to yield 85 mg of tert-butyl 4-{3-[(3R)-3-{[(1S)-3-tert-butoxy-1-{5-[4-(2-{[(4-methylphenyl)sulfonyl]oxy}ethoxy)phenyl]

pyridin-3-yl}-3-oxopropyl]carbamoyl}piperidin-1-yl]-3-oxopropyl}piperidine-1-carboxylate.
UPLC (ACN-NH3): Rt.=1.44 min
MS (ES+): m/e=863.6 (M+H+)
MS (ES−): m/e=861.5 (M−H).

Example 28

Tert-butyl 4-{3-[(3R)-3-({1-[5-(4-chloro-3-cyano-phenyl)pyridin-3-yl]-3-methoxy-3-oxopropyl}carbamoyl)piperidin-1-yl]-3-oxopropyl}piperidine-1-carboxylate

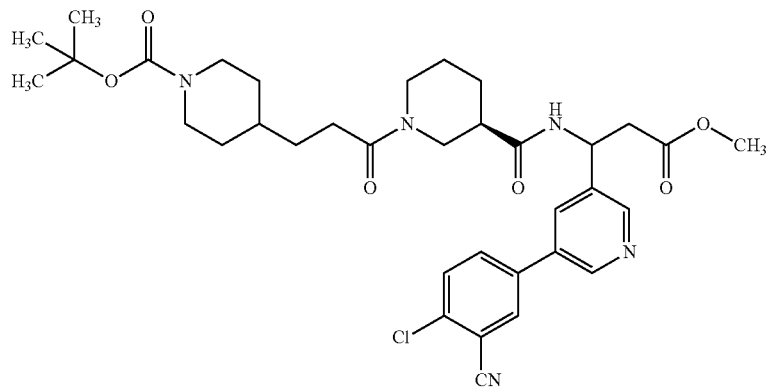 [SMILES: COC(=O)CC(NC(=O)[C@@H]1CCCN(C(=O)CCC2CCN(C(=O)OC(C)(C)C)CC2)C1)c1cncc(-c2ccc(Cl)c(C#N)c2)c1]

To 100.0 mg (0.16 mmol) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate (example 8c) in 4 ml toluene were added 3.8 mg tetrakis(triphenylphosphine)palladium(0), 35.7 mg (0.20 mmol) (4-chloro-3-cyano-phenyl)boronic acid in 1.0 ml ethanol and 29.6 mg (0.51 mmol) potassium fluoride in 1.0 ml water. The mixture was stirred at 100° C. for 6 hours, diluted with water and saturated sodium hydrogen carbonate solution and extracted with ethyl acetate. The organic phase was dried over sodium sulfate and concentrated in vacuum. Chromatography over 10 g silica gel (dichloromethane/ethanol 100/0-95/5-90/10) gave 44 mg (36%) Tert-butyl 4-{3-[(3R)-3-({1-[5-(4-chloro-3-cyanophenyl)pyridin-3-yl]-3-methoxy-3-oxopropyl}carbamoyl)piperidin-1-yl]-3-oxopropyl}piperidine-1-carboxylate.
UPLC (ACN-HCOOH): Rt.=1.27 min
MS (ES+): m/e=668.6 (M+H+)
MS (ES−): m/e=664.5 (M−H), 710.5 (M+HCOO−)

Example 29

Tert-butyl-4-{3-[(3R)-3-{[(1S-1-{5-[(3-bromo-4-cyanobenzyl)oxy]pyridin-3-yl}-3-methoxy-3-oxo-propyl]carbamoyl}piperidin-1-yl]-3-oxopropyl}piperidine-1-carboxylate

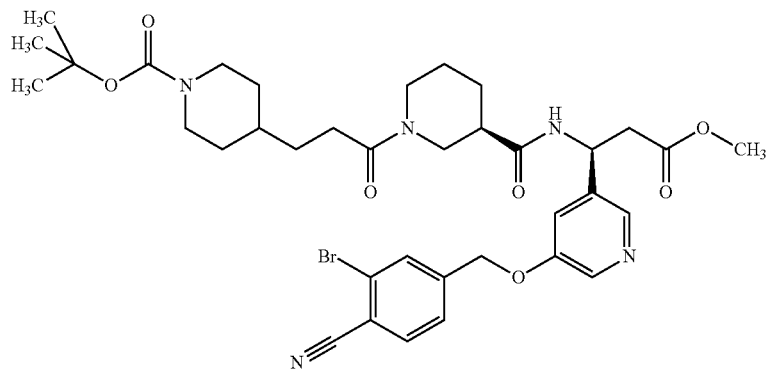 [SMILES: COC(=O)C[C@H](NC(=O)[C@@H]1CCCN(C(=O)CCC2CCN(C(=O)OC(C)(C)C)CC2)C1)c1cncc(OCc2ccc(C#N)c(Br)c2)c1]

To tert-butyl-4-{3-[(3R)-3-{[(1S)-1-(5-hydroxypyridin-3-yl)-3-methoxy-3-oxopropyl]carbamoyl}piperidin-1-yl]-3-oxopropyl}piperidine-1-carboxylate (100 mg, 0.18 mmol) in DMF (3 mL) was added sodium hydride (8 mg, 60% 0.2 mmol). The solution was cooled to 0° C. and 2-bromo-4-(bromomethyl)benzonitrile (55 mg, 0.2 mmol) while stirring. The mixture was warmed to room temperature and quenched by addition of water and ethyl acetate after 45 minutes. Phases were separated and the water phase was extracted with ethyl acetate. Combined organic extracts were concentrated in vacuum and the residue was purified by preparative HPLC to yield 46 mg of tert-butyl-4-{3-[(3R)-3-{[(1S)-1-{5-[(3-bromo-4-cyanobenzyl) oxy]pyridin-3-yl}-3-methoxy-3-oxopropyl]carbamoyl}piperidin-1-yl]-3-oxopropyl}piperidine-1-carboxylate.

| Column: | C18 Chromatorex 10 µm 30 × 125 mm |
|---|---|
| Solvent: | A = H2O + 0.1% HCOOH |
| | B = acetonitrile |
| Gradient: | 0 0.5 min 30% B, 0.5-7 min 30-70% B |
| Flow: | 120 mL/min |
| Temperature: | RT |
| Detection: | 276 nm |
| Rt.: | 5.31-5.70 min |

UPLC (ACN-HCOOH): Rt.=1.27 min
MS (ES+): m/e=740.3/742.3 (M+H+)

Example 30

Tert-butyl 4-{3-[(3R)-3-{[3-methoxy-1-{5-[3-(2-{[(4-methyl phenyl)sulfonyl]oxy}ethoxy)phenyl]pyridin-3-yl}-3-oxopropyl]carbamoyl}piperidin-1-yl]-3-oxopropyl}piperidine-1-carboxylate

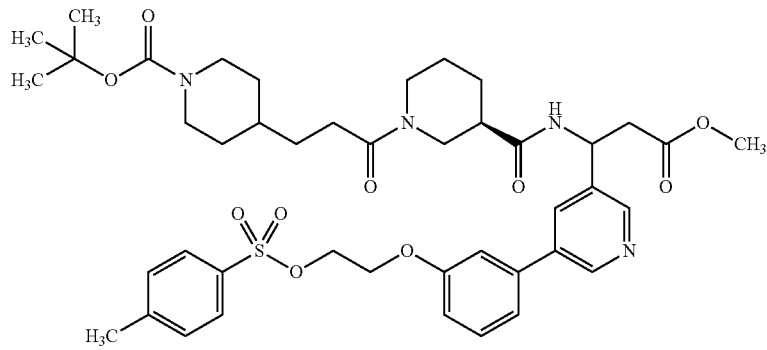 [SMILES: COC(=O)CC(NC(=O)[C@@H]1CCCN(C(=O)CCC2CCN(C(=O)OC(C)(C)C)CC2)C1)c1cncc(-c2cccc(OCCOS(=O)(=O)c3ccc(C)cc3)c2)c1]

98.0 mg (0.16 mmol) Tert-butyl 4-{3-[(3R)-3-({1-[5-(3-hydroxyphenyl)pyridin-3-yl]-3-methoxy-3-oxopropyl}carbamoyl)piperidin-1-yl]-3-oxopropyl}piperidine-1-carboxylate (example 6a) were dissolved in 6.1 ml N,N-dimethylformamide. 154 mg (0.47 mmol) cesium carbonate and 87.4 mg (0.24 mmol) ethylene glycol bis-p-toluenesulfonate were added. The mixture was stirred at room temperature for 68 hours and concentrated. The remainder was taken up with saturated ammonium chloride solution and ethyl acetate. The aqueous phase was extracted with 3×20 ml ethyl acetate. The extracts were dried over sodium sulfate and concentrated. Chromatography over 10 g silica gel (dichloromethane/ethanol 100/0-90/10) gave 70 mg (49%) tert-butyl 4-{3-[(3R)-3-{[3-methoxy-1-{5-[3-(2-{[(4-methylphenyl) sulfonyl]oxy}ethoxy)phenyl]pyridin-3-yl}-3-oxopropyl]carbamoyl}piperidin-1-yl]-3-oxopropyl}piperidine-1-carboxylate.

UPLC (ACN-HCOOH): Rt.=1.33 min

MS (ES+): m/e=821.3 (M+H+)

MS (ES−): m/e=865.5 (M+HCOO−)

Example 31

Tert-butyl 4-{3-[(3R)-3-{[3-methoxy-1-{5-[2-(2-{[(4-methyl phenyl)sulfonyl]oxy}ethoxy)phenyl]pyridin-3-yl}-3-oxopropyl]carbamoyl}piperidin-1-yl]-3-oxopropyl}piperidine-1-carboxylate

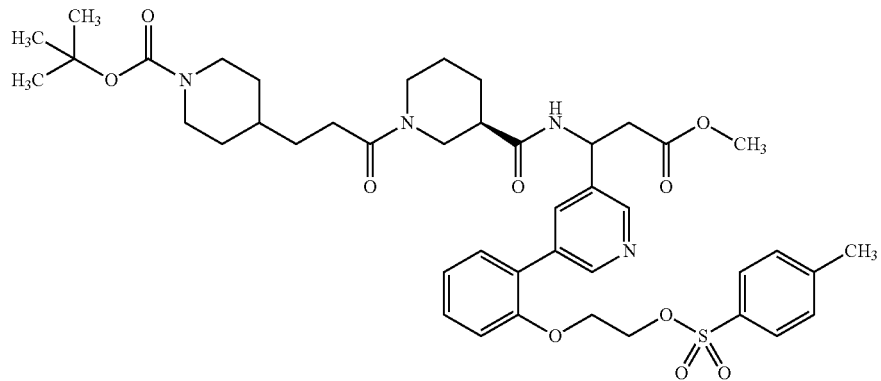 [SMILES: COC(=O)CC(NC(=O)[C@@H]1CCCN(C(=O)CCC2CCN(C(=O)OC(C)(C)C)CC2)C1)c1cncc(-c2ccccc2OCCOS(=O)(=O)c2ccc(C)cc2)c1]

108.0 mg (0.17 mmol) Tert-butyl 4-{3-[(3R)-3-({1-[5-(2-hydroxyphenyl)pyridin-3-yl]-3-methoxy-3-oxopropyl}carbamoyl)piperidin-1-yl]-3-oxopropyl}piperidine-1-carboxylate (example 8d) were dissolved in 6.7 ml N,N-dimethylformamide. 170 mg (0.52 mmol) cesium carbonate and 96.4 mg (0.26 mmol) ethylene glycol bis-p-toluenesulfonate were added. The mixture was stirred at room temperature for 68 hours and concentrated. The remainder was taken up with saturated ammonium chloride solution and ethyl acetate. The aqueous phase was extracted with 3×20 ml ethyl acetate. The extracts were dried over sodium sulfate and concentrated. Chromatography over 10 g silica gel (dichloromethane/ethanol 100/0-90/10) gave 55 mg (37%) tert-butyl 4-{3-[(3R)-3-{[3-methoxy-1-{5-[2-(2-{[(4-methylphenyl)sulfonyl]oxy}ethoxy)phenyl]pyridin-3-yl}-3-oxopropyl]carbamoyl}piperidin-1-yl]-3-oxopropyl}piperidine-1-carboxylate.

UPLC (ACN-HCOOH): Rt.=1.30 min

MS (ES$^+$): m/e=821.3 (M+H$^+$)

MS (ES$^-$): m/e=865.5 (M+HCOO$^-$)

Example 32

Tert-butyl 4-{3-[(3R)-3-({1-[5-(4-chloro-3-nitrophenyl)pyridin-3-yl]-3-methoxy-3-oxopropyl}carbamoyl)piperidin-1-yl]-3-oxopropyl}piperidine-1-carboxylate

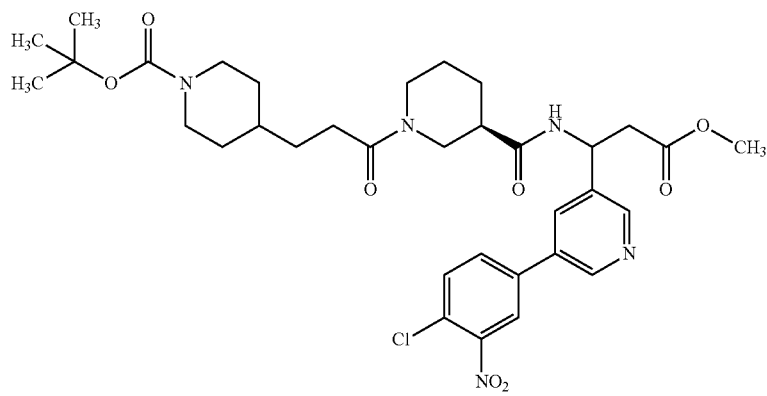 [SMILES: COC(=O)CC(NC(=O)[C@@H]1CCCN(C(=O)CCC2CCN(C(=O)OC(C)(C)C)CC2)C1)c1cncc(-c2ccc(Cl)c([N+](=O)[O-])c2)c1]

To 171.5 mg (0.28 mmol) tert-butyl 4-{3-[(3R)-3-{[1-(5-bromopyridin-3-yl)-3-methoxy-3-oxopropyl]carbamoyl}piperidin-1-yl]-3-oxopropyl}piperidine-1-carboxylate (example 8c) in 7 ml toluene were added 6.5 mg (0.01 mmol) tetrakis(triphenylphosphine)palladium(0), 68.0 mg (0.34 mmol) (4-chloro-3-nitro-phenyl)boronic acid in 1.7 ml ethanol and 50.7 mg (0.87 mmol) potassium fluoride in 1.7 ml water. The mixture was stirred at 100° C. for 60 hours, diluted with water and extracted with ethyl acetate. The organic phase was dried over sodium sulfate and concentrated in vacuum. Chromatography over 10 g silica gel (dichloromethane/ethanol 100/0-95/5-90/10) gave 100 mg (47%) tert-butyl 4-{3-[(3R)-3-({1-[5-(4-chloro-3-nitro-phenyl)pyridin-3-yl]-3-methoxy-3-oxopropyl}carbamoyl)piperidin-1-yl]-3-oxopropyl}piperidine-1-carboxylate.

UPLC (ACN-HCOOH): Rt.=1.30 min
MS (ES$^+$): m/e=686.2 (M+H$^+$)
MS (ES$^-$): m/e=730.4 (M+HCOO$^-$)

Example 33

Tert-butyl 4-{3-[(3R)-3-({1-[5-fluoro-4'-(2-{[(4-methyl phenyl)sulfonyl]oxy}ethoxy)biphenyl-3-yl]-3-methoxy-3-oxopropyl}carbamoyl)piperidin-1-yl]-3-oxopropyl}piperidine-1-carboxylate

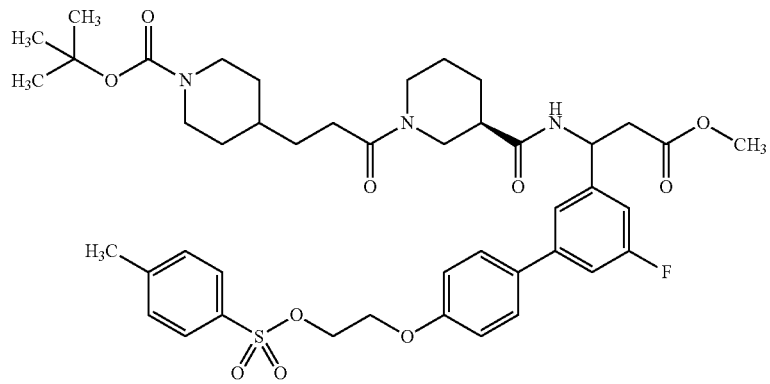 [SMILES: COC(=O)CC(NC(=O)[C@@H]1CCCN(C(=O)CCC2CCN(C(=O)OC(C)(C)C)CC2)C1)c1cc(F)cc(-c2ccc(OCCOS(=O)(=O)c3ccc(C)cc3)cc2)c1]

178.0 mg (0.28 mmol) 4-(3-{(R)-3-[1-(5-fluoro-4'-hydroxy-biphenyl-3-yl)-2-methoxycarbonyl-ethylcarbamoyl]-piperidin-1-yl}-3-oxo-propyl)-piperidine-1-carboxylic acid tert-butyl ester (example 17d) were dissolved in 10.7 ml N,N-dimethylformamide. 272 mg (0.84 mmol) cesium carbonate and 154.6 mg (0.42 mmol) ethylene glycol bis-p-toluenesulfonate were added. The mixture was stirred at room temperature for 70 hours and concentrated. The remainder was taken up with saturated ammonium chloride solution and ethyl acetate. The aqueous phase was extracted with 3×20 ml ethyl acetate. The extracts were dried over sodium sulfate and concentrated. Chromatography over 10 g silica gel (dichloromethane/ethanol 100/0-95/5) gave 167 mg which were further purified by HPLC to yield 27 mg (11%) tert-butyl 4-{3-[(3R)-3-({1-[5-fluoro-4'-(2-{[(4-methylphenyl)sulfonyl]oxy}ethoxy)biphenyl-3-yl]-3-methoxy-3-oxopropyl}carbamoyl)piperidin-1-yl]-3-oxopropyl}piperidine-1-carboxylate.

UPLC (ACN-HCOOH): Rt.=1.47 min
MS (ES$^+$): m/e=838.4 (M+H$^+$)
MS (ES$^-$): m/e=882.4 (M+HCOO$^-$)

Example 34

Tert-butyl 4-{3-[(3R)-3-{[(1S)-3-tert-butoxy-1-(5-{[4-(2-{[(4-methylphenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate

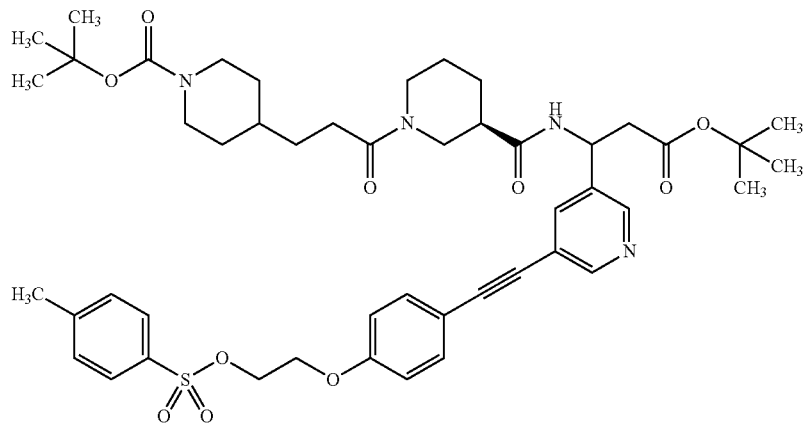 [SMILES: Cc1ccc(S(=O)(=O)OCCOc2ccc(C#Cc3cncc(C(CC(=O)OC(C)(C)C)NC(=O)[C@@H]4CCCN(C(=O)CCC5CCN(C(=O)OC(C)(C)C)CC5)C4)c3)cc2)cc1]

Example 34a

Tert-butyl 4-{3-[(3R)-3-{[(1S)-3-tert-butoxy-1-{5-[(4-hydroxyphenyl)ethynyl]pyridin-3-yl}-3-oxopropyl]carbamoyl}piperidin-1-yl]-3-oxopropyl}piperidine-1-carboxylate

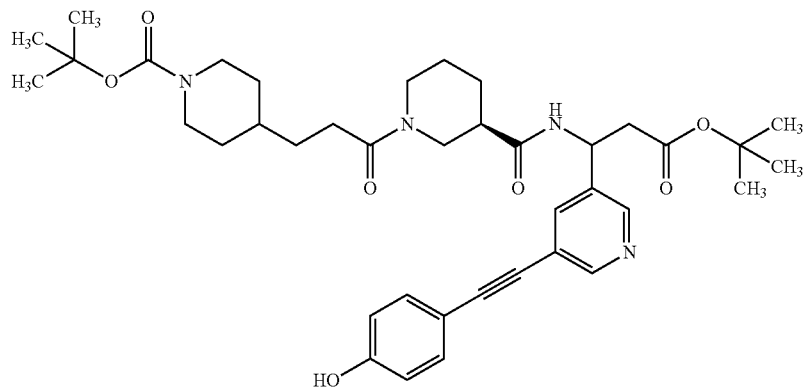 [SMILES: CC(C)(C)OC(=O)CC(NC(=O)[C@@H]1CCCN(C(=O)CCC2CCN(C(=O)OC(C)(C)C)CC2)C1)c1cncc(C#Cc2ccc(O)cc2)c1]

To a degassed solution of tert-butyl 4-[3-((3R)-3-{[(1S)-1-(5-bromopyridin-3-yl)-3-tert-butoxy-3-oxopropyl]carbamoyl}piperidin-1-yl)-3-oxopropyl]piperidine-1-carboxylate (400 mg, 0.61 mol), copper iodide (14 mg, 70 µmol), tetrakis(triphenylphosphine)palladium(0) (71 mg, 60 µmol) and 4-[(trimethylsilyl)ethynyl]phenol (234 mg, 1.23 mmol) in 1,2-dimethoxyethan (3.5 mL) and n-butyl amine (0.91 mL) was added a 1 M tetra-n-butyl ammonium fluoride solution in THF (800 µL, 0.8 mmol) over 60 minutes at 80° C. After 10 additional minutes at 80° C. the mixture was diluted with water after cooling to room temperature and extracted with ethyl acetate. The organic phase was dried over sodium sulfate and concentrated in vacuum. The residue was purified by preparative HPLC to yield 338 mg of tert-butyl 4-{3-[(3R)-3-{[(1S)-3-tert-butoxy-1-{5-[(4-hydroxyphenyl)ethynyl]pyridin-3-yl}-3-oxopropyl]carbamoyl}piperidin-1-yl]-3-oxopropyl}piperidine-1-carboxylate

| Column: | C18 YMC-ODS AQ 10 µm 51 × 200 mm |
|---|---|
| Solvent: | A = H2O + 0.1% HCOOH |
| | B = acetonitrile |
| Gradient: | 0-1 min 65% B, 1-10 min 65-85% B, |
| Flow: | 150 mL/min |
| Temperature: | RT |
| Detection: | 276 nm |
| Rt.: | 7.36-8.67 min |

UPLC (ACN-HCOOH): Rt.=1.31 min
MS (ES$^+$): m/e=689.5 (M+H$^+$)

Example 34b

Tert-butyl 4-{3-[(3R)-3-{[(1S)-3-tert-butoxy-1-(5-{[4-(2-{[(4-methyl phenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate Tert-butyl 4-{3-[(3R)-3-{[(1S)-3-tert-butoxy-1-{5-[(4-hydroxyphenyl)ethynyl]pyridin-3-yl}-3-oxopropyl]carbamoyl}piperidin-1-yl]-3-oxopropyl}piperidine-1-carboxylate (60 mg, 0.09 mmol) was dissolved in N,N-dimethylformamide (10 mL). Cesium carbonate (71 mg, 0.22 mmol) and ethane-1,2-diyl bis(4-methylbenzenesulfonate (48 mg, 0.13 mmol) were added. The mixture was stirred at room temperature for 25 hours while the addition of cesium carbonate (71 mg, 0.22 mmol) and ethane-1,2-diyl bis(4-methylbenzenesulfonate (48 mg, 0.13 mmol) was repeated after 4 and 6 hours. The mixture was quenched by addition of saturated aqueous ammonium chloride solution and extracted with diethyl ether and ethyl acetate. The combined extracts were washed with brine and dried over sodium sulfate. The solution was concentrated under reduced pressure and the residue was purified by chromatography on silica gel (ethyl acetate in hexane 20% to 100% followed by dioxane in ethyl acetate 0 to 50%) to yield 48 mg of tert-butyl 4-{3-[(3R)-3-{[(1S)-3-tert-butoxy-1-(5-{[4-(2-{[(4-methylphenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate.

UPLC (ACN-HCOOH): Rt.=1.51 min
MS (ES$^+$): m/e=887.7 (M+H$^+$)

Example 35

Tert-butyl 4-{3-[(3R)-3-{[(1S)-3-tert-butoxy-1-(5-{[3-(2-{[(4-methyl phenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate

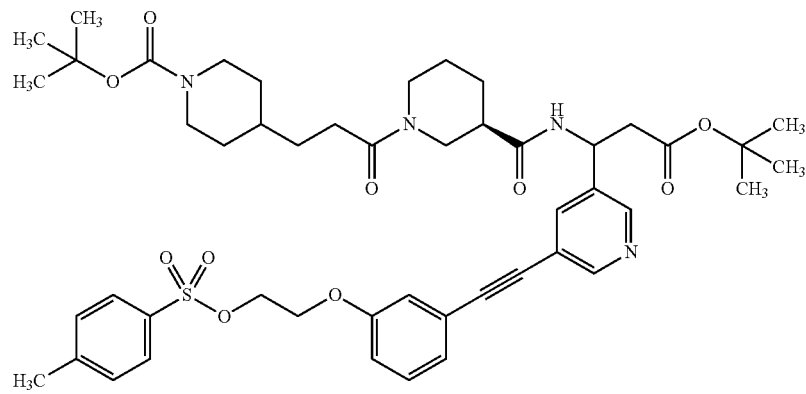 [SMILES: Cc1ccc(S(=O)(=O)OCCOc2cccc(C#Cc3cncc(C(CC(=O)OC(C)(C)C)NC(=O)[C@@H]4CCCN(C(=O)CCC5CCN(C(=O)OC(C)(C)C)CC5)C4)c3)c2)cc1]

Example 35a

Tert-butyl 4-{3-[(3R)-3-{[(1S)-3-tert-butoxy-1-{5-[(3-hydroxyphenyl)ethynyl]pyridin-3-yl}-3-oxopropyl]carbamoyl}piperidin-1-yl]-3-oxopropyl}piperidine-1-carboxylate

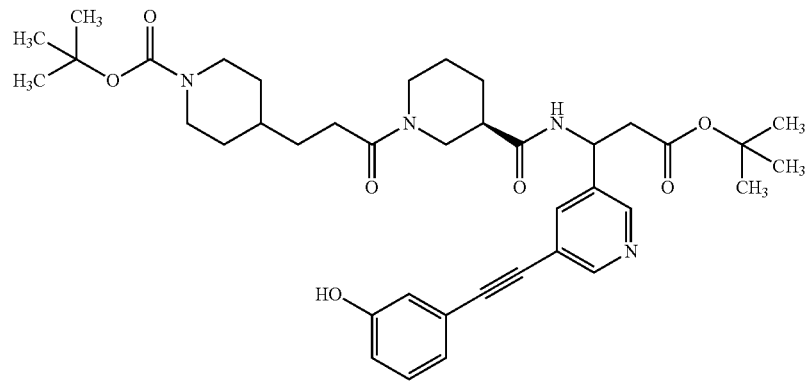 [SMILES: CC(C)(C)OC(=O)CC(NC(=O)[C@@H]1CCCN(C(=O)CCC2CCN(C(=O)OC(C)(C)C)CC2)C1)c1cncc(C#Cc2cccc(O)c2)c1]

To a degassed solution of tert-butyl 4-[3-((3R)-3-{[(1S)-1-(5-bromopyridin-3-yl)-3-tert-butoxy-3-oxopropyl]carbamoyl}piperidin-1-yl)-3-oxopropyl]piperidine-1-carboxylate (example 27c, 300 mg, 0.46 mmol), copper iodide (13 mg, 70 µmol) and tetrakis(triphenylphosphine)palladium(0) (53 mg, 50 µmol) in DMF (1.5 mL) and n-butyl amine (0.68 mL) was added a solution of 3-ethynylphenol (103 mg, 0.88 mmol) in DMF (1.0 mL) over 35 minutes at 100° C. After 5 additional minutes at 100° C. the mixture was diluted with DMSO and purified by preparative HPLC to yield 289 mg of tert-butyl 4-{3-[(3R)-3-{[(1S)-3-tert-butoxy-1-{5-[(3-hydroxyphenyl)ethynyl]pyridin-3-yl}-3-oxopropyl]carbamoyl}piperidin-1-yl]-3-oxopropyl}piperidine-1-carboxylate.

| Column: | C18 YMC-ODS AQ 10 µm 51 × 200 mm |
|---|---|
| Solvent: | A = H2O + 0.1% HCOOH |
| | B = acetonitrile |
| Gradient: | 0-1 min 65% B, 1-10 min 65-85% B, |
| Flow: | 240 mL/min |
| Temperature: | RT |
| Detection: | 276 nm |
| Rt.: | 7.86-9.09 min |

UPLC (ACN-HCOOH): Rt.=1.33 min

MS (ES$^+$): m/e=689.6 (M+H$^+$)

Example 35b

Tert-butyl 4-{3-[(3R)-3-{[(1S)-3-tert-butoxy-1-(5-{[3-(2-{[(4-methyl phenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate Tert-butyl 4-{3-[(3R)-3-{[(1S)-3-tert-butoxy-1-{5-[(3-hydroxyphenyl)ethynyl]pyridin-3-yl}-3-oxopropyl]carbamoyl}piperidin-1-yl]-3-oxopropyl}piperidine-1-carboxylate (40 mg, 0.06 mmol) was dissolved in N,N-dimethylformamide (6.7 mL). Cesium carbonate (47 mg, 0.15 mmol) and ethane-1,2-diyl bis(4-methylbenzenesulfonate (32 mg, 0.09 mmol) were added. The mixture was stirred at room temperature for 4 hours and stored for 72 hours at 5° C. The addition of cesium carbonate (47 mg, 0.15 mmol) and ethane-1,2-diyl bis(4-methylbenzenesulfonate (32 mg, 0.09 mmol) was repeated and the mixture was stirred at room temperature for 3 hours. The mixture was quenched by addition of saturated aqueous ammonium chloride solution and extracted with ethyl acetate. The combined extracts were washed with brine and dried over sodium sulfate. The solution was concentrated under reduced pressure and the residue was purified by chromatography on silica gel (ethyl acetate in hexane 20% to 100% followed by dioxane in ethyl acetate 0 to 50%) to yield 24 mg of tert-butyl 4-{3-[(3R)-3-{[(1S)-3-tert-butoxy-1-(5-{[3-(2-{[(4-methylphenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate.

UPLC (ACN-HCOOH): Rt.=1.50 min

MS (ES$^+$): m/e=887.5 (M+H$^+$)

Example 36

Tert-butyl 4-{3-[(3R)-3-{[(1S)-3-tert-butoxy-1-(5-{2-[4-(2-{[(4-methyl phenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate

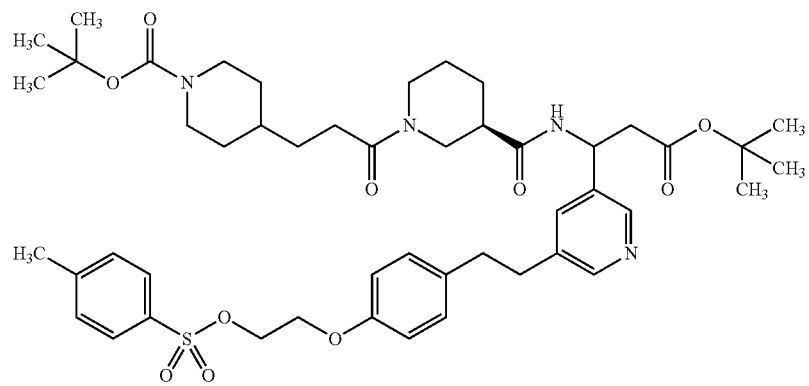 [SMILES: Cc1ccc(S(=O)(=O)OCCOc2ccc(CCc3cncc(C(CC(=O)OC(C)(C)C)NC(=O)[C@@H]4CCCN(C(=O)CCC5CCN(C(=O)OC(C)(C)C)CC5)C4)c3)cc2)cc1]

Example 36a

Tert-butyl 4-{3-[(3R)-3-{[(1 S)-3-tert-butoxy-1-{5-[2-(4-hydroxyphenyl)ethyl]pyridin-3-yl}-3-oxopropyl]carbamoyl}piperidin-1-yl]-3-oxopropyl}piperidine-1-carboxylate

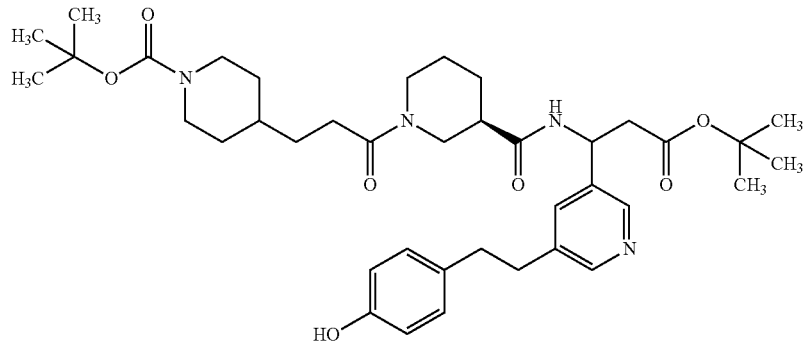 [SMILES: CC(C)(C)OC(=O)CC(NC(=O)[C@@H]1CCCN(C(=O)CCC2CCN(C(=O)OC(C)(C)C)CC2)C1)c1cncc(CCc2ccc(O)cc2)c1]

Tert-butyl 4-{3-[(3R)-3-{[(1 S)-3-tert-butoxy-1-{5-[(4-hydroxyphenyl)ethynyl]pyridin-3-yl}-3-oxopropyl]carbamoyl}piperidin-1-yl]-3-oxopropyl}piperidine-1-carboxylate (190 mg, 0.28 mmol) in ethyl acetate (8.1 mL) and methanol (1.34 mL) was stirred for 4.45 hours at room temperature under a hydrogen atmosphere in the presence of palladium on charcoal (10%, 19 mg). The suspension was filtrated through celite, which were washed thoroughly with methanol. The solution was concentrated under reduced pressure and purified by preparative HPLC to yield 89 mg of tert-butyl 4-{3-[(3R)-3-{[(1S)-3-tert-butoxy-1-{5-[2-(4-hydroxyphenyl)ethyl]pyridin-3-yl}-3-oxopropyl]carbamoyl}piperidin-1-yl]-3-oxopropyl}piperidine-1-carboxylate.

| | |
|---|---|
| Column: | C18 YMC-ODS AQ 10 µm 51 × 200 mm |
| Solvent: | A = H2O + 0.1% HCOOH |
| | B = acetonitrile |
| Gradient: | 0-1 min 40% B, 1-10 min 40-80% B, |
| Flow: | 240 mL/min |
| Temperature: | RT |
| Detection: | 276 nm |
| Rt.: | 4.40-4.74 min |

UPLC (ACN-HCOOH): Rt.=1.18 min
MS (ES+): m/e=693.6 (M+H+)

Example 36b

Tert-butyl 4-{3-[(3R)-3-{[(1S)-3-tert-butoxy-1-(5-{2-[4-(2-{[(4-methyl phenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate Tert-butyl 4-{3-[(3R)-3-{[(1S)-3-tert-butoxy-1-{5-[(4-hydroxyphenyl)ethyl]pyridin-3-yl}-3-oxopropyl]carbamoyl}piperidin-1-yl]-3-oxopropyl}piperidine-1-carboxylate (67 mg, 0.10 mmol) was dissolved in N,N-dimethylformamide (9.7 mL). Cesium carbonate (79 mg, 0.24 mmol) and ethane-1,2-diyl bis(4-methylbenzenesulfonate) (54 mg, 0.15 mmol) were added. The mixture was stirred at room temperature for 4 hours, quenched by addition of saturated aqueous ammonium chloride solution and extracted with ethyl acetate. The combined extracts were washed with brine and dried over sodium sulfate. The solution was concentrated under reduced pressure and the residue was purified by chromatography on silica gel (ethyl acetate in hexane 20% to 100% followed by dioxane in ethyl acetate 0 to 60%) to yield 64 mg of tert-butyl 4-{3-[(3R)-3-{[(1S)-3-tert-butoxy-1-(5-{2-[4-(2-{[(4-methylphenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate.

UPLC (ACN-NH3): Rt.=1.48 min
MS (ES+): m/e=891.6 (M+H+)

Example 37

Tert-butyl 4-{3-[(3R)-3-{[(1S)-3-tert-butoxy-1-(5-{2-[3-(2-{[(4-methyl phenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate

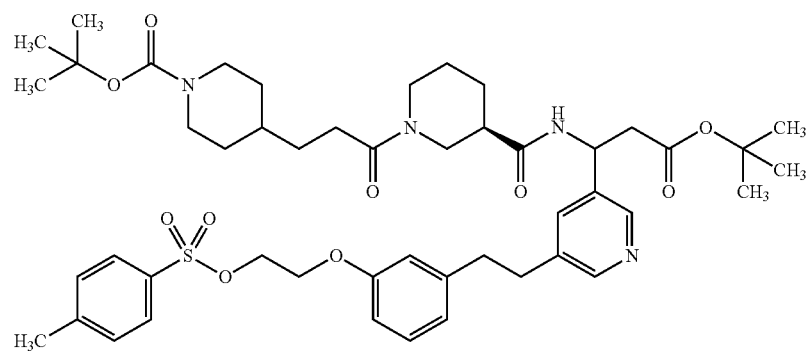 [SMILES: Cc1ccc(S(=O)(=O)OCCOc2cccc(CCc3cncc(C(CC(=O)OC(C)(C)C)NC(=O)[C@@H]4CCCN(C(=O)CCC5CCN(C(=O)OC(C)(C)C)CC5)C4)c3)c2)cc1]

Example 37a

Tert-butyl 4-{3-[(3R)-3-{[(1S)-3-tert-butoxy-1-{5-[(3-hydroxyphenyl)ethyl]pyridin-3-yl}-3-oxopropyl]carbamoyl}piperidin-1-yl]-3-oxopropyl}piperidine-1-carboxylate

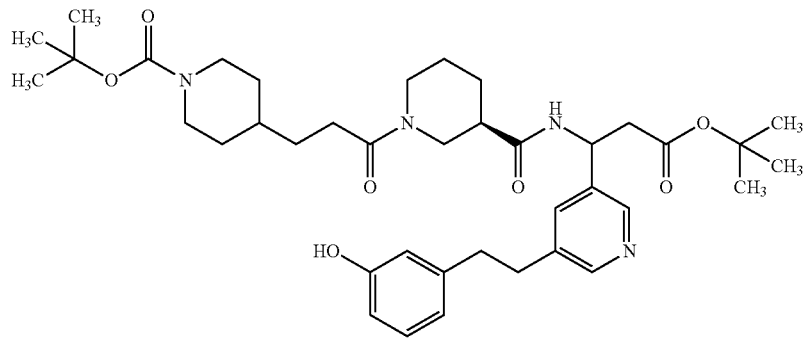 [SMILES: CC(C)(C)OC(=O)CC(NC(=O)[C@@H]1CCCN(C(=O)CCC2CCN(C(=O)OC(C)(C)C)CC2)C1)c1cncc(CCc2cccc(O)c2)c1]

Tert-butyl 4-{3-[(3R)-3-{[(1S)-3-tert-butoxy-1-{5-[(3-hydroxyphenyl)ethynyl]pyridin-3-yl}-3-oxopropyl]carbamoyl}piperidin-1-yl]-3-oxopropyl}piperidine-1-carboxylate (200 mg, 0.29 mmol) in ethyl acetate (8.5 mL) and methanol (1.4 mL) was stirred for 7 hours at room temperature under a hydrogen atmosphere in the presence of palladium on charcoal (10%, 20 mg), while the addition of palladium on charcoal (10%, 20 mg) was repeated after 4 hours. The suspension was filtrated through celite, which were washed thoroughly with methanol. The solution was concentrated under reduced pressure and the residue was purified by preparative HPLC to yield 125 mg of tert-butyl 4-{3-[(3R)-3-{[(1S)-3-tert-butoxy-1-{5-[2-(3-hydroxyphenyl)ethyl]pyridin-3-yl}-3-oxopropyl]carbamoyl}piperidin-1-yl]-3-oxopropyl}piperidine-1-carboxylate.

| | |
|---|---|
| Column: | C18 Chromatorex 10 μm 125 × 30 mm |
| Solvent: | A = H2O + 0.1% HCOOH |
| | B = acetonitrile |
| Gradient: | 0-0.5 min 45% B, 0.5-6 min 45-70% B, |
| Flow: | 150 mL/min |
| Temperature: | RT |
| Detection: | 228 nm |
| Rt.: | 1.52-2.49 min |

UPLC (ACN-HCOOH): Rt.=1.19 min
MS (ES+): m/e=693.5 (M+H+)

Example 37b

Tert-butyl 4-{3-[(3R)-3-{[(1S)-3-tert-butoxy-1-(5-{2-[3-(2-{[(4-methylphenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate Tert-butyl 4-{3-[(3R)-3-{[(1S)-3-tert-butoxy-1-{5-[(3-hydroxyphenyl)ethyl]pyridin-3-yl}-3-oxopropyl]carbamoyl}piperidin-1-yl]-3-oxopropyl}piperidine-1-carboxylate (67 mg, 0.10 mmol) was dissolved in N,N-dimethylformamide (9.7 mL). Cesium carbonate (79 mg, 0.24 mmol) and ethane-1,2-diyl bis(4-methylbenzenesulfonate (54 mg, 0.15 mmol) were added. The mixture was stirred at room temperature for 4 hours, quenched by addition of saturated aqueous ammonium chloride solution and extracted with ethyl acetate. The combined extracts were washed with brine and dried over sodium sulfate. The solution was concentrated under reduced pressure and the residue was purified by chromatography on silica gel (ethyl acetate in hexane 20% to 100% followed by dioxane in ethyl acetate 0 to 50%) to yield 49 mg of tert-butyl 4-{3-[(3R)-3-{[(1S)-3-tert-butoxy-1-(5-{2-[3-(2-{[(4-methylphenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate.

UPLC (ACN-HCOOH): Rt.=1.43 min
MS (ES+): m/e=891.5 (M+H+)

Example 38

(3S)-3-[3-(2-[$^{18}$F]Fluoroethoxy)phenyl]-3-[({(3R)-1-[3-(piperidin-4-yl)propanoyl]piperidin-3-yl}carbonyl)amino]propanoic acid

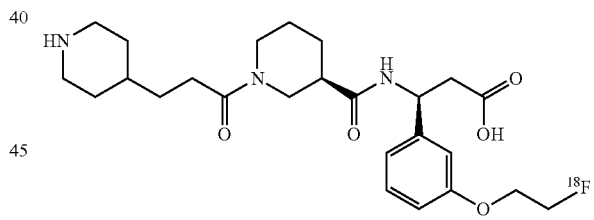

Radiosynthesis Via Direct Labeling:

[$^{18}$F]Fluoride was produced by an $^{18}$O (p, n)$^{18}$F nuclear reaction by bombardment of a 98% $^{18}$O-enriched water target with an 11MeVproton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M $K_2CO_3$ solution and 10 mL water). The radioactivity was eluted with a solution mixture (1.0 mg $K_2CO_3$ in 0.5 ml water and 5.27 mg $K_{222}$ in 1.5 ml MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then the diastereomeric mixture of tert-butyl 4-{3-[(3R)-3-({3-methoxy-1-[3-(2-{[(4-methylphenyl)sulfonyl]oxy}ethoxy)phenyl]-3-oxopropyl}carbamoyl)piperidin-1-yl]-3-oxopropyl}piperidine-1-carboxylat (example 21, 2.0 mg, 2.69 μmol) in dry MeCN (300 μL) was added to the dried

[¹⁸F]KF-K$_{222}$. After heating at 100° C. for 10 min in a sealed vial the vessel was cooled and 0.5 M NaOH (100 μL) was added. Stirring was continued for 10 min at 25° C. before 1 M HCl (200 μL) was added. The resealed vial was then again heated for 10 min at 100° C. After cooling the reaction mixture was diluted with 4 mL water and given on a semiprep HPLC (Zorbax Bonus RP 5 μm C18-HL (9.4×250 mm), 17/83/0.1-acetonitrile/water/triflouro acetic acid (volume-to-volume-to-volume ratio), 4 mL/min, retention time of (3S)-3-[3-(2-[¹⁸F]fluoro-ethoxy)phenyl]-3-[({(3R)-1-[3-(piperidin-4-yl)propanoyl]piperidin-3-yl}carbonyl)amino]propanoic acid: 18.3-19.5 min; retention time of (3R)-3-[3-(2-[¹⁸F]fluoro-ethoxy)phenyl]-3-[({(3R)-1-[3-(piperidin-4-yl)propanoyl]piperidin-3-yl}-carbonyl)amino]propanoic acid: 12.8-14.0 min). The collected fraction was diluted with 20 mL water and given on a preconditioned Sep-Pak™ Light C18 cartridge (preconditioned with 5 ml EtOH and 10 mL water). The cartridge was washed with 5 mL water and then the activity was eluted with 1.5 mL of EtOH. After complete evaporation of the EtOH under a stream of nitrogen at 90° C. the final tracer was taken up in water (300 μL) to get 73 to 297 MBq (3S)-3-[3-(2-[¹⁸F]fluoro-ethoxy)phenyl]-3-[({(3R)-1-[3-(piperidin-4-yl)propanoyl]piperidin-3-yl}-carbonyl)amino]propanoic acid (radiochemical yield: 14±5.4% d.c.; synthesis time: 116±9.6 min). The radiochemical purity was >99%. The F-18 labeled product was confirmed by co-injection with the F-19 cold standard (example 1) on an analytical HPLC (column: ACE, C18 RP, 50×4.6 mm, 3μ, 2 ml/min (Agilent), solvent A: H2O+0.1% TFA, solvent B: MeCN+0.1% TFA, gradient: 5% B to 40% B in 7 min).

Radiosynthesis Via Indirect Labeling:

[¹⁸F]Fluoride was produced by an ¹⁸O (p,n)¹⁸F nuclear reaction by bombardment of a 98% ¹⁸O-enriched water target with an 11MeVproton beam at the RDS111 cyclotron. The aqueous [¹⁸F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (1.0 mg K$_2$CO$_3$ in 0.5 ml water and 5.27 mg K$_{222}$ in 1.5 ml MeCN) from the QMA cartridge into a 5 mL conic Wheaton vial. The solvent was evaporated under a stream of nitrogen at 110° C. Azeotropic drying was repeated three times with 1.0 mL portions of acetonitrile. 500 μL of o-dichlorobenzene (o-DCB) was added to the dried [¹⁸F]KF-K$_{222}$. After heating at 100° C. for 2 min in a sealed vial the vessel was cooled and then 4-nitro-benzenesulfonic acid 2-bromo-ethyl ester (10 mg, 32.24 μmol) was added. The resealed vial was heated again for 10 min at 130° C. Afterwards the reaction mixture was cooled again and two needles with tubings were sticked through Teflon membrane sealed reaction vial. One tubing is connected to a nitrogen flow regulator and the other tubing to a second vial equipped with 400 μL DMF. Using a constant small flow of nitrogen gas through the reaction mixture, this mixture was heated for additional 20 min at 100° C., while leading this nitrogen stream to the second vial where the nitrogen stream constantly bubbles through the 400 μL DMF. With the heating and the nitrogen stream the formed 2-[¹⁸F]fluoro-1-bromo-ethane in vial 1 is constantly driven to vial 2. After 20 min the distillation is stopped because no further increase of radioactivity in vial 2 could be detected.

In a separate vial tert-butyl-4-{3-[(3R)-3-{[1-(5-hydroxy-pyridin-3-yl)-3-methoxy-3-oxopropyl]carbamoyl}piperidin-1-yl]-3-oxopropyl}piperidine-1-carboxylate (example 4e, 2.50 mg, 4.58 μmol) was dissolved in 100 μL DMF. Then 2 M NaOH solution was added (20 μL, 40.0 μmol) and after standing for 1 min at 25° C. this mixture was added to vial 2 containing the 2-[¹⁸F]fluoro-1-bromo-ethane in 400 μL DMSO. The sealed vial 2 was heated for 25 min at 100° C. After cooling additional 100 μL 2 M NaOH was added to the reaction mixture and stirring was continued for 15 min at 25° C. The solution was acidified with 200 μL 4 M HCl and heated for 10 min at 100° C. in the sealed vial. The reaction mixture was neutralized with 4 M NaOH, diluted with 3 mL water and given on a semiprep HPLC (Zorbax Bonus RP 5 μm C18-HL (9.4×250 mm), 17/83/0.1-acetonitrile/water/triflouro acetic acid (volume-to-volume-to-volume ratio), 4 mL/min, retention time of (3S)-3-[3-(2-[¹⁸F]fluoro-ethoxy)phenyl]-3-[({(3R)-1-[3-(piperidin-4-yl)propanoyl]piperidin-3-yl}carbonyl)amino]propanoic acid: 13.4-14.7 min; retention time of (3R)-3-[3-(2-[¹⁸F]fluoro-ethoxy)phenyl]-3-[({(3R)-1-[3-(piperidin-4-yl)propanoyl]piperidin-3-yl}carbonyl)amino]propanoic acid: 8.6-9.7 min). The collected fraction was diluted with 20 mL water and given on a preconditioned Sep-Pak™ Light C18 cartridge (preconditioned with 5 ml EtOH and 10 mL). The cartridge was washed with 5 mL water and then the activity was eluted with 1.5 mL of EtOH. After complete evaporation of the EtOH under a stream of nitrogen at 90° C. the final tracer was taken up in water (100 μL) to get 10 to 15 MBq (3S)-3-[3-(2-[¹⁸F]fluoro-ethoxy)-phenyl]-3-[({(3R)-1-[3-(piperidin-4-yl)propanoyl]piperidin-3-yl}carbonyl)amino]propanoic acid (radiochemical yield: 3±1.7% d.c.; synthesis time: 195±14.3 min). The radiochemical purity was >99%. The F-18 labeled product was confirmed by co-injection with the F-19 cold standard (example 1) on an analytical HPLC (column: ACE, C18 RP, 50×4.6 mm, 3μ, 2 ml/min (Agilent), solvent A: H2O+0.1% TFA, solvent B: MeCN+0.1% TFA, gradient: 5% B to 40% B in 7 min).

Example 39

(3S)-3-[4-(2-[¹⁸F]Fluoroethoxy)phenyl]-3-[({(3R)-1-[3-(piperidin-4-yl)propanoyl]piperidin-3-yl}carbonyl)amino]propanoic acid

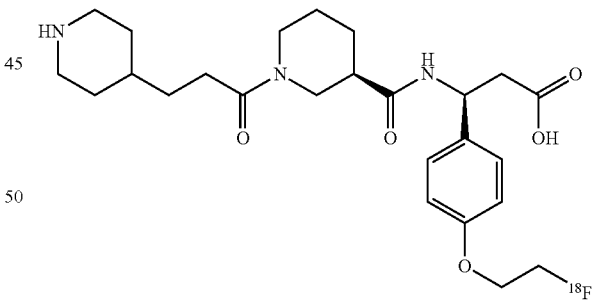

[¹⁸F]Fluoride was produced by an ¹⁸O (p,n)¹⁸F nuclear reaction by bombardment of a 98% ¹⁸O-enriched water target with an 11MeVproton beam at the RDS111 cyclotron. The aqueous [¹⁸F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (1.0 mg K$_2$CO$_3$ in 0.5 ml water and 5.27 mg K$_{222}$ in 1.5 ml MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then the diastereomeric mixture of tert-butyl 4-{3-[(3R)-3-({3-methoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate (example 22, 2.0 mg, 2.69 μmol) in dry MeCN (300 μL) was added to the dried [$^{18}$F]KF-K$_{222}$. After heating at 100° C. for 10 min in a sealed vial the vessel was cooled and 0.5 M NaOH (100 μL) was added. Stirring was continued for 10 min at 25° C. before 1 M HCl (200 μL) was added. The resealed vial was then again heated for 10 min at 100° C. After cooling the reaction mixture was diluted with 4 mL water and given on a semiprep HPLC (Zorbax Bonus RP 5 μm C18-HL (9.4×250 mm), 19/81/0.1-acetonitrile/water/triflouro acetic acid (volume-to-volume-to-volume ratio), 4 mL/min, retention time of (3S)-3-[4-(2-[$^{18}$F]fluoroethoxy)phenyl]-3-[({(3R)-1-[3-(piperidin-4-yl)propanoyl]piperidin-3-yl}carbonyl)amino] propanoic acid: 10.3-12.4 min; retention time of (3R)-3-[4-(2-[$^{18}$F]fluoroethoxy)phenyl]-3-[({(3R)-1-[3-(piperidin-4-yl)propanoyl]piperidin-3-yl}carbonyl)amino]propanoic acid: 8.3-10.3 min). The collected fraction was diluted with 20 mL water and given on a preconditioned Sep-Pak™ Light C18 cartridge (preconditioned with 5 ml EtOH and 10 mL). The cartridge was washed with 5 mL water and then the activity was eluted with 1.5 mL of EtOH. After complete evaporation of the EtOH under a stream of nitrogen at 90° C. the final tracer was taken up in water (300 μL) and sterile filtrated to get 115 to 151 MBq (3S)-3-[4-(2-[$^{18}$F]fluoroethoxy)phenyl]-3-[({(3R)-1-[3-(piperidin-4-yl)propanoyl]piperidin-3-yl}carbonyl)amino]propanoic acid (radiochemical yield: 11±4.0% d.c.; synthesis time: 108±10.5 min). The radiochemical purity was >99%. The F-18 labeled product was confirmed by co-injection with the F-19 cold standard (example 2) on an analytical HPLC (column: ACE, C18 RP, 50×4.6 mm, 3μ, 2 ml/min (Agilent), solvent A: H2O+0.1% TFA, solvent B: MeCN+0.1% TFA, gradient: 5% B to 50% B in 7 min).

Example 40

(3S)-3-[5-(2-[$^{18}$F]Fluoroethoxy)pyridin-3-yl]-3-[({(3R)-1-[3-(piperidin-4-yl)propanoyl]piperidin-3-yl}carbonyl)amino]propanoic acid

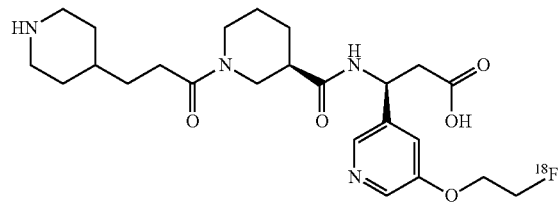 [SMILES: O=C(O)C[C@H](NC(=O)[C@@H]1CCCN(C(=O)CCC2CCNCC2)C1)c1cncc(OCC[18F])c1]

Labeling of tert-Butyl 4-{3-[(3R)-3-({3-methoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylate

[$^{18}$F]Fluoride was produced by an $^{18}$O (p, n)$^{18}$F nuclear reaction by bombardment of a 98% $^{18}$O-enriched water target with an 11MeVproton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (1.0 mg K$_2$CO$_3$ in 0.5 ml water and 5.27 mg K$_{222}$ in 1.5 ml MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then the diastereomeric mixture of tert-butyl 4-{3-[(3R)-3-({3-methoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylate (example 24, 2.0 mg, 2.68 μmol) in dry MeCN (300 μL) was added to the dried [$^{18}$F]KF-K$_{222}$. After heating at 100° C. for 10 min in a sealed vial the vessel was cooled and 0.5 M NaOH (100 μL) was added. Stirring was continued for 10 min at 25° C. before 1 M HCl (200 μL) was added. The resealed vial was then again heated for 10 min at 100° C. After cooling the reaction mixture was diluted with 4 mL water and given on a semi prep HPLC (Phenomenex Gemini 5 μm C18 110A (S/N: 337148-3; 10.0×250 mm), 10/90/0.1-acetonitrile/water/trifluoro acetic acid (volume-to-volume-to-volume ratio), 4 mL/min, retention time of (3S)-3-[5-(2-[$^{18}$F]fluoroethoxy)pyridin-3-yl]-3-[({(3R)-1-[3-(piperidin-4-yl)propanoyl]piperidin-3-yl}carbonyl)amino]propanoic acid: 15.1-17.0 min; retention time of (3R)-3-[5-(2-[$^{18}$F]fluoroethoxy)pyridin-3-yl]-3-[({(3R)-1-[3-(piperidin-4-yl)propanoyl]piperidin-3-yl}carbonyl)amino]propanoic acid: 8.0-8.4 min). The collected fraction was diluted with 40 mL water and given on a preconditioned Sep-Pak™ Plus C18 cartridge (preconditioned with 5 ml EtOH and 10 mL). The cartridge was washed with 5 mL water and then the activity was eluted with 1.5 mL of EtOH. After complete evaporation of the EtOH under a stream of nitrogen at 90° C. the final tracer was taken up in water (300 μL) to get 113 to 168 MBq (3S)-3-[5-(2-[$^{18}$F]fluoroethoxy)pyridin-3-yl]-3-[({(3R)-1-[3-(piperidin-4-yl)propanoyl]piperidin-3-yl}carbonyl)amino]propanoic acid (radiochemical yield: 8.7±1.5% d.c.; synthesis time: 132±15.4 min). The radiochemical purity was >99%. The F-18 labeled product was confirmed by co-injection with the F-19 cold standard (example 3) on an analytical HPLC (column: Phenomenex Gemini, C18 RP, 50×4.6 mm, 3 μ, 1.5 ml/min (Agilent), solvent A: H2O+0.1% TFA, solvent B: MeCN+0.1% TFA, isocratic 12% B for 7 min).

Labeling of tert-Butyl 4-{3-[(3R)-3-({(1S)-3-methoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylate

[$^{18}$F]Fluoride was produced by an $^{18}$O (p, n)$^{18}$F nuclear reaction by bombardment of a 98% $^{18}$O-enriched water target with an 11MeVproton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (1.0 mg K$_2$CO$_3$ in 0.5 ml water and 5.27 mg K$_{222}$ in 1.5 ml MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then tert-butyl 4-{3-[(3R)-3-({(1S)-3-methoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylate (example 24, 2.0 mg, 2.68 μmol) in dry MeCN (300 μL) was added to the dried [$^{18}$F]KF-K$_{222}$. After heating at 100° C. for 10 min in a sealed vial the vessel was cooled and 0.5 M NaOH (100

μL) was added. Stirring was continued for 10 min at 25° C. before 1 M HCl (200 μL) was added. The resealed vial was then again heated for 10 min at 100° C. After cooling the reaction mixture was diluted with 4 mL water and given on a semi prep HPLC (Phenomenex Gemini 5 μm C18 110A (S/N: 337148-3; 10.0×250 mm), 10/90/0.1-acetonitrile/water/trifluoro acetic acid (volume-to-volume-to-volume ratio), 4 mL/min, retention time of (3S)-3-[5-(2-[$^{18}$F]Fluoroethoxy)pyridin-3-yl]-3-[({(3R)-1-[3-(piperidin-4-yl)propanoyl]piperidin-3-yl}carbonyl)amino]propanoic acid: 15.4-18.4 min). The collected fraction was diluted with 40 mL water and given on a preconditioned Sep-Pak™ Plus C18 cartridge (preconditioned with 5 ml EtOH and 10 mL). The cartridge was washed with 5 mL water and then the activity was eluted with 1.5 mL of EtOH. After complete evaporation of the EtOH under a stream of nitrogen at 90° C. the final tracer was taken up in water (300 μL) to get 127 to 435 MBq (3S)-3-[5-(2-[$^{18}$F]Fluoroethoxy)pyridin-3-yl]-3-[({(3R)-1-[3-(piperidin-4-yl)propanoyl]piperidin-3-yl}carbonyl)amino]propanoic acid (radiochemical yield: 19.5±4.6% d.c.; synthesis time: 117±10 min). The radiochemical purity was >99% and the specific activity was between 38 and 107 GBq/μmol. The F-18 labeled product was confirmed by co-injection with the F-19 cold standard (example 3) on an analytical HPLC (column: Phenomenex Gemini, C18 RP, 50×4.6 mm, 3 μ, 1.5 ml/min (Agilent), solvent A: H2O+0.1% TFA, solvent B: MeCN+0.1% TFA, isocratic 12% B for 7 min).

Labeling of tert-Butyl 4-{3-[(3R)-3-({(1S)-3-tert-butoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylate

[$^{18}$F]Fluoride was produced by an $^{18}$O (p,n)$^{18}$F nuclear reaction by bombardment of a 98% $^{18}$O-enriched water target with an 11MeVproton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (2.28 mg Cs$_2$CO$_3$ in 0.5 ml water and 5.27 mg K$_{222}$ in 1.5 mL MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then tert-butyl 4-{3-[(3R)-3-({(1S)-3-tert-butoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylate (example 25, 4.0 mg, 5.08 μmol) in dry MeCN (400 μL) was added to the dried [$^{18}$F]CsF-K$_{222}$. After heating at 100° C. for 20 min in a sealed vial the vessel was cooled and 1 M HCl (400 μL) was added. The resealed vial was then again heated for 12 min at 100° C. After cooling the reaction mixture was diluted with 4 mL water and given on a semi prep HPLC (Phenomenex Gemini 5 μm C18 110A (S/N: 337148-3; 10.0×250 mm), 9/91/0.1-acetonitrile/water/trifluoro acetic acid (volume-to-volume-to-volume ratio), 4 mL/min, retention time of (3S)-3-[5-(2-[$^{18}$F]Fluoroethoxy)pyridin-3-yl]-3-[({(3R)-1-[3-(piperidin-4-yl)propanoyl]piperidin-3-yl}carbonyl)amino]propanoic acid: 11.0-17.2 min). The collected fraction was diluted with 40 mL water and given on a preconditioned Sep-Pak™ Plus C18 cartridge (preconditioned with 5 ml EtOH and 10 mL). The cartridge was washed with 5 mL water and then the activity was eluted with 1.0 mL of EtOH. After complete evaporation of the EtOH under a stream of nitrogen at 90° C. the final tracer was taken up in water (300 μL) to get 154 to 1351 MBq (3S)-3-[5-(2-[$^{18}$F]Fluoroethoxy)pyridin-3-yl]-3-[({(3R)-1-[3-(piperidin-4-yl)propanoyl]piperidin-3-yl}carbonyl)amino]propanoic acid (radiochemical yield: 21.3±5.9% d.c.; synthesis time: 126±20 min). The radiochemical purity was >99% and the specific activity was between 28.5 and 61.2 GBq/μmol. The F-18 labeled product was confirmed by co-injection with the F-19 cold standard (example 3) on an analytical HPLC (column: Phenomenex Gemini, C18 RP, 50×4.6 mm, 3μ, 1.5 ml/min (Agilent), solvent A: H2O+0.1% TFA, solvent B: MeCN+0.1% TFA, isocratic 12% B for 7 min).

Example 41

(3S)-3-{5-[4-(2-[$^{18}$F]Fluoroethoxy)phenyl]pyridin-3-yl}-3-[({(3R)-1-[3-(piperidin-4-yl)propanoyl]piperidin-3-yl}carbonyl)amino]propanoic acid

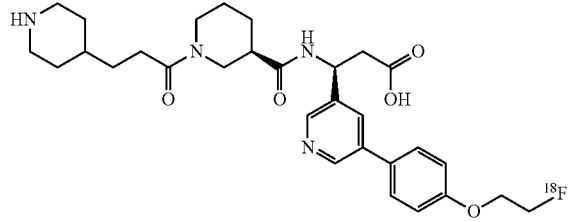 [SMILES: O=C(O)C[C@H](NC(=O)[C@@H]1CCCN(C(=O)CCC2CCNCC2)C1)c1cncc(-c2ccc(OCC[18F])cc2)c1]

Labeling of tert-Butyl 4-{3-[(3R)-3-{[3-methoxy-1-{5-[4-(2-{[(4-methylphenyl)sulfonyl]oxy}ethoxy)phenyl]pyridin-3-yl}-3-oxopropyl]carbamoyl}piperidin-1-yl]-3-oxopropyl}piperidine-1-carboxylate

[$^{18}$F]Fluoride was produced by an $^{18}$O (p, n)$^{18}$F nuclear reaction by bombardment of a 98% $^{18}$O-enriched water target with an 11MeVproton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (1.0 mg K$_2$CO$_3$ in 0.5 ml water and 5.27 mg K$_{222}$ in 1.5 ml MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then the diastereomeric mixture of tert-butyl 4-{3-[(3R)-3-{[3-methoxy-1-{5-[4-(2-{[(4-methylphenyl)sulfonyl]oxy}ethoxy)phenyl]pyridin-3-yl}-3-oxopropyl]carbamoyl}piperidin-1-yl]-3-oxopropyl}piperidine-1-carboxylate (example 26, 2.0 mg, 2.44 μmol) in dry MeCN (300 μL) was added to the dried [$^{18}$F]KF-K$_{222}$. After heating at 100° C. for 10 min in a sealed vial the vessel was cooled and 0.5 M NaOH (100 μL) was added. Stirring was continued for 10 min at 25° C. before 1 M HCl (200 μL) was added. The resealed vial was then again heated for 10 min at 100° C. After cooling the reaction mixture was diluted with 4 mL water and given on a semi prep HPLC (ACE 5 μm C18 HL (10.0×250 mm), gradient (20 min): 20/80/0.1-35/65/0.1 acetonitrile/water/trifluoro acetic acid (volume-to-volume-to-volume ratio), 4 mL/min, retention time of (3S)-3-{5-[4-(2-[$^{18}$F]fluoroethoxy)phenyl]

pyridin-3-yl}-3-[({(3R)-1-[3-(piperidin-4-yl)propanoyl]piperidin-3-yl}carbonyl)amino]propanoic acid: 15.5-16.8 min; retention time of (3R)-3-{5-[4-(2-[¹⁸F]fluoroethoxy)phenyl]pyridin-3-yl}-3-[({(3R)-1-[3-(piperidin-4-yl)propanoyl]piperidin-3-yl}carbonyl)amino]propanoic acid: 13.2-15.4 min). The collected fraction was diluted with 40 mL water and given on a preconditioned Sep-Pak™ Plus C18 cartridge (preconditioned with 5 ml EtOH and 10 mL). The cartridge was washed with 5 mL water and then the activity was eluted with 1.5 mL of EtOH. After complete evaporation of the EtOH under a stream of nitrogen at 90° C. the final tracer was taken up in water (300 µL) to get 65 to 163 MBq (3S)-3-{5-[4-(2-[¹⁸F]fluoroethoxy)phenyl]pyridin-3-yl}-3-[({(3R)-1-[3-(piperidin-4-yl)propanoyl]piperidin-3-yl}carbonyl)amino]propanoic acid (radiochemical yield: 9.0±1.0% d.c.; synthesis time: 128±1 0.0 min). The radiochemical purity was >99%. The F-18 labeled product was confirmed by co-injection with the F-19 cold standard (example 7) on an analytical HPLC (column: ACE, C18 RP, 50×4.6 mm, 3µ, 2 ml/min (Agilent), solvent A: H2O+0.1% TFA, solvent B: MeCN+0.1% TFA, isocratic 15% B in 7 min).

Labeling of tert-Butyl 4-{3-[(3R)-3-{[(1S)-3-tert-butoxy-1-{5-[4-(2-{[(4-methylphenyl)sulfonyl]oxy}ethoxy)phenyl]pyridin-3-yl}-3-oxopropyl]carbamoyl}piperidin-1-yl]-3-oxopropyl}piperidine-1-carboxylate

[¹⁸F]Fluoride was produced by an ¹⁸O (p,n)¹⁸F nuclear reaction by bombardment of a 98% ¹⁸O-enriched water target with an 11MeVproton beam at the RDS111 cyclotron. The aqueous [¹⁸F]fluoride solution was trapped in a small anion exchange Sep-Pak™ Plus QMA cartridge (Waters) (preconditioned with 5 ml 0.5 M K₂CO₃ solution and 10 mL water). The radioactivity was eluted with a solution mixture (2.28 mg Cs₂CO₃ in 0.5 ml water and 5.27 mg K₂₂₂ in 1.5 mL MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then tert-butyl 4-{3-[(3R)-3-{[(1S)-3-tert-butoxy-1-{5-[4-(2-{[(4-methylphenyl)sulfonyl]oxy}ethoxy)phenyl]pyridin-3-yl}-3-oxopropyl]carbamoyl}piperidin-1-yl]-3-oxopropyl}piperidine-1-carboxylate (example 27, 2.0 mg, 2.31 µmol) in dry MeCN (300 µL) was added to the dried [¹⁸F]CsF-K₂₂₂. After heating at 100° C. for 15 min in a sealed vial the vessel was cooled and 1 M HCl (150 µL) was added. The resealed vial was then again heated for 10 min at 100° C. After cooling the reaction mixture was neutralized with 1 M NaOH (150 µL) and diluted with 4 mL water and given on a semi prep HPLC (ACE 5 µm C18 HL (10.0×250 mm), 21/79/0.1-acetonitrile/water/trifluoro acetic acid (volume-to-volume-to-volume ratio), 4 mL/min, retention time of (3S)-3-{5-[4-(2-[¹⁸F]fluoroethoxy)phenyl]pyridin-3-yl}-3-[({(3R)-1-[3-(piperidin-4-yl)propanoyl]piperidin-3-yl}carbonyl)amino]propanoic acid: 13.0 min). The collected fraction was diluted with 30 mL water and given on a preconditioned Sep-Pak™ Plus C18 cartridge (preconditioned with 5 ml EtOH and 10 mL). The cartridge was washed with 5 mL water and then the activity was eluted with 1.0 mL of EtOH. After complete evaporation of the EtOH under a stream of nitrogen at 90° C. the final tracer was taken up in water (300 µL) to get 226 MBq (3S)-3-{5-[4-(2-[¹⁸F]fluoroethoxy)phenyl]pyridin-3-yl}-3-[({(3R)-1-[3-(piperidin-4-yl)propanoyl]piperidin-3-yl}carbonyl)amino]propanoic acid (radiochemical yield: 11% d.c.; synthesis time: 113 min). The radiochemical purity was >99%. The F-18 labeled product was confirmed by co-injection with the F-19 cold standard (example 7) on an analytical HPLC (column: ACE, C18 RP, 50×4.6 mm, 3µ, 2 ml/min (Agilent), solvent A: H2O+0.1% TFA, solvent B: MeCN+0.1% TFA, isocratic 15% B in 7 min).

Example 42

(3S)-3-[5-(3-Cyano-4-[¹⁸F]fluorophenyl)pyridin-3-yl]-3-[({(3R)-1-[3-(piperidin-4-yl)propanoyl]piperidin-3-yl}carbonyl)amino]propanoic acid

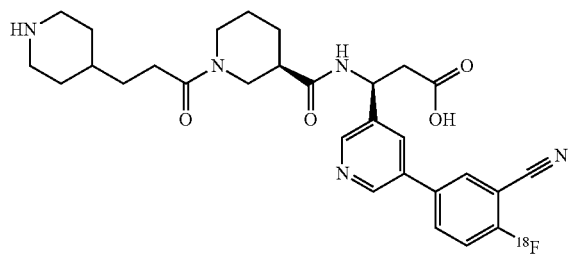 [SMILES: N#Cc1cc(-c2cncc([C@H](CC(=O)O)NC(=O)[C@@H]3CCCN(C(=O)CCC4CCNCC4)C3)c2)ccc1[18F]]

[¹⁸F]Fluoride was produced by an ¹⁸O (p, n)¹⁸F nuclear reaction by bombardment of a 98% ¹⁸O-enriched water target with an 11MeVproton beam at the RDS111 cyclotron. The aqueous [¹⁸F]fluoride solution was trapped in a small anion exchange Sep-Pak™ Plus QMA cartridge (Waters) (preconditioned with 5 ml 0.5 M K₂CO₃ solution and 10 mL water). The radioactivity was eluted with a solution mixture (2.8 mg KHCO₃ in 100 µL water and 10.4 mg K₂₂₂ in 1.9 mL MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then the diastereomeric mixture of 4-[3-((R)-3-{1-[5-(4-chloro-3-cyano-phenyl)-pyridin-3-yl]-2-methoxycarbonyl-ethylcarbamoyl}-piperidin-1-yl)-3-oxo-propyl]-piperidine-1-carboxylic acid tert-butyl ester (2.0 mg, 3.00 µmol) in dry DMSO (300 µL) was added to the dried [¹⁸F]KHF₂—K₂₂₂. After heating at 160° C. for 10 min in a sealed vial the vessel was cooled and 0.5 M NaOH (100 µL) was added. Stirring was continued for 5 min at 25° C. before 1 M HCl (200 µL) was added. The resealed vial was then again heated for 5 min at 70° C. After cooling the reaction mixture was diluted with 4 mL water and given on a semi prep HPLC (ACE 5 µm C18 HL (10.0×250 mm), gradient (20 min): 20/80/0.1-30/70/0.1 acetonitrile/water/trifluoro acetic acid (volume-to-volume-to-volume ratio), 4 mL/min, retention time of (3S)-3-[5-(3-cyano-4-[¹⁸F]fluorophenyl)pyridin-3-yl]-3-[({(3R)-1-[3-(piperidin-4-yl)propanoyl]piperidin-3-yl}carbonyl)amino]propanoic acid: 12.0-11.8 min; retention time of (3R)-3-[5-(3-cyano-4-[¹⁸F]fluorophenyl)pyridin-3-yl]-3-[({(3R)-1-[3-(piperidin-4-yl)propanoyl]piperidin-3-yl}carbonyl)amino]propanoic acid: 10.0-10.5 min). The collected fraction was diluted with 30 mL water and given on a preconditioned Sep-Pak™ Light C18 cartridge (preconditioned with 5 ml EtOH and 10 mL). The cartridge was washed with 5 mL water and then the activity was eluted with 0.7 mL of EtOH. After complete evaporation of the EtOH under a stream of nitrogen at 90° C. the final tracer was taken up in water (200 µL) to get 12 to 111 MBq (3S)-3-[5-(3-cyano-4-[¹⁸F]fluorophenyl)pyridin-3-yl]-3-[({(3R)-1-[3-(piperidin-4-yl)propanoyl]piperidin-3-yl}carbonyl)amino]propanoic acid (ra-

Example 43

(3S)-3-[5-(4-Cyano-3-[$^{18}$F]fluorophenyl)pyridin-3-yl]-3-[({(3R)-1-[3-(piperidin-4-yl)propanoyl]piperidin-3-yl}carbonyl)amino]propanoic acid

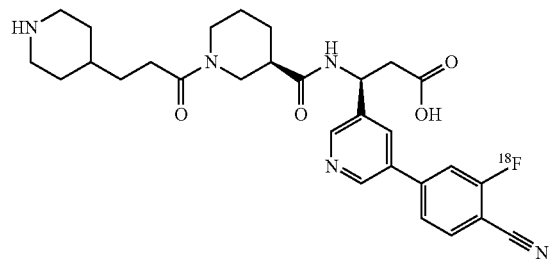 [SMILES: N#Cc1ccc(-c2cncc([C@H](CC(=O)O)NC(=O)[C@@H]3CCCN(C(=O)CCC4CCNCC4)C3)c2)cc1[18F]]

[$^{18}$F]Fluoride was produced by an $^{18}$O (p, n)$^{18}$F nuclear reaction by bombardment of a 98% $^{18}$O-enriched water target with an 11MeVproton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (2.8 mg KHCO$_3$ in 100 μL water and 10.4 mg K$_{222}$ in 1.9 mL MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then the diastereomeric mixture of tert-butyl 4-{3-[(3R)-3-({1-[5-(4-chloro-3-cyanophenyl)pyridin-3-yl]-3-methoxy-3-oxopropyl}carbamoyl)piperidin-1-yl]-3-oxopropyl}piperidine-1-carboxylate (example 28, 1.0 mg, 1.87 μmol) in dry DMSO (300 μL) was added to the dried [$^{18}$F]KHF$_2$—K$_{222}$. After heating at 160° C. for 15 min in a sealed vial the vessel was cooled and 0.5 M NaOH (100 μL) was added. Stirring was continued for 10 min at 25° C. before 1 M HCl (200 μL) was added. The resealed vial was then again heated for 10 min at 70° C. After cooling the reaction mixture was diluted with 4 mL water and given on a semi prep HPLC (ACE 5 μm C18 HL (10.0×250 mm), gradient (20 min): 20/80/0.1-30/70/0.1 acetonitrile/water/trifluoro acetic acid (volume-to-volume-to-volume ratio), 4 mL/min, retention time of (3S)-3-[5-(4-cyano-3-[$^{18}$F]fluorophenyl)pyridin-3-yl]-3-[({(3R)-1-[3-(piperidin-4-yl)propanoyl]piperidin-3-yl}carbonyl)amino] propanoic acid: 11.5-12.2 min; retention time of (3R)-3-[5-(4-cyano-3-[$^{18}$F]fluorophenyl)pyridin-3-yl]-3-[({(3R)-1-[3-(piperidin-4-yl)propanoyl]piperidin-3-yl}carbonyl)amino] propanoic acid: 9.9-10.8 min). The collected fraction was diluted with 15 mL water and given on a preconditioned Sep-Pak™ Light C18 cartridge (preconditioned with 5 ml EtOH and 10 mL). The cartridge was washed with 5 mL water and then the activity was eluted with 1.0 mL of EtOH. After complete evaporation of the EtOH under a stream of nitrogen at 90° C. the final tracer was taken up in water (100 μL) to get 7 to 38 MBq (3S)-3-[5-(4-cyano-3-[$^{18}$F]fluorophenyl)pyridin-3-yl]-3-[({(3R)-1-[3-(piperidin-4-yl)propanoyl]piperidin-3-yl}carbonyl)amino]propanoic acid (radiochemical yield: 2.4±1.0% d.c.; synthesis time: 111±10.6 min). The radiochemical purity was >99%. The F-18 labeled product was confirmed by co-injection with the F-19 cold standard (example 10) on an analytical HPLC (column: ACE, C18 RP, 50×4.6 mm, 3μ, 2 ml/min (Agilent), solvent A: H2O+0.1% TFA, solvent B: MeCN+0.1% TFA, isocratic 15% B in 7 min).

Example 44

(3S)-3-(5-{[4-(2-[$^{18}$F]Fluoroethoxy)phenyl]ethynyl}pyridin-3-yl)-3-[({(3R)-1-[3-(piperidin-4-yl)propanoyl]piperidin-3-yl}carbonyl)amino]propanoic acid

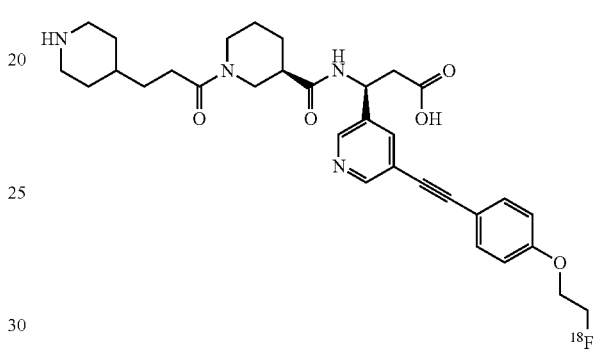

[$^{18}$F]Fluoride was produced by an $^{18}$O (p, n)$^{18}$F nuclear reaction by bombardment of a 98% $^{18}$O-enriched water target with an 11MeVproton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (2.28 mg Cs$_2$CO$_3$ in 0.5 ml water and 5.25 mg K$_{222}$ in 1.5 mL MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then tert-butyl 4-{3-[(3R)-3-{[(1S)-3-tert-butoxy-1-(5-{[4-(2-{[(4-methylphenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate (example 34, 2.0 mg, 2.25 μmol) in dry MeCN (300 μL) was added to the dried [$^{18}$F]CsF-K$_{222}$. After heating at 100° C. for 15 min in a sealed vial the vessel was cooled and 1 M HCl (150 μL) was added. The resealed vial was then again heated for 12 min at 100° C. After cooling the reaction mixture was diluted with 4 mL water and given on a semi prep HPLC (ACE 5 μm C18 (10.0×250 mm), 28/72/0.1-acetonitrile/water/trifluoro acetic acid (volume-to-volume-to-volume ratio), 4 mL/min, retention time of (3S)-3-(5-{[4-(2-[$^{18}$F]fluoroethoxy)phenyl]ethynyl}pyridin-3-yl)-3-[({(3R)-1-[3-(piperidin-4-yl)propanoyl]piperidin-3-yl}carbonyl)amino]propanoic acid: 17.8 min). The collected fraction was diluted with 15 mL water and given on a preconditioned Sep-Pak™ Light C18 cartridge (preconditioned with 5 ml EtOH and 10 mL). The cartridge was washed with 5 mL water and then the activity was eluted with 1.0 mL of EtOH. After complete evaporation of the EtOH under a stream of nitrogen at 90° C. the final tracer was taken up in water (100 μL) to get 44 MBq (3S)-3-(5-{[4-(2-[$^{18}$F]fluoroethoxy)phenyl]ethynyl}pyridin-3-yl)-3-

[({(3R)-1-[3-(piperidin-4-yl)propanoyl]piperidin-3-yl}carbonyl)amino]propanoic acid (radiochemical yield: 5.0% d.c.; synthesis time: 139 min). The radiochemical purity was >99%. The F-18 labeled product was confirmed by co-injection with the F-19 cold standard (example 15) on an analytical HPLC (column: ACE, C18 RP, 50×4.6 mm, 3 μ, 2 ml/min (Agilent), solvent A: H2O+0.1% TFA, solvent B: MeCN+0.1% TFA, isocratic 20% B in 7 min).

Example 45

(3S)-3-(5-{[3-(2-[$^{18}$F]Fluoroethoxy)phenyl]ethynyl}pyridin-3-yl)-3-[({(3R)-1-[3-(piperidin-4-yl)propanoyl]piperidin-3-yl}carbonyl)amino]propanoic acid

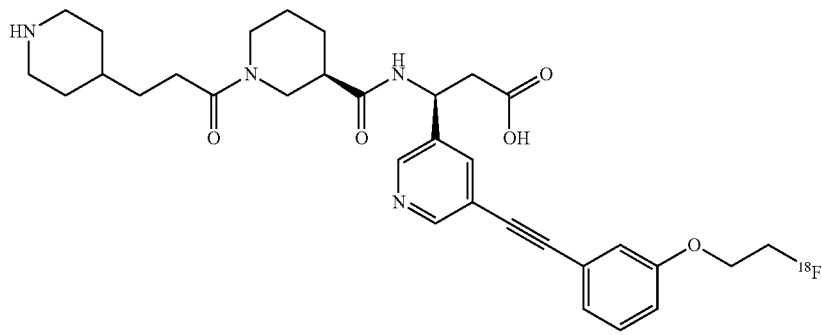 [SMILES: O=C(O)C[C@H](NC(=O)[C@@H]1CCCN(C(=O)CCC2CCNCC2)C1)c1cncc(C#Cc2cccc(OCC[18F])c2)c1]

[$^{18}$F]Fluoride was produced by an $^{18}$O (p, n)$^{18}$F nuclear reaction by bombardment of a 98% $^{18}$O-enriched water target with an 11MeV proton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (2.28 mg Cs$_2$CO$_3$ in 500 μL water and 5.25 mg K$_{222}$ in 1.5 mL MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then tert-butyl 4-{3-[(3R)-3-{[(1S)-3-tert-butoxy-1-(5-{[3-(2-{[(4-methylphenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate (example 35, 2.0 mg, 2.25 μmol) in dry MeCN (300 μL) was added to the dried [$^{18}$F]CsF-K$_{222}$. After heating at 100° C. for 15 min in a sealed vial the vessel was cooled and 1 M HCl (150 μL) was added. The resealed vial was then again heated for 10 min at 100° C. After cooling the reaction mixture was diluted with 4 mL water and given on a semi prep HPLC (ACE 5 μm C18 HL (10.0×250 mm), 31/69/0.1-acetonitrile/water/trifluoro acetic acid (volume-to-volume-to-volume ratio), 4 mL/min, retention time of (3S)-3-(5-{[3-(2-[$^{18}$F]Fluoroethoxy)phenyl]ethynyl}pyridin-3-yl)-3-[({(3R)-1-[3-(piperidin-4-yl)propanoyl]piperidin-3-yl}carbonyl)amino]propanoic acid: 14.9 min). The collected fraction was diluted with 15 mL water and given on a preconditioned Sep-Pak™ Light C18 cartridge (preconditioned with 5 ml EtOH and 10 mL). The cartridge was washed with 5 mL water and then the activity was eluted with 0.5 mL of EtOH. After complete evaporation of the EtOH under a stream of nitrogen at 90° C. the final tracer was taken up in water (100 μL) to get 63 MBq (3S)-3-(5-{[3-(2-[$^{18}$F]Fluoroethoxy)phenyl]ethynyl}pyridin-3-yl)-3-[({(3R)-1-[3-(piperidin-4-yl)propanoyl]piperidin-3-yl}carbonyl)amino]propanoic acid (radiochemical yield: 5.0% d.c.; synthesis time: 115 min). The radiochemical purity was >99%. The F-18 labeled product was confirmed by co-injection with the F-19 cold standard (example 16) on an analytical HPLC (column: ACE, C18 RP, 50×4.6 mm, 3 μ, 2 ml/min (Agilent), solvent A: H2O+ 0.1% TFA, solvent B: MeCN+0.1% TFA, isocratic 23% B in 7 min).

Example 46

(3S)-3-(5-{2-[4-(2-[$^{18}$F]Fluoroethoxy)phenyl]ethyl}pyridin-3-yl)-3-[({(3R)-1-[3-(piperidin-4-yl)propanoyl]piperidin-3-yl}carbonyl)amino]propanoic acid

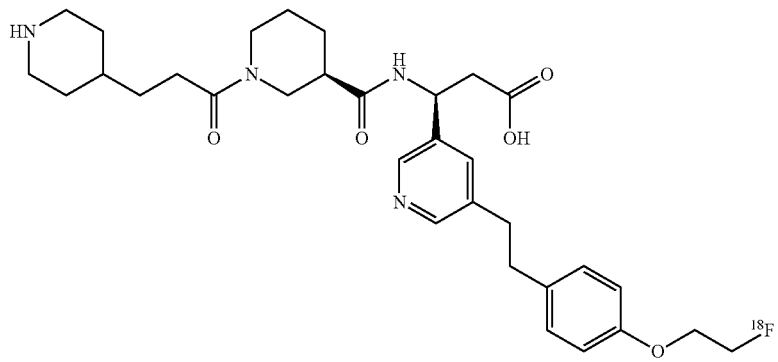 [SMILES: O=C(O)C[C@H](NC(=O)[C@@H]1CCCN(C(=O)CCC2CCNCC2)C1)c1cncc(CCc2ccc(OCC[18F])cc2)c1]

[¹⁸F]Fluoride was produced by an ¹⁸O (p, n)¹⁸F nuclear reaction by bombardment of a 98% ¹⁸O-enriched water target with an 11MeVproton beam at the RDS111 cyclotron. The aqueous [¹⁸F]fluoride solution was trapped in a small anion exchange Sep-Pak™ Plus QMA cartridge (Waters) (preconditioned with 5 ml 0.5 M $K_2CO_3$ solution and 10 mL water). The radioactivity was eluted with a solution mixture (1.0 mg $K_2CO_3$ in 0.5 ml water and 5.27 mg $K_{222}$ in 1.5 ml MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then tert-butyl 4-{3-[(3R)-3-{[(1S)-3-tert-butoxy-1-(5-{2-[4-(2-{[(4-methylphenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate (example 36, 3.0 mg, 3.37 µmol) in dry MeCN (300 µL) was added to the dried [¹⁸F]KF-$K_{222}$. After heating at 100° C. for 15 min in a sealed vial the vessel was cooled and 1 M HCl (150 µL) was added. The resealed vial was then again heated for 10 min at 100° C. After cooling the reaction mixture was diluted with 4 mL water and given on a semi prep HPLC (Phenomenex Synergi Hydro-RP 4 µm (250×10 mm), 18/82/0.1-acetonitrile/water/trifluoro acetic acid (volume-to-volume-to-volume ratio), 4 mL/min, retention time of (3S)-3-(5-{2-[4-(2-[¹⁸F]fluoroethoxy)phenyl]ethyl}pyridin-3-yl)-3-[({(3R)-1-[3-(piperidin-4-yl)propanoyl]piperidin-3-yl}carbonyl)amino]propanoic acid: 17.8 min). The collected fraction was diluted with 15 mL water and given on a preconditioned Sep-Pak™ Light C18 cartridge (preconditioned with 5 ml EtOH and 10 mL). The cartridge was washed with 5 mL water and then the activity was eluted with 1.0 mL of EtOH. After complete evaporation of the EtOH under a stream of nitrogen at 90° C. the final tracer was taken up in water (100 µL) and sterile filtrated to get 52 MBq (3S)-3-(5-{2-[4-(2-[¹⁸F]fluoroethoxy)phenyl]ethyl}pyridin-3-yl)-3-[({(3R)-1-[3-(piperidin-4-yl)propanoyl]piperidin-3-yl}carbonyl)amino]propanoic acid (radiochemical yield: 5.5% d.c.; synthesis time: 145 min). The radiochemical purity was >99%. The F-18 labeled product was confirmed by co-injection with the F-19 cold standard on an analytical HPLC (column: Phenomenex Synergi Hydro, C18 RP, 50×4.6 mm, 4µ, 2 ml/min (Agilent), solvent A: H2O+0.1% TFA, solvent B: MeCN+0.1% TFA, isocratic 18% B in 7 min).

Example 47

(3S)-3-(5-{2-[3-(2-[¹⁸F]Fluoroethoxy)phenyl]ethyl}pyridin-3-yl)-3-[({(3R)-1-[3-(piperidin-4-yl)propanoyl]piperidin-3-yl}carbonyl)amino]propanoic acid

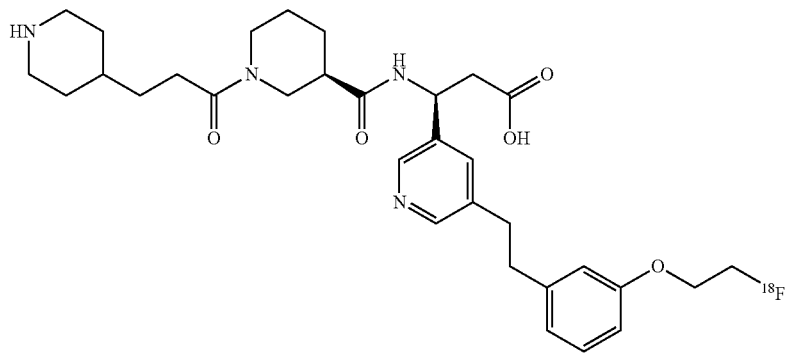 [SMILES: O=C(O)C[C@H](NC(=O)[C@@H]1CCCN(C(=O)CCC2CCNCC2)C1)c1cncc(CCc2cccc(OCC[18F])c2)c1]

[¹⁸F]Fluoride was produced by an ¹⁸O (p, n)¹⁸F nuclear reaction by bombardment of a 98% ¹⁸O-enriched water target with an 11MeVproton beam at the RDS111 cyclotron. The aqueous [¹⁸F]fluoride solution was trapped in a small anion exchange Sep-Pak™ Plus QMA cartridge (Waters) (preconditioned with 5 ml 0.5 M $K_2CO_3$ solution and 10 mL water). The radioactivity was eluted with a solution mixture (2.28 mg $Cs_2CO_3$ in 0.5 ml water and 5.27 mg $K_{222}$ in 1.5 mL MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then tert-butyl 4-{3-[(3R)-3-{[(1S)-3-tert-butoxy-1-(5-{2-[3-(2-{[(4-methylphenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate (example 37, 2.5 mg, 2.81 µmol) in dry MeCN (200 µL) was added to the dried [¹⁸F]CsF-$K_{222}$. After heating at 100° C. for 10 min in a sealed vial the vessel was cooled and 1 M HCl (150 µL) was added. The resealed vial was then again heated for 8 min at 100° C. After cooling the reaction mixture was diluted with 4 mL water and given on a semi prep HPLC (ACE 5 µm C18 HL (10.0×250 mm), 25/75/0.1-acetonitrile/water/trifluoro acetic acid (volume-to-volume-to-volume ratio), 4 mL/min, retention time of (3S)-3-(5-{2-[3-(2-[¹⁸F]fluoroethoxy)phenyl]ethyl}pyridin-3-yl)-3-[({(3R)-1-[3-(piperidin-4-yl)propanoyl]piperidin-3-yl}carbonyl)amino]propanoic acid: 13.2 min). The collected fraction was diluted with 15 mL water and given on a preconditioned Sep-Pak™ Light C18 cartridge (preconditioned with 5 ml EtOH and 10 mL). The cartridge was washed with 5 mL water and then the activity was eluted with 1.0 mL of EtOH. After complete evaporation of the EtOH under a stream of nitrogen at 90° C. the final tracer was taken up in water (200 µL) to get 290 MBq (3S)-3-(5-{2-[3-(2-[$^{18}$F]fluoroethoxy)phenyl]ethyl}pyridin-3-yl)-3-[({(3R)-1-[3-(piperidin-4-yl)propanoyl]piperidin-3-yl}carbonyl)amino]propanoic acid (radiochemical yield: 19.1% d.c.; synthesis time: 88 min). The radiochemical purity was >99%. The F-18 labeled product was confirmed by co-injection with the F-19 cold standard (example 19) on an analytical HPLC (column: ACE, C18 RP, 50×4.6 mm, 3µ, 2 ml/min (Agilent), solvent A: H2O+0.1% TFA, solvent B: MeCN+0.1% TFA, gradient: 5% B to 50% B in 7 min).

Example 48

(3S)-3-(3-{2-[2-(2-[$^{18}$F]Fluoroethoxy)ethoxy]ethoxy}phenyl)-3-[({(3R)-1-[3-(piperidin-4-yl)propanoyl]piperidin-3-yl}carbonyl)amino]propanoic acid

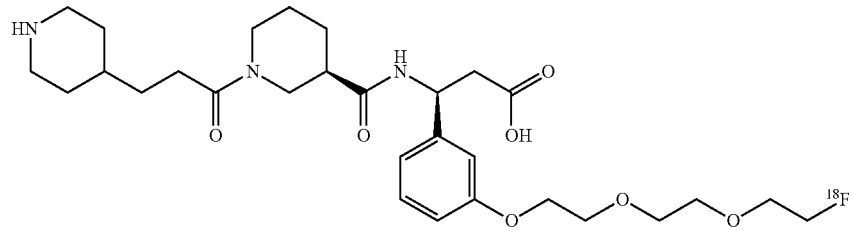 [SMILES: O=C(O)C[C@H](NC(=O)[C@@H]1CCCN(C(=O)CCC2CCNCC2)C1)c1cccc(OCCOCCOCC[18F])c1]

[$^{18}$F]Fluoride was produced by an $^{18}$O (p, n)$^{18}$F nuclear reaction by bombardment of a 98% $^{18}$O-enriched water target with an 11MeVproton beam at the RDS111 cyclotron. The aqueous [$^{18}$F]fluoride solution was trapped in a small anion exchange Sep-Pak™ Plus QMA cartridge (Waters) (preconditioned with 5 ml 0.5 M K$_2$CO$_3$ solution and 10 mL water). The radioactivity was eluted with a solution mixture (1.0 mg K$_2$CO$_3$ in 0.5 ml water and 5.27 mg K$_{222}$ in 1.5 ml MeCN) from the QMA cartridge into a 5 mL conic Wheaton vial. The solvent was evaporated under a stream of nitrogen at 110° C. Azeotropic drying was repeated three times with 1.0 mL portions of acetonitrile. Then tri(ethylene glycol) di-p-toluenesulfonate (10 mg, 21.81 µmol) in dry MeCN (500 µL) was added to the dried [$^{18}$F]KF-K$_{222}$. After heating at 100° C. for 10 min in a sealed vial the vessel was cooled, diluted with 4 mL water and given on a semi prep HPLC ACE 5 µm C18 HL (10.0×250 mm), 50/50/0.1-acetonitrile/water/trifluoro acetic acid (volume-to-volume-to-volume ratio), 4 mL/min, retention time of toluene-4-sulfonic acid 2-[2-(2-[$^{18}$F]-fluoroethoxy)ethoxy]ethyl ester: 12.5 min). The collected fraction was diluted with 20 mL water and given on a preconditioned Sep-Pak™ Light C18 cartridge (preconditioned with 5 ml EtOH and 10 mL). The cartridge was washed with 5 mL water and then the activity was eluted with 1.0 mL of MeCN. Afterwards the MeCN was completely evaporated at 90° C. under a slow stream of nitrogen gas to get the pure prosthetic group toluene-4-sulfonic acid 2-[2-(2-[$^{18}$F]fluoroethoxy)ethoxy]ethyl ester (570 MBq).

In a separate vial tert-butyl-4-{3-[(3R)-3-{[1-(5-hydroxy-pyridin-3-yl)-3-methoxy-3-oxopropyl]carbamoyl}piperidin-1-yl]-3-oxopropyl}piperidine-1-carboxylate (example 4e, 2.50 mg, 4.58 µmol) was dissolved in 300 µL DMF. Then 2 M NaOH solution was added (20 µL, 40.0 µmol) and after standing for 1 min at 25° C. this mixture was added to vial 1 containing the dried toluene-4-sulfonic acid 2-[2-(2-[$^{18}$F]fluoroethoxy)ethoxy]ethyl ester. The sealed vial 2 was heated for 20 min at 100° C. After cooling additional 100 µL 1 M NaOH was added to the reaction mixture and stirring was continued for 10 min at 25° C. The solution was acidified with 200 µL 2 M HCl and heated for 10 min at 100° C. in the sealed vial. The reaction mixture was diluted with a 4 mL mixture of water/MeCN (1:1) and given on a semi prep HPLC ACE 5 µm C18 HL (10.0×250 mm), gradient (20 min): 15/85/0.1-50/50/0.1 acetonitrile/water/trifluoro acetic acid (volume-to-volume-to-volume ratio), 4 mL/min, retention time of (3S)-3-(3-{2-[2-(2-[$^{18}$F]fluoroethoxy)ethoxy]ethoxy}phenyl)-3-[({(3R)-1-[3-(piperidin-4-yl)propanoyl]piperidin-3-yl}carbonyl)amino]propanoic acid: 28.3 min; retention time of (3R)-3-(3-{2-[2-(2-[$^{18}$F]fluoroethoxy)ethoxy]ethoxy}phenyl)-3-[({(3R)-1-[3-(piperidin-4-yl)propanoyl]piperidin-3-yl}carbonyl)amino]propanoic acid: 29.0 min). The collected fraction was diluted with 20 mL water and given on a preconditioned Sep-Pak™ Plus C18 cartridge (preconditioned with 5 ml EtOH and 10 mL). The cartridge was washed with 5 mL water and then the activity was eluted with 2.0 mL of EtOH. After complete evaporation of the EtOH under a stream of nitrogen at 90° C. the final tracer was taken up in water (100 µL) to get 34 MBq (3S)-3-(3-{2-[2-(2-[$^{18}$F]fluoroethoxy)ethoxy]ethoxy}phenyl)-3-[({(3R)-1-[3-(piperidin-4-yl)propanoyl]piperidin-3-yl}carbonyl)amino]propanoic acid (radiochemical yield: 4.5% d.c.; synthesis time: 172 min). The radiochemical purity was >99%. The F-18 labeled product was confirmed by co-injection with the F-19 cold standard (example 4) on an analytical HPLC (column: ACE, C18 RP, 50×4.6 mm, 3 µ, 2 ml/min (Agilent), solvent A: H2O+0.1% TFA, solvent B: MeCN+0.1% TFA, isocratic 20% B in 7 min).

Reference Compound (3S)-3-[({(3R)-1-[3-(Piperidin-4-yl)propanoyl]piperidin-3-yl}carbonyl)amino]-3-{6-[$^3$H]Pyridin-3-yl}propanoic acid

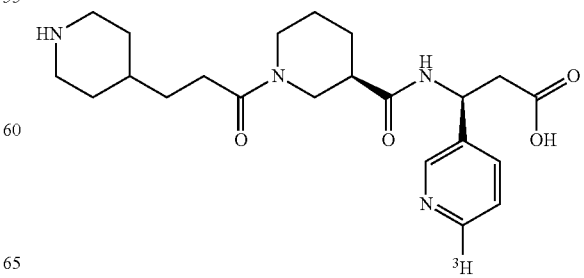

(3S)-3-(6-Bromopyridin-3-yl)-3-{[(3R)-1-(3-piperidin-4-yl-propanoyl)piperidine-3-carbonyl]amino}propanoic acid (1.85 mg, 3.73 µmol) was dissolved in a mixture of DMF (500 µL) and Et3N (25 µL). To this solution palladium on charcoal (20%) (6.45 mg) was added and the mixture was connected to a tritium manifold to tritiate over night with tritium gas. Afterwards the reaction mixture was 3 times cryostatically evaporated in the manifold. The obtained crude product was purified on a semi prep HPLC (Kromasil 100° C.8 5 µm (250×4.6 mm), eluent: 35 mM ammonia/methanol, flow: 1 mL/min). The collected fraction contained 2061 MBq (S)-3-{5-3H-pyridin-3-yl}-3-{[(R)-1-(3-piperidin-4-yl-propanoyl)-piperidin-3-carbonyl]-amino}-propanoic acid (radiochemical yield: 12.6%; radiochemical purity: 98%; specific activity: 7.81 Ci/mmol).

Example 49

Affinities of GPIIb/IIIa Antagonists Towards Human GPIIb/IIIa Receptors

Figure 1:
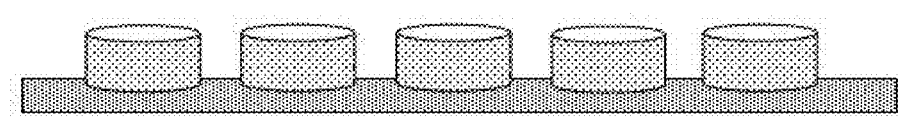
FIG. 1: Affinity assay: In the first step human GPIIb/IIIa purified from human platelets was immobilized on a 96-well solid plate. After 48 hours the plates were washed and the unspecific binding sites were blocked with Roti®-Block. 2. In the next step, the plates were simultaneously incubated with a tritium labeled known GPIIb/IIIa binder ($^3$H) mixed with increasing concentrations of the novel small molecule compounds (inhibitor, $^{19}$F). The higher the affinity of the inhibitor, the lower the bound fraction of the tritiated known GPIIb/IIIa binder ($^3$H) was. The fraction of tritiated compound ($^3$H), which is not displaced by inhibitor, was measured in a microplate scintillation counter.
Figure 1:
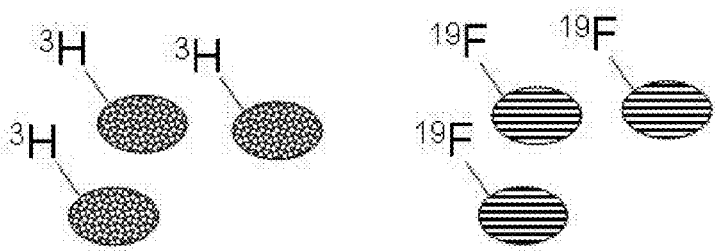
Figure 1:
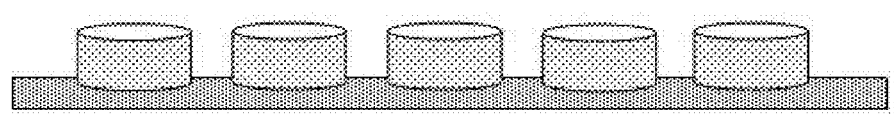
Figure 1:
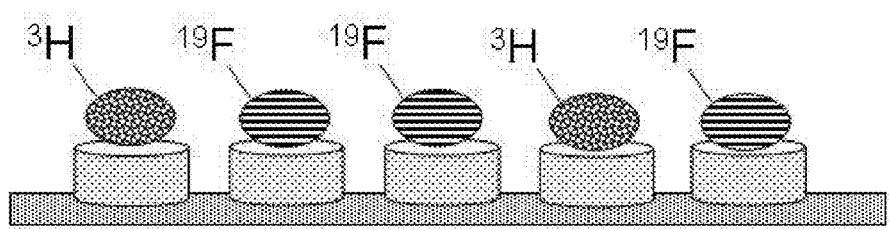

The whole procedure of the used GPIIb/IIIa assay is schematic demonstrated in FIG. 1.

Purified human glycoprotein IIb/IIIa (20 mM Tris-HCl, 0.1 M NaCl, 0.1% Triton X-100, 1 mM $CaCl_2$, 0.05% $NaN_3$, 50% Glycerol, pH 7.4) was purchased from Enzyme Research Laboratories Inc. (South Bend, Ind.). The GPIIb/IIIa receptor was diluted in phosphate-buffered saline (Dulbecco's Phosphate Buffered Saline (D-PBS (+)) with calcium and magnesium, GIBCO®, Invitrogen) with 0.01% bovine serum albumin (albumin from bovine serum-lyophilized powder, >96%, Sigma).

The GPIIb/IIIa receptor was immobilized 48 hours at least (100 µL per well, 48 to maximum 96 hours) on a 96-well solid plate (Immuno Plate MaxiSorp™, Nunc, Roskilde, Denmark) at 277 K to 280 K and at a concentration of 0.1 µg per well to 1 µg per well. As negative control one row of the plate (n=8) was incubated just with 2% bovine serum albumin (200 µL per well, albumin from bovine serum-lyophilized powder, >96%, Sigma, diluted in D-PBS (+)).

After washing three times with the wash buffer (230 µL per well, Dulbecco's Phosphate Buffered Saline (D-PBS (−)) contains no calcium or magnesium, GIBCO®, Invitrogen) residual exposed plastic and unspecific binding sites were blocked by incubating the plate with a special blocking solution (200 µL per well, Roti®-Block, Carl Roth GmbH Co KG, Karlsruhe) containing 2% bovine serum albumin (Albumin from bovine serum-lyophilized powder, >96%, Sigma) 1 hour at room temperature.

After washing three times with the wash buffer 50 µL of tritiated reference compound (60 nM, $^3$H-labeled compound) and 50 µL of novel compound (inhibitor, $^{19}$F) were simultaneously added to each well and incubated for 1 hour at room temperature. Several concentrations of each novel inhibitor (0.1, 1, 2, 5, 10, 20 50, 100, 200, 500, 1000, 2000, 5000, 10000 and 20000 nM) were investigated. At each concentration of inhibitor a fourfold determination was performed. The results for the examined inhibitors are summarized in table 1.

The maximum value of tritiated reference compound was determined without addition of inhibitor (n=8). To exclude unspecific binding of $^3$H— reference compound wells without glycoprotein receptors were used as negative controls (n=12, identically treated just without GPIIb/IIIa receptors).

After one hour the plate was washed three times with phosphate-buffered saline (200 µL per well, Dulbecco's Phosphate Buffered Saline (D-PBS (+)), GIBCO®, Invitrogen). Following 140 µL of liquid scintillation cocktail (MicroScint™ 40 aqueous, Perkin Elmer) was added to each well. After 15 min at room temperature the plates were measured at the microplate scintillation counter (TopCount NXT v2.13, Perkin Elmer, Packard Instrument Company).

FIG. 1 shows a schematic diagram of GPIIb/IIIa assay. In the first step human glycoprotein IIb/IIIa, which is purified from human platelets, was immobilized on a 96-well solid plate. After 48 hours at least the plates were washed and the unspecific binding sites were blocked with Roti®-Block. In the next step, the plates were simultaneously incubated with a tritium labeled reference compound and the novel small molecule compound (inhibitor). The higher the affinity of the inhibitor, the smaller is the bound fraction of reference compound. The fraction of tritiated reference compound, which is not displaced by inhibitor, was measured at a microplate scintillation counter.

The results are summarized in table 1.

TABLE 1

Binding affinity of compounds towards human GPIIb/IIIa receptor.

| Example | $IC_{50}$ human [nM] |
| --- | --- |
| 1 | 101 |
| 2 | 29 |
| 3 | 20 |
| 4 | 84 |
| 5 | 16 |
| 6 | 16 |
| 7 | 11 |
| 8 | 14 |
| 9 | 21 |
| 10 | 15 |
| 11 | 14 |
| 12 | 8 |
| 13 | 7 |
| 14 | 15 |
| 15 | 5 |
| 16 | 6 |
| 17 | 35 |
| 18 | 3 |
| 19 | 3 |
| 20 | 7 |

The higher the affinity of the inhibitor, the smaller is the bound fraction of tritium-labeled reference compound. By means of this assay the active diastereomers identified and the affinities (IC50 values) could be determined. The studies described above indicate that compounds of formula I are useful as contrast agents for the imaging of thrombi. The good correlation between IC50-values and the actual thrombus accumulation are described in Example 50.

Example 50

Ex Vivo Characterization
Binding to Human Thrombi:

The binding of compounds to thrombi was further investigated in an ex vivo blood flow model similar to that described in "Wakhloo, A. K. et al. Thrombus and stroke 2008, in vitro models 57-66" but modified with regard to thrombus development. Briefly, an open handmade tube-set consisting of tygon-tubes (Tygon R-1000, part No AAU00007: I.D. 3.2 mm, O.D. 6.4 mm, Saint Gobain Performance Plastics North America), intermediate tubes (Intrafix® Infusion set, B. Braun, Melsungen, Germany) an open reservoir (10 mL Combitip, Eppendorf) and a chamber made of a piece of polyethylene-Tube, (INTRAMEDIC Polyethylene Tubing, Clay Adams, PE160, length: 6.5 cm)

containing a loop of a roughened thread (fishing line: Okuma UltraMax whitefish, diameter: 0.14 mm, length: 5 cm; sandpaper: CAMI Grit designation: 600, CP918a, VSM) was used for thrombus formation. The connection between the intermediate tube and the thrombus chamber was made by trimmed tips (epTIPS, 200 μL, Eppendorff, Hamburg/Germany). The Reservoir and the thrombus chamber were fixed by clamps and stands. A peristaltic-pump (Minipuls 3, Gilson, Middelton/USA) was used to pump the blood around thereby adjusting the flow in the middle of the thrombus chamber to 70-90 cm per second, which was monitored by ultrasound Doppler measurement (Vevo 770 High-Resolution In Vivo Micro-Imaging System, Visual-Sonics, Toronto/Ontario, Canada; Scanhead: RMV 704, 40 MHz). The volume of the entire tube-set was 7.5 or 15 mL.

For each experiment fresh blood was taken from a volunteer using 10 mL citrate-tubes (Sarstedt S-Monovette 02.1067.001, 10 mL, Citrate 3.13%) and immediately laid into the turning-device of an incubator at a temperature of 37° C. (Heraeus miniTherm CTT with integrated rotation- and turning device, turning speed: 19 rotations per minute, Heraeus Instruments GmbH, Hanau/Germany). As needed, two tubes were taken out of the turning-device and 15 mL were transferred to a 20 mL Syringe (Omnifix®, B. Braun, Melsungen/Germany) and gently mixed with 0.75 mL $CaCl_2$—Solution before the peristaltic pump was started and the whole content of the syringe was transferred into the reservoir of the tube-set via a cell strainer (BD Falcon™ cell strain, 40 μm, BD, Franklin Lakes, N.J. USA). After 7 minutes 1 MBq or 0.5 MBq (15 mL or 7.5 mL) of the compound was added to the reservoir by means of a pipette, thereby mixing the content gently with the tip of the pipette. The blood was left circulating for another 3 minutes. Then, the pump was stopped, aliquots were taken from the blood and the thrombus together with the roughened thread was removed from the thrombus-chamber before both was weighted and measured in a gamma counter (Automatic Gamma Counter Wizard[2] 3, Perkin Elmer). Then the thrombus together with the thread was incubated in Plasmin-solution (Plasmin from Human Plasma, Sigma Aldrich, stock-solution: 500 μg in 500 μL 150 μM Tris-buffer (pH 7.8), 20 μL stock-solution to 230 μL saline solution 0.9%) for 48 hours to separate the platelets from the thread and to determine the netto weight of the thrombus. Finally the activity of the compound in blood and thrombus as well as the ratio between both was determined (cpm/weight [mg]). The results for the investigated compounds are summarized in table 2.

TABLE 2

In vitro clot-to-blood ratios and corresponding $IC_{50}$-values

| Example # $^{18}$F-compound | in vitro clot-to-blood ratio* | Example # corresponding $^{19}$F-compound | $IC_{50}$ human [nM] |
|---|---|---|---|
| 38 | 19 ± 1 (n = 9) | 1 | 101 |
| 39 | 34 ± 4 (n = 4) | 2 | 29 |
| 40 | 71 ± 4 (n = 3) | 3 | 20 |
| 41 | 83 ± 14 (n = 6) | 7 | 11 |
| 42 | 58 ± 10 (n = 6) | 9 | 21 |
| 46 | 191 ± 30 (n = 4) | 18 | 3 |
| 47 | 178 ± 48 (n = 4) | 19 | 3 |

*Ratio of in vitro clot-to-blood ± standard error of the mean (SEM) 3 minutes post-injection of $^{18}$F-labeled compound in the described in vitro thrombus model.

To verify the specificity of the compound, a competition experiment was conducted in which the cold compound was added to the reservoir together with the hot compound. The final plasma concentration of the cold compound was 2.8 μM. The results are summarized in the table 3.

TABLE 3

Competition experiments

| Example # | Accumulation Thrombus [$10^3$ cpm/mg]* | Thrombus competition [$10^3$ cpm/mg]* |
|---|---|---|
| 38 | 41 ± 3 (n = 5) | 10 ± 1 (n = 5) |
| 39 | 86 ± 9 (n = 6) | 12 ± 1 (n = 6) |
| 40 | 202 ± 11 (n = 3) | 8 ± 1 (n = 3) |
| 41 | 44 ± 7 (n = 6) | 5 ± 1 (n = 5) |
| 42 | 39 ± 5 (n = 6) | 5 ± 1 (n = 6) |
| 46 | 285 ± 76 (n = 4) | 17 ± 1 (n = 4) |
| 47 | 258 ± 59 (n = 4) | 14 ± 2 (n = 3) |

*Values ± standard error of the mean (SEM) 3 minutes post-injection of $^{18}$F-labeled compound in the described in vitro thrombus model.

The competition experiments showed that the accumulation of the tracer can be displaced by addition of the cold compound and verify that the binding is specific.

Figure 2:
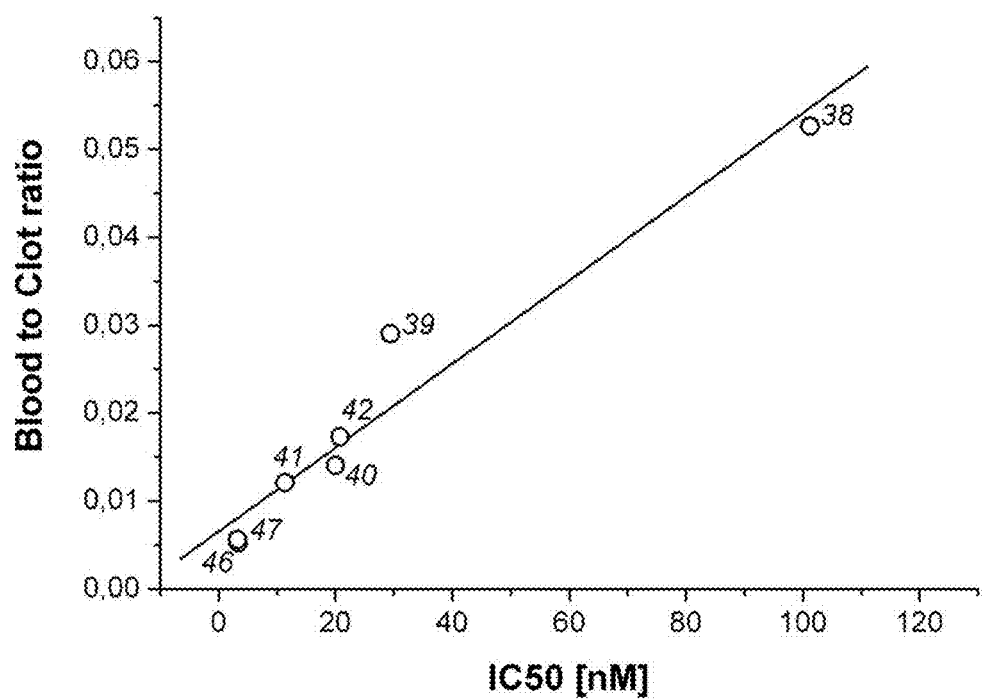
FIG. 2: The diagram shows the blood-to-clot ratio versus IC50 values of the investigated compounds. Each point is marked with the accompanying example number. The blood-to-clot ratios decrease with increasing affinity.

The strong specific binding of the compounds to thrombi shown in table 2 and 3 (in vitro clot-to-blood ratio) correlates well to the $IC_{50}$-values determined before (FIG. 2 and Example 49). The accumulation of compounds within thrombi or the clot-to-blood ratios grows with increasing affinity.

Example 51

Plasma Protein Binding

The determination of the plasma protein binding of compounds was performed by means of an equilibrium dialysis in a 96-well HT plate. Solutions of test compound (0.3 μM and 3 μM) were prepared in buffer (50 mM phosphate buffer) and 10% plasma. A 96 well HT dialysis plate (Teflon) was assembled so that each well was divided in two compartments by a semi-permeable cellulose membrane (regenerated Cellulose, MWCO 12-14K). The phosphate buffer solution (150 μL) was added to one side of the membrane and the plasma solution to the other side (150 μL). The compounds were added to the plasma solution side and were incubated at 37 degree. The unbound fraction of the compound could pass through the membrane and equilibrium between the two sides could be reached (6-8 h, 37° C.). Both solutions were analyzed for each compound (plasma-free and plasma-containing) by LC-MS. Both solutions for each compound were diluted with buffer or plasma to reach the same matrix (10% plasma) for analysis and were precipitated by the addition of methanol. The fraction unbound (Fu) was calculated as the quotient of the equilibrium concentrations of the compound in plasma-free and plasma-containing solution.

The results are summarized in table 4. The extent of plasma protein binding has been investigated in human and monkey. Examples showed no significant binding to plasma proteins, with a fraction unbound (Fu) greater than 10% in all investigated species.

TABLE 4

Plasma protein binding in human and monkey plasma at a concentration of 0.3 µM and 3 µM

| Example # | Species | Strain | Concentration (µM) | Fu (Mari) % |
|---|---|---|---|---|
| 1 | Human | Caucasian | 3 | 90 |
| 1 | Human | Caucasian | 0.3 | 91 |
| 1 | Monkey | Cynomolgus | 3 | 93 |
| 1 | Monkey | Cynomolgus | 0.3 | 99 |
| 3 | Human | Caucasian | 3 | 100 |
| 3 | Human | Caucasian | 0.3 | 96 |
| 3 | Monkey | Cynomolgus | 3 | 100 |
| 3 | Monkey | Cynomolgus | 0.3 | 100 |
| 7 | Human | Caucasian | 3 | 54 |
| 7 | Human | Caucasian | 0.3 | 50 |
| 7 | Monkey | Cynomolgus | 3 | 58 |
| 7 | Monkey | Cynomolgus | 0.3 | 54 |

Example 52

In Vitro Metabolic Stability in Liver Microsomes

Human liver microsomes in suspension (protein content 0.5 mg/mL) were used for metabolic stability studies. The incubation concentration was 0.3 µM. The hole incubation volume was 3.03 mL in which 2.4 mL of a microsome suspension in phosphate buffer (7.4 pH) was activated by addition of 0.6 mL of a NADPH regeneration system (cofactor mixture: 1.2 mg NADP, 3 IU Glucose-6-Phosphat Dehydrogenase, 14.6 mg Glucose-6-Phosphat und 4.9 mg MgCl2 in phosphate buffer, pH 7.4). After addition of 30 µL of test compound the assay was started. The compound was dissolved in an organic solvent and diluted with the same liver microsome medium in order to keep the organic content below the recommended concentration (dimethylsulfoxide DMSO <0.2% and methanol <1%). The suspension was incubated at 37 degree for 60 minutes under continuous stirring (Tec Control Shaker RS 485 at 300 UpM). At different time points (2, 8, 16, 30, 45 and 60 min) 250 µL aliquots were taken and mixed with cold methanol. The samples were frozen over night at −20° C. The solutions were centrifuged for 15 min at 3000 g. The clear supernatant (100 µL) was used to determine the concentration. The analysis was performed with an Agilent 1200 HPLC system with a LCMS/MS detector.

The susceptibility of investigated compounds to degradation by phase-I oxidative metabolism was investigated using liver microsomes from different species. Compound 1 and 3 revealed very high metabolic stability in human, monkey and rat (calculated $CL_{blood}$=0.0001 L/h/kg). The recovery was almost 100% for all investigated species. Extrapolation of the in vitro to in vivo clearance (Clint) suggests a very low metabolic clearance in human, mouse, rat and monkey.

TABLE 5

In vitro metabolic stability in human, monkey, rat and mouse microsomes

| Example # | Species | Strain | Sex | $CL_{blood}$ (L/h/kg) |
|---|---|---|---|---|
| 1 | Human | Caucasian | mix | 0.0001 |
| 1 | Monkey | Cynomolgus | female | 0.0001 |
| 1 | Rat | Wistar | male | 0.0001 |
| 3 | Human | Caucasian | mix | 0.0001 |
| 3 | Monkey | Cynomolgus | female | 0.0001 |
| 3 | Rat | Wistar | male | 0.0001 |
| 3 | Mouse | NMRI | female | 0.0001 |

Example 53

Pharmacokinetics in Mice

The biodistribution of the compound described in example 41 was determined in nude mice. Briefly, the mice received 185 KBq of the compound each. At different time points (1, 3, 10, 30, 120 minutes p.i., 3 mice per group) the animals were sacrificed and the organs of interest or aliquots thereof were removed, weighted and finally measured in a gamma counter (Automatic Gamma Counter Wizard$^2$ 3, Perkin Elmer).

Figure 3:
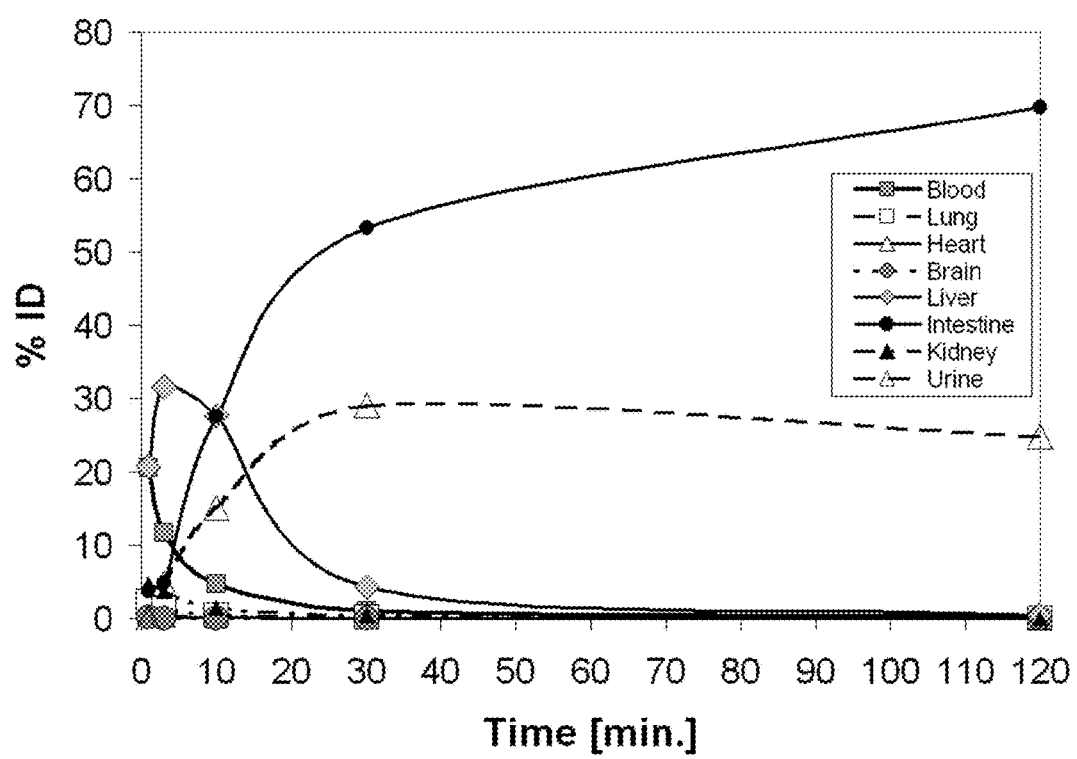
FIG. 3: Biodistribution of the compound described in example 41 in mice. The compound was rapidly eliminated from the blood and was quickly excreted over the kidney and liver. There was almost no background in the whole rest of the body after 15 minutes p. i.

The compound was rapidly eliminated from the blood and there was no enhancement in the vessel-wall. The compound was quickly excreted over the kidney and liver and there was almost no background in the whole rest of the body after 15 minutes p.i. (FIG. 3).

Example 54

Blood Clearance in a Cynomolgus Monkey

Figure 4:
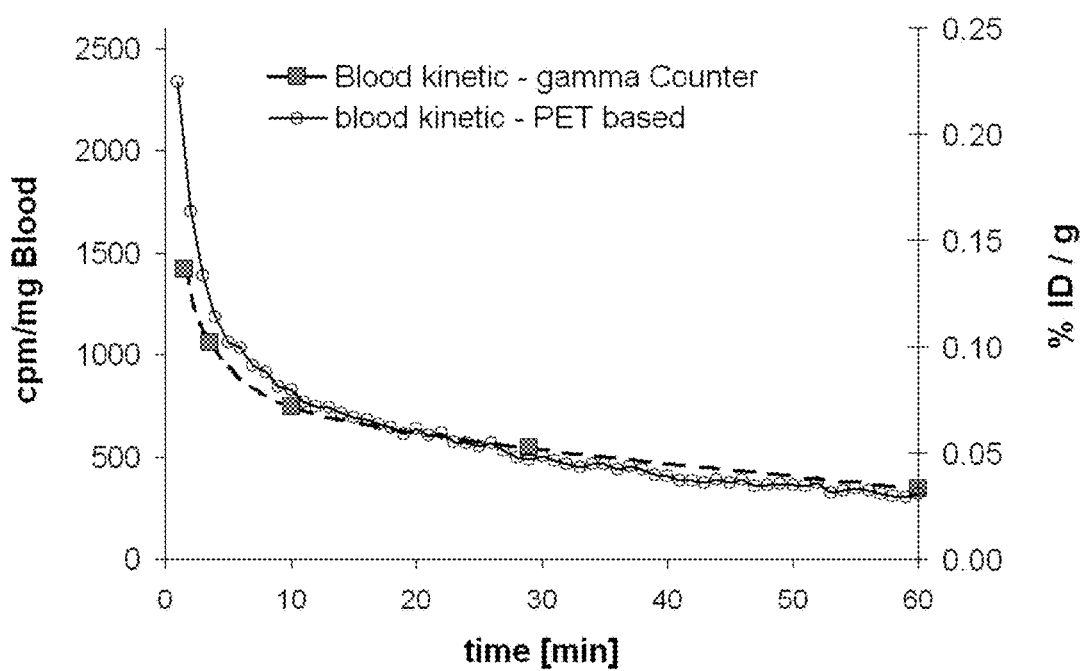
FIG. 4: Blood kinetics of the compound described in example 40 in cynomolgus monkey.

The blood clearance of the compound described in example 40 has been determined in a cynomolgus monkey. A female cynomolgus monkey was anesthetized with a mixture of Xylazin (Rompun®, Bayer HealthCare, Leverkusen, Germany), 0.12 mL/kg bodyweight and Ketamine (Ketavet®, Pfizer) 0.12 mL/kg bodyweight i.m. The monkey was placed inside the PET-scanner (Inveon PET/CT, Siemens Medical, Erlangen) and 25 MBq of the compound has been injected i.v. while PET-imaging was performed continuously from shortly before up to 60 minutes post injection. Venous blood samples were taken at 3, 10, 30 and 60 minutes p.i. and were measured in a gamma-counter (Automatic Gamma Counter Wizard$^2$ 3, Perkin Elmer). Additionally, the blood-concentration of the compound was measured from the PET-Image over the whole imaging period (FIG. 4).

It was found that the compound described in example 40 was rapidly cleared from the blood. There was only marginal signal visible in any other tissue. The brain was completely free of contrast.

This result correlates well with the results from the pharmacokinetic study in mice and underlines again the advantageous pharmacokinetic profile of the compound. Moreover, it shows that there is also no cross reaction to any other structures (e.g. integrines) at the healthy endothelium.

Example 55

Thrombus-Imaging in Cynomolgus Monkeys

The ability of the compound described in example 40 for the imaging of thrombi was investigated in a PET-study with cynomolgus monkeys (female, 2.8-3.2 kg).

Monkey 1:

The first monkey was anesthetized with a mixture of Xylazin (Rompun®, Bayer HealthCare, Leverkusen, Germany), 0.12 mL/Kg and Ketamine (Ketavet®, Pfizer) 0.12 mL/Kg b.w. i.m. and additionally analgesized by an i.m. injection of 6 µg Buprenorphine per kg. While the investigation, small amounts of Ketamine have been injected i.m. if required. The left common carotid artery was exposed surgically and a polyethylene-tube (INTRAMEDIC Polyethylene Tubing, Clay Adams, PE50), which was roughened previously by sandpaper (600—CAMI Grit designation), was inserted into the vessel, advanced into the descending aorta and was left there for 30 minutes to allow for the development of a thrombus on the rough surface of the tube. Meanwhile, the monkey was placed inside the PET-scanner (Inveon PET/CT, Siemens Medical, Erlangen). Then the monkey received 25 MBq of the compound i.v. and a PET-scan was taken from shortly before up to 60 minutes post injection. The image revealed a bright signal inside the descending aorta alongside the roughened part of the tube (FIG. 5), while there was only sparse signal in any tissue around the tube. Surprisingly there was only a very thin layer of thrombus covering the rough part of the tube visible after removal of the roughened tube from the animal. The thickness of this layer was far below 1 mm (see also removed thrombus of Monkey 2, FIG. 7) and therewith also far below the resolution of the image, which is approximately 1 mm. This also means, that even slightest thrombi, even if their size is far less than the resolution of the imaging-device, can be visualized due to the massive accumulation of compound on the platelets of the thrombi.

At the end of the experiment the tube was removed carefully from the vessel before it was weighted and measured in a gamma counter (Automatic Gamma Counter Wizard$^2$ 3, Perkin Elmer). Then the thrombus together with the tube was incubated in Plasmin-solution (Plasmin from Human Plasma, Sigma Aldrich, Plasmin-stock-solution: 500 μg Plasmin in 500 μL Tris-buffer (150 μM, pH 7.8), 20 μL Plasmin-stock-solution to 230 μL saline solution 0.9%) for 48 hours to separate the platelets from the tube and to determine the netto weight of the thrombus. Finally the activity of the compound in blood and thrombus as well as the ratio between the two was determined (cpm/weight [mg]).

Monkey 2:

The experiment was repeated with the same compound in another monkey with a slightly different preparation of the thrombogenic tube: This tube was roughened at only two short sections with a gap in between. Apart from that, the experimental design including the determination of the in vivo clot-to-blood ratio was as described above for monkey 1.

Unlike the thrombus of the first monkey now found two separate strong signals showed up in the PET image with a gap in between (FIG. 6). After removing the thrombogenic tube from the vessel, two separate thrombi could be found at the roughened parts of the tube (FIG. 7) proving that the signals were solely deriving from thrombus and not from the tube alone. As already known from monkey 1, these two thrombi were also extremely thin (FIG. 7).

Monkey 3, Dose Reduction & Venous Thrombus

The experiment was repeated with the same compound in another monkey, but with the reduced dose of 15 MBq for the whole animal. In addition to the arterial catheter, this animal also received a venous catheter, also made of PE50-catheter-tube and roughened at some parts with gaps in between as described above. This catheter was inserted into the left femoral vein and advanced into the upper caval vein. Both catheters were left in the vessels for 30 minutes before the compound was injected intravenously. PET imaging was performed from shortly before to 60 minutes after injection.

As in the other monkeys, all arterial and venous thrombi showed a bright signal in the image (FIG. 8). As before, most of the signal was vanished from the blood and other tissues around the thrombi within some minutes.

Clot-to-Blood Ratio In Vivo:

The in vivo clot-to-blood ratio was determined from 5 thrombi out of the above described monkey experiments. As already mentioned above the thrombi had been removed from the vessels after imaging and had been weighted and measured in a gamma-counter (Automatic Gamma Counter Wizard$^2$ 3, Perkin Elmer) together with blood samples taken from the animal. After incubation of the thrombi in Plasmin (Plasmin from Human Plasma, Sigma Aldrich, Plasmin-stock-solution: 500 μg Plasmin in 500 μL Tris-buffer (150 μM, pH 7.8), 20 μL Plasmin-stock-solution to 230 μL saline solution 0.9%) and removal of the thrombi from the catheter tubes, the netto weight of the thrombi was calculated and the concentration of the compound in thrombus (clot) and blood, as well as the ratio between the two was calculated. The in vivo clot-to-blood ratio was surprisingly high (126+/−52, Table 6) and significantly above the ratio described in the closest prior art (US 2007/0189970 A1).

TABLE 6

Clot-to-blood ratios in vivo (Cynomolgus monkey)

| Clot [cpm/mg] | Blood [cpm/mg] | Clot/Blood |
|---|---|---|
| 25578 | 130 | 196 |
| 7204 | 100 | 72 |
| 9545 | 100 | 96 |
| 9011 | 90 | 100 |
| 14801 | 90 | 164 |
|  | mean | 126 |
|  | sd | 52 |

Table 6 shows the compound concentration in thrombus (clot) and blood and the resulting in vivo clot-to-blood ratio determined from 5 thrombi out of the monkey imaging experiments described above. It was found to be surprisingly high, and significantly higher than showed in the closest prior art (US 2007/0189970 A1)

CONCLUSION

The compound described in example 40 shows surprisingly high accumulation even in slightest venous and arterial thrombi in monkeys. There was almost no background in any surrounding tissue or organ in any of the investigated monkeys. The compound almost completely remains within the thrombus over a long time (60 minutes were shown). In contrast to the closest prior art (US 2007/0189970 A1) the dose given in the here described experiments was almost 50-fold lower and the in vivo clot-to-blood ratio was significantly higher at the same time.

The invention claimed is:
1. Compounds of Formula I:

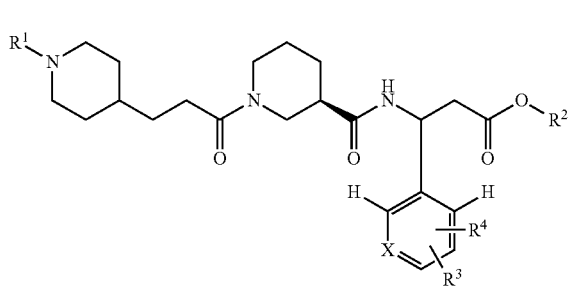

wherein
R$^1$ is hydrogen or an amine-protecting group;
R$^2$ is hydrogen or a carboxyl-protecting group;
wherein at least one of R$^1$ and R$^2$ is not H;
R$^3$ is selected from the group consisting of H, F, CF$_3$, COR$^9$, COOR$^{10}$, SOR$^{10}$, SO$_2$R$^{10}$, CN and NO$_2$;

$R^4$ is selected from the group consisting of OH, Halogen, —$NO_2$, —$N^+(Me)_3(W^-)$, —$I^+R^{11}(W^-)$—$O(CH_2)_n$-LG, —$(OCH_2CH_2)_m$-LG, Q, —$OCH_2$-Q; —$CH_2$—$CH_2$-Q, —CH=CH-Q and —C≡C-Q;

X is selected from CH or N;

LG is a leaving group;

$R^9$ is hydrogen or ($C_1$-$C_6$)alkyl;

$R^{10}$ is ($C_1$-$C_6$)alkyl;

$R^{11}$ is selected from the group consisting of phenyl, (4-methyl)phenyl, (4-methoxy)phenyl, 2-furanyl and 2-thienyl;

$W^-$ is selected from the group comprising $CF_3(S(O)_2O^-$, iodide anion, bromide anion and $CF_3C(O)O^-$;

Q is a group

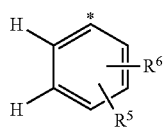

wherein * indicates the atom of connection of Q;

$R^5$ is selected from the group consisting of H, $CF_3$, $COR^9$, $COOR^{10}$, $SOR^{10}$, $SO_2R^{10}$, CN and $NO_2$;

$R^6$ is selected from the group consisting of OH, Halogen, —$NO_2$, —$N^+(Me)_3(W^-)$, —$I^+R^{11}(W^{31})$, —$O(CH_2)_n$-LG and —$(OCH_2CH_2)_m$-LG;

n is 1-3;

and m is 2-3;

with the proviso that if $R^4$ has the meaning of Halogen, —$NO_2$, —$N^+(Me)_3(W^-)$ or —$I^+R^{11}(W^-)$, $R^3$ has the meaning of $CF_3$, $COR^9$, $COOR^{10}$, $SOR^{10}$, $SO_2R^{10}$, CN or $NO_2$ and with the proviso that if $R^6$ has the meaning of Halogen, —$NO_2$, —$N^+(Me)_3(W^-)$ or —$I^+R^{11}(W^-)$, $R^5$ has the meaning of $CF_3$, $COR^9$, $COOR^{10}$, $SOR^{10}$, $SO_2R^{10}$, CN or $NO_2$;

including E and Z-isomers and diastereomers, mixtures thereof, and any pharmaceutically acceptable salt or complex thereof.

2. Compounds according to claim 1, wherein $R^1$ is hydrogen or an amine-protecting group;

$R^2$ is hydrogen or a carboxyl-protecting group;

wherein at least one of $R^1$ and $R^2$ is not H;

$R^3$ is H, F, $CF_3$, CN or $NO_2$;

$R^4$ is OH, Halogen, —$N^+(Me)_3(W^-)$, —$O(CH_2)_n$-LG, —$(OCH_2CH_2)_m$-LG, Q, —$OCH_2$-Q; —$CH_2$—$CH_2$-Q, —CH=CH-Q or —C≡C-Q;

X is CH or N;

LG is a leaving group;

$W^-$ is $CF_3(S(O)_2O^-$, a bromide anion or $CF_3C(O)O^-$;

Q is a group

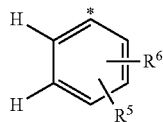

wherein * indicates the atom of connection of Q;

$R^5$ is H, $CF_3$, CN or $NO_2$;

$R^6$ is OH, Halogen, —$N^+(Me)_3(W^-)$, —$O(CH_2)_n$-LG or —$(OCH_2CH_2)_m$-LG;

n is 1-3;

and m is 2-3;

with the proviso that if $R^4$ has the meaning of Halogen or —$N^+(Me)_3(W^-)$, $R^3$ has the meaning of $CF_3$, CN or $NO_2$ and with the proviso that if $R^6$ has the meaning of Halogen or —$N^+(Me)_3(W^-)$, $R^5$ has the meaning of $CF_3$, CN or $NO_2$;

including E and Z-isomers and diastereomers and mixtures thereof.

3. Compounds according to claim 1, wherein $R^1$ is hydrogen or an amine-protecting group selected from the group consisting of tert-butyloxycarbonyl (BOC), carbobenzyloxy (Cbz) and 9-fluorenylmethyl-oxycarbonyl (FMOC);

$R^2$ is hydrogen or a carboxyl-protecting group selected from the group consisting of methyl, ethyl, propyl, tert-butyl, benzyl and p-methoxybenzyl;

wherein at least one of $R^1$ and $R^2$ is not H;

$R^3$ is H, F, $CF_3$, CN or $NO_2$;

$R^4$ is OH, Halogen, —$N^+(Me)_3(W^-)$, —$O(CH_2)_n$-LG, —$(OCH_2CH_2)_m$-LG, Q, —$OCH_2$-Q; —$CH_2$—$CH_2$-Q, —CH=CH-Q or —C≡C-Q;

X is CH or N;

LG is a leaving group selected from the group comprising methylsulfonyloxy and (4-methylphenyl) sulfonyloxy;

$W^-$ is $CF_3(S(O)_2O^-$, a bromide anion or $CF_3C(O)O^-$;

Q is a group

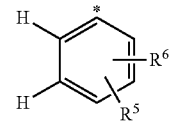

wherein * indicates the atom of connection of Q;

$R^5$ is H, $CF_3$, CN or $NO_2$;

$R^6$ is OH, Halogen, —$N^+(Me)_3(W^-)$, —$O(CH_2)_n$-LG or —$(OCH_2CH_2)_m$-LG;

n is 1-3;

and m is 2-3;

with the proviso that if $R^4$ has the meaning of Halogen or —$N^+(Me)_3(W^-)$, $R^3$ has the meaning of $CF_3$, CN or $NO_2$ and with the proviso that if $R^6$ has the meaning of Halogen or —$N^+(Me)_3(W^-)$, $R^5$ has the meaning of $CF_3$, CN or $NO_2$;

including E and Z-isomers and diastereomers and mixtures thereof.

4. Compounds according to claim 1, wherein $R^1$ is tert-butyloxycarbonyl (BOC);

$R^2$ is methyl or tert-butyl;

wherein at least one of $R^1$ and $R^2$ is not H;

$R^3$ is H;

$R^4$ is —$O(CH_2)_n$-LG;

X is N;

LG is methylsulfonyloxy or (4-methylphenyl)sulfonyloxy;

$W^-$ is $CF_3(S(O)_2O^-$, a bromide anion or $CF_3C(O)O^-$;

Q is a group

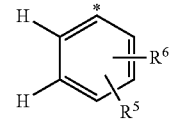

wherein * indicates the atom of connection of Q;
R⁵ is H, CF₃, CN or NO₂;
R⁶ is OH, Halogen, —N⁺(Me)₃(W⁻), —O(CH₂)ₙ-LG or —(OCH₂CH₂)ₘ-LG;
n is 1-3;
and m is 2-3;
with the proviso that if R⁶ has the meaning of Halogen or —N⁺(Me)₃(W⁻), R⁵ has the meaning of CF₃, CN or NO₂;
including E and Z-isomers and diastereomers and mixtures thereof.

5. Compounds of Formula I according to claim 1, selected from:

tert-butyl 4-{3-[(3R)-3-({(1S)-3-methoxy-1-[3-(2-{[(4-methylphenyl)sulfonyl]oxy}ethoxy)-phenyl]-3-oxopropyl}carbamoyl)piperidin-1-yl]-3-oxopropyl}piperidine-1-carboxylate, tert-butyl 4-{3-[(3R)-3-({3-methoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate, tert-butyl 4-{3-[(3R)-3-({(1S)-3-tert-butoxy-1-[4-(2-{[(4-methylphenyl)sulfonyl]oxy}ethoxy)phenyl]-3-oxopropyl}carbamoyl)piperidin-1-yl]-3-oxopropyl}piperidine-1-carboxylate, tert-butyl 4-{3-[(3R)-3-({(1S)-3-methoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylat, tert-butyl 4-{3-[(3R)-3-({(1S)-3-tert-butoxy-1-[5-(2-{[(4-methylphenyl)sulfonyl]oxy}ethoxy)pyridin-3-yl]-3-oxopropyl}carbamoyl)piperidin-1-yl]-3-oxopropyl}piperidine-1-carboxylate, tert-butyl 4-{3-[(3R)-3-{[3-methoxy-1-{5-[4-(2-{[(4-methylphenyl)sulfonyl]oxy}ethoxy)-phenyl]pyridin-3-yl}-3-oxopropyl]carbamoyl}piperidin-1-yl]-3-oxopropyl}piperidine-1-carboxylate, tert-butyl 4-{3-[(3R)-3-{[(1S)-3-tert-butoxy-1-{5-[4-(2-{[(4-methylphenyl)sulfonyl]oxy}-ethoxy)phenyl]pyridin-3-yl}-3-oxopropyl]carbamoyl}piperidin-1-yl]-3-oxopropyl}piperidine-1-carboxylate;

tert-butyl 4-{3-[(3R)-3-({1-[5-(4-chloro-3-cyanophenyl)pyridin-3-yl]-3-methoxy-3-oxopropyl}carbamoyl)piperidin-1-yl]-3-oxopropyl}piperidine-1-carboxylate, tert-butyl-4-{3-[(3R)-3-{[(1S)-1-{5-[(3-bromo-4-cyanobenzyl)oxy]pyridin-3-yl}-3-methoxy-3-oxopropyl]carbamoyl}piperidin-1-yl]-3-oxopropyl}piperidine-1-carboxylate, tert-butyl 4-{3-[(3R)-3-{[3-methoxy-1-{5-[3-(2-{[(4-methylphenyl)sulfonyl]oxy}ethoxy)-phenyl]pyridin-3-yl}-3-oxopropyl]carbamoyl}piperidin-1-yl]-3-oxopropyl}piperidine-1-carboxylate, tert-butyl 4-{3-[(3R)-3-{[3-methoxy-1-{5-[2-(2-{[(4-methylphenyl)sulfonyl]oxy}ethoxy)-phenyl]pyridin-3-yl}-3-oxopropyl]carbamoyl}piperidin-1-yl]-3-oxopropyl}piperidine-1-carboxylate, tert-butyl 4-{3-[(3R)-3-({1-[5-(4-chloro-3-nitrophenyl)pyridin-3-yl]-3-methoxy-3-oxopropyl}carbamoyl)piperidin-1-yl]-3-oxopropyl}piperidine-1-carboxylate, tert-butyl 4-{3-[(3R)-3-({1-[5-fluoro-4'-(2-{[(4-methylphenyl)sulfonyl]oxy}ethoxy)biphenyl-3-yl]-3-methoxy-3-oxopropyl}carbamoyl)piperidin-1-yl]-3-oxopropyl}piperidine-1-carboxylate, tert-butyl 4-{3-[(3R)-3-{[(1S)-3-tert-butoxy-1-(5-{[4-(2-{[(4-methylphenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate, tert-butyl 4-{3-[(3R)-3-{[(1S)-3-tert-butoxy-1-(5-{[3-(2-{[(4-methylphenyl)sulfonyl]oxy}ethoxy)phenyl]ethynyl}pyridin-3-yl)-3-oxopropyl]carbamoyl}piperidin-1-yl]-3-oxopropyl}piperidine-1-carboxylate, tert-butyl 4-{3-[(3R)-3-{[(1S)-3-tert-butoxy-1-(5-{2-[4-(2-{[(4-methylphenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate, tert-butyl 4-{3-[(3R)-3-{[(1S)-3-tert-butoxy-1-(5-{2-[3-(2-{[(4-methylphenyl)sulfonyl]oxy}ethoxy)phenyl]ethyl}pyridin-3-yl)-3-oxopropyl]carbamoyl}piperidin-1-yl]-3-oxopropyl}piperidine-1-carboxylate, tert-butyl 4-[3-((3R)-3-{[1-(4-hydroxyphenyl)-3-methoxy-3-oxopropyl]carbamoyl}piperidin-1-yl)-3-oxopropyl]piperidine-1-carboxylate, tert-butyl 4-{3-[(3R)-3-({(1S)-1-[3-hydroxyphenyl]-3-methoxy-3-oxopropyl}carbamoyl)-piperidin-1-yl]-3-oxopropyl}piperidine-1-carboxylate, tert-butyl 4-{3-[(3R)-3-({(1S)-1-[5-(hydroxy)pyridin-3-yl]-3-methoxy-3-oxopropyl}-carbamoyl)piperidin-1-yl]-3-oxopropyl}piperidine-1-carboxylate, tert-butyl 4-{3-[(3R)-3-({1-[5-(3-hydroxyphenyl)pyridin-3-yl]-3-methoxy-3-oxopropyl}-carbamoyl)piperidin-1-yl]-3-oxopropyl}piperidine-1-carboxylate, tert-butyl 4-{3-[(3R)-3-({1-[5-(4-hydroxyphenyl)pyridin-3-yl]-3-methoxy-3-oxopropyl}-carbamoyl)piperidin-1-yl]-3-oxopropyl}piperidine-1-carboxylate, tert-butyl 4-{3-[(3R)-3-({1-[5-(2-hydroxyphenyl)pyridin-3-yl]-3-methoxy-3-oxopropyl}-carbamoyl)piperidin-1-yl]-3-oxopropyl}piperidine-1-carboxylate, tert-butyl 4-{3-[(3R)-3-{[(1-(5-fluoro-4'-hydroxybiphenyl-3-yl)-3-methoxy-3-oxopropyl]-carbamoyl}piperidin-1-yl]-3-oxopropyl}piperidine-1-carboxylate, tert-butyl 4-{3-[(3R)-3-{[(1S)-3-tert-butoxy-1-(4-hydroxyphenyl)-3-oxopropyl]-carbamoyl}piperidin-1-yl]-3-oxopropyl}piperidine-1-carboxylate, tert-butyl 4-{3-[(3R)-3-{[(1S)-3-tert-butoxy-1-(5-hydroxypyridin-3-yl)-3-oxopropyl]-carbamoyl}piperidin-1-yl]-3-oxopropyl}piperidine-1-carboxylate, tert-butyl 4-{3-[(3R)-3-({(1S)-3-tert-butoxy-1-[5-(4-hydroxyphenyl)pyridin-3-yl]-3-oxopropyl}carbamoyl)piperidin-1-yl]-3-oxopropyl}piperidine-1-carboxylate, tert-butyl 4-(3-{(3R)-3-[(3-tert-butoxy-1-{5-[(4-hydroxyphenyl)ethynyl]pyridin-3-yl}-3-oxopropyl)carbamoyl]piperidin-1-yl}-3-oxopropyl)piperidine-1-carboxylate, tert-butyl 4-{3-[(3R)-3-{[(1S)-3-tert-butoxy-1-{5-[(3-hydroxyphenyl)ethynyl]pyridin-3-yl}-3-oxopropyl]carbamoyl}piperidin-1-yl]-3-oxopropyl}piperidine-1-carboxylate, tert-butyl 4-(3-{(3R)-3-[(3-tert-butoxy-1-{5-[2-(4-hydroxyphenyl)ethyl]pyridin-3-yl}-3-oxopropyl)carbamoyl]piperidin-1-yl}-3-oxopropyl)piperidine-1-carboxylate, and tert-butyl 4-(3-{(3R)-3-[(3-tert-butoxy-1-{5-[2-(3-hydroxyphenyl)ethyl]pyridin-3-yl}-3-oxopropyl)carbamoyl]piperidin-1-yl}-3-oxopropyl)piperidine-1-carboxylate.

6. A kit comprising a sealed vial containing a predetermined quantity of a compound selected from the compounds of Formula I according to claim 1, stereoisomers thereof and 7. Compounds of the formula I of claim 1, wherein:
$R^9$ is hydrogen or $(C_1$-$C_4)$ alkyl;
$R^{10}$ is $(C_1$-$C_4)$ alkyl; and
$R^{11}$ is selected from the group consisting of (4-methoxy) phenyl and 2-thienyl.

8. Compounds of the formula I of claim 1, wherein:
$R^9$ is hydrogen, methyl, ethyl or tert-butyl;
$R^{10}$ is methyl, ethyl or tert-butyl; and
$R^{11}$ is selected from the group consisting of (4-methoxy) phenyl and 2-thienyl.

9. Compounds of Formula II:

wherein
$R^1$ is hydrogen or an amine-protecting group;
$R^2$ is hydrogen or a carboxyl-protecting group;
wherein at least one of $R^1$ and $R^2$ is not hydrogen;
$R^3$ is selected from the group consisting of H, F, $CF_3$, $COR^9$, $COOR^{10}$, $SOR^{10}$, $SO_2R^{10}$, CN and $NO_2$;
$R^7$ is selected from the group consisting of Y, —O(CH$_2$)$_n$—Y, —(OCH$_2$CH$_2$)$_m$—Y, Z, —OCH$_2$—Z; —CH$_2$—CH$_2$—Z, —CH=CH—Z and —C≡C—Z;
X is selected from CH or N;
Y is selected from $^{18}$F or F;
$R^9$ is hydrogen or $(C_1$-$C_6)$alkyl;
$R^{10}$ is $(C_1$-$C_6)$alkyl;
Z is a group wherein * indicates the atom of connection of Z;
$R^5$ is selected from the group consisting of H, $CF_3$, $COR^9$, $COOR^{10}$, $SOR^{10}$, $SO_2R^{10}$, CN and $NO_2$;
$R^8$ is selected from the group consisting of Y, —O(CH$_2$)$_n$—Y and —(OCH$_2$CH$_2$)$_m$—Y;
n is 1-3;
and m is 2-3;
with the proviso that if $R^7$ has the meaning Y, $R^3$ has the meaning of $CF_3$, $COR^9$, $COOR^{10}$, $SOR^{10}$, $SO_2R^{10}$, CN or $NO_2$ and
with the proviso that if $R^8$ has the meaning Y, $R^5$ has the meaning of $CF_3$, $COR^9$, $COOR^{10}$, $SOR^{10}$, $SO_2R^{10}$, CN or $NO_2$;
including E and Z-isomers and diastereomers, mixtures thereof, and any pharmaceutically acceptable salt or complex thereof.

10. Compounds according to claim 9, wherein
$R^1$ is hydrogen or an amine-protecting group;
$R^2$ is hydrogen or a carboxyl-protecting group;
wherein at least one of $R^1$ and $R^2$ is not hydrogen;
$R^3$ is H, F, $CF_3$, CN or $NO_2$;
$R^7$ is Y, —O(CH$_2$)$_n$—Y, —(OCH$_2$CH$_2$)$_m$—Y, Z, —OCH$_2$—Z; —CH$_2$—CH$_2$—Z, —CH=CH—Z or —C≡C—Z;
X is CH or N;
Y is $^{18}$F or F;
Z is a group wherein * indicates the atom of connection of Z;
$R^5$ is H, $CF_3$, CN or $NO_2$;
$R^8$ is Y, —O(CH$_2$)$_n$—Y or —(OCH$_2$CH$_2$)$_m$—Y;
n is 1-3;
and m is 2-3;
with the proviso that if $R^7$ has the meaning of Y, $R^3$ has the meaning of $CF_3$, CN or $NO_2$ and
with the proviso that if $R^8$ has the meaning of Y, $R^5$ has the meaning of $CF_3$, CN or $NO_2$;
including E and Z-isomers and diastereomers and mixtures thereof.

11. Compounds according to claim 9, wherein
$R^1$ is hydrogen or an amine-protecting group selected from the group consisting of tert-butyloxycarbonyl (BOC), carbobenzyloxy (Cbz) and 9-fluorenylmethyloxycarbonyl (FMOC);
$R^2$ is hydrogen or a carboxyl-protecting group selected from the group consisting of methyl, ethyl, propyl, tert-butyl, benzyl and p-methoxybenzyl;
wherein at least one of $R^1$ and $R^2$ is not hydrogen;
$R^3$ is H, F, $CF_3$, CN or $NO_2$;
$R^7$ is Y, —O(CH$_2$)$_n$—Y, —(OCH$_2$CH$_2$)$_m$—Y, Z, —OCH$_2$—Z; —CH$_2$—CH$_2$—Z, —CH=CH—Z or —C≡C—Z;
X is N;
Y is $^{18}$F or F;
Z is a group wherein * indicates the atom of connection of Z;
$R^5$ is H, $CF_3$, CN or $NO_2$;
$R^8$ is Y, —O(CH$_2$)$_n$—Y or —(OCH$_2$CH$_2$)$_m$—Y;
n is 1-3;
and m is 2-3;
with the proviso that if $R^7$ has the meaning of Y, $R^3$ has the meaning of $CF_3$, CN or $NO_2$ and
with the proviso that if $R^8$ has the meaning of Y, $R^5$ has the meaning of $CF_3$, CN or $NO_2$;
including E and Z-isomers and diastereomers and mixtures thereof.

12. Compounds according to claim 9, wherein
R¹ is tert-butyloxycarbonyl (BOC);
R² is methyl or tert-butyl;
R³ is H;
R⁷ is —O(CH₂)ₙ—Y;
X is N;
Y is ¹⁸F or F;
Z is a group

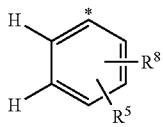

wherein * indicates the atom of connection of Z;
R⁵ is H, CF₃, CN or NO₂;
R⁸ is Y, —O(CH₂)ₙ—Y or —(OCH₂CH₂)ₘ—Y;
n is 1-3;
and m is 2-3;
with the proviso that if R⁸ has the meaning of Y, R⁵ has the meaning of CF₃, CN or NO₂;
including E and Z-isomers and diastereomers and mixtures thereof.

13. Compounds of Formula II according to claim 9, selected from:

3-({[(3R)-1-{3-[1-(tert-butoxycarbonyl)piperidin-4-yl]propanoyl}piperidin-3-yl]carbonyl}amino)-3-[3-(2-fluoroethoxy)phenyl]propanoic acid, 3-({[(3R)-1-{3-[1-(tert-butoxycarbonyl)piperidin-4-yl]propanoyl}piperidin-3-yl]carbonyl}amino)-3-[4-(2-fluoroethoxy)phenyl]propanoic acid, tert-butyl 4-{3-[(3R)-3-({(1S)-3-tert-butoxy-1-[5-(2-fluoroethoxy)pyridin-3-yl]-3-oxopropyl}carbamoyl)piperidin-1-yl]-3-oxopropyl}piperidine-1-carboxylate, tert-butyl-4-{3-[(3R)-3-{[(1S)-1-(3-{2-[2-(2-fluoroethoxy)ethoxy]ethoxy}phenyl)-3-methoxy-3-oxopropyl]carbamoyl}piperidin-1-yl]-3-oxopropyl}piperidine-1-carboxylate, tert-butyl-4-{3-[(3R)-3-{[(1S)-1-(5-{2-[2-(2-fluoroethoxy)ethoxy]ethoxy}pyridin-3-yl)-3-methoxy-3-oxopropyl]carbamoyl}piperidin-1-yl]-3-oxopropyl}piperidine-1-carboxylate, tert-butyl 4-{3-[(3R)-3-{[1-{5-[3-(2-fluoroethoxy)phenyl]pyridin-3-yl}-3-methoxy-3-oxopropyl]carbamoyl}piperidin-1-yl]-3-oxopropyl}piperidine-1-carboxylate, 3-({[(3R)-1-{3-[1-(tert-butoxycarbonyl)piperidin-4-yl]propanoyl}piperidin-3-yl]carbonyl}amino)-3-{5-[3-(2-fluoroethoxy)phenyl]pyridin-3-yl}propanoic acid, tert-butyl 4-(3-{(3R)-3-[(1-{5-[4-(2-fluoroethoxy)phenyl]pyridin-3-yl}-3-methoxy-3-oxopropyl)carbamoyl]piperidin-1-yl}-3-oxopropyl)piperidine-1-carboxylate, 3-({[(3R)-1-{3-[1-(tert-butoxycarbonyl)piperidin-4-yl]propanoyl}piperidin-3-yl]carbonyl}amino)-3-{5-[4-(2-fluoroethoxy)phenyl]pyridin-3-yl}propanoic acid, tert-butyl 4-(3-{(3R)-3-[(1-{5-[2-(2-fluoroethoxy)phenyl]pyridin-3yl}-3-methoxy-3-oxopropyl)carbamoyl]piperidin-1-yl}-3-oxopropyl)piperidine-1-carboxylate, 3-({[(3R)-1-{3-[1-(tert-butoxycarbonyl)piperidin-4-yl]propanoyl}piperidin-3-yl]-carbonyl}amino)-3-{5-[2-(2-fluoroethoxy)phenyl]pyridin-3-yl}propanoic acid, tert-butyl 4-{3-[(3R)-3-({1-[5-(3-cyano-4-fluorophenyl)pyridin-3-yl]-3-methoxy-3-oxopropyl}carbamoyl)piperidin-1-yl]-3-oxopropyl}piperidine-1-carboxylate, 3-({[(3R)-1-{3-[1-(tert-butoxycarbonyl)piperidin-4-yl]propanoyl}piperidin-3-yl]carbonyl}amino)-3-[5-(3-cyano-4-fluorophenyl)pyridin-3-yl]propanoic acid, tert-butyl 4-{3-[(3R)-3-({1-[5-(4-cyano-3-fluorophenyl)pyridin-3-yl]-3-methoxy-3-oxopropyl}carbamoyl)piperidin-1-yl]-3-oxopropyl}piperidine-1-carboxylate, 3-({[(3R)-1-{3-[1-(tert-butoxycarbonyl)piperidin-4-yl]propanoyl}piperidin-3-yl]carbonyl}amino)-3-[5-(4-cyano-3-fluorophenyl)pyridin-3-yl]propanoic acid, tert-butyl 4-{3-[(3R)-3-({1-[5-(4-fluoro-3-nitrophenyl)pyridin-3-yl]-3-methoxy-3-oxopropyl}carbamoyl)piperidin-1-yl]-3-oxopropyl}piperidine-1-carboxylate, 3-({[(3R)-1-{3-[1-(tert-butoxycarbonyl)piperidin-4-yl]propanoyl}piperidin-3-yl]carbonyl}amino)-3-[5-(4-fluoro-3-nitrophenyl)pyridin-3-yl]propanoic acid, tert-butyl 4-{3-[(3R)-3-{[(1S)-1-{5-[(3-cyano-4-fluorobenzyl)oxy]pyridin-3-yl}-3-methoxy-3-oxopropyl]carbamoyl}piperidin-1-yl]-3-oxopropyl}piperidine-1-carboxylate, tert-butyl 4-{3-[(3R)-3-{[(1S)-1-{5-[(4-cyano-3-fluorobenzyl)oxy]pyridin-3-yl}-3-methoxy-3-oxopropyl]carbamoyl}piperidin-1-yl]-3-oxopropyl}piperidine-1-carboxylate, tert-butyl 4-{3-[(3R)-3-{[(1S)-3-tert-butoxy-1-(5-{[4-(2-fluoroethoxy)phenyl]ethynyl}-pyridine-3-yl)-3-oxopropyl]carbamoyl}piperidin-1-yl]-3-oxopropyl}piperidine-1-carboxylate, tert-butyl 4-{3-[(3R)-3-{[(1S)-3-tert-butoxy-1-(5-{[3-(2-fluoroethoxy)phenyl]ethynyl}pyridin-3-yl)-3-oxopropyl]carbamoyl}piperidin-1-yl]-3-oxopropyl}piperidine-1-carboxylate, tert-butyl 4-{3-[(3R)-3-({1-[5-fluoro-4'-(2-fluoroethoxy)biphenyl-3-yl]-3-methoxy-3-oxopropyl}carbamoyl)piperidin-1-yl]-3-oxopropyl}piperidine-1-carboxylate, 3-({[(3R)-1-{3-[1-(tert-butoxycarbonyl)piperidin-4-yl]propanoyl}piperidin-3-yl]carbonyl}amino)-3-[5-fluoro-4'-(2-fluoroethoxy)biphenyl-3-yl]propanoic acid, tert-butyl 4-{3-[(3R)-3{[(1S)-3-tert-butoxy-1-({[4-(2-fluoroethoxy)phenyl]ethyl}pyridin-3-yl)-3-oxopropyl]carbamoyl}piperidin-1-yl]-3-oxopropyl}piperidine-1-carboxylate, tert-butyl 4-{3-[(3R)-3-{[(1S)-3-tert-butoxy-1-({[3-(2-fluoroethoxy)phenyl]ethyl}pyridin-3-yl)-3-oxopropyl]carbamoyl}piperidin-1-yl]-3-oxopropyl}piperidine-1-carboxylate, (E/Z) tert-butyl 4-{3-[(3R)-3-{[(1S)-3-tert-butoxy-1-({[3-(2-fluoroethoxy)phenyl]ethenyl}pyridin-3-yl)-3-oxopropyl]carbamoyl}piperidin-1-yl]-3-oxopropyl}piperidine-1-carboxylate, tert-butyl 4-{3-[(3R)-3-{[(1S)-1-{3-[2-[¹⁸F]fluoroethoxy]phenyl}-3-methoxy-3-oxopropyl]carbamoyl}piperidin-1-yl]-3-oxopropyl}piperidine-1-carboxylate (3S)-3-({[(3R)-1-{3-[1-(tert-butoxycarbonyl)piperidin-4-yl]propanoyl}piperidin-3-yl]-carbonyl}amino)-3-{3-[2-[⁸F]fluoroethoxy]phenyl}propanoic acid, tert-butyl 4-{3-[(3R)-3-({1-[4-(2-[¹⁸F]fluoroethoxy)phenyl]-3-methoxy-3-oxopropyl}-carbamoyl)piperidin-1-yl]-3-oxopropyl}piperidine-1-carboxylate, 3-({[(3R)-1-{3-[1-(tert-butoxycarbonyl)piperidin-4-yl]propanoyl}piperidin-3-yl]carbonyl}amino)-3-{4-[2-[¹⁸F]fluoroethoxy]phenyl}propanoic acid, tert-butyl 4-{3-[(3R)-3-({(1S)-3-tert-butoxy-1-[5-(2-[¹⁸F]fluoroethoxy)pyridin-3-yl]-3-oxopropyl}carbamoyl)piperidin-1-yl]-3-oxopropyl}piperidine-1-carboxylate, tert-butyl 4-{3-[(3R)-3-({(1S)-1-[5-(2-[$^{18}$F]fluoroethoxy)pyridin-3-yl]-3-methoxy-3-oxopropyl}carbamoyl)piperidin-1-yl]-3-oxopropyl}piperidine-1-carboxylate, (3S)-3-({[(3R)-1-{3-[1-(tert-butoxycarbonyl)piperidin-4-yl]propanoyl}piperidin-3-yl]carbonyl}amino)-3-{5-[2-[$^{18}$F]fluoroethoxy]pyridin-3-yl}propanoic acid, tert-butyl 4-(3-{(3R)-3-[(1-{5-[2-[$^{18}$F]fluoroethoxy]pyridin-3-yl}-3-methoxy-3-oxopropyl)carbamoyl]piperidin-1-yl}-3-oxopropyl)piperidine-1-carboxylate, 3-({[(3R)-1-{3-[1-(tert-butoxycarbonyl)piperidin-4-yl]propanoyl}piperidin-3-yl]-carbonyl}amino)-3-{5-[2-[$^{18}$F]fluoroethoxy]pyridin-3-yl}propanoic acid, tert-butyl 4-{3-[(3R)-3-{[(1S)-1-(5-{4-[2-[$^{18}$F]fluoroethoxy]phenyl}pyridin-3-yl)-3-methoxy-3-oxopropyl]carbamoyl}piperidin-1-yl]-3-oxopropyl}piperidine-1-carboxylate, (3S)-3-({[(3R)-1-{3-[1-(tert-butoxycarbonyl)piperidin-4-yl]propanoyl}piperidin-3-yl]-carbonyl}amino)-3-(5-{4-[2-[$^{18}$F]fluoroethoxy]phenyl}pyridin-3-yl)propanoic acid, tert-butyl 4-{3-[(3R)-3-{[(1S)-3-tert-butoxy-1-(5-{4-[2-[$^{18}$F]fluoroethoxy]phenyl}pyridin-3-yl)-3-oxopropyl]carbamoyl}piperidin-1-yl]-3-oxopropyl}piperidine-1-carboxylate, tert-butyl 4-(3-{(3R)-3-[(1-{5-[3-cyano-4-[$^{18}$F]fluorophenyl]pyridin-3-yl}-3-methoxy-3-oxopropyl)carbamoyl]piperidin-1-yl}-3-oxopropyl)piperidine-1-carboxylate, 3-({[(3R)-1-{3-[1-(tert-butoxycarbonyl)piperidin-4-yl]propanoyl}piperidin-3-yl]carbonyl}amino)-3-[5-(3-cyano-4-[$^{18}$F]fluorophenyl)pyridin-3-yl]propanoic acid, tert-butyl 4-(3-{(3R)-3-[(1-{5-[4-cyano-3-[$^{18}$F]fluorophenyl]pyridin-3-yl}-3-methoxy-3-oxopropyl)carbamoyl]piperidin-1-yl}-3-oxopropyl)piperidine-1-carboxylate, 3-({[(3R)-1-{3-[1-(tert-butoxycarbonyl)piperidin-4-yl]propanoyl}piperidin-3-yl]carbonyl}amino)-3-{5-[4-cyano-3-[$^{18}$F]fluorophenyl]pyridin-3-yl}propanoic acid, tert-butyl 4-{3-[(3R)-3-{[(1S)-3-tert-butoxy-1-(5-{[4-(2-[$^{18}$F]fluoroethoxy)phenyl]ethynyl}pyridine-3-yl)-3-oxopropyl]carbamoyl}piperidin-1-yl]-3-oxopropyl}piperidine-1-carboxylate, tert-butyl 4-{3-[(3R)-3-{[(1S)-3-tert-butoxy-1-(5-{[3-(2-[$^{18}$F]fluoroethoxy)phenyl]ethynyl}pyridin-3-yl)-3-oxopropyl]carbamoyl}piperidin-1-yl]-3-oxopropyl}piperidine-1-carboxylate, tert-butyl 4-{3-[(3R)-3-{[(1S)-3-tert-butoxy-1-({[4-(2-[$^{18}$F]fluoroethoxy)phenyl]ethyl}pyridin-3-yl)-3-oxopropyl]carbamoyl}piperidin-1-yl]-3-oxopropyl}piperidine-1-carboxylate, tert-butyl 4-{3-[(3R)-3-{[(1S)-3-tert-butoxy-1-({[3-(2-[$^{18}$F]fluoroethoxy)phenyl]ethyl }pyridin-3-yl)-3-oxopropyl]carbamoyl}piperidin-1-yl]-3-oxopropyl}piperidine-1-carboxylate, tert-butyl 4-{3-[(3R)-3-({1-[3-(2-{2-[2-[$^{18}$F]fluoroethoxy]ethoxy}ethoxy)phenyl]-3-methoxy-3-oxopropyl}carbamoyl)piperidin-1-yl]-3-oxopropyl}piperidine-1-carboxylate, and 3-({[(3R)-1-{3-[1-(tert-butoxycarbonyl)piperidin-4-yl]propanoyl}piperidin-3-yl]carbonyl}amino)-3-[3-(2-{2-[2-[$^{18}$F]fluoroethoxy]ethoxy}ethoxy)phenyl]propanoic acid.

14. Compounds of the formula II of claim 9, wherein:
$R^9$ is hydrogen or ($C_1$-$C_4$) alkyl; and
$R^{10}$ is ($C_1$-$C_4$) alkyl.

15. Compounds of the formula II of claim 9, wherein:
$R^9$ is hydrogen, methyl, ethyl or tert-butyl; and
$R^{10}$ is methyl, ethyl or tert-butyl.

* * * * *